United States Patent
Janssen et al.

(10) Patent No.: US 10,048,250 B2
(45) Date of Patent: Aug. 14, 2018

(54) MOLECULAR TARGETS AND COMPOUNDS, AND METHODS TO IDENTIFY THE SAME, USEFUL IN THE TREATMENT OF FIBROTIC DISEASES

(71) Applicants: Richard Antonius Jozef Janssen, Leiden (NL); Annemarie Nicolette Lekkerkerker, Palo Alto, CA (US); Thomas Van Es, Voorschoen (NL); Johannes Melchior Petrus Stallen, Leiden (NL)

(72) Inventors: Richard Antonius Jozef Janssen, Leiden (NL); Annemarie Nicolette Lekkerkerker, Palo Alto, CA (US); Thomas Van Es, Voorschoen (NL); Johannes Melchior Petrus Stallen, Leiden (NL)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 15/669,213

(22) Filed: Aug. 4, 2017

(65) Prior Publication Data
US 2018/0045713 A1 Feb. 15, 2018

Related U.S. Application Data

(62) Division of application No. 14/775,790, filed as application No. PCT/EP2014/054441 on Mar. 7, 2014, now abandoned.

(60) Provisional application No. 61/781,220, filed on Mar. 14, 2013.

(51) Int. Cl.
| | |
|---|---|
| *G01N 33/50* | (2006.01) |
| *C07K 16/28* | (2006.01) |
| *C12N 15/113* | (2010.01) |
| *C07K 16/40* | (2006.01) |

(52) U.S. Cl.
CPC ..... *G01N 33/5055* (2013.01); *C07K 16/2869* (2013.01); *C07K 16/40* (2013.01); *C12N 15/113* (2013.01); *C12N 2310/14* (2013.01); *C12N 2310/531* (2013.01)

(58) Field of Classification Search
CPC ............ G01N 33/5055; C07K 16/2869; C07K 16/40; C12N 15/113; C12N 2310/531; C12N 2310/14
See application file for complete search history.

(56) References Cited

U.S. PATENT DOCUMENTS

| | | |
|---|---|---|
| 6,004,753 A | 12/1999 | Henry et al. |
| 6,277,981 B1 | 8/2001 | Tu et al. |
| 6,416,951 B1 | 7/2002 | Schmidt et al. |
| 6,500,615 B1 | 12/2002 | Schmidt et al. |
| 2003/0198627 A1 | 10/2003 | Arts et al. |

FOREIGN PATENT DOCUMENTS

| | | |
|---|---|---|
| KR | 2013-0005086 | 1/2013 |
| WO | WO02/077642 | 10/2002 |
| WO | WO04/044587 | 5/2004 |
| WO | WO04/094636 | 11/2004 |

OTHER PUBLICATIONS

Czimmerer Z., et al.; Identification of novel markers of alternative activation and potential endogenous PPARligand production mechanisms in human IL-4 stimulated differentiating macrophages; Immunobiology (2012) 217: 1301-1314.
Duluc D., et al; Tumor-associated leukemia inhibitory factor and IL-6 skew monocyte differentiation into tumor-associated macrophage-like cells; Blood (2007) 110: 4319-4330.
Sanyal R., et al; A novel cell surface marker for M2 macrophages and plasma cells; Immunology and Cell Biology (2017) 95: 611-619.
Schupp JC., et al; Macrophage Activation in Acute Exacerbation of Idiopathic Pulmonary Fibrosis; PLoS ONE10(1) (2015) e01 16775.
Kuek L Eon, et al.; The MS4A family: counting past 1, 2 and 3: Immunology and Cell Biology (2015), 1-13.
Tomay Federica; Regulation and function of the tetraspain-like molecule MS4A4A in alternatively activated and tumor-associated macrophages: Universita' Delgli Studi Di Milano Thesis Publication Feb. 2015, 1-160.
Ambros V (2004) The functions of animal microRNAs Nature 431(7006):350-355.
Atamas SP et al (2003) Pulmonary and activation-regulated chemokine stimulates collagen production in lung fibroblasts Am J Respir Cell Mol Biol 29(6):743-749.
Bartel DP (2004) MicroRNAs: genomics, biogenesis, mechanism, and function Cell 116:281-297.
Bustin SA et al (2009) The MIQE guidelines: minimum information for publication of quantitative real-time PCR experiments Clin Chem 55(4):611-622.
Chen CJ et al (1992) Multitarget-ribozyme directed to cleave at up to nine highly conserved HIV-1 env RNA regions inhibits HIV-1 replication—potential effectiveness against most presently sequenced HIV-1 isolates Nucleic Acids Res 20(17):4581-4589.
Chiang MY et al (1991) Antisense oligonucleotides inhibit intercellular adhesion molecule 1 expression by two distinct mechanisms J. Biol. Chem. 266(27)18162-18171.

(Continued)

*Primary Examiner* — Ruixiang Li
(74) *Attorney, Agent, or Firm* — Klauber & Jackson LLC

(57) ABSTRACT

The present invention relates to methods and assays for identifying agents useful in the treatment of fibrotic conditions. The invention provides polypeptide and nucleic acid TARGETs, siRNA sequences based on these TARGETs and antibodies against the TARGETs. The invention is further related to pharmaceutical composition comprising siRNA sequences based on the TARGETs and antibodies against the TARGETs for use in the treatment of fibrotic conditions. The invention further provides in vitro methods for reduction or inhibition of macrophage differentiation into alternatively-activated macrophages (M2).

33 Claims, 10 Drawing Sheets

(56) References Cited

OTHER PUBLICATIONS

Cox TR et al (2011) Remodeling and homeostasis of the extracellular matrix: implications for fibrotic diseases and cancer Disease Model Mech 4(2):165-178.

Cullen BR (2004) Derivation and function of small interfering RNAs and microRNAs Virus Research 102(1):3-9.

Duffield JS et al (2005) Selective depletion of macrophages reveals distinct, opposing roles during liver injury and repair J Clin Invest 115(1):56-65.

Fujiwara Y et al (2011) Oleanolic acid inhibits macrophage differentiation into the M2 phenotype and glioblastoma cell proliferation by suppressing the activation of STAT3 Oncology Reports 26(6):1533-1537.

He L et al (2004) MicroRNAs: small RNAs with a big role in gene regulation. Nat. Rev. Genet. 5(7):522-531.

Ho SP et al (1996) Potent antisense oligonucleotides to the human multidrug resistance-1 mRNA are rationally selected by mapping RNA-accessible sites with oligonucleotide libraries Nucl Acids Res 24(10):1901-1907.

Ho SP et al (1998) Mapping of RNA accessible sites for antisense experiments with oligonucleotide libraries Nature Biotechnology 16(1):59-63.

Kunisch E et al (2004) Macrophage specificity of three anti-CD68 monoclonal antibodies (KP1, EBM11, and PGM1) widely used for immunohistochemistry and flow cytometry Ann Rheum Dis 63(7):774-784.

Lima WF et al (1992) Implication of RNA structure on antisense oligonucleotide hybridization kinetics Biochem 31 (48):12055-12061.

Mantovani A et al (2004) The chemokine system in diverse forms of macrophage activation and polarization Trends Immunol 25(12):677-686.

Meneghin A et al (2007) Infectious disease, the innate immune response, and fibrosis J Clin Invest 117(3):530-538.

Mishra RK et al (1994) In vitro selection of antisense oligonucleotides targeted to a hairpin structure Life Sciences 317 (11):977-982.

Murphy CA et al (2003) Divergent pro- and anti-inflammatory roles for IL-23 and IL-12 in joint autoimmune Inflammation J Exp Med 198(12)1951-1957.

Murray PJ et al (2011) Protective and pathogenic functions of macrophage subsets Nat Rev Immunol 11(11):723-737.

Prasse A et al (2006) A vicious circle of alveolar macrophages and fibroblasts perpetuates pulmonary fibrosis via CCL18 Am J Respir Crit Care Med 173(7):781-792.

Prasse A et al (2007) CCL18 as an indicator of pulmonary fibrotic activity in idiopathic interstitial pneumonias and systemic sclerosis Arthritis Rheum 56(5):1685-1693.

Prasse A et al (2009) Serum CC-chemokine ligand 18 concentration predicts outcome in idiopathic pulmonary fibrosis Am J Respir Crit Care Med 179(8):717-723.

Prasse Antje et al (2009) Non-invasive biomarkers in pulmonary fibrosis Respirology 14(6):788-795.

Sethupathy P et al (2006) TarBase: A comprehensive database of experimentally supported animal microRNA targets RNA 12(2):192-197.

Sica A et al (2012) Macrophage plasticity and polarization: in vivo veritas J Clin Invest. 122(3):787-795.

Song E et al (2000) Influence of alternatively and classically activated macrophages on fibrogenic activities of human Fibroblasts Cell Immunol 204(1):19-28.

Stull RA et al (1992) Predicting antisense oligonucleotide inhibitory efficacy: a computational approach using histograms and thermodynamic indices Nucl. Acids Res. 20(13):3501-3508.

Talal A et al (2012) a monoclonal antibody directed at the Lysyl Oxidase-Like 2 (LOXL2) enzyme appears safe and well tolerated in patients with liver disease Hepatology 56(Suppl.1):809A.

Thannickal VJ et al (2004) Mechanisms of pulmonary fibrosis Annu Rev Med 55:395.

Ventura M et al (1993) Activation of HIV-specific ribozyme activity by self-cleavage Nucleic Acids Res. 21 (14):3249-3255.

Wynn TA (2004) Fibrotic disease and the T(H)1/T(H)2 paradigm Nat Rev Immunol 4(8):583-594.

Wynn TA (2008) Cellular and molecular mechanisms of fibrosis J Pathol 214(2):199-210.

Ying SY el al (2004) Intron-derived microRNAs—fine tuning of gene functions Gene 342(1):25-28.

MOLECULAR TARGETS AND COMPOUNDS, AND METHODS TO IDENTIFY THE SAME, USEFUL IN THE TREATMENT OF FIBROTIC DISEASES

CROSS REFERENCE TO RELATED APPLICATIONS

The present application is a Divisional Application of pending National Stage application Ser. No. 14/775,790, filed Nov. 3, 2015, which claims priority from PCT Application No. PCT/EP2014/054441 filed Mar. 7, 2014, which in turn, claims priority from U.S. Provisional Application Ser. No. 61/781,220 filed Mar. 14, 2013. Applicants claim the benefits of 35 U.S.C. § 120 as to the U.S. Non-Provisional applications and the PCT application, and priority under 35 U.S.C. § 119 as to the said Provisional application, and the entire disclosures of all applications are incorporated herein by reference in their entireties.

TECHNICAL FIELD OF THE INVENTION

The present invention is in the field of molecular biology and biochemistry. The present invention relates to methods for identifying agents useful in treatment of fibrotic disease, in particular, agents that reduce or inhibit macrophage differentiation into the alternatively-activated (M2) phenotype. Reduction or inhibition of differentiation into the alternatively-activated (M2) phenotype is useful in the prevention and/or treatment of fibrotic conditions and other diseases where alternatively-activated (M2) macrophages play a role. In particular, the present invention provides methods for identifying agents for use in the prevention and/or treatment of fibrotic diseases.

BACKGROUND OF THE INVENTION

Fibrosis is characterized by excessive deposition of scar tissue by fibroblasts and it is currently one of the largest groups of diseases for which there is no therapy. Fibrosis is responsible for morbidity and mortality associated with organ failure in a variety of chronic diseases affecting the lungs, heart, kidneys, liver and skin. It has been estimated that nearly 45% of all deaths in the developed world are caused by or related to fibrotic conditions which include: cardiovascular disease, pulmonary fibrosis, diabetic nephropathy and liver cirrhosis (Wynn et. al., 2004).

Fibrosis and, especially, idiopathic pulmonary fibrosis (IPF) is a disease that is receiving increasing attention. The pathogenesis of fibrosis has been relatively undefined and only recently the various cellular and molecular processes that contribute to this disease have been unveiled. The overall consensus is that fibrosis is a result of an imbalance in the immune and repair response following infection and/or tissue damage (reviewed by Lekkerkerker et al 2012). These responses are the result of an intricate interplay between various cell types such as epithelial cells, fibroblasts, macrophages, fibrocytes, smooth muscle cells and endothelial cells. An imbalance in the activity in one or more of these cell types is expected to contribute to fibrosis.

Macrophages are responsible for immune surveillance and tissue homeostasis. They are able to engulf pathogens using a broad repertoire of pathogen recognition receptors (PRRs) and destroy them via degradation within lysosomes. Within the process of tissue homeostasis, macrophages play an essential role in removing dead and dying cells and toxic materials. Furthermore, macrophages are crucial in the orchestration of the wound healing process. To perform these important functions, macrophages consist of different subpopulations which are strategically positioned throughout the body (Mantovani et al., 2004).

During an immune response, monocytes are recruited from the circulation in the tissues and differentiate into macrophages. Following tissue damage and/or infection, macrophages exhibit primarily a pro-inflammatory phenotype and secrete pro-inflammatory mediators such as TNFα and IL-1. These pro-inflammatory macrophages are often called classically activated macrophages or M1 macrophages. Various chronic inflammatory disease and autoimmune diseases, such as, for example, rheumatoid arthritis, are associated with activation of M1 macrophages (Murphy et al., 2003).

To prevent an exacerbated immune response and collateral damage to surrounding tissue the M1 macrophage response needs to be tightly controlled. Macrophages that play a role in wound healing have been designated as alternatively-activated macrophages or, otherwise, M2 macrophages. This subset of macrophages secretes anti-inflammatory mediators and is strongly associated with Th2 mediated inflammation and antagonizes M1 macrophages to regulate the immune response.

A major initiator of fibrosis is the persistence of exogenous and endogenous stimuli of pathogens or tissue injury (Meneghin et al., 2007). Both classically activated (M1) and alternatively-activated (M2) macrophages are involved in the process of fibrosis. Nevertheless, M2 macrophages are considered to be the predominant macrophage subtype contributing to fibrosis (Song et al., 2000; Murray et al., 2011; Wynn, 2004). Furthermore, alveolar macrophages isolated from IPF patients are predominantly of a M2 macrophage phenotype (Thannickal et al., 2004).

A key characteristic of many fibrotic diseases is abnormal or exaggerated deposition of extracellular matrix degradation (ECM) (Cox et al, 2011). M2 macrophages can directly affect fibrosis by the excretion of pro-fibrotic mediators, such as tissue inhibitors of metalloproteinases and thereby directly inhibiting ECM turnover (Duffield et al., 2005). M2 macrophages also produce fibronectin, a key component of the ECM and thus contribute, directly to the buildup of excessive ECM. Besides the direct effect of M2 macrophages on fibrosis, M2 macrophages also indirectly contribute to fibrosis through activation of other cell types such as T cells, fibroblasts, and endothelial cells and thereby aggravating fibrosis (Wynn, 2008).

A hallmark of M2 macrophages is the production of CCL18, also known as pulmonary activation-related chemokine (PARC), and it is highly expressed in alveolar macrophages of IPF patients (Prasse et al., 2006, 2007, 2009). Other markers of M2 macrophages have been also identified, among them CD206 and CD163 (Mantovani et al, 2004). Prasse et al. showed that CCL18 concentration within the serum of idiopathic pulmonary fibrosis (IPF) patients strongly correlates with severity of IPF and is a predictive value for mortality (Prasse and Probst et al., 2009). In addition, CCL18 production is strongly increased in the lungs of patients with pulmonary fibrosis and affects cells such as fibroblasts, functioning directly as a pro-fibrotic factor (Atamas et al., 2003). Given that CCL18 is predominantly produced by M2 macrophages, it is likely that a misbalance between M1 and M2 macrophages favoring the M2 macrophages is involved in fibrosis. Recent studies have shown that M1 macrophages can convert into M2 macrophages indicating a dynamic balance between both macrophage subtypes (Duffield et al. 2005). Therefore, interfering in the M1/M2 balance, in particular preventing the occurrence of the M2 phenotype, provides a strategy to intervene in the process of fibrosis.

Over the past few decades much effort has been put into the development of in vitro and in vivo models to unravel the molecular mechanisms regulating fibrotic processes. Employment of primary cells and, preferably, those from fibrosis patients will provide us with better insights in the molecular processes involved in fibrotic disease. It is, however, important to use these cells under physiological conditions and in a disease-relevant context. The study of macrophages in functional assays relevant for fibrosis in combination with functional genomics can give invaluable insight into possible molecular mechanisms contributing to fibrosis and identify novel genetic targets for treatment of fibrosis. Therefore, there is a clear need to understand molecular and cellular processes related to fibrosis and to provide new methods of identifying targets, novel targets, and compounds useful for treatment of fibrosis.

SUMMARY OF THE INVENTION

The present invention is based on the discovery that agents that inhibit the expression and/or activity of the TARGETS disclosed herein are capable of reducing or inhibiting the differentiation of macrophages into alternatively-activated macrophages (M2 macrophages), as indicated by a inhibition of expression and/or release of markers of M2 macrophages, in particular a suppression of the release or expression of CCL18 and/or CD206. The present invention, therefore, provides TARGETS which play a role in the differentiation of macrophages into M2 macrophages, methods for screening for agents capable of down-regulating the expression and/or activity of TARGETS and the use of these agents in the prevention and/or treatment of fibrotic diseases, in particular diseases associated with alternatively-activated macrophages, by inhibiting the differentiation of macrophages into M2 macrophages. The present invention provides TARGETS which are involved in the formation and biology of M2 macrophages, in particular with fibrosis and fibrotic diseases. In a particular aspect, the present invention provides TARGETS which are involved in or otherwise associated with development of fibrosis.

The present invention relates to a method for identifying a compound useful for the treatment of fibrosis, said method comprising: contacting a test compound with a TARGET polypeptide, fragments and structurally functional derivatives thereof, determining a binding affinity of the test compound to said polypeptide or an activity of said polypeptide, contacting the test compound with a population of macrophage cells, measuring a property related to differentiation of macrophages into M2 macrophages, and identifying a compound capable of reducing or inhibiting macrophage differentiation into M2 macrophages and which either demonstrate a binding affinity to said polypeptide or are able to inhibit the activity of said polypeptide.

The present invention further relates to a method for identifying a compound useful for the treatment of fibrosis, said method comprising: contacting a test compound with population of macrophage cells and expressing a TARGET polypeptide, measuring expression and/or amount of said polypeptide in said cells, measuring a property related to differentiation of macrophages into M2 macrophages, and identifying a compound which reduces the expression and/or amount of said polypeptide and which is capable of reducing or inhibiting the differentiation of macrophages into M2 macrophages.

The present invention relates to a method for identifying a compound capable of reducing or inhibiting differentiation of macrophages into M2 macrophages said method comprising: contacting a test compound with a TARGET polypeptide, fragments or structurally functional derivatives thereof, determining a binding affinity of the test compound to said polypeptide or an activity of said polypeptide, contacting the test compound with a population of macrophage cells, measuring a property related to differentiation of macrophages into M2 macrophages, and identifying a compound capable of inhibiting macrophage differentiation into M2 macrophages and which demonstrates a binding affinity to said polypeptide and/or is able to inhibit the activity of said polypeptide.

The present invention provides a method for identifying a compound capable of reducing or inhibiting differentiation of macrophages into M2 macrophages said method comprising: contacting a test compound with a TARGET polypeptide, fragments or structurally functional derivatives thereof, determining a binding affinity of the test compound to said polypeptide or expression or an activity of said polypeptide, and identifying a compound capable of inhibiting macrophage differentiation into M2 macrophages as a compound which demonstrates a binding affinity to said polypeptide and/or is able to inhibit the expression or activity of said polypeptide.

The present invention also relates to:
a) pharmaceutical compositions comprising an antibody or a fragment thereof which specifically binds to a TARGET polypeptide, for use in the treatment of a fibrotic condition.
b) pharmaceutical compositions comprising an agent selected from the group consisting of an antisense polynucleotide, a ribozyme, a small interfering RNA (siRNA) and a short-hairpin RNA (shRNA) for use in the treatment of a fibrotic condition, wherein said agent comprises a nucleic acid sequence complementary to, or engineered from, a naturally-occurring polynucleotide sequence of about 17 to about 30 contiguous nucleotides of a nucleic acid sequence selected encoding a TARGET polypeptide for use in the treatment of a fibrotic condition.

Another aspect of this invention relates to an in vitro method of reducing or inhibiting the differentiation of macrophages into alternatively-activated (M2) macrophages, said method comprising contacting a population of macrophage cells with an inhibitor of the activity or expression of a TARGET polypeptide.

DETAILED DESCRIPTION

Definitions

Figure 1:
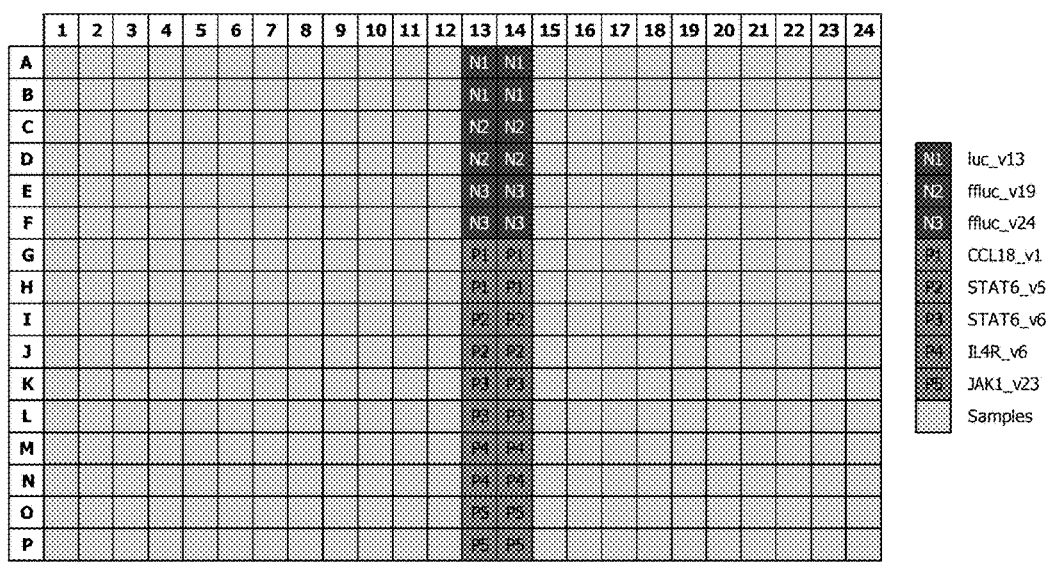
FIG. 1 shows the plate layout of the primary screen. Layout of the library plates with the negative control viruses (N1, N2, and N3) and the positive control viruses (P1, P2, P3, P4, and P5) in column 13 and 14. The remainder of the plate consisted of random viruses (Samples) from the Adenoviral library.

The following terms are intended to have the meanings presented below and are useful in understanding the description and intended scope of the present invention.

The term 'agent' means any molecule, including polypeptides, polynucleotides, natural products and small molecules. In particular the term agent includes compounds such as test compounds or drug candidate compounds.

The term 'activity inhibitory agent' or 'activity inhibiting agent' means an agent, e.g. a polypeptide, small molecule, compound designed to interfere or capable of interfering selectively with the activity of a specific polypeptide or protein normally expressed within or by a cell.

The term 'agonist' refers to an agent that stimulates the receptor the agent binds to in the broadest sense.

As used herein, the term 'antagonist' is used to describe an agent that does not provoke a biological response itself upon binding to a receptor, but blocks or dampens agonist-mediated responses, or prevents or reduces agonist binding and, thereby, agonist-mediated responses.

The term 'assay' means any process used to measure a specific property of an agent, including a compound. A 'screening assay' means a process used to characterize or select compounds based upon their activity from a collection of compounds.

The term 'binding affinity' is a property that describes how strongly two or more compounds associate with each other in a non-covalent relationship. Binding affinities can be characterized qualitatively, (such as 'strong', 'weak', 'high', or low') or quantitatively (such as measuring the KD).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays and methods of the present invention. As such, these compounds comprise organic or inorganic compounds, derived synthetically or from natural sources. The compounds include inorganic or organic compounds such as polynucleotides (e.g. siRNA or cDNA), lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical or cellular indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethyl-phosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'endogenous' shall mean a material that a mammal naturally produces. Endogenous in reference to the term 'enzyme', 'protease', 'kinase', or G-Protein Coupled Receptor ('GPCR') shall mean that which is naturally produced by a mammal (for example, and not by limitation, a human). In contrast, the term non-endogenous in this context shall mean that which is not naturally produced by a mammal (for example, and not by limitation, a human). Both terms can be utilized to describe both in vivo and in vitro systems. For example, and without limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is feasible.

The term 'expressible nucleic acid' means a nucleic acid coding for or capable of encoding a proteinaceous molecule, peptide or polypeptide, and may include an RNA molecule, or a DNA molecule.

The term 'expression' comprises both endogenous expression and non-endogenous expression, including overexpression by transduction.

The term 'expression inhibitory agent' or 'expression inhibiting agent' means an agent, e.g. a polynucleotide designed to interfere or capable of interfering selectively with the transcription, translation and/or expression of a specific polypeptide or protein normally expressed within or by a cell. More particularly and by example, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary such expression inhibitory molecules include ribozymes, microRNAs, double stranded siRNA molecules, self-complementary single-stranded siRNA molecules, genetic antisense constructs, and synthetic RNA antisense molecules with modified stabilized backbones.

The term "'RNAi inhibitor" refers to any molecule that can down regulate, reduce or inhibit RNA interference function or activity in a cell or organism. An RNAi inhibitor can down regulate, reduce or inhibit RNAi (e.g., RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. A RNAi inhibitor can be an siNA molecule, an antisense molecule, an aptamer, or a small molecule that interacts with or interferes with the function of RISC, a miRNA, or an siRNA or any other component of the RNAi pathway in a cell or organism. By inhibiting RNAi (e.g. RNAi mediated cleavage of a target polynucleotide, translational inhibition, or transcriptional silencing), an RNAi inhibitor of the invention can be used to modulate (e.g., down regulate) the expression of a target gene.

The term "microRNA" or "miRNA" or "miR" as used herein refers to its meaning as is generally accepted in the art. More specifically, the term refers a small double-stranded RNA molecules that regulate the expression of target messenger RNAs either by mRNA cleavage, translational repression/inhibition or heterochromatic silencing (see for example Ambros, 2004, Nature, 431, 350-355; Barrel, 2004, Cell, 1 16, 281-297; Cullen, 2004, Virus Research., 102, 3-9; He et al, 2004, Nat. Rev. Genet., 5, 522-531; Ying et al, 2004, Gene, 342, 25-28; and Sethupathy et al, 2006, RNA, 12:192-197). As used herein, the term includes mature single stranded miRNAs, precursor miR-NAs (pre-miR), and variants thereof, which may be naturally occurring. In some instances, the term "miRNA" also includes primary miRNA transcripts and duplex miRNAs.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic acid residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'hybridization' means any process by which a strand of nucleic acid binds with a complementary strand through base pairing. The term 'hybridization complex' refers to a complex formed between two nucleic acid sequences by virtue of the formation of hydrogen bonds between complementary bases. A hybridization complex may be formed in solution (for example, C0t or R0t analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency. The term 'standard hybridization conditions' refers to salt and temperature conditions substantially equivalent to 5×SSC and 65° C. for both hybridization and wash. However, one skilled in the art will appreciate that such 'standard hybridization conditions' are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20NC below the predicted or determined Tm with washes of higher stringency, if desired.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression, enhanced expression, activity, or increased activity of a protein or polypeptide.

The term 'ligand' means an endogenous, naturally occurring molecule specific for an endogenous, naturally occurring receptor.

The term 'pharmaceutically acceptable salts' refers to the non-toxic, inorganic and organic acid addition salts, and base addition salts, of compounds which inhibit the expression or activity of TARGETS as disclosed herein. These salts can be prepared in situ during the final isolation and purification of compounds useful in the present invention.

The term 'polypeptide' relates to proteins (such as TARGETS), proteinaceous molecules, fragments of proteins, monomers or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, particularly 80 percent, most particularly 90 percent, and in a special embodiment 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A special embodiment of polynucleotide is the polyribonucleotide of from about 17 to about 22 nucleotides, more commonly described as small interfering RNAs (siRNAs—double stranded siRNA molecules or self-complementary single-stranded siRNA molecules (shRNA)). Another special embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'subject' includes humans and other mammals.

The term 'TARGET' or 'TARGETS' means the protein(s) identified in accordance with the assays described herein and determined to be involved in differentiation of macrophages into M2 macrophages, otherwise referred to as an alternatively-activated macrophages. The term TARGET or TARGETS includes and contemplates alternative species forms, isoforms, and variants, such as splice variants, allelic variants, alternate in frame exons, and alternative or premature termination or start sites, including known or recognized isoforms or variants thereof such as indicated in Table 1. The NCBI accession numbers are provided to assist a skilled person to identify the transcripts and polypeptides. However, the term TARGET or TARGETS is not limited to those particular versions of the sequences and encompasses functional variants of nucleic acids and polypeptides corresponding to those sequences.

'Therapeutically effective amount' or 'effective amount' means that amount of a compound or agent that will elicit the biological or medical response in or of a subject that is being sought by or is accepted by a medical doctor or other clinician.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). Accordingly, 'treating' refers to both therapeutic treatment and prophylactic or preventative measures. Those in need of treating include those already with the disorder as well as those in which the disorder is to be prevented. The related term 'treatment,' as used herein, refers to the act of treating a disorder, symptom, disease or condition. In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter or of a physiologically measurable parameter), or both. In a further embodiment, 'treating' or 'treatment' relates to slowing the progression of the disease.

The term "vectors" also relates to plasmids as well as to viral vectors, such as recombinant viruses, or the nucleic acid encoding the recombinant virus.

The term "vertebrate cells" means cells derived from animals having vertebral structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine, murine, such as mice and rats, and rabbits.

As used herein the term 'fibrotic diseases' refers to diseases characterized by excessive or persistent scarring, particularly due to excessive or abnormal production, deposition of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular aspects, the term fibrotic diseases refers to idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis and Peyronie's disease. More particularly, the term "fibrotic diseases" refers to idiopathic pulmonary fibrosis (IPF).

The term "M2 macrophage phenotype" or "alternatively-activated macrophages" or "M2 macrophages" is used throughout to refer to the subtype of macrophages which are activated by interleukin-4 (IL-4), IL-10, or a combination thereof, and demonstrating the ability to express particular markers e.g. CCL-18, CD206 and CD163 (Mantovani et al., 2004, Prasse 2007) many subtypes of M2 phenotype are covered by this term. They would be known to a skilled person. (e.g. described in Mantovani et al., 2004, 2012).

The term "M1 macrophage phenotype" or "classically-activated macrophages" or "M1 macrophages" is used throughout to refer to the subtype of macrophages activated by bacterial lipopolysaccharide (LPS) and interferon-$\gamma$ (IFN-$\gamma$). and demonstrating characteristics which include production of large amounts of pro-inflammatory signaling and effector molecules such as TNF$\alpha$.

The term "M0 macrophage phenotype" or "M0 macrophages" refers to monocyte derived naive macrophages that have not yet differentiated into either M1 or M2 macrophages, characterized by the absence of CCL18 and TNF$\alpha$.

Targets

Applicant's invention is relevant to the treatment, prevention and alleviation of fibrotic conditions and disorders, particularly associated with increased numbers of M2 macrophages or enhanced differentiation of macrophages into M2 macrophages.

The present invention is based on extensive work by the present inventors to develop an in vitro (cell-free or cell based) assay system suitable to provide a scientifically valid substitute for the naturally occurring in vivo process of macrophage differentiation. The process of differentiation of macrophages into M2 macrophages is known to be involved in fibrosis, however it is a complex process. The present invention provides an artificial model for the natural system using distinct and quantifiable in vitro parameters which is suitable for the identification of compounds able to inhibit the differentiation of macrophages into M2 macrophages, and, thus, identify compounds that may be useful in the treatment and/or prevention of fibrosis.

The present invention provides methods for assaying for drug candidate compounds useful in treatment of fibrotic conditions, particularly useful in reducing or inhibiting the differentiation of macrophages into M2 macrophages, comprising contacting the compound with a cell expressing a TARGET, and determining the relative amount or degree of inhibition of differentiation of macrophages into M2 macrophages in the presence and/or absence of the compound. The present invention provides methods for assaying for drug candidate compounds useful in treatment of fibrotic conditions, particularly useful in reducing or inhibiting the differentiation of macrophages into M2 macrophages, comprising contacting the compound with a cell expressing a TARGET, and determining the relative amount or degree of inhibition of the expression or activity of the TARGET, whereby inhibition of expression or activity of the TARGET is associated with or results in inhibition of or reduced differentiation of macrophages into M2 macrophages in the presence and/or absence of the compound. Such methods may be used to identify target proteins that act to inhibit said differentiation; alternatively, they may be used to identify compounds that down-regulate or inhibit the expression or activity of TARGET proteins. The invention provides methods for assaying for drug candidate compounds useful in the treatment of fibrosis, comprising contacting the compound with a TARGET, under conditions wherein the expression or activity of the TARGET may be measured, and determining whether the TARGET expression or activity is altered in the presence of the compound, contacting a population of macrophage cells with said test compound and measuring a property related to differentiation of macrophages into M2 macrophages. Exemplary such methods can be designed and determined by the skilled artisan. Particular such exemplary methods are provided herein.

The present invention is based on the inventors' discovery that the TARGET polypeptides and their encoding nucleic acids, identified as a result of screens described below in the Examples, are factors involved in fibrosis and in particular in differentiation of macrophages into M2 macrophages. A reduced activity or expression of the TARGET polypeptides and/or their encoding polynucleotides is causative, correlative or associated with reduced or inhibited differentiation of macrophages into M2 macrophages. Alternatively, a reduced activity or expression of the TARGET polypeptides and/or their encoding polynucleotides is causative, correlative or associated with decrease of the markers of M2 macrophages.

In a particular embodiment of the invention, the TARGET polypeptide comprises an amino acid sequence selected from the group consisting of SEQ ID NO: 26-50 as listed in Table 1.

A particular embodiment of the invention comprises the GPCR TARGETs identified as SEQ ID NO: 26 and 38-41. A particular embodiment of the invention comprises the protease TARGETs identified as SEQ ID NO: 27 and 50. A particular embodiment of the invention comprises the phosphatase TARGET identified as SEQ ID NO: 28. A particular embodiment of the invention comprises the secreted/extracellular TARGETs identified as SEQ ID NO: 29, 30-35, 36 and 43-44. A particular embodiment of the invention comprises the receptor TARGETs identified as SEQ ID NO: 37, 45-47. A particular embodiment of the invention comprises the ion channel TARGET identified as SEQ ID NO: 42. A particular embodiment of the invention comprises the kinase TARGET identified as SEQ ID NO: 48. A particular embodiment of the invention comprises the transporter TARGETs identified as SEQ ID NO: 49.

Methods of the Invention

In one aspect, the present invention relates to a method for identifying a compound useful for the treatment of fibrosis, said method comprising:

a) contacting a test compound with a polypeptide comprising an amino acid sequence selected from the group consisting of SEQ ID NOs: 26-50, fragments and functional derivatives thereof;

TABLE 1

| Target Gene Symbol | GenBank Nucleic Acid Acc #: | SEQ ID NO: DNA | GenBank Protein Acc # | SEQ ID NO: Protein | NAME | Class |
|---|---|---|---|---|---|---|
| S1PR2 | NM_004230.3 | 1 | NP_004221.3 | 26 | sphingosine-1-phosphate receptor 2 | GPCR |
| USP22 | NM_015276.1 | 2 | NP_056091.1 | 27 | ubiquitin specific peptidase 22 | Protease |
| BPNT1 | NM_006085.4 | 3 | NP_006076.4 | 28 | 3'(2'), 5'-bisphosphate nucleotidase 1 | Phosphatase |
| C1RL | NM_016546.2 | 4 | NP_057630.2 | 29 | complement component 1, r subcomponent-like | Secreted/Extracellular |
| DCN | NM_133505.2 | 5 | NP_598012.1 | 30 | decorin | Secreted/Extracellular |
|  | NM_133507.2 | 6 | NP_598014.1 | 31 |  |  |
|  | NM_133506.2 | 7 | NP_598013.1 | 32 |  |  |
|  | NM_133504.2 | 8 | NP_598011.1 | 33 |  |  |
|  | NM_001920.3 | 9 | NP_001911.1 | 34 |  |  |
|  | NM_133503.2 | 10 | NP_598010.1 | 35 |  |  |
| EFEMP2 | NM_016938.4 | 11 | NP_058634.4 | 36 | EGF containing fibulin-like extracellular matrix protein 2 | Secreted/Extracellular |
| EFNB2 | NM_004093.3 | 12 | NP_004084.1 | 37 | ephrin-B2 | Receptor |
| GPR155 | NM_001033045.3 | 13 | NP_001028217.1 | 38 | G protein-coupled receptor 155 | GPCR |
|  | NM_152529.6 | 14 | NP_689742.4 | 39 |  |  |
|  | NM_001267050.1 | 15 | NP_001253979.1 | 40 |  |  |
|  | NM_001267051.1 | 16 | NP_001253980.1 | 41 |  |  |
| KCNMB4 | NM_014505.5 | 17 | NP_055320.4 | 42 | potassium large conductance calcium-activated channel, subfamily M, beta member 4 | Ion channel |
| LIF | NM_002309.4 | 18 | NP_002300.1 | 43 | leukemia inhibitory factor | Secreted/Extracellular |
|  | NM_001257135.1 | 19 | NP_001244064.1 | 44 |  |  |
| MS4A4A | NM_148975.2 | 20 | NP_683876.1 | 45 | membrane-spanning 4-domains, subfamily A, member 4A | Receptor |
|  | NM_024021.3 | 21 | NP_076926.2 | 46 |  |  |
|  | NM_001243266.1 | 22 | NP_001230195.1 | 47 |  |  |
| RAF1 | NM_002880.3 | 23 | NP_002871.1 | 48 | v-raf-1 murine leukemia viral oncogene homolog 1 | Kinase |
| SLC15A3 | NM_016582.2 | 24 | NP_057666.1 | 49 | solute carrier family 15, member 3 | Transporter |
| ZMPSTE24 | NM_005857.4 | 25 | NP_005848.2 | 50 | zinc metallopeptidase STE24 | Protease | b) measuring a binding affinity of the test compound to said polypeptide;

c) contacting the test compound with a population of macrophage cells;

d) measuring a property related to differentiation of macrophages into M2 macrophages; and e) identifying a compound capable of reducing or inhibiting macrophage differentiation into M2 macrophages and demonstrating binding affinity to said polypeptide.

In a further aspect, the present invention relates to a method for identifying a compound that reduces or inhibits differentiation of macrophages into M2 macrophages, said method comprising:
a) contacting a test compound with a nucleic acid encoding an amino acid selected from the group consisting of SEQ ID NOs: 26-50 or a fragment or functional derivative thereof;
b) identifying and/or measuring a binding affinity of the test compound to said nucleic acid;
c) contacting the test compound with a population of macrophage cells;
d) measuring a property related to differentiation of macrophages into M2 macrophages; and
e) identifying a compound capable of reducing or inhibiting macrophage differentiation into M2 macrophages and demonstrating binding affinity to said polypeptide.

In one aspect, the present invention relates to a method for identifying a compound that reduces or inhibits differentiation of macrophages into M2 macrophages, said method comprising:
a) contacting a test compound with a polypeptide comprising an amino acid sequence selected from the group consisting of SEQ ID NOs: 26-50, fragments and functional derivatives thereof or with a nucleic acid encoding an amino acid selected from the group consisting of SEQ ID NOs: 26-50 or a functional derivative thereof;
b) identifying and/or measuring a binding affinity of the test compound to said polypeptide or nucleic acid;
c) contacting the test compound with a population of macrophage cells;
d) measuring a property related to or indicating differentiation of macrophages into M2 macrophages; and
e) identifying a compound capable of inhibiting or reducing macrophage differentiation into M2 macrophages and demonstrating binding affinity to said polypeptide or nucleic acid.

In a further aspect of the above method, the nucleic acid encoding an amino acid selected from the group consisting of SEQ ID NOs: 26-50 or a functional derivative thereof may be selected from the group consisting of SEQ ID NOs: 1-25.

The order of taking these measurements is not believed to be critical to the practice of the present invention, which may be practiced in any order. In a particular aspect the method steps (c) and (d) may be performed before performing steps (a) and (b). For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide.

In another aspect, steps (a)-(d) method may also be performed simultaneously in a cell-based assay by contacting a test compound with a population of macrophages, measuring a binding affinity of the test compound to a TARGET polypeptide and a property related to differentiation of macrophages into M2 macrophages, and identifying a compound capable of inhibiting of macrophage differentiation into said M2 macrophages and which demonstrates binding affinity to said polypeptide.

The binding affinity of a compound with the polypeptide TARGET can be measured by methods known in the art, such as using surface plasmon resonance biosensors (Biacore®), by saturation binding analysis with a labeled compound (for example, Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, for example, in the range of 100 nM to 1 pM; a moderate- to low-affinity binding relates to high Kd, $IC_{50}$ and $EC_{50}$ values, for example in the micromolar range.

In one aspect, the assay method includes contacting a TARGET polypeptide with a compound that exhibits a binding affinity in the micromolar range. In an aspect, the binding affinity exhibited is at least 10 micromolar. In an aspect, the binding affinity is at least 1 micromolar. In an aspect, the binding affinity is at least 500 nanomolar.

In a particular aspect a test compound is selected based its ability to bind to a TARGET class or from a known libraries of compounds having ability to bind to a TARGET class.

In further aspect, the present invention relates to a method for identifying a compound useful for the treatment of fibrosis, said method comprising:
a) contacting a test compound with a polypeptide comprising an amino acid sequence selected from the group consisting of SEQ ID NOs: 26-50, functional fragments and functional derivatives thereof;
b) measuring an activity of said polypeptide;
c) contacting the test compound with a population of macrophage cells;
d) measuring a property related to differentiation of macrophages into alternatively-activated macrophages; and
e) identifying a compound capable of reducing or inhibiting differentiation of macrophages into M2 macrophages and inhibiting the activity of said polypeptide.

In an additional aspect, the present invention relates to a method for identifying a compound that reduces or inhibits differentiation of macrophages into M2 macrophages, said method comprising:
a) contacting a test compound with a polypeptide comprising an amino acid sequence selected from the group consisting of SEQ ID NOs: 26-50, functional fragments and functional derivatives thereof;
b) measuring an activity of said polypeptide;
c) contacting the test compound with a population of macrophage cells;
d) measuring a property related to differentiation of macrophages into alternatively-activated macrophages; and
e) identifying a compound capable of reducing or inhibiting differentiation of macrophages into M2 macrophages and inhibiting the activity of said polypeptide.

In a further aspect, the present invention relates to a method for identifying a compound that reduces or inhibits differentiation of macrophages into M2 macrophages, said method comprising:
   a) contacting a test compound with a polypeptide comprising an amino acid sequence selected from the group consisting of SEQ ID NOs: 26-50, functional fragments and functional derivatives thereof or with a nucleic acid encoding an amino acid selected from the group consisting of SEQ ID NOs: 26-50 or a functional derivative thereof;
   b) measuring the expression or an activity of said polypeptide;
   c) identifying a compound capable of inhibiting the expression or activity of said polypeptide whereby inhibition of expression or activity of said polypeptide results in or is associated with reduction or inhibition of differentiation of macrophages into M2 macrophages.

In an additional aspect of the above method, the nucleic acid encoding an amino acid selected from the group consisting of SEQ ID NOs: 26-50 or a functional derivative thereof may be selected from the group consisting of SEQ ID NOs: 1-25.

The order of taking these measurements is not believed to be critical to the practice of the present invention, which may be practiced in any order. In a particular aspect of the method steps (c) and (d) may be performed before performing steps (a) and (b). For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide.

Table 1 lists the TARGETS identified using applicants' knock-down library in the M2 differentiation assay exemplified herein, including the class of polypeptides identified. TARGETS have been identified in polypeptide classes including kinases, proteases, enzymes, ion channels, GPCRs, and extracellular proteins, for instance. A skilled artisan would be aware of different methods of measuring activity of those classes both in cell-free preparations as well in cell-based assays. A variety of methods exists and might be adapted to a particular target. Those adaptations are a matter of routine experimentation and rely on the existent techniques and methods. Some exemplary methods are described herein.

Ion channels are membrane protein complexes and their function is to facilitate the diffusion of ions across biological membranes. Membranes, or phospholipid bilayers, build a hydrophobic, low dielectric barrier to hydrophilic and charged molecules. Ion channels provide a high conducting, hydrophilic pathway across the hydrophobic interior of the membrane. The activity of an ion channel can be measured using classical patch clamping. High-throughput fluorescence-based or tracer-based assays are also widely available to measure ion channel activity. These fluorescent-based assays screen compounds on the basis of their ability to either open or close an ion channel thereby changing the concentration of specific fluorescent dyes across a membrane. In the case of the tracer-based assay, the changes in concentration of the tracer within and outside the cell are measured by radioactivity measurement or gas absorption spectrometry.

Specific methods to determine the inhibition by the compound by measuring the cleavage of the substrate by the polypeptide, which is a protease, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

G-protein coupled receptors (GPCR) are capable of activating an effector protein, resulting in changes in second messenger levels in the cell. The TARGETs represented by SEQ ID NO: 26, 38-41 are GPCRs. The activity of a GPCR can be measured by measuring the activity level of such second messengers. Two important and useful second messengers in the cell are cyclic AMP (cAMP) and $Ca^{2+}$. The activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

In another aspect the present relation relates to a method for identifying a compound useful for the treatment of fibrosis, said method comprising
   a) contacting a test compound with population of macrophage cells expressing a polypeptide comprising an amino acid sequence selected from the group consisting of SEQ ID NOs: 26-50;
   b) measuring expression, activity and/or amount of said polypeptide in said cells;
   c) measuring a property related to differentiation of macrophages into M2 macrophages; and
   d) identifying a compound producing reduction of expression, activity and/or amount of said polypeptide and capable of reducing or inhibiting differentiation of macrophages into M2 macrophages.

In a further aspect the present relation relates to a method for identifying a compound that reduces or inhibits differentiation of macrophages into M2 macrophages, said method comprising
   a) contacting a test compound with population of macrophage cells expressing a polypeptide comprising an amino acid sequence selected from the group consisting of SEQ ID NOs: 26-50;
   b) measuring expression, activity and/or amount of said polypeptide in said cells;
   c) optionally measuring a property related to differentiation of macrophages into M2 macrophages; and
   d) identifying a compound producing reduction of expression, activity and/or amount of said polypeptide and capable of reducing or inhibiting differentiation of macrophages into M2 macrophages.

In particular aspect the method steps of the invention related to measuring of binding to a TARGET or activity are performed with a population of mammalian cells, in particular human cells, which have been engineered so as to express said TARGET polypeptide. In an alternative aspect the methods of the invention are performed using a population of macrophages, which have been engineered so as to express said TARGET polypeptide. This can be achieved by expression of the TARGET polypeptide in the cells using appropriate techniques known to a skilled person. In a specific embodiment, this can be achieved by over-expression of the TARGET polypeptide in the cells using appropriate techniques known to a skilled person. Alternatively, the method of the invention maybe performed with a population of macrophages which are known to naturally express said TARGET polypeptide.

In particular aspect the measurements of expression and/ or amount of a TARGET polypeptide and a measurement of a property related to differentiation of macrophages into M2 macrophages can be done in separate steps using different populations of macrophage cells. The measurements in steps (b) and (c) can also be performed in reverse order. The order of taking these measurements is not believed to be critical to the practice of the present invention, which may be practiced in any order.

One particular means of measuring the activity or expression of the polypeptide is to determine the amount of said polypeptide using a polypeptide binding agent, such as an antibody, or to determine the activity of said polypeptide in a biological or biochemical measure, for instance the amount of phosphorylation of a target of a kinase polypeptide.

TARGET gene expression (mRNA levels) can be measured using techniques well-known to a skilled artisan. Particular examples of such techniques include northern analysis or real-time PCR. Those methods are indicative of the presence of nucleic acids encoding TARGETs in a sample, and thereby correlate with the expression of the transcript from the polynucleotide.

The population of cells may be exposed to the compound or the mixture of compounds through different means, for instance by direct incubation in the medium, or by nucleic acid transfer into the cells. Such transfer may be achieved by a wide variety of means, for instance by direct transfection of naked isolated DNA, or RNA, or by means of delivery systems, such as recombinant vectors. Other delivery means such as liposomes, or other lipid-based vectors may also be used. Particularly, the nucleic acid compound is delivered by means of a (recombinant) vector such as a recombinant virus.

In vivo animal models of fibrotic diseases may be utilized by the skilled artisan to further or additionally screen, assess, and/or verify the agents or compounds identified in the present invention, including further assessing TARGET modulation in vivo. Such animal models include, but are not limited to, lung fibrosis models (e.g Bleomycin model, irradiation model, silica model, (inducible) transgenic mouse model, FITC model, adoptive transfer model), renal fibrosis models (e.g. COL4A3-deficiency model, nephrotoxic serum nephritis model; unilateral ureteral obstruction model) and liver fibrosis models (e.g CCL4 intoxication model).

A population of macrophage cells in the methods of the invention does not have to be pure or require a particular degree of purity. A population of mammalian cells wherein some of said cells are macrophage cells is sufficient to practice the methods of present invention. The number or amount of macrophage cells should be sufficient to determine whether there are significant or relevant changes in differentiation into M2 macrophages or in relative amounts of M2 macrophages, including versus other types such as M1 macrophages, or should be sufficient to evaluate differences, such as a significant decrease or increase, in a macrophage marker or factor. In particular aspect said marker is CCL18. In one aspect such population of macrophage cells can be derived from another cell type (e.g. monocytes) or any other cells that can potentially differentiate into macrophage cells. It should be understood that a population of macrophage cells can be also obtained directly from an organ or alternatively grown using appropriate medium. The techniques of generating a population of macrophage cells are known to a person skilled in the art. Some of such techniques are provided in the Examples of the invention.

In a specific embodiment the methods may additionally comprise the step of comparing the compound to be tested to a control. Suitable controls should always be in place to insure against false positive or negative readings. In a particular embodiment of the present invention the screening method comprises the additional step of comparing the compound to a suitable control. In one embodiment, the control may be a cell or a sample that has not been in contact with the test compound. In an alternative embodiment, the control may be a cell that does not express the TARGET; for example in one aspect of such an embodiment the test cell may naturally express the TARGET and the control cell may have been contacted with an agent, e.g. an siRNA, which inhibits or prevents expression of the TARGET. Alternatively, in another aspect of such an embodiment, the cell in its native state does not express the TARGET and the test cell has been engineered so as to express the TARGET, so that in this embodiment, the control could be the untransformed native cell. The control may also alternatively utilize a known inhibitor of differentiation of macrophages into M2 macrophages or a compound known not to have any significant effect on the M2 macrophages. Whilst exemplary controls are described herein, this should not be taken as limiting; it is within the scope of a person of skill in the art to select appropriate controls for the experimental conditions being used.

Examples of negative controls include, but not limited to, cells that have been not treated with any compound, cells treated with a compound known not to be an inhibitor of differentiation of macrophages into M2 macrophages, compounds known not to interfere with the pathways involved in differentiation of macrophages into M2 macrophages. Examples of positive controls include, but not limited to, cells contacted with compounds known to inhibit activity or expression of STATE, IL4R, JAK1 or CCL18, cells contacted with a compound known to inhibit the differentiation of macrophages into M2 macrophages.

In a particular embodiment the binding and activity testing in the invention methods is performed in an in vitro cell-free preparation.

In an alternative embodiment the binding and activity testing in the invention methods is performed in a cell.

In a particular aspect the invention methods activity and binding testing is performed in a mammalian cell, particularly a human cell. More specifically these steps are performed in macrophage cells.

It should be understood that the cells expressing the polypeptides may be cells naturally expressing the polypeptides, or the cells may be may be transfected to express the polypeptides. Also, the cells may be transduced to overexpress the polypeptide, or may be transfected to express a non-endogenous form of the polypeptide, which can be differentially assayed or assessed.

The polynucleotide expressing the TARGET polypeptide in cells might be included within a vector. The polynucleic acid is operably linked to signals enabling expression of the nucleic acid sequence and is introduced into a cell utilizing, particularly, recombinant vector constructs, which will express the nucleic acid once the vector is introduced into the cell. A variety of viral-based systems are available, including adenoviral, retroviral, adeno-associated viral, lentiviral, herpes simplex viral or a sendai viral vector systems. All may be used to introduce and express a TARGET polypeptide in the target cells.

In a particular embodiment the assay methods of the invention involve measurement of the inhibition of release or expression of a marker of alternatively-activated macrophages (M2 macrophage marker).

Many of the M2 macrophage markers are known to a skilled person. The selection of such markers depends on the availability of reagents, scale of the practiced assay methods and other factors related to a specific assay design. In a specific embodiment a M2 macrophage marker is selected from the group consisting of CCL18, CCL13, TGFβ, CCL22, CCL17, soluble fibronectin, folate receptor β, CD206, and CD163. In a specific embodiment the M2 macrophage marker is CCL18 or CD206.

The means of measuring such markers, depending on the assay setup and throughput, are known to a skilled artisan. Although human ELISA's are commercially available their sensitivity is not always to detect low levels of the markers. Therefore, the assay might be optimized on the Meso Scale Discovery platform (MSD) (Meso Scale Discovery, Maryland, US) as a sandwich immunoassay where signaling molecules are specifically captured and detected by antibodies. MSD technology uses micro-plates with carbon electrodes integrated at the bottom of the plates; Biological reagents, immobilized to the carbon simply by passive adsorption, retain high biological activity. MSD assays use electro-chemiluminescent labels for ultra-sensitive detection. The detection process is initiated at electrodes located at the bottom of the micro-plates. Labels near the electrode only are excited and detected reducing background signal. The antibodies for such assay might be purchased from different producers and the skilled artisan is in the position to choose correct antibodies to perform the assay.

Alternatively the expression levels of the M1 and M2 phenotype markers can be measured using known methods including quantitative real time polymerase chain reaction (Q-PCR/qPCR/qrt-PCR). qPCR is a laboratory technique based on PCR, which is used to amplify and simultaneously quantify a targeted DNA molecule. For one or more specific sequences in a DNA sample, Real Time-PCR enables both detection and quantification. The quantity can be either an absolute number of copies or a relative amount when normalized to DNA input or additional normalizing genes.

In a specific embodiment the methods of the invention utilize cells that have been triggered by a factor which induces macrophage differentiation into M2 macrophages (M2 inducing factor). Many of such factors have been described in the literature and they are well-known to a skilled person. In a particular embodiment the methods of the invention utilize cells that have been triggered by one or more M2 inducing factors selected from the group consisting of IL4, IL10, IL13, immune complexes, and lipopolysaccharides. An immune complex is formed from the integral binding of an antibody to a soluble antigen. The bound antigen and antibody act as a specific epitope, and is referred to as a singular immune complex.

In more particular embodiment the assay methods are performed using cells that have been triggered by a combination of IL10 and IL4.

In a particular embodiment the assay methods might be supplemented by additional steps of: measuring a property related to the differentiation of macrophages into classically-activated (M1) macrophages, and identifying a compound that does not inhibit said differentiation. In a specific embodiment said property is the level and/or expression of a marker of the M1 macrophage phenotype (M1 macrophage marker), and a compound is identified which does not increase the levels of said marker.

In a particular embodiment TNFα is used as a marker of the M1 macrophage phenotype. Many other alternative M1 macrophage markers have been described in the literature and will be known to a skilled person.

Candidate Compounds

Expression-Inhibiting Agents

In a particular embodiment the methods of the invention a test compound is selected from the group consisting of an antisense polynucleotide, a ribozyme, short-hairpin RNA (shRNA), microRNA (miRNA) and a small interfering RNA (siRNA).

A special embodiment of these methods comprises the expression-inhibitory agent selected from the group consisting of antisense RNA, antisense oligodeoxynucleotide (ODN), a ribozyme that cleaves the polyribonucleotide coding for SEQ ID NO: 26-50, a small interfering RNA (siRNA) or microRNA (miRNA) that is sufficiently homologous to a portion of the polyribonucleotide corresponding to SEQ ID NO: 1-25, such that the expression-inhibitory agent interferes with the translation of the TARGET polyribonucleotide to the TARGET polypeptide.

The down regulation of gene expression using antisense nucleic acids can be achieved at the translational or transcriptional level. Antisense nucleic acids of the invention are particularly nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Particularly, the antisense sequence is at least about 15-30, and particularly at least 17 nucleotides in length. The preparation and use of antisense nucleic acids, DNA encoding antisense RNAs and the use of oligo and genetic antisense is known in the art.

In a more specific embodiment a test compound comprises a nucleic acid sequence complementary to, or engineered from, a naturally-occurring polynucleotide sequence of about 17 to about 30 contiguous nucleotides of a TARGET polynucleotide.

The skilled artisan can readily utilize any of several strategies to facilitate and simplify the selection process for antisense nucleic acids and oligonucleotides effective in inhibition of TARGET and differentiation of macrophages into alternatively-activated macrophages. Predictions of the binding energy or calculation of thermodynamic indices between an oligonucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide sequences or antisense targets utilizing various criteria recognized by the skilled artisan, including for example the absence of self-complementarity, the absence of hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.). In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

The antisense nucleic acids are particularly oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Specific examples of some particular oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RNA-DNA duplex activates the endogenous enzyme ribonuclease (RNase) H, which cleaves the mRNA component of the hybrid molecule. Oligonucleotides may also contain one or more substituted sugar moieties. Particular oligonucleotides comprise one of the following at the 2' position: OH, SH, SCH3, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Exemplary ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase T (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

In a particular embodiment the methods of the invention might be practiced using antisense polynucleotide, siRNA or shRNA comprising an antisense strand of 17-25 nucleotides complementary to a sense strand, wherein said sense strand is selected from 17-25 continuous nucleotides of a TARGET polynucleotide.

A particular inhibitory agent is a small interfering RNA (siRNA, particularly small hairpin RNA, "shRNA"). siRNA, particularly shRNA, mediate the post-transcriptional process of gene silencing by double stranded RNA (dsRNA) that is homologous in sequence to the silenced RNA. siRNA according to the present invention comprises a sense strand of 15-30, particularly 17-30, most particularly 17-25 nucleotides complementary or homologous to a contiguous 17-25 nucleotide sequence selected from the group of sequences described in SEQ ID NO: 1-25, more particularly from the group of sequences described in SEQ ID NOs: 64-109, and an antisense strand of 15-30, particularly 17-30, most particularly 17-25, more specifically 19-21 nucleotides complementary to the sense strand. More particular siRNA according to the present invention comprises a sense strand selected from the group of sequences comprising SEQ ID NOs: 64-109. The most particular siRNA comprises sense and anti-sense strands that are 100 percent complementary to each other and the TARGET polynucleotide sequence. Particularly the siRNA further comprises a loop region linking the sense and the antisense strand.

A self-complementing single stranded shRNA molecule polynucleotide according to the present invention comprises a sense portion and an antisense portion connected by a loop region linker. Particularly, the loop region sequence is 4-30 nucleotides long, more particularly 5-15 nucleotides long and most particularly 8 or 12 nucleotides long. In a most particular embodiment the linker sequence is UUGCUAUA or GUUUGCUAUAAC (SEQ ID NO: 110). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO 2004/094636 and US 2003/0198627, are hereby incorporated by reference).

Particular inhibitory agents include MicroRNAs (referred to as "miRNAs"). miRNA are small non-coding RNAs, belonging to a class of regulatory molecules found in many eukaryotic species that control gene expression by binding to complementary sites on target messenger RNA (mRNA) transcripts.

In vivo miRNAs are generated from larger RNA precursors (termed pre-miRNAs) that are processed in the nucleus into approximately 70 nucleotide pre-miRNAs, which fold into imperfect stem-loop structures. The pre-miRNAs undergo an additional processing step within the cytoplasm where mature miRNAs of 18-25 nucleotides in length are excised from one side of the pre-miRNA hairpin by an RNase III enzyme.

miRNAs have been shown to regulate gene expression in two ways. First, miRNAs binding to protein-coding mRNA sequences that are exactly complementary to the miRNA induce the RNA-mediated interference (RNAi) pathway. Messenger RNA targets are cleaved by ribonucleases in the RISC complex. In the second mechanism, miRNAs that bind to imperfect complementary sites on messenger RNA transcripts direct gene regulation at the posttranscriptional level but do not cleave their mRNA targets. miRNAs identified in both plants and animals use this mechanism to exert translational control over their gene targets.

Low Molecular Weight Compounds

Particular drug candidate compounds are low molecular weight compounds. Low molecular weight compounds, for example with a molecular weight of 500 Dalton or less, are likely to have good absorption and permeation in biological systems and are consequently more likely to be successful drug candidates than compounds with a molecular weight above 500 Dalton (Lipinski et al., 2001)). Peptides comprise another particular class of drug candidate compounds. Peptides may be excellent drug candidates and there are multiple examples of commercially valuable peptides such as fertility hormones and platelet aggregation inhibitors. Natural compounds are another particular class of drug candidate compound. Such compounds are found in and extracted from natural sources, and which may thereafter be synthesized. The lipids are another particular class of drug candidate compound.

Antibodies

Another preferred class of drug candidate compounds is an antibody. The present invention also provides antibodies directed against the TARGETS. These antibodies may be endogenously produced to bind to the TARGETS within the cell, or added to the tissue to bind to the TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized Examples of such immunogenic proteins include but are not limited to keyhole limpet hemocyanin, serum albumin, bovine thyroglobulin, and soybean trypsin inhibitor Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boerner, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGETS. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET; the other one is for another domain of the TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

A special aspect of the methods of the present invention relates to the down-regulation or blocking of the expression of a TARGET polypeptide by the induced expression of a polynucleotide encoding an intracellular binding protein that is capable of selectively interacting with the TARGET polypeptide. An intracellular binding protein includes an activity-inhibitory agent and any protein capable of selectively interacting, or binding, with the polypeptide in the cell in which it is expressed and neutralizing the function of the polypeptide. Particularly, the intracellular binding protein may be an antibody, particularly a neutralizing antibody, or a fragment of an antibody or neutralizing antibody having binding affinity to an epitope of the TARGET polypeptide of SEQ ID NO: 26-50. More particularly, the intracellular binding protein is a single chain antibody.

Pharmaceutical Compositions, Related Uses and Methods

The antibodies or a fragments thereof which specifically bind to a TARGET polypeptide and expression inhibiting agents selected from the group consisting of an antisense polynucleotide, a ribozyme, a small interfering RNA (siRNA), microRNA (miRNA) and a short-hairpin RNA (shRNA) that may be used as therapeutic agents for the treatment of conditions in mammals that are causally related or attributable to differentiation of macrophages into M2 macrophages.

The present invention relates to pharmaceutical compositions comprising an antibody or a fragment thereof which specifically binds to a TARGET polypeptide, for use in the treatment of a fibrotic condition. In a particular embodiment a fibrotic condition is fibrotic diseases associated with differentiation of macrophages into M2 macrophages.

In particular aspect, the present invention provides a method of treating a mammal having, or at risk of having a fibrotic disease, said method comprising administering an effective condition-treating or condition-preventing amount of one or more of the pharmaceutical compositions comprising an antibody or a fragment thereof which specifically binds to a TARGET polypeptide. In a particular aspect, the present invention provides a method of treating a mammal having, or at risk of having idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In specific embodiment, said antibody is a monoclonal antibody. In alternative embodiment said antibody is a single chain antibody. In particular embodiment said fibrotic condition is a fibrotic condition associated with differentiation of macrophages into M2 macrophages.

In another aspect the present invention provides an antibody or a fragment thereof which specifically binds to a TARGET polypeptide for use in the treatment, and/or prophylaxis of a fibrotic condition. In a specific embodiment, said fibrotic condition is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In specific embodiment, said antibody is a monoclonal antibody. In alternative embodiment said antibody is a single chain antibody. In particular embodiment said fibrotic condition is a fibrotic condition associated with differentiation of macrophages into M2 macrophages.

In yet another aspect, the present invention provides an antibody or a fragment thereof which specifically binds to a TARGET polypeptide, or a pharmaceutical composition comprising an antibody or a fragment thereof which specifically binds to a TARGET polypeptide for use in the manufacture of a medicament for the treatment, or prophylaxis of a fibrotic condition. In a specific embodiment, said fibrotic condition is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In specific embodiment, said antibody is a monoclonal antibody. In alternative embodiment said antibody is a single chain antibody. In particular embodiment said fibrotic condition is a fibrotic condition associated with differentiation of macrophages into M2 macrophages.

A particular regimen of the present method comprises the administration to a subject suffering from a fibrotic disease involving differentiation of macrophages into M2 macrophages, of an effective amount of an antibody or a fragment thereof which specifically binds to a TARGET polypeptide for a period of time sufficient to reduce the level of abnormal fibrosis in the subject, and preferably terminate the processes responsible for said fibrotic condition. A special embodiment of the method comprises administering of an effective amount of an antibody or a fragment thereof which specifically binds to a TARGET polypeptide to a subject patient suffering from or susceptible to the development of a fibrotic disease, for a period of time sufficient to reduce or prevent, respectively, fibrotic condition in said patient, and preferably terminate, the processes responsible for said fibrotic condition. In specific embodiment, said antibody is a monoclonal antibody. In alternative embodiment said antibody is a single chain antibody. In particular embodiment said fibrotic condition is a fibrotic condition associated with differentiation of macrophages into M2 macrophages.

The present invention further relates to compositions comprising said agents, wherein said agent is selected from the group consisting of an antisense polynucleotide, a ribozyme, a small interfering RNA (siRNA), microRNA (miRNA), and a short-hairpin RNA (shRNA), wherein said agent comprises a nucleic acid sequence complementary to, or engineered from, a naturally-occurring polynucleotide sequence of about 17 to about 30 contiguous nucleotides of a nucleic acid sequence selected from the group consisting of SEQ ID NO: 1-25. These agents are, otherwise, referred herein to as expression inhibitory agents.

In particular aspect, the present invention provides a method of treating a mammal having, or at risk of having a fibrotic disease, said method comprising administering an effective condition-treating or condition-preventing amount of one or more of the pharmaceutical compositions comprising said expression inhibitory agent. In a particular aspect, the present invention provides a method of treating a mammal having, or at risk of having idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In particular embodiment said fibrotic condition is a fibrotic condition associated with differentiation of macrophages into M2 macrophages.

In another aspect the present invention provides expression inhibitory agents for use in the treatment, and/or prophylaxis of a fibrotic condition. In a specific embodiment, said fibrotic condition is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In particular embodiment said fibrotic condition is a fibrotic condition associated with differentiation of macrophages into M2 macrophages.

In yet another aspect, the present invention provides expression inhibitory agents, or a pharmaceutical composition comprising said expression inhibitory agents for use in the manufacture of a medicament for the treatment, or prophylaxis of a fibrotic condition. In a specific embodiment, said fibrotic condition is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, and/or diseases associated with differentiation of macrophages into M2 macrophages. In particular embodiment said fibrotic condition is a fibrotic condition associated with differentiation of macrophages into M2 macrophages.

A particular regimen of the present method comprises the administration to a subject suffering from a fibrotic disease involving differentiation of macrophages into M2 macrophages, of an effective amount of an expression inhibitory agent for a period of time sufficient to reduce the level of abnormal fibrosis in the subject, and preferably terminate the processes responsible for said fibrotic condition. A special embodiment of the method comprises administering of an effective amount of an antibody or a fragment thereof which specifically binds to a TARGET polypeptide to a subject patient suffering from or susceptible to the development of a fibrotic disease, for a period of time sufficient to reduce or prevent, respectively, fibrotic condition in said patient, and preferably terminate, the processes responsible for said fibrotic condition In particular embodiment said fibrotic condition is a fibrotic condition associated with differentiation of macrophages into M2 macrophages.

Another aspect of the present invention relates to compositions, comprising a DNA expression vector capable of expressing a polynucleotide capable of inhibition of expression of a TARGET polypeptide and described as an expression inhibitory agent.

The present invention provides compounds, compositions, and methods useful for modulating the expression of the TARGET genes, specifically those TARGET genes associated with a fibrotic disease and for treating such conditions by RNA interference (RNAi) using small nucleic acid molecules. In particular, the instant invention features small nucleic acid molecules, i.e., short interfering nucleic acid (siNA) molecules including, but not limited to, short interfering RNA (siRNA), double-stranded RNA (dsRNA), micro-RNA (miRNA), short hairpin RNA (shRNA) and circular RNA molecules and methods used to modulate the expression of the TARGET genes and/or other genes involved in pathways of the TARGET gene expression and/or activity.

A particular aspect of these compositions and methods relates to the down-regulation or blocking of the expression of the TARGET by the induced expression of a polynucleotide encoding an intracellular binding protein that is capable of selectively interacting with the TARGET. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of a TARGET selected from the group consisting of SEQ ID NO: 26-50. More preferably, the intracellular binding protein is a single chain antibody.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

A particular embodiment of this composition comprises the expression-inhibiting agent selected from the group consisting of antisense RNA, antisense oligodeoxynucleotide (ODN), a ribozyme that cleaves the polyribonucleotide coding for a TARGET selected from the group consisting of SEQ ID NO: 1-25, a small interfering RNA (siRNA), and a microRNA that is sufficiently homologous to a portion of the polyribonucleotide coding for a TARGET selected from the group consisting of SEQ ID NO: 1-25, such that the siRNA or microRNA interferes with the translation of the TARGET polyribonucleotide to the TARGET polypeptide.

The polynucleotide expressing the expression-inhibiting agent, or a polynucleotide expressing the TARGET polypeptide in cells, is particularly included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaiviral vector systems, and all may be used to introduce and express polynucleotide sequence for the expression-inhibiting agents or the polynucleotide expressing the TARGET polypeptide in the target cells.

Particularly, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US 2003/0180258 and US 2004/0071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention may use retroviral vector systems. Retroviruses are integrating viruses that infect dividing cells, and their construction is known in the art. Retroviral vectors can be constructed from different types of retrovirus, such as, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

As discussed hereinabove, recombinant viruses may be used to introduce DNA encoding polynucleotide agents useful in the present invention. Recombinant viruses according to the invention are generally formulated and administering in the form of doses of between about 104 and about 1014 pfu. In the case of AAVs and adenoviruses, doses of from about 106 to about 1011 pfu are particularly used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_1$, and trp promoters. Among the eukaryotic (including viral) promoters useful for practice of this invention are ubiquitous promoters (e.g. HPRT, vimentin, actin, tubulin), therapeutic gene promoters (e.g. MDR type, CFTR, factor VIII), tissue-specific promoters, including animal transcriptional control regions, which exhibit tissue specificity and have been utilized in transgenic animals, e.g. chymase gene control region which is active in mast cells (Liao et al., (1997), Journal of Biological Chemistry, 272: 2969-2976), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), beta-globin gene control region which is active in myeloid cells (Mogram, et al. (1985) Nature 315:338-40; Kollias, et al. (1986) Cell 46:89-94), the CMV promoter and the Visna LTR (Sidiropoulos et al., (2001), Gene Therapy, 8:223-231)

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Further promoters which may be of use in the practice of the invention include promoters which are active and/or expressed in macrophages or other cell types contributing to inflammation such as dendritic cells, monocytes, neutrophils, mast cells, endothelial cells, epithelial cells, muscle cells, etc.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et. al. (1987) Proc. Natl. Acad Sci. USA 84:7413-7); sec Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringoid, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589, 466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET; a nucleic acid would be able to replicate, translate a message, or hybridize to a complementary mRNA of the TARGET; a vector would be able to transfect a target cell and express the antisense, antibody, ribozyme or siRNA as described hereinabove; an antibody would bind a the TARGET polypeptide domain.

A particular biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Particular sterile injectable preparations can be a solution or suspension in a non-toxic parenterally acceptable solvent or diluent. Examples of pharmaceutically acceptable carriers are saline, buffered saline, isotonic saline (for example, monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The compounds or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J). In general, these polymers are at least partially soluble in aqueous solutions, such as water, buffered salt solutions, or aqueous alcohol solutions, that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semipermeable matrices of solid hydrophobic polymers containing the antibody, which matrices are in the form of shaped articles, for example, films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As used herein, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, for example, $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are particular. The data obtained from cell culture assays and animal studies are used in formulating a range of dosage for human use. The dosage of such compounds lies particularly within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to targeted tissues, complexed with cationic lipids, packaged within liposomes, or delivered to targeted cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Administration of an expression-inhibiting agent or an antibody of the present invention to the subject patient includes both self-administration and administration by another person. The patient may be in need of treatment for an existing disease or medical condition, or may desire prophylactic treatment to prevent or reduce the risk for diseases and medical conditions affected by differentiation of macrophages into alternatively-activated macrophages. The expression-inhibiting agent of the present invention may be delivered to the subject patient orally, transdermally, via inhalation, injection, nasally, rectally or via a sustained release formulation.

In Vitro Methods

The present invention also provides an in vitro method of reducing or inhibiting the differentiation of macrophages into M2 macrophages, said method comprising contacting a population of macrophage cells with an inhibitor of the activity or expression of a TARGET polypeptide. In a particular embodiment said inhibitor is an antibody. In an alternative embodiment said antibody is a monoclonal antibody The present invention further relates to an in vitro method of inhibiting the differentiation of macrophages into M2 macrophages, said method comprising contacting a population of macrophage cells with an inhibitor selected from the group consisting of an antisense polynucleotide, a ribozyme, a small interfering RNA (siRNA) and a short-hairpin RNA (shRNA), wherein said inhibitor comprises a nucleic acid sequence complementary to, or engineered from, a naturally-occurring polynucleotide sequence of about 17 to about 30 contiguous nucleotides of a nucleic acid encoding a TARGET polypeptide.

The down regulation of gene expression using antisense nucleic acids can be achieved at the translational or transcriptional level. Antisense nucleic acids of the invention are particularly nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Particularly, the antisense sequence is at least about 15-30, and particularly at least 17 nucleotides in length. The preparation and use of antisense nucleic acids, DNA encoding antisense RNAs and the use of oligo and genetic antisense is known in the art.

EXAMPLES

The invention is further illustrated using examples provided below. It would be obvious to a person skilled in the art that the examples might be easily modified or adapted to particular types of conditions, scale or cell types using routine adaptations.

Example 1 describes the M2 screening assay.
Example 2 describes the M2 re-screen.
Example 3 describes the M1 counter assay.
Example 4 describes the M2 assay using CD206 marker.
Example 5 describes on target and toxicity assessment of selected shRNA constructs.
Example 6 describes infection units (IU)-based on target screen and toxicity assessment of selected shRNA constructs.
Example 7 describes the analysis of expression of TARGETs in macrophages.

Example 1

Screening Adenoviral Library Using the M2 Macrophage Differentiation Assay 1.1 Background of the Assay M2 macrophages can be generated by priming M0 macrophages derived from human peripheral monocytes with a combination of IL-4 and IL-10. The polarized M2 macrophages express high levels of secreted CCL18 and the surface-bound markers CD163 and CD206. Furthermore, a person of skill in the art will appreciate that several positive controls may also be selected based on available literature on the signaling pathway of IL-4 and IL-10 and the read-out, CCL18.

1.2 Cell Cultures

To obtain M0 macrophages, buffy coats from healthy donors and not older than 50 years, were purchased via the blood bank (Sanquin, The Netherlands) for isolation of peripheral blood mononuclear cells PBMCs. The isolation was performed using a Ficoll-Paque PLUS gradient (GE healthcare, cat#17-1440-03) and subsequently the CD14+ monocytes were extracted using CD14 MicroBeads (Miltenyi, cat. #130-050-201). After the CD14 isolation a QC regarding the purity was performed on the isolated CD14+ fraction based on CD14 fluorescent labelled antibody staining using flow cytometric analysis (Facscalibur BD) and CellQuest Pro software.

To differentiate the CD14 positive cells into M0 macrophages, the cells were seeded in 96-well plates with RPMI Glutamax medium, containing 10% FBS, 1% P/S and 100 ng/mL M-CSF. In total four plates were seeded per donor at a cell density of 20,000 cells/well and cultured for six days. On day six, one plate from both donors containing the M0 macrophages were harvested for RNA isolation and the other three plates were refreshed. Ten days after seeding, the second plate from both donors containing M0 macrophages was harvested for RNA isolation. The other two plates from each donor were triggered with 20 ng/ml IFNγ and 5 ng/mL IFNγ or 20 ng/mL IL-10 and 20 ng/mL LPS in RPMI Glutamax medium containing 10% FBS and 1% P/S, to generate M1 or M2, respectively. The cells were cultured for another three days before the macrophages were harvested for RNA isolation. After harvest, specific cell markers were tested using flow cytometry to confirm the M0, M1 and M2 phenotypes. This was done by assessing the expression markers CD163 and CD206. The CD163 and CD206 expression were enhanced in the M2 macrophages and decreased in the M1 macrophages compared to the M0 macrophages, in both donors.

1.3 Positive and Negative Controls

STAT6 _v5 was used together with CCL18_v1, IL-4R_v6, JAK1_v23 and STAT6 _v6 as positive controls, based on public available resources (for example, Sica et al, 2012) regarding the IL-10 and IL-4 pathway. Ffluc_v19, ffluc_v24 and luc_v13 are shRNA against non-expressed genes (firefly luciferase and luciferase, respectively) and were used as negative controls.

TABLE 2

Overview of the knock-down sequences of the controls in M2 macrophage assay

| Control code | Control name | Sequence | SEQ ID NO |
|---|---|---|---|
| N1 | luc_v13 | GGTTACCTAAGGGTGTGGC | 51 |
| N2 | ffluc_v19 | GAATCGATATTGTTACAAC | 52 |
| N3 | ffluc_v24 | GCATAAGGCTATGAAGAGA | 53 |
| P1 | CCL18_v1 | GTCTATACCTCCTGGCAGA | 54 |
| P2 | STAT6_v5 | GCCAAAGACCTGTCCATTC | 55 |
| P3 | STAT6_v6 | GTCCCAGCTACCATCAAGA | 56 |
| P4 | IL4R_v6 | CCCGGCAGATTTCAGAATC | 57 |
| P5 | JAK1_v23 | GAGTCTGTGGTCAGCATTA | 58 |

1.4 CCL18 384-Well Luminescent ELISA

The CCL18 detection assay using high binding MSD plates was developed and automated. The antibody pair used in the commercial CCL18 ELISA was used with a 384-well Meso Scale Discovery (MSD) assay (see:http://www.mesoscale.com/CatalogSystemWeb/WebRoot/technology/ecl/walkthrough.htm), for an overview of the MSD technology). Automation was performed on the Bravo system (Agilent). Automation was performed using the Bravo system. White 384-well high binding plates (Lumitrac 600, Greiner Bio-one) were used and coated with CCL18 capture antibody (Human CCL18/PARC MAb (Clone 64507), Mouse IgG1, R&D Systems) in PBS incubated o/n at 4° C. The plates were blocked with 5% BSA in PBS-Tween at RT for one hour. After blocking and washing of the plates, a single concentration of CCL18 and a standard curve was added to the plate and incubated for two hours at RT. Hereafter, the plates were washed and incubated with biotin labeled CCL18 detection antibody (CCL18/PARC Biotinylated Affinity Purified PAb, Goat IgG, R&D Systems). Subsequently, the plates were washed three times in wash buffer (PBS-Tween) and incubated with Streptavidin-HRP (Cat# DY998, R&D Systems) in reagent buffer (1% BSA in PBS-Tween). After 30 minutes incubation at room temperature while shaking, the plates were washed three times in wash buffer before luminescent substrate (BM Chemiluminescence ELISA Substrate (HRP), Roche) was added which prepared 15 minutes in advance. After approximately five minutes the plates were measured on an Envision machine (PerkinElmer) using Victor Wallac software.

1.5 Screening Protocol

Figure 2:
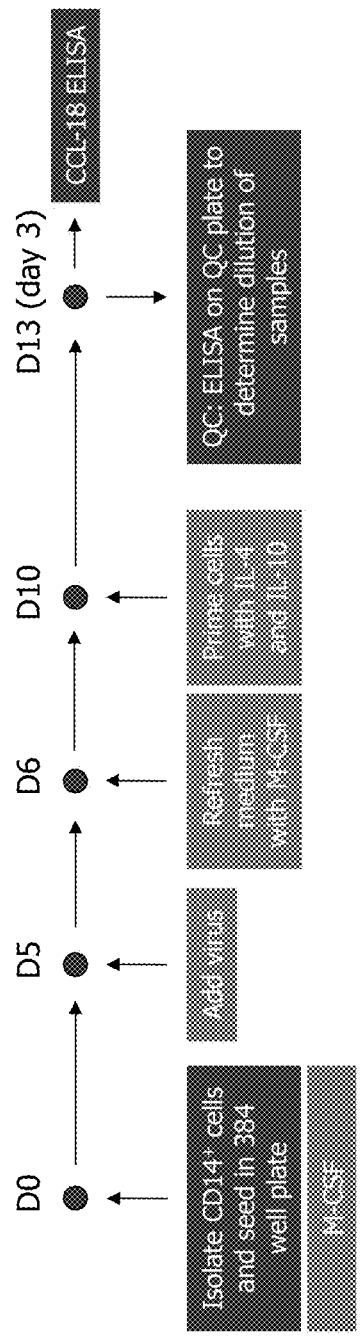
FIG. 2 depicts the primary screen set-up.

The primary screen was performed using shRNA constructs comprising the complete adenoviral shRNA library (12210 shRNA constructs designed against 4438 genes). The library consisted of 34×384-well plates and the screen was performed in biological duplicate. MOI4 was chosen based on the pilot screen. All individual 384-well source plates contained 12 negative and 20 positive control viruses positioned in column 13 and 14 (FIG. 1). Additional QC plates were also measured. The QC plates contained only the control viruses positioned in column 13 and 14 in order to determine the sample dilution factor. The remainder of the wells consisted of cells that were not transduced with adenovirus to assess the performance of the negative controls and the intra-plate variation. In total three dilutions were made of the QC samples from all three donors used (donor CQ, CR and CU). Column 21 was used for the CCL18 standard, to determine the optimal dilution factor for each donor separately. Three out of the five positive controls should give more than 40% inhibition compared to the negative controls. The set-up of the protocol is outline in FIG. 2.

To perform the screen, 5,000 CD14+ cells/well were seeded in 384-well culture plates on day 0 with RPMI Glutamax medium (cat #: 1870-010). containing 10% fetal bovine serum (FBS), 1% penicillin/streptomycin P/S and 100 ng/mL Macrophage colony stimulating factor (M-CSF). After five days, the M0 macrophages were transduced with the adenoviruses followed by a refreshment step one day later. On day ten the cells were primed with RPMI Glutamax medium containing 10% FBS, 1% P/S, 20 ng/mL IL-4 and 20 ng/mL IL-10 to trigger the cells to differentiate into M2 macrophages. Medium was harvested on day 13 and secreted CCL18 was detected using a CCL18 384-well luminescent ELISA (as described in 1.4) after measuring a QC plate to determine sample dilution.

1.6 QC, Data Analysis and Hit Identification

The sample population had a non-Gaussian distribution based on a Shapiro-Wilk test and normalization was required. The robust Z-score was used, that utilizes median and median absolute deviation (MAD) instead of the mean and SD (Zhang et al., 2006). This normalization method is less sensitive to extreme values and asymmetry in the distribution and therefore suitable for the skewed sample distribution observed with the raw data points. Potential plate effects were assessed using the heat maps.

To correct for these positional effects a normalization method, similar to the robust Z-score was used. The method is referred as the B-score and attempts to correct for possible plate edge/row/column effects and the plate center effect. The calculation is similar to the robust Z-score, except for the median calculation that is replaced by median value of the plate adjusted for each well separately depending on its position on the plate (Malo et al. 2006).

After calculating the B-score, the control and sample performance was determined for each plate separately and compared to each other. To assess the performance of the duplicate values, the Spearman correlation coefficient based on the sample values was calculated. Based on the performance of the positive controls and the negative controls, a B-score cut-off was selected for hit calling. Kappa statistics was used as a statistical measure of inter-replicate agreement of the hits after hit calling.

1.7 Results

On all three QC plates the untransduced samples showed little intra-plate variation (data not shown) and the negative controls remained within the 25% reduction and induction range compared to the no virus control.

The average Spearman correlation coefficient of the primary screen was 0.87, ranging from 0.81 till 0.92 per plate pair.

Figure 3:
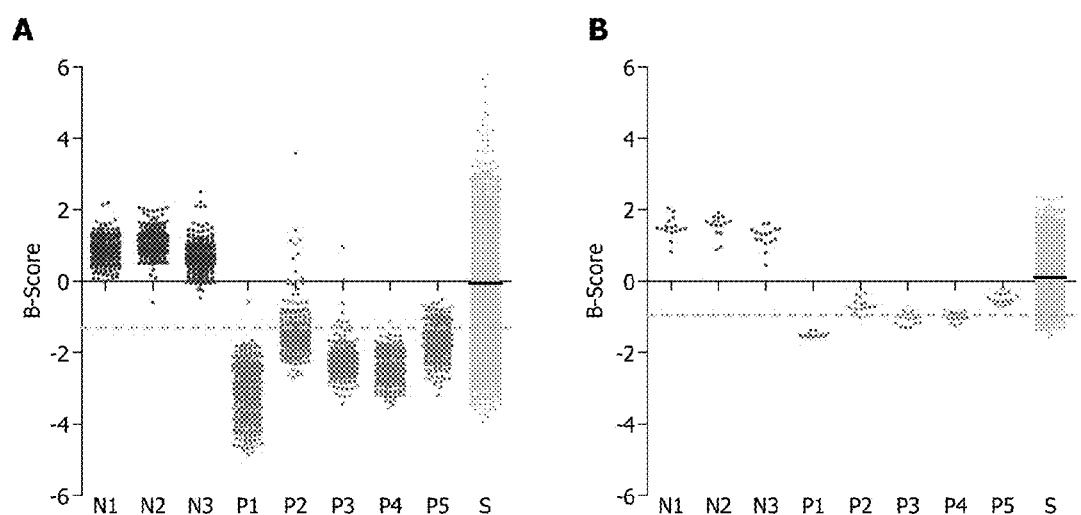
FIG. 3 shows B-score values for the individual controls and samples in primary screen. The graphs show the B-score of the negative controls (N1, N2, and N3), the positive controls (P1, P2, P3, P4, and P5) and the samples (S) for the complete screen (A) and the four separate analyzed plates (B). The dashed lines indicate the cut-off used for hit calling.

A B-score cut-off of −1.3 was used for hit calling (FIG. 3A). Four plates were analyzed separately and a cut-off of −0.95 was used for hit calling (FIG. 3 B). With these cut-offs none of the negative controls were identified as a hit and more than 95% of the positive controls were identified as a hit.

In total 999 shRNA hits were identified in the primary screen with an average kappa value of 0.80 on the plates with a cut-off of −1.3 and an average kappa value of 0.72 on the plates with a cut-off of −0.95. An overview of the assay statistical analysis is shown in Table 3. In this table the assay performance is summarized.

TABLE 3

Assay parameters overview of the primary screen.

| Readout | Cut-off | # source plates | Average Hit rate (%) | Average Spearman | Range Spearman | Average Kappa |
|---------|---------|-----------------|----------------------|------------------|----------------|---------------|
| CCL18 | −1.30 | 33 | 8.4 | 0.87 | 0.81-0.92 | 0.80 |
| CCL18 | −0.95 | 2 | 7.5 | | | 0.72 |

Example 2

Figure 4:
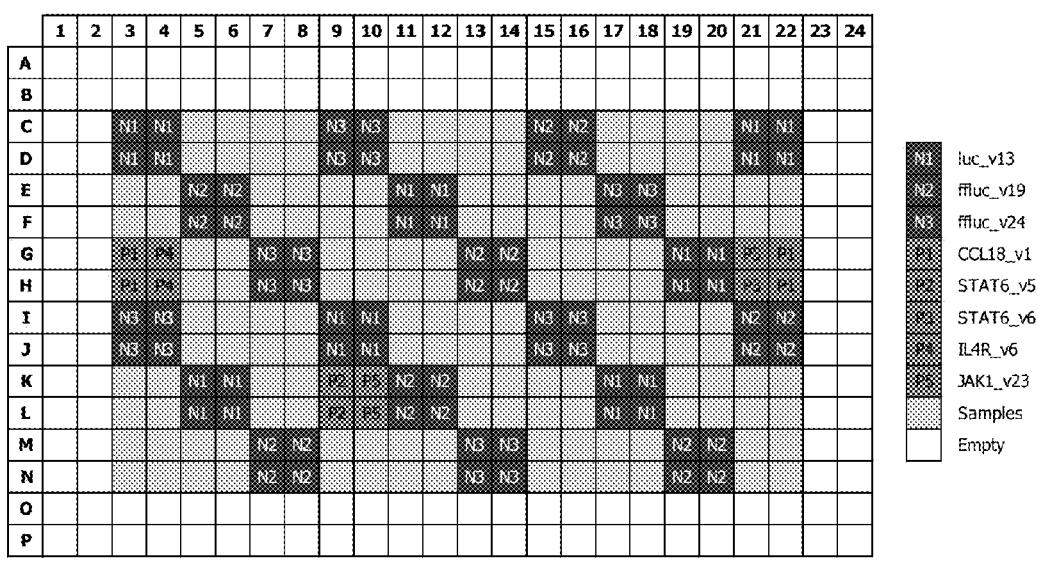
FIG. 4 shows rescreen plate layout. Layout of the library plates with the negative control viruses and the positive control viruses distributed over the plate. The remaining of the plate consisted of randomly distributed viruses which were identified as hits in the primary screen. The outer wells were not used.

Re-screen of Identified Hits Using M2 Macrophage Differentiation Assay 2.1 Background The primary screen was followed by the rescreen for which the same assay set up was used as described in Example 1. The 999 viruses identified in the primary M2 macrophage differentiation screen (Example 1) were further evaluated in the rescreen. For the rescreen a different transduction plate layout was designed. In this layout the outer wells were omitted and the negative controls were arranged in such a way to allow detection of possible plate effects. Furthermore, >30% of the plate content consisted of negative controls as the hit calling analysis is performed based on the mean of the negative controls. All identified hits from the primary screen were repropagated and were distributed randomly over the plate The adenoviral shRNA constructs from the adenoviral library that were identified as a hit in the primary screen of Example 1 as well as the same control viruses were re-propagated for the rescreen. The new propagations of the controls (same controls were used as in the Example 1) and a representative part of the hit set were tested in the pilot rescreen to assess the quality of the viruses and to establish an optimal transduction volume for the rescreen. Similar criteria as used as for development of the primary screen 2.2 Re-Screen Protocol The rescreen consisted of eight 384-well plates and was performed in biological duplicate, at MOI4 in one donor. The cells were obtained according to the same protocol as in Example 1. All individual 384-well source plates contained 80 negative and 12 positive control viruses distributed over the plate as shown in FIG. 4. The assay set up was identical to the primary M2 macrophage differentiation screen (see Example 1). A QC plate was included in the assay, containing only the controls according to the plate layout. The QC plate was used to determine the dilution factor for the supernatant in which the CCL18 secretion was measured. The samples were diluted 1:37.5.

2.3 Data Analysis

Normalization of the data was done using the Robust Z score based on the mean negative controls. The robust Z score based on negatives, is calculated by dividing the readout value minus the median of the negative controls by the MAD (median absolute deviation) of the negative controls. To assess the performance of the duplicate values, the Spearman correlation coefficient based on the sample values was calculated.

2.4 Results

Figure 5:
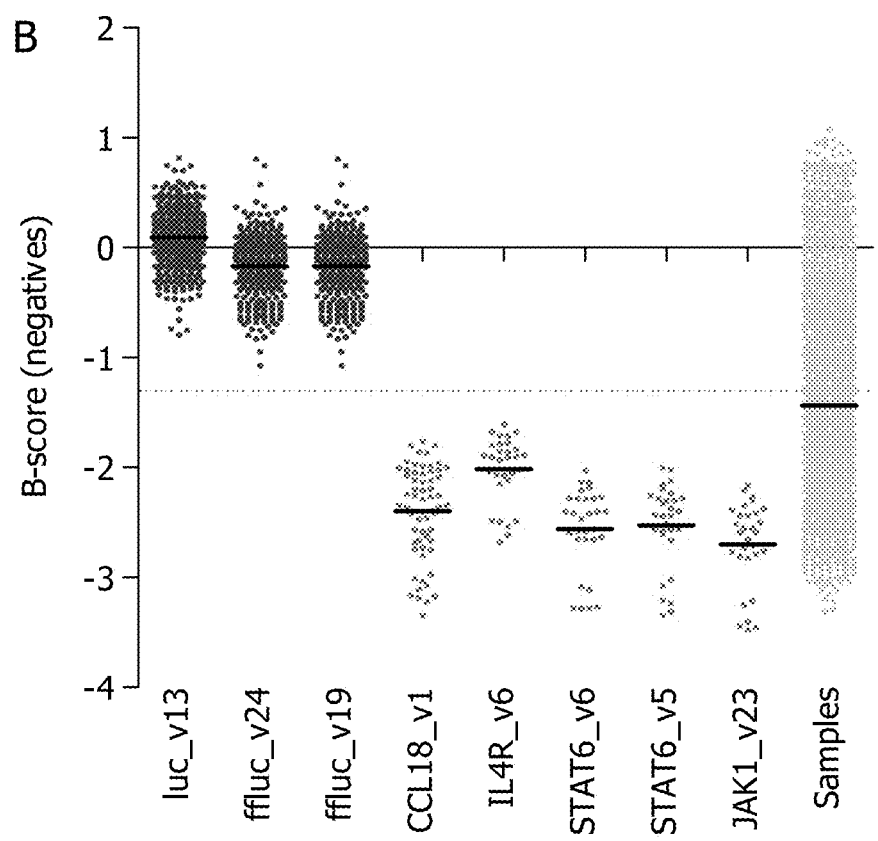
FIG. 5 shows B-score values for the individual controls and samples in re-screen. The graphs show the B-score of the negative controls, the positive controls and the samples. The dashed lines indicate the cut-off used for hit calling.

In FIG. 5 the control and sample performance of the rescreen is shown, in which a clear separation of the positive and negative controls can be seen. A strong correlation between the duplicate data points was observed with an average Spearman of 0.93, ranging from 0.91 till 0.96 per duplicate plate. Based on the performance of the positive controls compared to the negative controls, a B-score cut-off of −1.3 was used for hit calling. With this cut-off none of the negative controls were identified as a hit and 100% of the positive controls were identified as a hit.

The rescreen was performed successfully and with a cut-off of −1.3 resulted in 619 hits. After QC and thorough analysis, these 619 hits represent 616 genes and are designated confirmed candidate TARGETs (Table 4). Based on the rescreen, 616 genes were taken forward for the validation phase.

TABLE 4

Assay parameters overview of the rescreen.

| Readout | Cut-off B-score | # Source plates | Confirmation rate % | # Hits | Average Spearman |
|---------|-----------------|-----------------|---------------------|--------|------------------|
| CCL18 | −1.30 | 8 | 58 | 619 | 0.93 (0.91-0.96) |

Example 3

M1 Counter Assay

3.1 Background of the Assay 600 confirmed candidate TARGETs were identified in the primary screen and rescreen that inhibitions of which inhibited differentiation of macrophages into M2 macrophages (Example 1 and 2). To assess that these shRNA do not interfere with development of classically activated M1 macrophages, a M1 counter screen can be developed to exclude the shRNA constructs inhibiting expression of targets which in turn inhibit the M1 phenotype.

A hallmark of M1 macrophages is the secretion of TNFα (Mantovani, 2004). The expression of TNFα upon triggering with LPS and IFNγ (known to polarize macrophages to the M1 phenotype), allows the M1 macrophages to be distinguished from M0 and M2 macrophages. Hence, a M1 counter screen might be performed in which secreted TNFα can be used as a read-out. To establish a robust and reproducible M1 counter assay the following aspects should be assessed: determination of TNFα secretion, optimization of the M1 counter screen assay, and selection of positive and negative controls.

3.2 Cell Donors and Cell Protocol

To obtain macrophages, buffy coats from healthy donors were purchased via the blood bank (Sanquin, The Netherlands) for isolation of peripheral blood mononuclear cells PBMCs. The isolation was performed using a Ficoll-Paque gradient (GE healthcare) and subsequently the CD14+ cells were extracted using CD14 MicroBeads (Miltenyi, cat. #130-050-201). After the CD14 isolation a QC regarding the purity was performed on the PBMCs and the isolated CD14+ fraction using flow cytometric analysis (Facscalibur BD) and CellQuest Pro software with CD14 fluorescent labelled antibody staining

3.3 TNFα HTRF Assay

The secreted TNFα was measured using the homogeneous time-resolved fluorescence (HTRF) technique according to manufacturers' protocol (Cisbio Bioassays, cat. #: 62TNFPEC). The signal was measured on an envision machine (Perkin Elmer) at 665 and 620 nm and analyzed using Victor Wallac software. A calibration curve was used to correlate the raw fluorescent signals to the TNFα concentration.

To confirm the specificity of the read-out, the secretion of TNFα by M1 macrophages was compared to the secretion by M2 macrophages. The TNFα secretion by M1 macrophages was strongly enhanced, whereas in supernatants obtained from M2 macrophages TNFα could not be detected. The TNFα HTRF was therefore suitable to distinguish M1 macrophages from M2 macrophages.

3.4 Positive and Negative Controls

In addition to the positive control virus TNF_v12, a selection of new putative positive controls, targeting genes in the M1 pathway (MYD88, TLR4, NFKB1, TRAF6 and TNFα) was assessed for TNFα inhibition to further validate the M1 counter screen. The TRAF6_v4 positive control showed more than 60% inhibition in donor EK and treatment with the TNF_v9 positive control resulted in more than 40% TNFα reduction in donor EK. The MYD88_v4 positive control showed around 40% inhibition in donor EL. Only the TNF_v12 positive control showed in both donors over 60% inhibition compared to the average of the negative controls. All these positive controls were taken forward to develop M1 counter screen.

TABLE 5

Summary of the controls

| Control code | Control name | Sequence | SEQ ID NO |
|---|---|---|---|
| N1 | luc_v13 | GGTTACCTAAGGGTGTGGC | 51 |
| N2 | ffluc_v19 | GAATCGATATTGTTACAAC | 52 |
| N3 | ffluc_v24 | GCATAAGGCTATGAAGAGA | 53 |
| P1 | MYD88_v4 | GGAACAGACAAACTATCGA | 59 |
| P2 | TRAF6_v4 | GTTCTGGTCATGGATCTCT | 60 |
| P3 | TNF_v12 | CGTGGAGCTGAGAGATAAC | 61 |

3.5 Set-Up of M1 Counter Assay

Figure 6:
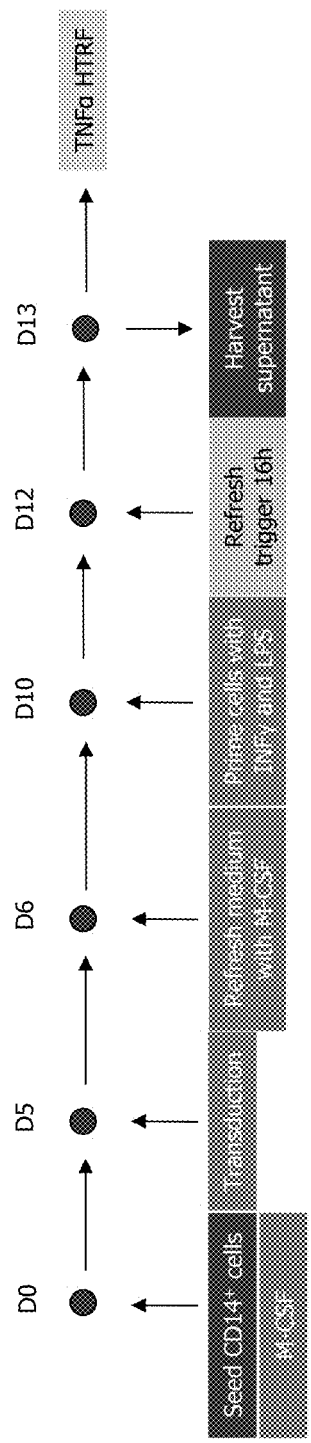
FIG. 6 shows the experimental setup of the M1 counter screen.
Figure 7:
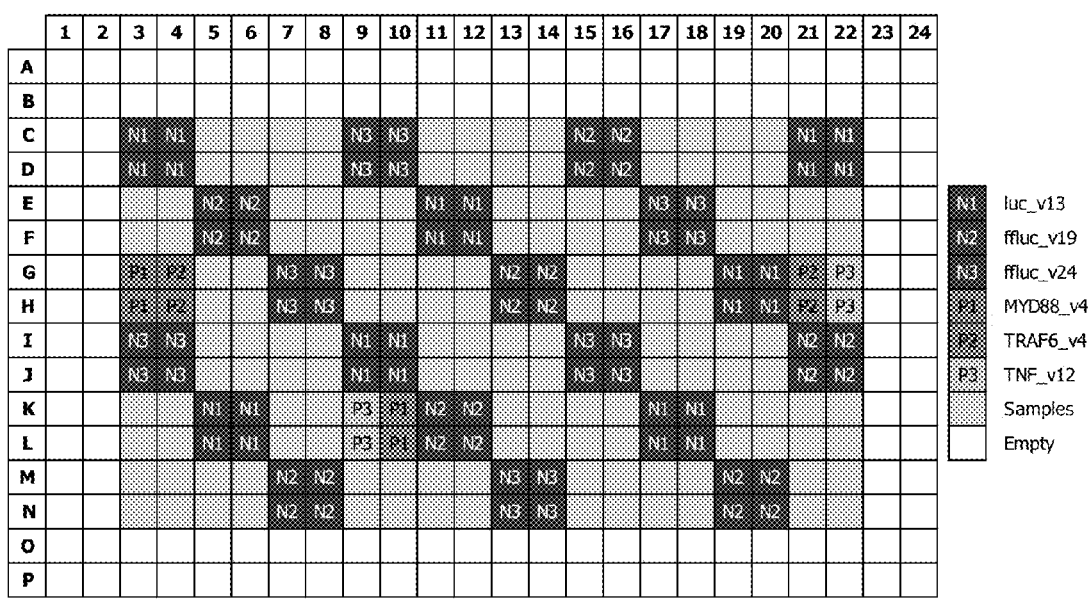
FIG. 7 shows plate layout of the M1 counter screen. Layout of the 384-well plates with the negative control viruses (N1, N2, and N3), the TNF_v12 positive control viruses (P3), the other positive control viruses (P1 and P2) and the random viruses (Samples) from the adenoviral library. The outer wells were left empty.

The experimental setup was as follows: On day 0 5,000 CD14+ cells/well were seeded in 384-well plates with medium containing M-CSF. Five days later the transduction was preformed followed by a refresh the next day. On day ten the trigger containing 20 ng/mL IFN-γ and 5 ng/mL LPS was added and refreshed on day 12. The trigger was refreshed 16 hours before harvest. The supernatants were harvested on day 13 in which the secreted TNFα was determined using a TNFα HTRF assay (FIG. 6). The M1 counter screen consisted of eight 384-well source plates similar to the viral repropagation aliquot set of the rescreen. The layout was therefore identical to that of the rescreen except for the CCL18 positive controls which were replaced by three positive controls for the TNFα read-out: MYD88_v4, TRAF6_v6 and TNF_v12 (FIG. 7). The screen was performed in two donors (donors EO and EP) at MOI8 in one batch. In addition, one QC plate for each donor containing only the virus controls was included in the experimental setup. These plates were assessed first, using the TNFα HTRF, to determine which donor provided the most optimal assay window.

In both donors the reduction in TNFα secretion was over 40% after transduction with the TNF_v12 positive control compared to the average of the negative controls. A different donor ET was selected for analysis of the complete set based on a slightly higher TNFα concentration as compared to donor ES.

3.6 Data Analysis

Normalization of the TNFα data was performed using the robust Z-score based on the mean negative controls. Positional effects were corrected by subsequently calculating the B-score.

The average Spearman from donor ET was 0.77, ranging from 0.70 till 0.86 per duplicate plate, indicating a strong correlation between duplicates. Based on the performance of the TNF_v12 positive controls compared to the negative controls, a B-score cut-off of >−1.3 was used for hit calling. With these cut-offs 1.67% of the negative controls were identified as a hit and 90.60% of the TNF_v12 positive controls were identified as a hit.

3.7 Results 729 hits were identified in the counter screen. Since the same virus set of the rescreen was used, and the results of the counter screen were compared with the results of the M2 macrophage differentiation rescreen (Example 1). This resulted in the identification of a total of 408 confirmed candidate TARGETs which did not affect M1 differentiation (Table 6). These 408 confirmed candidate Targets were taken forward for further validation.

TABLE 6

Results M1 counter screen

| Read-out | Cut-off Robust Z-score | # Source plates | # Hits | Average Spearman |
|---|---|---|---|---|
| TNFα | >−1.3 | 8 | 729 | 0.77 (0.70-0.86) |

Example 4

M2 Assay Using CD206 Marker 4.1 Background of the Assay

To confirm that the candidate shRNA constructs inhibited M2 differentiation, a validation assay with a different read-out to the primary CCL18 read-out can be developed. Two surface markers, CD163 and CD206, are known to be expressed on M2 macrophages and can be used to distinguish between M0, M1 and M2 macrophages (Murray el al., 2011). During the M2 assay development and throughout the screening phase, both CD163 and CD206 expression levels were used for QC analysis to assess macrophage differentiation (see Example 1). M2 primed macrophages showed enhanced expression of CD163 and CD206 compared to M0 and M1 macrophages. The induction of CD206 expression upon M2 priming was more profound than CD163 and it was therefore decided to develop a validation assay with CD206 as read-out.

4.2 CD206 Detection Method (ICC)

For indirect labelling, a mouse-anti-human CD206 primary antibody (BD Pharmingen, cat. 555953) in combination with a goat-anti-mouse Alexa488 secondary antibody (Invitrogen, cat. A-11001) was used. Both the primary and secondary antibodies were tested in different dilutions to find the most optimal staining conditions.

These results were obtained when the primary antibody was used in a 1:200 dilution and the secondary antibody was used in a 1:500 dilution. The images were taken on the GE INcell Analyzer 2000 with a 10× objective in the DAPI (nuclei) and the FITC (Alexa488) channel. Using this indirect labelling the CD206 expression in M2 primed macrophages was strongly enhanced compared to M0 macrophages and reduced in the M1 macrophages.

4.3 Algorithm to Quantify CD206

Figure 8:
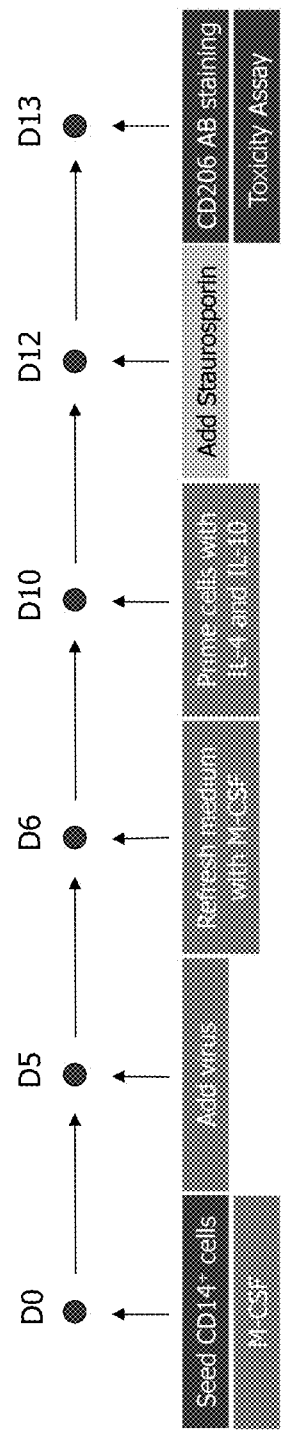
FIG. 8 shows the schematic overview of the M2 validation screen.

To quantify the CD206 ICC staining in a high throughput screening format an algorithm was developed. The output of the algorithm should provide a representative value of the number of CD206 expressing macrophages observed in the imaged areas (FIG. 8). Based on the FACS data from previous experiments, M0, M1 and M2 macrophages all express some level of CD206. M2 macrophages could only be distinguished from M1 and M0 populations based on the enhanced expression of CD206.

The algorithm calculated the number of CD206 positive cells by using a threshold for the CD206 expression. Next, based on the nuclei count, the total number of cells in the well was determined and this number was used to determine the percentage of CD206 positive cells, i.e. M2 macrophages. By applying this algorithm percentage of M2 macrophages can be determined. It should be noted that the absolute values differed between donors, but a robust window was observed within a single donor.

4.4 Positive and Negative Controls

The three negative control viruses used in the Examples 1 and 2 were also tested in the M2 validation assay. The negative controls should not inhibit or induce the read-out more than 25% compared to the no virus control. All three negative controls fulfilled this criterion and were selected as negative controls for the M2 validation assay.

For the selection of positive controls various viruses, which target CD206 (also named Mannose Receptor C type 1 (MRC1)), were tested in the M2 validation assay. Four out of the six viruses targeting CD206 resulted in >60% reduction compared to the average of the negative controls. Two viruses, MRC1_v1 and MRC1_v2, gave the most consistent results in all donors tested and were therefore selected as positive controls for the M2 validation assay read-out.

In addition, the panel of positive controls used in Example 1 was also included in the CD206 assay. The STAT6_v5 and STAT6_v6 positive controls inhibited the percentages of CD206 more than 40% and were therefore also selected as positive controls for the M2 validation assay. The CCL18_v1 positive control did not or only minimally affect CD206 expression. This is expected as CCL18 is an end stage molecule in the IL-4/IL-10 pathway and is therefore unlikely to affect CD206 expression, except through a possible autocrine or paracrine loop.

TABLE 7

Summary of controls used in CD206 screen

| Control code | Name | Sequence | SEQ ID NO |
|---|---|---|---|
| N1 | luc_v13 | GGTTACCTAAGGGTGTGGC | 51 |
| N2 | ffluc_v19 | GAATCGATATTGTTACAAC | 52 |
| N3 | ffluc_v24 | GCATAAGGCTATGAAGAGA | 53 |
| P1 | CCL18_v1 | GTCTATACCTCCTGGCAGA | 54 |
| P2 | IL4R_v6 | CCCGGCAGATTTCAGAATC | 57 |
| P3 | MRC1_v1 | GACTTAGCTAGCATCAATA | 62 |
| P4 | STAT6_v6 | GTCCCAGCTACCATCAAGA | 56 |
| P5 | JAK1_v23 | GAGTCTGTGGTCAGCATTA | 58 |
| P6 | MRC1_v2 | GGATATTGTCCATTGAAAT | 63 |

4.5 Toxicity Assessment Assay

A toxicity assay was developed as part of the validation to exclude false positive hits due to toxic effects. The commercially available Cell Titer Blue (CTB) reagent (Promega, cat. G8081) can be used to measure the metabolic capacity of the cells. The CTB reagent contains a dye, resazurin, which viable cells can convert into resorufin which is highly fluorescent. The CTB reagent was added to the cells in a one in five dilution either by replacing the medium or adding it directly to the medium on the cells. After 24 hours, the relative fluorescent units (RFU), representing viability, were measured on an Envision machine.

To evaluate the sensitivity of the CTB reaction in the macrophages, various cell densities were seeded and the viability was measured. This resulted in a strong correlation between number of cells and RFU signals, indicating that the assay is very sensitive and suitable for measuring cell viability in macrophages. Subsequently, the cells were treated with control virus from the shRNA adenoviral library to assess the toxicity.

To exclude false positive candidate TARGETs, the shRNA constructs from the adenoviral library should not show more than 30% cellular toxicity compared to the no virus controls. Therefore, the macrophages were treated with either no virus or a negative control virus (ffluc_v24). Additionally, staurosporin was added to the cells as a positive control for toxicity. Furthermore, the positive control IL4R_v6 was also included as a positive control since treatment with the IL4R_v6 positive control resulted in a significant decrease in nuclei counts, which indicate toxicity. This observation was done in multiple donors during assay development of the CD206 validation screen.

The RFU of the negative controls was comparable to the no virus control and therefore not toxic. In the staurosporin-treated macrophages the signal and thus viability, decreased dramatically. Treatment with the IL4R_v6 positive control induced around 30% toxicity in M0 and M2 macrophages and more than 50% in M1 macrophages.

4.6 Set-Up of the Screening Protocol for CD206 Read-Out shRNAs against 408 candidate TARGETs, which followed from the M2 macrophage screen (Example 1) and M1 counter screen (Example 2), were tested in the M2 CD206 validation screen which consisted of thirteen 96-well virus source plates. The screen was performed in biological duplicate, at MOI4. The combined protocol together with toxicity assay is presented in FIG. 9.

Figure 9:
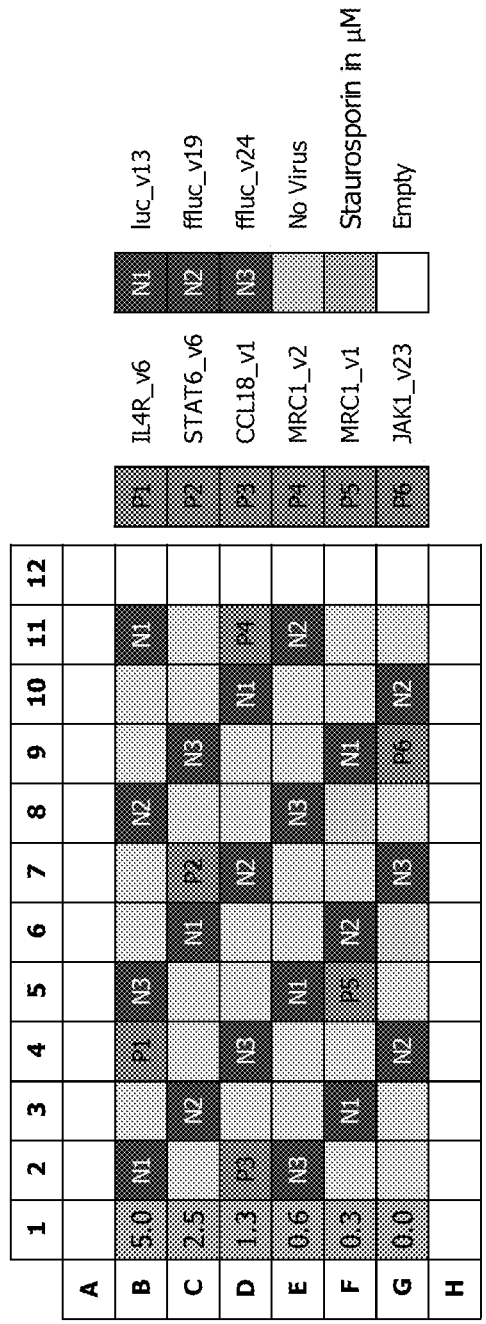
FIG. 9 shows the M2 validation screen plate layout. Layout of the validation screen source plates containing the negative control viruses (N1, N2, and N3), the positive control viruses (P1, P2, P3, P4, P5, and P6), no virus wells and candidate Targets from the adenoviral library (the rest of the wells). The edges of the plates were left empty, except for the wells as indicated in column one in which various concentrations of stauroporin were added.

To perform the screen, on day 0 CD14+ cells were seeded in 96-well µclear plates with medium containing M-CSF to allow the cells to differentiate to M0 macrophages. On day five the transduction was performed followed by a refreshment of the medium one day later. On day ten the interleukins were added to obtain the M2 macrophages. Three days later the cells were fixed for the CD206 ICC assay or CTB was added to measure cytotoxicity. The shRNA adenovirus layout and the experimental setup were identical to the pilot screen, except for column one were staurosporin was added on day 12 to induce toxicity (FIG. 9).

4.7 Results

Figure 10:
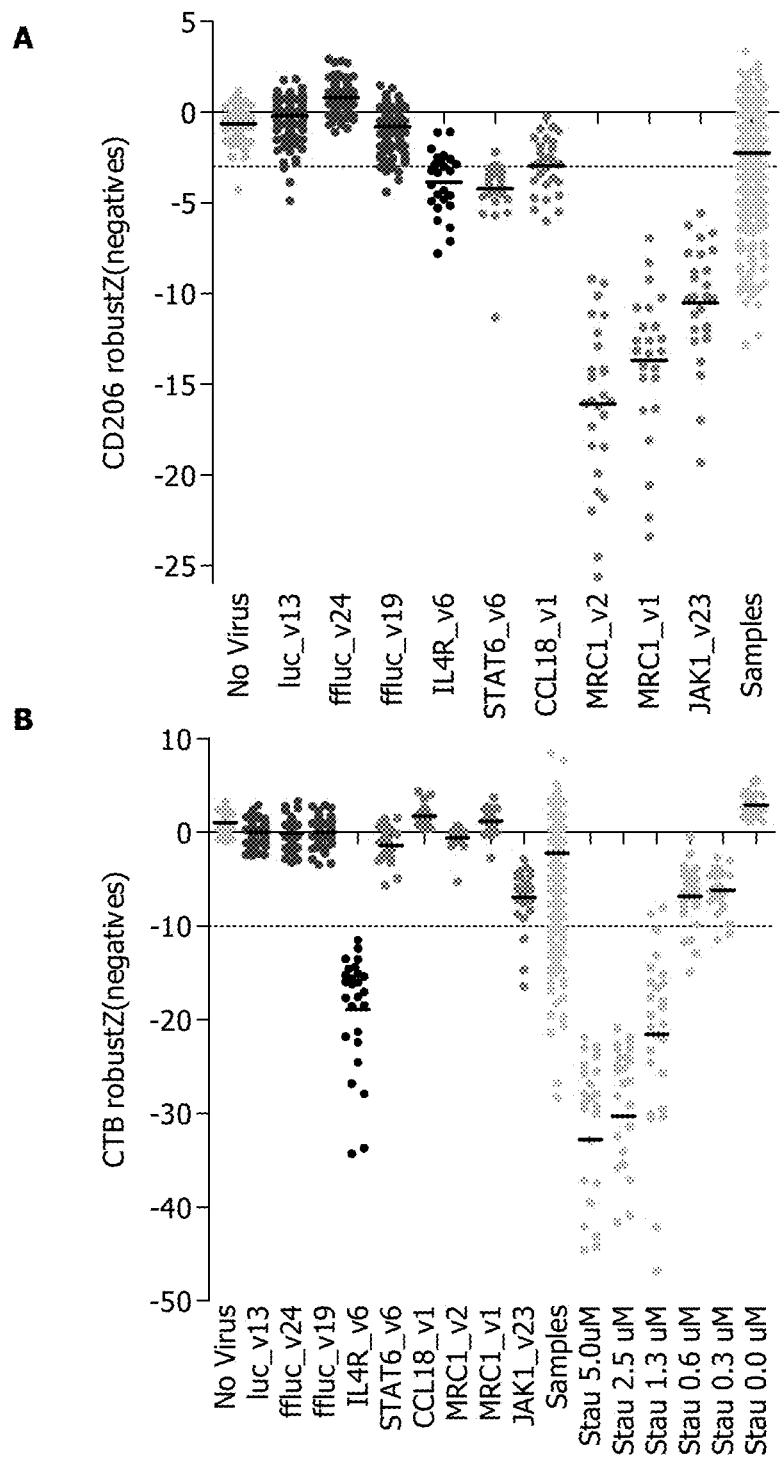
FIG. 10 shows the results of the M2 validation screen. The graphs represent the performance of the controls containing no virus and negative controls compared to positive controls in the CD206 screen (A) and the CTB screen (B). The hit calling cut-offs for the CD206 screen (−3) and for the CTB screen (−10) are indicated with the dashed lines. All values depicted are normalized data points using the Robust Z score.

The average Spearman with the CD206 assay was 0.73, ranging from 0.54 to 0.86 per duplicate plate, which indicates a strong correlation between replicates. The control performance demonstrated a clear separation between the positive controls (MRC1_v1, MRC1_v2 and JAK1_v23) and the negative controls. The negative controls performed in the same range as the no virus controls, indicating the absence of a-specific viral effects on the read-out. The cut-off for hit-calling was determined based on the separation between the positive and negative controls. Furthermore, the cut-off was also based on the percentage of CD206 positive cells in M0 macrophages which consisted of ~60% CD206 positive cells (FIG. 10A). Based on these parameters a robust Z score cut-off of ≤−3 was chosen. None of the negative controls were identified as a hit and 100% of the MRC1_v1, MRC1_v2 and JAK1_v23 positive controls were identified as a hit.

To eliminate false positive hits due to toxicity, the CTB data was analyzed. The Spearman calculations showed a strong replicate correlation. The average Spearman was 0.82, ranging from 0.70 to 0.93 per duplicate plate. The cut-off for hit-calling was based on the 30% signal reduction level, relative to the no virus control. This corresponded to a Robust Z-score value of −10. As a positive control for toxicity various staurosporin concentrations and the IL4R_v6 virus were used to introduce toxicity. The IL4R_v6 Robust Z scores were lower than the 30% inhibition score of −10 which corresponds with previous obtained data. The addition of various staurosporin concentrations resulted in a dose-respond curve, indicating the sensitivity of the CTB assay (FIG. 10B). Based on these results the cut-off for hit calling was determined to be >−10.

Both, the CD206 screen and the CTB screen were performed successfully based on the Spearman values and the control performance. In total 371 candidate Targets passed the toxicity assay using a cut-off of >−10 (Table 8). From the CD206 screen 73 viruses were identified as a hit with a cut-off of ≤−3. From these 73 confirmed candidate TARGETs, 17 virus constructs were identified as toxic. This resulted in a selection of shRNA constructs against 56 candidate Targets that inhibited the M2 phenotype and classified not to induce toxic effects. These 56 candidate TARGETs were taken forward to the "on target" validation.

TABLE 8

Hit performance in M2 validation and toxicity screen.

| Read-out | Cut-off Robust Z-score | # Source plates | # Hits | Average Spearman |
|---|---|---|---|---|
| CD206 | ≤−3 | 13 | 73 | 0.73 (0.54-0.86) |
| CTB | >−10 | 13 | 371 | 0.82 (0.70-0.93) |

Example 5

"on Target" and Toxicity Assessment of Selected shRNA Constructs 5.1 Background

To exclude that the knockdown constructs have an effect on expression of a different mRNA then the intended mRNA, so called off-target effect, an on target validation was performed with the confirmed candidate Targets. The 56 confirmed candidate TARGETs that passed the screens of Examples 1-3, were selected for the on target validation. To this end, multiple adenoviral-shRNA targeting different sites of the same confirmed candidate Target were designed and tested using the primary screen and the M1 counter screen setup. The confirmed candidate Targets are designated 'on-target' if at least two independent shRNA sequences, including the original sequence, pass the criteria of the M2 and M1 validation screens.

The following additional shRNA constructs have been used in "on-target" analysis and demonstrated the ability to inhibit the expression of the target:

5.2 Controls Used in "on Target" Analysis

Two different control panels were used for M1 and M2 differentiation assays as described in Examples 3 and 1 correspondingly.

5.3 Protocol for M2 and M1 "on Target" Screens and Toxicity Assessment

For the on target validation a different virus layout was designed. In that layout the outer wells were omitted and >30% of the plate was filled with negative controls in order to enable hit calling based on negative controls and correction for potential plate effects. Positive controls were included for both the M2 and M1 on target validation. Furthermore, a serial dilution of Staurosporin was added in column one on untransduced cells as reference for the toxicity assay. All adenoviral-shRNAs directed against the candidate TARGETs were randomly distributed over the plate. "No-virus" controls (samples without virus treatment) were positioned on the plates on spots without viruses.

The experimental setup of the M2 and M1 assays (Examples 1 and 3) was adjusted for the "on target" validation. CD14+ cells were isolated as described in Example 1 (1.2). On day zero, 5,000 (M2) or 10,000 (M1) CD14+ cells/well were seeded in 384-well culture plates with RPMI Glutamax medium containing 10% FBS, 1% P/S and 100 ng/ml M-CSF. After five days, the M0 macrophages were transduced with the adenoviruses followed by medium refreshment one day later. On day ten the cells were primed with RPMI Glutamax medium containing 10% FBS, 1% P/S and the required cytokines to prime the cells towards M2 (20 ng/ml IL-4 and 20 ng/ml IL-10) or M1 (20 ng/ml INFγ and 5 ng/ml LPS) macrophages. The M1 priming condition was refreshed 16 hours before harvesting the supernatants. On day 13, the M2 and M1 supernatants were harvested and the CTB reagent was added to the cells. CCL18 and TNFα were measured for the M2 and M1 on target validation, respectively. The toxicity was assessed 24 hours after addition of CTB.

5.4 Data Analysis 5.4.1 M2 "on Target" Screen Data Analysis

The B-score analysis was applied to normalize the CCL18 data obtained from the M2 on target screen followed by assessing the replicate performance using the Spearman rank correlation coefficient. The average Spearman correlation for the M2 on target screen was 0.95 indicating a strong correlation between replicates. The control performance demonstrated a clear separation between the positive controls (CCL18_v1, STAT6_v6 and JAK1_v23) and the negative controls. The negative controls performed in the same range as the "no virus" controls. Based on these results a B-score cut-off of ≤−1.6 was used for hit calling.

5.4.2 CTB Assay in M2 "on Target" Screen Data Analysis

The data obtained from the CTB assessment in the M2 on target validation screen was also analyzed using the B-score normalization and Spearman rank correlation. The average Spearman correlation for the M2 CTB screen was 0.89 which indicated a strong correlation between replicates. The cut-off for hit calling was based on the 30% signal reduction level, relative to the no virus controls which corresponded to a B-score value of −8. As a positive control for toxicity various Staurosporin concentrations and the IL4R_v6 virus were used to introduce toxicity. The IL4R_v6 positive control was identified as a hit at a cut-off of −8. The addition of various Staurosporin concentrations resulted in a dose-response curve, indicating that the CTB assay is a sensitive measurement for toxicity. Based on these results the cut-off for hit calling of nontoxic targets in M2 macrophages was set at a B-score of >−8.

5.4.3 M1 "on Target" Screen Data Analysis

The TNFα data derived from the M1 on target screen were also analyzed using the B-score normalization. The average Spearman for M1 on target assay was 0.84 indicating a strong correlation between replicates. The control performance demonstrated a clear separation between two of the positive controls (TNF_v12, TRAF6 v6), whereas TRAF6_v4 and MYD88_v4 showed less inhibition of the TNFα signal. The negative controls showed a small effect compared to the no virus condition, which was also observed in previous M1 assay. This effect is within 25% margin compared to the no virus control and therefore passes the assay criteria. Based on these results a cut-off of >−3 was used for hit calling.

5.4.4 CTB Assay in M1 "on Target" Screen Data Analysis

Based on the CTB read-out of the M1 on target toxicity assay, the B-score was used for normalization and the replicate performance was assessed. The average Spearman for M1 on target assay was 0.83. The cut-off for hit calling was based on the 30% signal reduction level, relative to the no virus control. This corresponded to a B-score value of −8. As a positive control for toxicity various staurosporin concentrations and the IL4R_v6 virus were used to introduce toxicity. The addition of various staurosporin concentrations resulted in a dose-respond curve, indicating the sensitivity of the CTB assay. Based on these results the cut-off for hit calling was determined to be >−8

5.5 Results

When at least two independent shRNA sequences, passed the cut-off criteria of the M2 and M1 "on target" validation screen without observing toxicity, the shRNA was designated as "on target". Based on these criteria, 14 gene targets were identified as on target. Summary of the results is presented in Table 14.

Example 6

M2 and M1 "on Target" Screen Using Different IU and Tox Assessment 6.1 Background The 34 targets for which the original construct was not identified as hit in Example 5 were retested in a different "on target" screen. The plate layout and the experimental set-up were identical to the "on target" validation in Example 5. The transduction was performed using two source plates, one containing virus constructs with a relatively low IU and one containing virus constructs with a relatively high IU.

6.2 Protocol for M2 and M1 "on Target" Screens

For both the M2 and M1 screens, multiple virus dilutions were made of the two source plates and used to transduce the cells. This was done in such a way that all virus constructs were added at a MOI range of 3-5 for the M2 screens and 6.5-9 for the M1 screens. By doing this, the performance of all virus constructs were more comparable to the performance of the negative and positive controls which were added in a MOI of 4 and 8 for the M2 and M1 assays, respectively.

6.3 Data Analysis

Data was normalized using the B-score. For the determination of B scores, negative controls with MOIs comparable to the samples were used. The replicate performance was analyzed using the Spearman correlations and were al >0.4. In all four screens an adequate window was observed between the positive and negative controls. The cut-offs for hit calling were based on the control performance (Table 9).

6.4 Results

When at least two independent shRNA sequences, including the original hit, were confirmed in the screens the target was declared "on target". In total 13 targets are found to be on target based on the results of the IU based M2 and M1 on target validation and toxicity screens.

TABLE 9

Assay overview IU based on target screens

| Read-out | Spearman | COF |
|---|---|---|
| CCL18 | 0.82 | ≤−3 |
| TNFα | 0.67 | >−3 |
| M2 CTB | 0.79 | >−6 |
| M1 CTB | 0.74 | >−8 |

When combined with the results of the Example 5, 27 confirmed candidate Targets were designated on target and therefore considered confirmed Targets. These targets were taken forward into further target validation.

Example 7

Analysis of Expression of the TARGETs in Macrophages and BALF

7.1 Background

To confirm mRNA expression of the identified targets in macrophages, mRNA was isolated from these cells to perform whole transcriptome sequencing. To be relevant for fibrotic conditions the TARGETs should be expressed in relevant tissue of the disease. Therefore, in addition to confirm the expression of the TARGETs in patient material alveolar macrophages (AM) were isolated from lung tissue from an IPF patient.).

Whole transcriptome sequencing, or mRNA-seq, is a cDNA sequencing application that can be used to profile the entire mRNA population and that enables mapping and quantification of all transcripts. With no probes or primer design needed, mRNA-seq has the potential to provide relatively unbiased sequence information from polyA-tailed RNA for analysis of gene expression, novel transcripts, novel isoforms, alternative splice sites, and rare transcripts in a single experiment, depending on read depth.

7.2 Sample Preparation for the mRNA-Seq Study in Macrophages

To obtain macrophages, buffy coats from two healthy donors, were purchased via the blood bank (Sanquin, The Netherlands) for isolation of PBMCs. The isolation was performed using a Ficoll gradient and subsequently the CD14+ cells were extracted using CD14 MicroBeads (Miltenyi, cat. 130-050-201). After the CD14 isolation a QC regarding the purity was performed on the PBMCs and the isolated CD14+ fraction using flow cytometric analysis.

To differentiate the CD14 positive cells into M0 macrophages, the cells were seeded in 96-well plates with RPMI Glutamax medium, containing 10% FBS, 1% P/S and 100 ng/mL M-CSF. In total four plates were seeded per donor at a cell density of 20,000 cells/well and cultured for six days. On day six, one plate from both donors containing the M0 macrophages were harvested for RNA isolation and the other three plates were refreshed. Ten days after seeding, the second plate from both donors containing M0 macrophages was harvested for RNA isolation. The other two plates from each donor were triggered with 20 ng/mL IFNγ and 5 ng/mL IFNγ or 20 ng/mL IL-10 and 20 ng/mL LPS in RPMI Glutamax medium containing 10% FBS and 1% P/S, to generate M1 or M2, respectively. The cells were cultured for another three days before the macrophages were harvested for RNA isolation. After harvest, specific cell markers were tested using flow cytometry to confirm the M0, M1 and M2 phenotypes. This was done by assessing the expression markers CD163 and CD206. The CD163 and CD206 expression were enhanced in the M2 macrophages and decreased in the M1 macrophages compared to the M0 macrophages, in both donors.

7.4 RNA Determination

Total RNA was isolated from M0 and M2 macrophages as well as AM using a commercially available RNA isolation kit (RNeasy Mini Kit, Qiagen). Concentration and purity was checked using the NanoDrop 2000 (Thermo Scientific).

7.5 mRNA Analysis

The quality and integrity of the RNA sample(s) was analyzed on a RNA 6000 Lab-on-a-Chip using the Bioanalyzer 2100 (Agilent Technologies). Sample quality met the requirements for sample preparation. The Illumina® mRNA-Seq Sample Prep Kit was used to process the samples. The sample preparation was performed according to the Illumina protocol "Preparing Samples for Sequencing of mRNA" (1004898 Rev. D). Briefly, mRNA was isolated from total RNA using the poly-T-oligo-attached magnetic beads. After fragmentation of the mRNA, cDNA synthesis was performed. This was used for ligation with the sequencing adapters and PCR amplification of the resulting product. The quality and yield after sample preparation was measured with a DNA 1000 Lab-on-a-Chip (Agilent Technologies) and all samples passed the quality control. The size of the resulting products was consistent with the expected product with a broad size distribution between 300-600 bp.

7.6 Clustering and DNA Sequencing

Clustering and DNA sequencing using the Illumina HiSeq 2000 (Solexa) were performed according manufacturer's protocols. A total of 6.5 pmol of DNA was used. Two sequencing reads of 100 cycles each using the Read 1 and Read 2 sequencing primers were performed with the flow cell.

7.7 Raw Data Processing

Image analysis, base-calling, and quality check was performed with the Illumina data analysis pipeline RTA v1.13.48 and/or OLB v1.9 and CASAVA v1.8.2. QA analysis performed to evaluate the quality of an Illumina sequencing run was based on quality metrics for a standard run of good quality using the Solexa technology. All lanes of the flow cell passed the QA analysis. Additionally, detailed error rate information based on an Illumina supplied Phi X control was reported. The Phi X control is spiked into the sample in a small amount (up to 5% of the reads). The reads from the Illumina control DNA were removed by the Illumina pipeline during processing of the data. The error rate is calculated after alignment of the reads passing the quality filter to the Phi X reference genome using the ELAND aligner in the Illumina pipeline. All error rates were within the allowed criteria.

7.8 Data Analysis

Reads obtained from the Illumina HiSeq 2000 sequencer were filtered by quality scores with a minimum threshold of Q25 and minimum length of 50 bases. Reads were then aligned to the human reference genome (hg19) with the Bowtie v0.12.7 aligner for each sample. New isoforms were identified with the Cufflinks v2.02 package using default settings and the known transcriptome annotation as mask (Homo_sapiens.GRCh37.65.gff). After new isoform identification for each sample, the newly detected isoforms were merged for all samples and added to the standard transcriptome annotation. Finally, FPKM (Fragments PerKilobase of transcript per Million fragments mapped) values were calculated with Cufflinks for each sample and reported in the default Cufflinks output. The FPKM values are a quantitative representation of the mRNAs in the samples and therefore in the cells used for the mRNA-seq analysis and the screening assays. Highly abundant mRNAs result in high FPKM values whereas low FPKM values represent low copy numbers of the mRNA.

7.9 Sample Preparation for the Expression Study in Alveolar Macrophages from Patient Material IPF patient tissue sample was obtained from Tissue Solutions. Isolation of alveolar macrophages was performed by adherence on a T80 cell culture flask. Part of the cells was used for flow cytometric analysis to determine the quantity of the macrophage population in this cell preparation. For this, a mouse-anti-human CD68-FITC antibody (Miltenyi, cat. 130-096-964) was used to detect the CD68 expression marker, which is known to be expressed on alveolar macrophages (Kunisch et al, 2004). In total 73% of the gated cells were found to be CD68 positive, representing the macrophage population.

The remainder of the cells were lysed and used for RNA isolation using the RNeasy Mini Kit (Qiagen, cat. 74106). Reverse transcription was performed using the TaqMan® Reverse Transcription Reagents (Applied Bioscience, cat. N8080234) to generate cDNA. This cDNA was quantified on the LightCycler® 480 Real-Time PCR System (Roche Diagnostics) using TaqMan® Fast Advanced Master Mix (Life Technologies, cat. 4444964) with commercially available validated TaqMan® Assays (Life Technologies or Qiagen). A set of four housekeeping genes was tested to confirm the quality of the sample. Roche LightCycler refers to Cp as the cycle number that crosses the threshold, also referred to Ct in other instruments. Bustin et al., 2009) proposes to unify the different nomenclatures to Cq (quantification cycle).

7.10 Results mRNA-Seq

The results of this mRNA-seq analysis are included in Table 12 and were used as selection criteria for the TARGETs. Expression data are listed as FPKM values and used as selection criteria for the TARGETS. Genes were considered to be expressed if FKPM values were determined. The results demonstrate that the TARGETs are expressed in both M0 and M2 macrophages 7.11 Results of qPCR on AM The results of this analysis are included in Table 15. Expression data are listed as Cq values and used as selection criteria for the TARGETS. Genes were considered to be expressed with Cq values up to 35, C values above 35 were considered as "not expressed". The results demonstrate that the TARGETs are expressed in AM.

Example 8

Testing siRNA Against the TARGETs in the CCL18 Assay 8.1 Background

To exclude that the shRNA knockdown constructs have an effect on expression of a different mRNA then the intended mRNA, so called off-target effect, an on-target validation was performed with the confirmed candidate Targets using siRNA constructs against selected TARGETS.

8.2 Controls Used in siRNA "on Target" Analysis siRNA against CCL18, JAK1 and STATE were used as positive controls and non-targeting siRNA (Thermo Fisher Scientific Biosciences GMBH) was used as a negative control.

8.3 Protocol for M2 "on Target" siRNA Assay and Toxicity Assessment

The experimental setup was as follows: On day 0 CD14+ 20,000 cells/well were seeded in 96-well plates with RPMI Glutamax medium containing 10% FBS, 1% P/S and 100 ng/ml M-CSF. Five days later the siRNA transfection was preformed. Cells were transfected using 0.02-0.2 μL/well of Dharmafect 1 (Thermo, Cat # T-2001-03). OnTarget Plus siRNA (Thermo Fisher Scientific Biosciences GMBH) in the final concentration of 20 nM were used as smart pools of 4 constructs per well. For EFEMP2 each siRNA construct was also tested individually. One day after cells were primed with RPMI Glutamax medium containing 10% FBS, 1% P/S and the required cytokines to prime the cells towards M2 (20 ng/mL IL-4 and 20 ng/mL IL-10). On day 8 cells the Staurosporin was added to the control wells on each plate (one single row on each plate). On day 9 supernatants were harvested and the CTB reagent was added to the cells. On the same day RNA isolation is performed using standard MagMax Total RNA isolation kit (Ambion, Cat # AM1830) together with Cell Titer Blue assay (Promega, Cat # G808B) as a quality control. The CCL18 is measured in the supernatant using ELISA as described for Example 1.

8.4 Data Analysis

Normalized percentage inhibition (NPI) analysis was used to quantify the effect of siRNA constructs on the read-out. CCL18 siRNA was used as a positive control and non-targeting siRNA as a negative control in the calculations. Normalized percentage inhibition (NPT) was calculated by dividing the difference between sample measurements and the average of positive controls through the difference between positive and negative controls.

Example 9

TARGET Expression in Animal Models of Fibrosis 9.1 Background

To study the expression of the TARGET genes in vivo, several mouse and rat models of fibrosis were tested and expression in specific tissues like kidney, lung and skin were determined.

9.2 Mouse UUO (Unilateral Ureteral Obstruction) Renal Fibrosis Model

Unilateral ureteral obstruction was performed on Balb/c female mice (from Harlan-France), with 10 mice/group. On day 0, mice were anaesthetized by intra-peritoneal injection and after incision of the skin, the left ureter was dissected out and ligatured with 4.0 silk at two points along its length. The ureter was then sectioned between the 2 ligatures. Intact mice were used as control. Mice were sacrificed by exsanguinations with scissors under anaesthesia after 10 or 21 days.

9.3 Rat 5/6 NTX (5/6 Nephrectomy) Renal Fibrosis Model

Nephrectomy was performed on Sprague-Dawley male rats (from CERJ-France), with 10 rats/group. At Day 0, rats were anaesthetized and after incision of the skin, the kidney capsule was removed while preserving the adrenal gland. The renal hilum was ligated and right kidney was removed. The ends of the left kidney are cut with a scalpel resulting in 5/6 nephrectomy. Rats were sacrificed after 4 or 8 weeks.

9.4 Mouse BLM (Bleomycine) Pulmonary Fibrosis Model

Lung fibrosis was induced on CD1 male mice (from CERJ-Francc) for bleomycin i.v. administration with 6 to 8 mice/group and on C57/Bl6 J female mice (from Janvier) for bleomycin i.t. administration with 14 mice/group.

For intravenous administration (i.v.) mice were injected intravenously with bleomycin (10 mg/kg; 100 μl/mouse) or saline as a control once per day for the first five consecutive days (Oku et al., 2004). Mice were sacrificed by exsanguinations with scissors under anaesthesia after 3 or 6 weeks.

For intra-peritoneal (i.p) administration mice were anaesthetized by intra-peritoneal injection (under a volume of 10 mL/kg) of anaesthetic solution (18 mL NaCl 0.9%+0.5 mL xylazine (5 mg/kg)+1.5 mL ketamine (75 mg/kg)). Bleomycin solution at 2 U/kg or saline was administered by intra-tracheal route (10 mg/kg; 40 μL/mouse). Mice were sacrificed by exsanguinations with scissors under anaesthesia after 3 weeks.

9.5 Mouse Scleroderma Model (SCL)

Scleroderma was induced on Balb/c female mice (from CERJ-France), with 15 mice per group. On day 0 mice were anesthetised by intra-peritoneal injection of a solution (Xylazine 5 mg/kg, ketamine 75 mg/kg) and shaved. A volume of 100 µl of bleomycin solution at 1 mg/ml or saline was injected subcutaneously with a 26g needle into the shaved backs of mice. Bleomycin was injected 5 days per week for 3 consecutive weeks. The total experimental period was 6 weeks. Mice were sacrificed by exsanguinations with scissors under anaesthesia after 6 weeks.

9.6 Gene Expression and Regulation in Animal Fibrosis Models

At the end of the in vivo experiment, animals were sacrificed and tissues (1/2 mouse kidney for UUO model, 1/3 rat kidney for 5/6 NTX model, a piece of skin for mouse scleroderma model and 1 lobe of lung for mouse lung fibrosis model) were collected in 2 ml-microtubes (Ozyme #03961-1-405.2) containing RNALater® stabilization solution (Ambion #AM7021). Tissues were disrupted with 1.4 mm ceramic beads (Ozyme #03961-1-103, BER1042) in a Precellys® 24 Tissue Homogenizer (Bertin Technologies). Total RNA was isolated, subjected to recombinant DNase digestion and purified using Qiazol® (Qiagen #79306) and NucleoSpin® RNA kit (Macherey-Nagel #740955.250) as recommended by the manufacturers. RNA was eluted with 60 µl RNase-free water. RNA concentration and purity were determined by absorbance at 260, 280 and 230 nm. cDNA was prepared from 500 ng total RNA by reverse transcription using a high-capacity cDNA RT kit (Applied Biosystems #4368814). 5 µl of 10 times diluted cDNA preparations were used for real-time quantitative PCR. qPCR was performed with gene-specific primers from Qiagen using SYBR Green technology. Reactions were carried out with a denaturation step at 95° C. for 5 min followed by 40 cycles (95° C. for 10 sec, 60° C. for 30 sec) in a ViiA7 real-time PCR system (Applied Biosystems).

The following rodent β-actin primers (Eurogentec) were used: 5'-ACCCTGTGCTGCTCACCG-3' (forward primer: SEQ ID NO 111) and 5'-AGGTCTCAAACATGATCTGGGTC-3' (reverse primer SEQ ID NO 112).

Mouse and rat assay mixes are listed in the table below.

TABLE 10

| Mouse and rat assay mixes (Qiagen) | | |
|---|---|---|
| TARGET | Mouse mix | Rat mix |
| BPNT1 | QT02530745 | QT00176540 |
| MS4A4A | QT01659476 | QT02375744 |
| S1PR2 | QT00262773 | QT00401884 |
| SLC15A3 | QT00139307 | QT01080009 |
| USP22 | QT01070531 | QT02386580 |
| ZMPSTE24 | QT01750329 | |
| LIF | QT00111090 | |
| EFEMP2 | QT00162134 | |

9.7 Data Analysis

Expression levels of each gene were estimated by their threshold cycle ($C_T$) values in control animals The quantification of relative changes in gene expression were expressed using the $2^{-\Delta\Delta C_T}$ method (where $\Delta\Delta C_T = (C_T\text{.target} - C_T\beta\text{-actin})_{diseased\ animal} - (C_T\text{.target} - C_T\beta\text{-actin})_{control\ animal}$. Statistical analysis of $2^{-\Delta\Delta C_T}$ values were performed using unpaired Student's t-test versus control group (*: $p<0.001$; : $p<0.01$; *: $p<0.05$)

9.8 Results

All tested mRNA are well expressed in fibrotic tissues (kidney, lung and skin) except for MS4A4A which is poorly expressed in kidney (see Table 11)

TABLE 11 mRNA expression levels in intact animals
(Ct > 30: low, 25 < Ct < 30: medium, Ct < 25: high)

| | BPNT1 | MS4A4A | S1PR2 | SLC15A3 | USP22 | EFEMP2 | LIF | ZMPSTE24 |
|---|---|---|---|---|---|---|---|---|
| Mouse UUO (10 days) | 20.7 | 31.1 | 28.2 | 28.7 | 23.1 | 24.7 | 30.7 | 21.8 |
| Mouse UUO (21 days) | 19.9 | 30.4 | 26.8 | 27.5 | 22.5 | 24.1 | 29.8 | 21.3 |
| Rat NTX (4 week) | 19.5 | >35 | 24.5 | 22.4 | 20.8 | — | — | — |
| Rat NTX (8 week) | 20.2 | 30.4 | 25.9 | 22.3 | 22.6 | — | — | — |
| Mouse BLM (i.v. 3 w) | 23.9 | 24.9 | 23.3 | 23.8 | 22.6 | — | — | — |
| Mouse BLM (i.v. 6 weeks) | 23.3 | 23.9 | 23.6 | 23.1 | 22.1 | — | — | — |
| Mouse BLM (single i.t.) | — | 26.1 | 24.5 | 24.9 | — | 23.4 | 21 | 24.6 |
| Mouse SCL | 23.1 | 24.3 | 25.1 | 28.3 | 23.4 | 25.2 | 29.5 | 24.9 |

Many genes are up or down regulated in mouse UUO model whereas only few regulations were observed in rat NTX model (4 & 8 weeks), and in lung and skin fibrosis models. EFEMP2 and LIF agenes are up regulated in at least one mouse fibrosis model. LIF is strongly upregulated in UUO at both times (10 and 21 days). ZMPSTE24 is significantly downregulated in UUO model at both times (10 and 21 days) (see Table 12)

TABLE 12 qPCR analysis of the fibrosis models

| | BPNT1 | MS4A4A | S1PR2 | SLC15A3 | USP22 | EFEMP2 | LIF | ZMPSTE24 |
|---|---|---|---|---|---|---|---|---|
| Mouse UUO (10 days) | −3.5 *** | 25.2 *** | 1.6 (***) | 2.1 *** | 1.3 (**) | 2.1 *** | 23.3 *** | −2.3 *** |
| Mouse UUO (21 days) | −3.9 *** | 65.1 *** | 4.1 *** | 5.7 *** | ns | 1.7 (***) | 14.2 *** | −3.9 *** |
| Rat NTX (4 week) | −1.3 () | ns | ns | ns | −1.3 () | — | — | — |
| Rat NTX (8 week) | −1.9 (**) | ns | 2.5 * | −1.6 (*) | ns | — | — | — |
| Mouse BLM (i.v. 3 w) | 1.5 (**) | ns | ns | 1.5 (*) | ns | — | — | — |
| Mouse BLM (i.v. 6 weeks) | ns | ns | ns | ns | ns | — | — | — |
| Mouse BLM (single i.t.) | | −1.2 (*) | −1.3 () | ns | | 1.4 (*) | 3.3 *** | ns |
| Mouse SCL | −1.2 (*) | ns | ns | 2.9 *** | 1.4 (**) | ns | 1.6 (*) | 1.2 (*) |

(fold > 1.8: significant fold induction vs intact animals;
fold < −1.8: significant fold inhibition vs intact animals;
ns: no significant change;
***: p < 0.001;
**: p < 0.01;
*: p < 0.05)

TABLE 13

Overview of the performance of TARGETs in the primary screen, rescreen, M1 counter screen, M2 CD206 validation assay and M2 toxicity assays.

| | Primary CCL18 screen | | CCL18 Rescreen | | M1 counterscreen | | M2 CD206 assay | | M2 CTB assay | | M2 nuclei count | |
|---|---|---|---|---|---|---|---|---|---|---|---|---|
| Gene symbol | B-score 1 | B-score 2 | B-score 1 | B-score 2 | B-score 1 | B-score 2 | Z-score 1 | Z-score 2 | Z-score 1 | Z-score 2 | Nuclei 1 | Nuclei 2 |
| BPNT1 | −3.13 | −3.21 | −2.00 | −2.12 | −0.84 | 1.07 | −4.14 | −4.40 | 1.12 | −1.02 | 1438 | 1834 |
| C1RL | −2.07 | −2.17 | −2.03 | −1.88 | 3.68 | 3.13 | −6.17 | −5.43 | 2.78 | 2.32 | 1391 | 1359 |
| DCN | −1.33 | −1.70 | −1.63 | −1.78 | 5.83 | 2.65 | −3.94 | −5.15 | −3.17 | −1.91 | 1164 | 1145 |
| EFEMP2 | −1.44 | −1.42 | −1.68 | −1.98 | −0.22 | 1.08 | −4.10 | −4.31 | 0.50 | 0.66 | 1303 | 1509 |
| EFNB2 | −1.93 | −1.63 | −1.52 | −1.64 | 0.92 | −1.23 | −3.26 | −3.07 | −0.03 | −0.38 | 1244 | 1192 |
| GPR155 | −2.68 | −1.82 | −2.21 | −2.34 | 1.75 | 1.45 | −9.27 | −8.54 | −1.65 | 0.82 | 1158 | 1431 |
| KCNMB4 | −2.32 | −2.08 | −1.83 | −1.67 | 2.87 | 2.65 | −10.09 | −12.84 | 5.11 | 0.88 | 1383 | 1393 |
| LIF | −1.56 | −1.39 | −1.80 | −1.84 | 10.29 | 9.83 | −3.00 | −3.46 | −0.94 | −1.13 | 1553 | 777 |
| MS4A4A | −1.61 | −1.77 | −2.19 | −2.18 | 9.88 | 6.06 | −3.07 | −3.75 | −0.11 | −0.26 | 1505 | 1379 |
| RAF1 | −2.17 | −2.47 | −2.11 | −2.52 | 7.43 | 5.95 | −3.28 | −3.36 | −3.07 | −1.68 | 1407 | 1390 |
| S1PR2 | −3.26 | −3.06 | −1.87 | −2.09 | 0.49 | −1.12 | −5.28 | −4.97 | 3.34 | 0.84 | 1509 | 1888 |
| SLC15A3 | −2.68 | −2.66 | −1.84 | −2.17 | 4.56 | 6.44 | −4.88 | −3.36 | −0.76 | −0.77 | 621 | 1068 |
| USP22 | −3.01 | −2.99 | −2.11 | −2.34 | 3.97 | 5.67 | −6.05 | −4.83 | −9.08 | −2.26 | 723 | 882 |
| ZMPSTE24 | −1.92 | −1.78 | −1.99 | −1.96 | −0.31 | −0.36 | −5.42 | −6.47 | −0.30 | 1.76 | 992 | 1206 |

This table gives an overview of the performance of the 56 candidate Targets that were shown to be on-target. The first column shows the Target gene symbol. Duplicate B-scores are shown for the primary CCL18 screen and rescreen where a cutoff of B-score robustZ

TABLE 14

Overview of the performance of the TARGETs in the on-target validation.
This table gives an overview of the performance of the Targets in the on-target
assays. The confirmed candidate Target gene symbol and the knock-down sequence of the
adenoviral constructs are shown. Results for the shRNAs which were considered a hit
are shown. If shRNA was a hit in both OT assays and was an original hit in the primary
screen the corresponding values are highlighted in bold. The on-target validation was
performed in two batches, A and B. Duplicate results are shown of the M2 CCL18 on-target
screen with a cutoff B-score ≤-1.6 for batch A or ≤-3 for batch B. Results of the M1
TNFα counter screen as readout are shown as B-score where non-hits were identified using
a cutoff of B-score >-3 for both batches. CTB results are shown for both M2 and M1 assays
as duplicate B-scores. Hits were included based on non-toxic effect in the M2 assay if
B-score >-8 and in the M1 assay if B-score >-8 (batch A) or B-score >-6 (batch B).
On-target indicates if at least 2 independent shRNAs including the original
shRNA give the same effect.

| Gene | Sequence | SEQ ID NO | OT M2 screen B-score 1 | OT M2 screen B-score 2 | OT M1 counter screen B-score 1 | OT M1 counter screen B-score 2 | OT M2 CTB assay B-score 1 | OT M2 CTB assay B-score 2 | OT M1 CTB assay B-score 1 | OT M1 CTB assay B-score 2 |
|---|---|---|---|---|---|---|---|---|---|---|
| BPNT1 | TGAAGCAACCATGCCCATC | 64 | -13.5 | -8.7 | -1.2 | -0.8 | -1.9 | -3.6 | 0.0 | 0.0 |
| BPNT1 | TGTGTTGCTGCTATGAACC | 65 | -8.4 | -9.9 | 0.3 | -2.3 | 0.4 | -3.3 | -2.2 | -4.9 |
| BPNT1 | GAGCTGATTGAAGACAGTC | 66 | -2.8 | -2.0 | 0.0 | 3.7 | 0.2 | 0.9 | 1.2 | 1.0 |
| BPNT1 | GTCTTCTTGACAATGTAAC | 67 | -12.4 | -9.2 | -0.7 | -2.7 | -2.4 | -4.9 | 0.6 | -0.6 |
| BPNT1 | CTACCACAACCATCTCAAC | 68 | -5.7 | -6.6 | 5.4 | 5.4 | 1.5 | -0.5 | -2.1 | -2.6 |
| C1RL | GAATGAGTCCCATAACTTT | 69 | -3.2 | -3.4 | -1.2 | 2.0 | -2.6 | -2.6 | -3.1 | -3.3 |
| C1RL | CCGTGGCTGTGAACTATAG | 70 | -4.2 | -6.2 | -1.1 | -1.6 | 0.2 | -0.8 | -0.7 | -0.4 |
| C1RL | GGTCTGTCTGCCCGATAAT | 71 | -5.9 | -4.6 | 0.5 | 0.2 | -0.2 | -0.9 | 0.1 | 0.5 |
| C1RL | CCAGAGTGTGAATGTGTTC | 72 | -3.7 | -5.6 | 0.7 | -1.7 | 0.6 | -0.6 | -1.3 | -0.1 |
| C1RL | GGTGCTCAGCTATGTGGAC | 73 | -3.7 | -6.5 | 1.5 | 7.2 | -0.3 | -2.9 | -3.4 | -3.1 |
| DCN | GGTTGTCTACCTTCATAAC | 74 | -5.3 | -6.9 | 4.4 | 4.9 | 0.0 | -2.1 | -0.7 | -0.2 |
| DCN | GAAGATGAGGCTTCTGGGA | 75 | -4.9 | -6.8 | 0.4 | 1.0 | 2.5 | -2.4 | 3.1 | 1.6 |
| EFEMP2 | CCAAACCTGTGTCAACTTC | 76 | -5.2 | -5.0 | 1.7 | 2.0 | -2.0 | -3.7 | -1.1 | -1.3 |
| EFEMP2 | GAGATGGTCACCATGAATT | 77 | -8.7 | -9.0 | 2.5 | 2.0 | -0.9 | -3.2 | -2.0 | 2.0 |
| EFEMP2 | TGATGGTTACCGCAAGATC | 78 | -4.3 | -3.9 | -2.0 | 0.0 | -1.0 | 0.2 | 2.5 | 0.6 |
| EFNB2 | GCCTATCTATTGGAATTCC | 79 | -11.8 | -7.3 | 1.8 | 0.5 | -1.0 | -1.4 | -2.2 | -2.0 |
| EFNB2 | AATAAAGATCCAACAAGAC | 80 | -3.0 | -3.2 | -1.6 | -2.6 | -0.3 | -1.0 | -0.9 | -0.6 |
| EFNB2 | GCCAAACCAGACCAAGATA | 81 | -6.5 | -4.0 | 4.8 | 3.1 | 4.2 | 1.5 | 1.2 | 0.7 |
| GPR155 | CATCCAAACCTACCTCTAT | 82 | -6.5 | -6.3 | 2.0 | 3.9 | -4.3 | -5.1 | -0.9 | -3.2 |
| GPR155 | ATTGGCCTGTTCGCTAATC | 83 | -2.3 | -3.1 | 0.9 | 1.8 | 0.4 | -1.0 | -0.9 | -0.3 |
| GPR155 | GAGAGAGGGTACAAATTCC | 84 | -8.9 | -7.2 | -0.7 | -1.2 | -5.4 | -4.1 | 3.0 | 2.7 |
| GPR155 | CCAGAGCTGCATATTAGCC | 85 | -12.3 | -9.7 | 0.1 | 1.8 | -2.6 | -4.9 | -3.8 | -0.2 |
| KCNMB4 | ATTTGTGGTGGGCGTTCTC | 86 | -4.2 | -2.0 | -7.7 | -7.5 | 0.6 | 0.4 | -0.4 | 0.1 |
| KCNMB4 | AGAAGCTGTACTCATCGGC | 87 | -13.3 | -10.4 | -1.9 | -1.7 | -0.6 | -1.0 | -3.8 | -3.3 |
| LIF | CAACCTCATGAACCAGATC | 88 | -4.8 | -8.0 | 7.7 | 10.0 | -1.1 | -2.8 | -1.7 | -1.1 |
| LIF | CTCGGGTAAGGATGTCTTC | 89 | -3.4 | -2.0 | -2.3 | -0.4 | 1.0 | 1.9 | -1.7 | -0.2 |
| LIF | ACAACCTGGACAAGCTATG | 90 | -8.2 | -8.3 | 6.7 | 2.4 | -1.4 | -5.6 | -2.1 | -2.5 |
| MS4A4A | CCATCACCCTTACTGTAAC | 91 | -7.8 | -7.3 | 3.0 | 2.2 | -1.0 | -4.2 | -3.1 | -2.8 |
| MS4A4A | GCATGGTGCTCCTCTTAAG | 92 | -7.2 | -6.1 | 2.5 | 1.9 | -4.4 | -3.5 | -1.0 | 2.1 |

TABLE 14-continued

Overview of the performance of the TARGETs in the on-target validation.
This table gives an overview of the performance of the Targets in the on-target assays. The confirmed candidate Target gene symbol and the knock-down sequence of the adenoviral constructs are shown. Results for the shRNAs which were considered a hit are shown. If shRNA was a hit in both OT assays and was an original hit in the primary screen the corresponding values are highlighted in bold. The on-target validation was performed in two batches, A and B. Duplicate results are shown of the M2 CCL18 on-target screen with a cutoff B-score ≤-1.6 for batch A or ≤-3 for batch B. Results of the M1 TNFα counter screen as readout are shown as B-score where non-hits were identified using a cutoff of B-score >-3 for both batches. CTB results are shown for both M2 and M1 assays as duplicate B-scores. Hits were included based on non-toxic effect in the M2 assay if B-score >-8 and in the M1 assay if B-score >-8 (batch A) or B-score >-6 (batch B). On-target indicates if at least 2 independent shRNAs including the original shRNA give the same effect.

| Gene | Sequence | SEQ ID NO | OT M2 screen B-score 1 | OT M2 screen B-score 2 | OT M1 counter screen B-score 1 | OT M1 counter screen B-score 2 | OT M2 CTB assay B-score 1 | OT M2 CTB assay B-score 2 | OT M1 CTB assay B-score 1 | OT M1 CTB assay B-score 2 |
|---|---|---|---|---|---|---|---|---|---|---|
| RAF1 | GTTTGGCAACAGTAAAGTC | 93 | -16.4 | -11.9 | 7.1 | 3.1 | -3.1 | -5.2 | -3.3 | -5.8 |
| RAF1 | GAGGATGCAATTCGAAGTC | 94 | -11.3 | -9.2 | 7.3 | 5.9 | 0.8 | -1.8 | -1.0 | -0.5 |
| RAF1 | CCGAATGCAGGATAACAAC | 95 | -10.0 | -7.1 | 3.0 | -2.1 | -3.0 | -3.0 | -3.2 | -1.9 |
| RAF1 | GCACGCTTAGATTGGAATA | 96 | -4.8 | -5.4 | -1.9 | -0.9 | -3.6 | -0.8 | 0.4 | -1.6 |
| S1PR2 | CCTGAATTCCCTGCTCAAC | 97 | -7.6 | -7.1 | 3.4 | 3.9 | -2.4 | -1.7 | 0.7 | 0.5 |
| S1PR2 | GTTCCACTCGGCAATGTAC | 98 | -6.1 | -6.5 | 3.5 | 2.9 | 0.3 | 1.3 | -1.1 | -0.4 |
| S1PR2 | GTAGCCAATACCTTGCTCT | 99 | -7.6 | -8.9 | 5.1 | 6.4 | 0.2 | 0.2 | 1.8 | 3.3 |
| SLC15A3 | GGACTTTGGGAACATCAAC | 100 | -7.4 | -7.2 | 3.6 | -0.1 | -4.6 | -3.3 | -0.6 | -3.3 |
| SLC15A3 | CCTCCTCCTCTACCTCAAC | 101 | -8.2 | -6.1 | 6.4 | 6.1 | -7.7 | -3.4 | 2.5 | 1.5 |
| SLC15A3 | CCTCTATGCTTAAGCTCGC | 102 | -8.5 | -9.1 | 4.2 | 4.5 | -2.4 | -4.4 | 2.7 | 2.3 |
| SLC15A3 | GATGGAGCGCTTACACTAC | 103 | -4.1 | -5.1 | 4.8 | 3.6 | 3.3 | 3.3 | 4.4 | 1.5 |
| USP22 | GGACAGTCTCAACAATGAC | 104 | -7.4 | -5.4 | 1.5 | 2.8 | -3.0 | -1.3 | -4.8 | -5.4 |
| USP22 | GCTGTTGTTAACCATCAAG | 105 | -9.1 | -8.1 | 1.0 | 0.7 | -1.9 | -2.1 | -5.4 | -3.2 |
| USP22 | GCTGAAGCACAACCCGAAA | 106 | -3.3 | -4.3 | -0.5 | -1.5 | 1.2 | 0.3 | 3.7 | -0.7 |
| ZMPSTE24 | TGGTTGTTCTCAATGTGGC | 107 | -13.0 | -10.5 | 4.4 | 2.9 | -3.0 | -5.4 | -1.2 | -1.5 |
| ZMPSTE24 | GACTGAAGGCACTCTTATT | 108 | -2.3 | -3.7 | 0.5 | 0.8 | 1.8 | 0.5 | -0.1 | 0.6 |
| ZMPSTE24 | GCCATGGAGTCTTTATAAT | 109 | -6.8 | -4.7 | 3.0 | 5.8 | -1.5 | -1.7 | -1.8 | -2.2 |

TABLE 15

Overview of the expression of the TARGETs that were confirmed to be on-target by shRNA.

| Gene | Gene class | RNA seq M0 (AVG) | RNA seq M2 (AVG) | qPCR AM from IPF (Ct) |
|---|---|---|---|---|
| BPNT1 | Enzyme | 15.25 | 22.48 | 31.89 |
| C1RL | Secreted/Extracellular | 0.93 | 3.29 | 30.95 |
| DCN | Secreted/Extracellular | 0.10 | 0.11 | nt |
| EFEMP2 | Secreted/Extracellular | 0.69 | 0.41 | 31.64 |
| EFNB2 | Other | 0.02 | 0.03 | 33.46 |
| GPR155 | GPCR | 8.94 | 18.51 | 30.57 |
| KCNMB4 | Ion channel | 0.33 | 0.13 | 32.46 |
| LIF | Secreted/Extracellular | 2.98 | 0.57 | 31.60 |
| MS4A4A | Other | 234.68 | 467.98 | 23.80 |
| RAF1 | Kinase | 32.81 | 24.89 | 30.45 |
| S1PR2 | GPCR | 6.05 | 5.31 | 29.42 |
| SLC15A3 | Transporter | 504.20 | 636.80 | 27.00 |
| USP22 | Enzyme | 33.21 | 31.74 | 28.15 |
| ZMPSTE24 | Enzyme | 29.71 | 26.57 | 28.75 |

The confirmed candidate Target codes are shown with the corresponding gene class of the Target. Expression data obtained from RNA-seq is shown as an average FPKM value of two healthy donor derived M0 or M2 macrophages. mRNA expression is shown as Ct values (AM = alveolar macrophage, ND = Not Detectable, nt = not tested, AVG = average).

REFERENCES

Atamas S P, Luzina I G, Choi J et al. Pulmonary and activation-regulated chemokine stimulates collagen production in lung fibroblasts. *Am J Respir Cell Mol Biol* 2003; 29:743-9.

Bustin S A, Benes V, Garson J A, Hellemans J, Huggett J, Kubista M, Mueller R, Nolan T, Pfaffl M W, Shipley G L, Vandesompele J, Wittwer C T. The MIQE guidelines: minimum information for publication of quantitative real-time PCR experiments. *Clin Chem.* 2009 April; 55(4): 611-22

Duffield J S, Forbes S J, Constandinou C M et al. Selective depletion of macrophages reveals distinct, opposing roles during liver injury and repair. *J Clin Invest* 2005; 115: 56-65.

Cox T R and Erler J T *Disease Model Mech* 2011, 4(2):165-178.

Kunisch et al Macrophage specificity of three anti-CD68 monoclonal antibodies (KP1, EBM11, and PGM1) widely used for immunohistochemistry and flow cytometry *Ann Rheum Dis* 2004; 63:774-784

Mantovani A, Sica A, Sozzani S et al. The chemokine system in diverse forms of macrophage activation and polarization. *Trends Immunol* 2004; 25:677-86.

Mantovani A, Sica A, Macrophage plasticity and polarization: in vivo veritas. *J Clin Invest.* 2012; 122:787-795.

Murphy C A, Langrish C L, Chen Y et al. Divergent pro- and antiinflammatory roles for IL-23 and IL-12 in joint autoimmune inflammation. *J Exp Med* 2003; 198:1951-7

Murray P J, Wynn T A. Protective and pathogenic functions of macrophage subsets. *Nat Rev Immunol* 2011; 11:723-37.

Meneghin A, Hogaboam C M. Infectious disease, the innate immune response, and fibrosis. *J Clin Invest* 2007; 117: 530-8.

Prasse A, Pechkovsky D V, Toews G B et al. A vicious circle of alveolar macrophages and fibroblasts perpetuates pulmonary fibrosis via CCL18. *Am J Respir Crit Care Med* 2006; 173:781-92.

Prasse A, Pechkovsky D V, Toews G B et al. CCL18 as an indicator of pulmonary fibrotic activity in idiopathic interstitial pneumonias and systemic sclerosis. *Arthritis Rheum* 2007; 56:1685-93.

Prasse A, Probst C, Bargagli E et al. Scrum CC-chemokine ligand 18 concentration predicts outcome in idiopathic pulmonary fibrosis. *Am J Respir Crit Care Med* 2009; 179:717-23.

Prasse A, Muller-Quernheim J. Non-invasive biomarkers in pulmonary fibrosis. *Respirology* 2009; 14:788-95.

Sica Antonio, Mantovani Alberto Macrophage plasticity and polarization: in vivo veritas. J Clin Invest. (2012); 122 (3):787-795.

Song E, Ouyang N, Horbelt M et al. Influence of alternatively and classically activated macrophages on fibrogenic activities of human fibroblasts. *Cell Immunol* 2000; 204:19-28.

Thannickal V J, Toews G B, White E S et al. Mechanisms of pulmonary fibrosis. *Annu Rev Med* 2004; 55:395.

Wynn T A. Fibrotic disease and the T(H)1/T(H)2 paradigm. *Nat Rev Immunol* 2004; 4:583-9.

Wynn T A. Cellular and molecular mechanisms of fibrosis. *J Pathol* 2008; 214:199-210.

We claim:

1. A method for identifying a compound that inhibits macrophage differentiation into M2 macrophages, said method comprising:
   a) contacting a test compound with a polypeptide comprising the amino acid sequence set forth in SEQ ID NO: 26;
   b) measuring a binding affinity of the test compound to said polypeptide;
   c) contacting the test compound that demonstrates binding affinity to said polypeptide with a population of macrophage cells;
   d) measuring a property related to differentiation of macrophages into M2 macrophages; and
   e) identifying a compound capable of inhibiting macrophage differentiation into M2 macrophages.

2. The method according to claim 1, which additionally comprises the step of comparing the compound to be tested to a control.

3. The method of claim 1, wherein said polypeptide is coupled to a detectable label.

4. The method according to claim 1, wherein said polypeptide in steps (a) and (b) is present in an in vitro cell-free preparation.

5. The method according to claim 1, wherein said polypeptide in steps (a) and (b) is present in a cell.

6. The method according to claim 5, wherein the cell naturally expresses said polypeptide.

7. The method according to claim 5, wherein the cell has been engineered so as to express said polypeptide.

8. The method according to claim 5, wherein said cell is a mammalian cell.

9. The method of claim 8, wherein said cell is a macrophage cell.

10. The method of claim 1, wherein said property is the inhibition of release or expression of a marker of M2 macrophages.

11. The method of claim 10 wherein said property is an expression or release of a marker selected from the group consisting of CCL18, CCL13, TGFβ, CCL22, CCL17, soluble fibronectin, folate receptor β, CD206, and CD163.

12. The method according to claim 1 wherein said cells have been triggered by a factor which induces macrophage differentiation into M2 macrophages (M2 inducing factor).

13. The method according to claim 1, wherein said cells have been triggered by one or more M2 inducing factors selected from the group consisting of IL4, IL10, IL13, immune complexes and lipopolysaccharides.

14. The method of claim 1 wherein the method additionally comprises:
   measuring a property related to the differentiation of macrophages into classically-activated (M1) macrophages and identifying a compound that does not inhibit said differentiation.

15. The method of claim 14 wherein said property is the level and/or expression of a marker of the M1 macrophage phenotype, and a compound is identified which does not increase the levels of said marker.

16. The method of claim 15 wherein said marker is TNFα.

17. A method for identifying a compound that inhibits macrophage differentiation into M2 macrophages, said method comprising:
   a) contacting a test compound with a population of macrophage cells expressing a polypeptide comprising the amino acid sequence set forth in SEQ ID NO: 26;
   b) measuring expression, activity, and/or amount of said polypeptide in said cells;
   c) measuring a property related to differentiation of macrophages into M2 macrophages if the test compound reduces expression, activity, and/or amount of said polypeptide; and
   d) identifying a compound capable of inhibiting macrophage differentiation into M2 macrophages.

18. The method according to claim 17, which additionally comprises the step of comparing the compound to be tested to a control.

19. The method according to claim 17, wherein said polypeptide is coupled to a detectable label.

20. The method according to claim 17, wherein the cell naturally expresses said polypeptide.

21. The method according to claim 17, wherein the cell has been engineered so as to express said polypeptide.

22. The method of claim 17, wherein said property is the inhibition of release or expression of a marker of M2 macrophages.

23. The method of claim 22 wherein said property is an expression or release of a marker selected from the group consisting of CCL18, CCL13, TGFβ, CCL22, CCL17, soluble fibronectin, folate receptor β, CD206, and CD163.

24. The method according to claim 17 wherein said cells have been triggered by a factor which induces macrophage differentiation into M2 macrophages (M2 inducing factor).

25. The method according to claim 17, wherein said cells have been triggered by one or more M2 inducing factors selected from the group consisting of IL4, IL10, IL13, immune complexes and lipopolysaccharides.

26. A method for identifying a compound that inhibits macrophage differentiation into M2 macrophages, said method comprising:
   a) contacting a test compound with a polypeptide comprising the amino acid sequence set forth in SEQ ID NO: 26;
   b) measuring an activity of said polypeptide;
   c) contacting the test compound that inhibits the activity of said polypeptide with a population of macrophage cells;
   d) measuring a property related to differentiation of macrophages into M2 macrophages if the test compound reduces the activity of said polypeptide; and
   e) identifying a compound capable of inhibiting macrophage differentiation into M2 macrophages.

27. The method according to claim 26, which additionally comprises the step of comparing the compound to be tested to a control.

28. The method according to claim 26, wherein said polypeptide is coupled to a detectable label.

29. The method according to claim 26, wherein said polypeptide in steps (a) and (b) is present in a cell.

30. The method of claim 26, wherein said property is the inhibition of release or expression of a marker of M2 macrophages.

31. The method of claim 30 wherein said property is an expression or release of a marker selected from the group consisting of CCL18, CCL13, TGFβ, CCL22, CCL17, soluble fibronectin, folate receptor β, CD206, and CD163.

32. The method according to claim 26 wherein said cells have been triggered by a factor which induces macrophage differentiation into M2 macrophages (M2 inducing factor).

33. The method according to claim 26, wherein said cells have been triggered by one or more M2 inducing factors selected from the group consisting of IL4, IL10, IL13, immune complexes and lipopolysaccharides.

* * * * *

SEQUENCE LISTING

```
<160> NUMBER OF SEQ ID NOS: 112

<210> SEQ ID NO 1
<211> LENGTH: 3589
<212> TYPE: DNA
<213> ORGANISM: Homo sapiens

<400> SEQUENCE: 1
cggccgccct ggggacgcag acgccaaggc ccctccggcc agggccggga gccgggccgg      60
cctagccagt tctgaaagcc ccatggcccc agcaggcctc tgagcccac catgggcagc     120 ttgtactcgg agtacctgaa ccccaacaag gtccaggaac actataatta taccaaggag    180
acgctggaaa cgcaggagac gacctcccgc caggtggcct cggccttcat cgtcatcctc    240
tgttgcgcca ttgtggtgga aaaccttctg gtgctcattg cggtggcccg aaacagcaag    300
ttccactcgg caatgtacct gtttctgggc aacctggccg cctccgatct actggcaggc    360
gtggccttcg tagccaatac cttgctctct ggctctgtca cgctgaggct gacgcctgtg    420
cagtggtttg cccgggaggg ctctgccttc atcacgctct cggcctctgt cttcagcctc    480
ctggccatcg ccattgagcg ccacgtggcc attgccaagg tcaagctgta tggcagcgac    540
aagagctgcc gcatgcttct gctcatcggg gcctcgtggc tcatctcgct ggtcctcggt    600
ggcctgccca tccttggctg gaactgcctg ggccacctcg aggcctgctc cactgtcctg    660
cctctctacg ccaagcatta tgtgctgtgc gtggtgacca tcttctccat catcctgttg    720
gccatcgtgg ccctgtacgt gcgcatctac tgcgtggtcc gctcaagcca cgctgacatg    780
gccgccccgc agacgctagc cctgctcaag acggtcacca tcgtgctagg cgtctttatc    840
```

```
gtctgctggc tgcccgcctt cagcatcctc cttctggact atgcctgtcc cgtccactcc    900
tgcccgatcc tctacaaagc ccactacttt ttcgccgtct ccaccctgaa ttccctgctc    960
aaccccgtca tctacacgtg gcgcagccgg gacctgcggc gggaggtgct tcggccgctg   1020
cagtgctgga ggccggggt gggggtgcaa ggacggaggc ggggcgggac cccgggccac    1080
cacctcctgc cactccgcag ctccagctcc ctggagaggg gcatgcacat gcccacgtca   1140
cccacgtttc tggagggcaa cacggtggtc tgagggtggg ggtggaccaa caaccaggcc   1200
agggcagagg ggttcatgga gaggccactg ggtgacccca gatagagact tggggctact   1260
gagccagatg cccccgcccc acagacctgg gtgatgttgc aaatatttca cacctggaaa   1320
ggccagataa ggcactgact agtcacatag cagtgttgca gtgcggtcct gagggccagt   1380
ccagtggcta gtgtgacccc tttagaactg gatcctgggg aggccagggc aggggacctg   1440
tgaagagcca gggtgagggc aggcagcatt aaggggagc tcagggcagg agcactttac    1500
cacctggtac aaaggatttt ttttttttt tgagacggaa tcttgcactg ctgcccaggc    1560
tggagtgcag tggcgtgatc tcggctcacc gcaagctccg cctcctgggt tcatgtcgtt   1620
ctcctgcctc agcctcccaa gtagctggga ctataggcgc ctgccaccac acctggctaa   1680
ttttttgtac ctttagtaga gatggggttt caccgtgtta gccaggatgg tcttgatctc   1740
ctgacctcgt gatccgcccg cctcggcctc ccaaagtgct gggattacag gcgtgagcca   1800
ccgtgcccgg ctttttttt tttttttt ttttttttt tttttttga gatgaagtct        1860 cgctctgttg cccaggctgg agagtgcagt ggtacggtct cagctcactg caacctccac   1920
ctcccaggtt caagcgattc tccagcctga gcctcctgag tagctgggat tacaggtgcc   1980
taccaccacg cccaggtaat tttttttt tttgtatttt tagtagagac ggggtttcac     2040
catgttggcc aggctggtct cgaactcctg acctcatgat ccgcccgtgt tggcctccca   2100
aagtgtggga ttacaggcgt aagccacctc acctggcggt acaagaatt tctgcatttt    2160 cttcctggc ccctagtcct gcaccgattt ctccttttcg aatgtattcc tcctgccacc    2220
ttctctgggc aacttcgtgc gactacagaa ccactgtcct gaggagctag aggcctcctc   2280
tctgaccatc cagagcccaa atccacagct tccccaaatt tcatcagctg ccacttgacg   2340
acttctcccc gtctctctga ggcccggaaa ccacggctgg aggtggggag gggatggcgg   2400
ctgaggtcca ttcctcattc tcagacctca ttgctcagtt gcactatttg gggcacagaa   2460
taatcaccaa aagtgagaaa aacgagtttg ggtggctggg gaggactttg ggactcttga   2520
tgcaaggcgc aacttgagaa aattctgggt gtgatatttg cacagacacc ctcctttcaa   2580
aaacagccac cccccaagct attctcagct ccacacctgc agccccagct aaggtaccag   2640
gtctcctgag caaggcagag agaagccttg agccttctct gtgtcttctt tcaagaaccc   2700
cgctgtgtct tctttcaaga tttttttt gagacagttt caagatttt gttttgtttt      2760 tgagatggag tctcactgtg tcacccaggc tgaggtggca gtggttcaat ctccgttcac   2820
tgccacctcc acctcccggg ttcaagcgat tctcctgctt cagcctctcg agtagctggg   2880
actacaggca cctgccacca tgtctggcta attttttgtat ttttagtaga cagggttt    2940 cactacgttg gccaggctgg tctcaaactc ctgacctcaa gtgatccgcc cgcctcggcc   3000
tccccaattg ctgggattac aggcgtgagc cactgtgccc ggccttcttc tttcaagtta   3060
tatagaatgg agcatggggg tggcagtggc tagggacatt tcctggggac actctcccct   3120
aaccccccag aaggacttca caaaaacctg tggataatgg aagggatgtt acggtacaaa   3180
cgtatattta tgtgtgtgtg tgtgtatgtg tgtgcgcgcg cgcgtgtgca cataggcgtg   3240
```

| | |
|---|---|
| atgtctgtga ccctcctctc ctcgtcacat ttcccccaga atgaatgctg tcctgtctgc | 3300 |
| tcatgtttgt gttgaagctg ccaaagtcgg ggagctctgg tcctgcccag accccttttgg | 3360 |
| aattgctggc ccatcctccc actggagagc tggggtgcag ctcaccttgg ggaaggaaac | 3420 |
| ctcatgcctc agagtaattt cttgtgaatg caaagcctgg gggagcgggt ctttgggggg | 3480 |
| caaggagcca gtcaggggct tgtttcccct catagagctc cccagacgtg cctccgcaat | 3540 |
| gcctgaaacc cagacctagg ctaataaacg gttcaatttc tgttaaaaa | 3589 |

<210> SEQ ID NO 2
<211> LENGTH: 5220
<212> TYPE: DNA
<213> ORGANISM: Homo sapiens

<400> SEQUENCE: 2

| | |
|---|---|
| gcagccgcag ctcgggggcg gtgcctgcct tgcagcctcc cctcggcgat cgcgcagccc | 60 |
| catctttgtc cggcctccgc gctttgttct cggcgcccgg gccttggcca gcctggccag | 120 |
| ccgccgagca gccccacgc cgcgctggcg tcgtcctcgc ctccctcgcc gccgcccccc | 180 |
| gcgcgcggcc gggccttgcc ccccatggtg tcccggccag agcccgaggg cgaggccatg | 240 |
| gacgccgagc tggcggtagc gccgccgggc tgctcgcacc tgggcagctt caaggtggac | 300 |
| aactggaagc agaacctgcg ggccatctac cagtgcttcg tgtggagcgg cacggctgag | 360 |
| gcccgcaagc gcaaggccaa gtcctgtatc tgccatgtct gtggcgtcca cctcaacagg | 420 |
| ctgcattcct gcctctactg tgtcttcttc ggctgtttca caagaagca tattcacgag | 480 |
| catgcgaagg cgaagcggca aacctggcc attgatctga tgtacggagg catctactgt | 540 |
| tttctgtgcc aggactacat ctatgacaaa gacatggaaa taatcgccaa ggaggagcag | 600 |
| cgaaaagctt ggaaaatgca aggcgttgga gagaagtttt caacttggga accaaccaaa | 660 |
| cgggagcttg aactgctgaa gcacaacccg aaaaggagaa agatcacctc gaactgcacc | 720 |
| ataggtctgc gtgggctgat caaccttggg aacacatgct tcatgaactg catcgtgcag | 780 |
| gccctgaccc acacgccact ctgcgggac ttcttcctgt ctgacaggca ccgctgtgag | 840 |
| atgcagagcc cagctcctg tctggtctgt gagatgtcct cactgtttca ggagtttttac | 900 |
| tctggacacc ggtcccctca catcccgtat aagttgctgc acctggtgtg gacccacgcg | 960 |
| aggcacctag caggctacga gcagcaggac gcccacgagt tcctcatcgc ggccctggac | 1020 |
| gtgctccacc gacactgcaa aggtgatgac aatgggaaga aggccaacaa ccccaaccac | 1080 |
| tgcaactgca tcatagacca gatcttcaca ggcgggttgc agtcagacgt cacctgccaa | 1140 |
| gtctgccatg gagtctccac caccatcgac cccttctggg acatcagctt ggatctcccc | 1200 |
| ggctcttcca ccccattctg gccctgagc ccagggagcg agggcaacgt ggtaaacggg | 1260 |
| gaaagccacg tgtcgggaac caccacgctc acggactgcc tgcgacgatt caccagacca | 1320 |
| gagcacttgg gcagcagcgc caagatcaag tgcagcggtt gccatagcta ccaggagtcc | 1380 |
| acaaagcagc tcactatgaa gaaactgccc atcgtagcct gttttcatct caaacgattt | 1440 |
| gaacactcag ccaagctgcg gcggaagatc accacgtatg tgtccttccc cctggagctg | 1500 |
| gacatgaccc ctttcatggc ctccagcaaa gagagcagga tgaatggaca gtaccagcag | 1560 |
| cccacggaca gtctcaacaa tgacaacaag tattccctgt ttgctgttgt taaccatcaa | 1620 |
| gggaccttgg agagtggcca ctacaccagc tttatccggc agcacaaaga ccagtggttc | 1680 |
| aagtgtgacg atgccatcat caccaaggcc agcatcaagg acgtcctgga cagcgaaggg | 1740 |

```
tacttgctgt tctatcacaa acagttcctg gaatacgagt agccttatct gcagctggtc    1800
agaaaaacaa aggcaatgca ttggcaagcc tcacaaagtg atcctccctg ccccccccct    1860
cccccaagtc tcccgccgcc tccccggcct ggtgacacca cctcccatgc agatgtggcc    1920
cctctgcacc tgggacccat cgggtcggga tggaccacac ggacggggag gctcctggag    1980 ctgcttttgaa gatggatgag atgaggggtg tgctctgggt gggaggagca gcgtacaccc    2040
gtcaccagaa catctcttgt gtcatgacat gggggtgcaa cggggggcctc acagcacaga    2100 gtgaccgctg cctggcgttc cccagcactc ggtgtggaaa ggcccctacc tgctgtaaga    2160
ttatgggtcc atgaaagcag taagctggac acagaggtgt agtgtgcggg acagagggcc    2220
ttgcagatgc ctttctgttg gtgttttagt gttaaaatac ggagagtatg gaactcttca    2280
cctccatttt ctcagcggct gtgaagcagc ctcctagctt cggaagtacg gacactacgt    2340
cgcgttttca gcgtgtctg ttctgcaggt aacagcatca agctgcacgt ggaagcatct    2400
cgcggttttc tagaaacagg cattttctta tccctctccc gctccttttt ccacaaaggt    2460
gaatttcata aatgtaatac tagtaaagtg aatgaattac tgagtttata cagaaattta    2520
ggtaacttct cctttagtct caagagcgag tcttgctttt taatgggtgc cgtttatgtt    2580
gctgcccgcc ctgtgtgcct ggctcctctg ggtgccttgg tgtctgctgg tggctggcag    2640
tgggcgcagc ggaggagagt tgtgctgcag ctcatacggt gtgtctgtca tctcagtctg    2700
gagtaaatgc agtgtctgcc ggtgtctgat gggttctgtc cctcgtattt tctttgcctt    2760
ctatcccatt gcctggctac cgctgcctgg cagccaaggg tgttggtcgc gaagctggag    2820
tggcctctgg tggagcctgc atcttgtctc gtctgcctct gctttacatt tggtgtactt    2880
tcgggcgtgg tggcagtaaa atgacaccgt gattgagctt gtcagcagag ctgaaagaga    2940
aagtagaagg atgtgcattg tttcttgtaa gatatcttgc atgtatctgt gtattcaaat    3000
tcaaacagag atggtttgtc catttgtcca ctgagaaatt agaaactagg acaaggggg    3060 aggaaaagta ctgaaataca gtttatgaag caagtgtgtc tcgggctgtg cttgtcccag    3120
gagccccagc agcatctgaa ctgaggcttc ttcagtcctg caggaacagg atcatctgtc    3180
tcagcggtgg gcagatgttt tcatagacag ccagggagta aacactgttg gctctgtggg    3240
ctgtatggtc tctgccataa atagtacaga gatgtggctg tgtctagtac aactttaga    3300 cacagaaatc tgaatgacat atattgttct gtgtcaagaa acttagattt ttttttaac    3360 tatttaaaaa cgtgaaacct attcttagct cacaggccat ggagaagctg gtggggacca    3420
gacccagctc cttagctggc tgggctgggg aggggtagt gacagtggca gctgctactc    3480
actgctcagt gtggaaaaca caggacttgg caatcacagc ccgcagaacc atcatgtgtg    3540
gcagaagcct gagggatgcg gtttcttgcc cacgtgctct gttcatttc tgttgttttt    3600 ctgcacttaa agaattcaca tggaagcatg ttttataaaa tgaattacca gagaaacaga    3660
gatgggccga gattttcaga aatggtccca tgtgaccaag ttctgctgtt tgggtgacag    3720 tgcttttgaag atctcctttg aggatgtgca gtcttttttt tttttttttt gagatggagt    3780
ttgttgccca ggctggagtg agtggcacag tctcggctca ctgcaacctc cacctcctgg    3840
gttcaagcag ttctcgtgcc gcagcctccc aagtagctgg gactacaggc atgcaccacc    3900
acgccaggct aattttttgta ttttagtag agatggggtt tcaccatgtc tcaaactcct    3960
gacctcaggc gatccaccca cctcagcgtc ccaaagtgct gggattatag gcgtgagcca    4020
ccgcacctgg cctatgagtg gtcttttaat taggaacaaa tctaatggaa aggagagttg    4080
actgaagttg gcccacagga ttgtgagctg ggcagtgcct tcatgaaggc ttgccacctt    4140
```

```
gggacgcccc agtttactgg ggtgtcttgc ggagtgcaga aggctttctg gcagctgcct      4200
gggtttggcc agaccctgcc tcccctcccg ccggccaacc cctagtcccc ttcctgtctc      4260
cacttgcatt caggggtggc tgctgttctg agaacattag aactgggaag agagatggag      4320
tcacatggat ttttggtggg cattattcta aactttcgta tccaagttag tcccccttat      4380
tccactgtgg cattgccgtt ctaagcagtt acctgatgcc tgctgctgaa gagctgctca      4440
caggaggcgc cggcggccct ggcactgccc cttgcattag gtcttgtgtt tgatgtgttc      4500
ttgtgaattt actttgtcag aacaaaatat ttacgcgttg ggttcaggaa tttctttttag     4560 ctccccatct ggctgtgaaa ttcaggaaac ctccgttgc ctagtaatca ccccatgtag       4620
gtgtacattg tgacaaagtg catctgacca ctaaggggcc cccttggtga ccccagcaca      4680
ttcacagcag tgttaaaatg gcctgcattt tggagatgct ggctggcctt tcagtgcctc      4740
ccaggaagac acatggcctt tccctcttca gatgcctgaa gggagtgctt tgaggcaggt      4800
gatgtgctgg gagtgtgggc ggcctccctc tggccccggg gccctctgtg gaccttggct      4860
ccctccgtgg acctgggctt cgtggtgagc actgcagcct ccctgggcat tccctccagc      4920
gccagcacca ctgcaacata tagacctgag tgctattgta ttttggcttg gtgtgtatgc      4980
tcttcattgt gtaaaattgc tgttcttttg acaatttaag tgattgtttt gtttactgta      5040
agtttgaaaa taaaaatgaa gaaaaaaatt ccaatgactg tgctgtgggtt ggagacttta    5100 tttaccaaga tgtttactct tcctttcccc ttccattttg aggagctgtg tcactcctcc     5160
tcccccccag tgctttgtag tctctcctat gtcataataa agctacattt tctctgagaa     5220

<210> SEQ ID NO 3
<211> LENGTH: 2461
<212> TYPE: DNA
<213> ORGANISM: Homo sapiens

<400> SEQUENCE: 3
gcgcgcagtt tcccgcatgc tcagtagctg aggtagggat gccatccttc tcaaaagact       60
tattgacagt gccaaagctc ggtactggac acaacgaggg acctgggtct acgataacgc      120
gcttttgctc ctcctgaagt gtctttggtc caacgttgtt ccagagtgta ccatggcttc      180
cagtaacact gtgttgatgc ggttggtagc ctccgcatat tctattgctc aaaaggcagg      240
aatgatagtc agacgtgtta ttgctgaagg agacctgggt attgtggaga agacctgtgc      300
aacagacctg cagaccaaag ctgaccgatt ggcacagatg agcatatgtt cttcattggc      360
ccggaaattc cccaaactca caattatagg ggaagaggat ctgccttctg aggaagtgga      420
tcaagagctg attgaagaca gtcagtggga agaaatactg aagcaaccat gcccatcgca      480
gtacagtgct attaaagaag aagatctcgt ggtctgggtt gatcctctgg atggaaccaa      540
ggaatatacc gaaggtcttc ttgacaatgt aacagttctt attggaattg cttatgaagg      600
aaaagccata gcaggagtta ttaaccagcc atattacaac tatgaggcag accagatgc       660 tgtgttgggg aggacaatct ggggagtttt aggtttaggc cctttgggt tcagctgaa        720 agaagtccct gctgggaaac acattatcac aactactcga tcccatagca acaagttggt      780
tactgactgt gttgctgcta tgaaccccga tgctgtgctg cgagtaggag gagcaggaaa      840
taagattatt cagctgattg aaggcaaagc ctctgcttat gtatttgcaa gtcctggttg      900
taagaagtgg gatacttgtg ctccagaagt tattttacat gctgtgggag gcaagttaac      960
cgatatccat gggaatgttc ttcagtacca caaggatgtg aagcatatga actctgcagg     1020
```

| | |
|---|---|
| agtcctggcc acactgagga attatgacta ctatgcaagc cgagttccag aatctattaa | 1080 |
| aaatgcactt gttccttaaa ggaaagtttc atttggccgg gcgcggtggc tcatgcctgt | 1140 |
| aatcccagca ctttgggagg ccgaggcagg tggatcactt gagctcagga gtttgagacc | 1200 |
| agcctgggca atatcgtgag accccatctc tacaaaaata caaattaact gggcatcctg | 1260 |
| tcatgcgcct gtcatcccag ctacttgaga ggctgaagca aagaatctc ttgagcccgg | 1320 |
| aaggcagagg ttgcagtgag ctgagatcgt gccactgcac tccagcctga gtgacaggag | 1380 |
| ttaagccctg tctcagaaaa aaaaaaaaca aaaacccaaa aagtacttaa agtttcattt | 1440 |
| acttagctag gagaaagact tggttctcaa aataatacat tttaagatta attgggtaga | 1500 |
| attagagttc cacctttatt cattgttgag cagtgattta tatttagtta ttatatttag | 1560 |
| gaatagaaaa tagaattaaa taatttaact tgattaatca accagaccaa ttttgacgtc | 1620 |
| tggagaactt ataaactcaa tatgttatat ttgttttcct gtatttaggt ggagaaatga | 1680 |
| gaaaagctt tagttccaat tgacagttca ggtcaatgtt caatgaacat tcctatcttc | 1740 |
| taaaccagat ttctcttttt ttttcctgag acggagtctc gctctgtagc ctaggctaga | 1800 |
| atgtagtggc gtgatctcgg ctcactgcaa gctccgcctc cgggttcat gccattctcc | 1860 |
| tgcctcagcc tcccgagtag ctgggactgc aggcaccgcc accacgcctg gctaatttt | 1920 |
| tgtatttta gtagagaagg tgtttcaccg tgttagccag gatggtcttg atctcctgac | 1980 |
| atcgtgatct gtctgcctcg gactcccaaa gtgctgggat tacaggtgtg agccaccgca | 2040 |
| cctggcctaa accagatttc tttagggcac aattttttct ggaatctcac tcttgttttt | 2100 |
| cacagtaatt ttaaaaacgt ttctactcca attaagaata tatatgatgt tattatatat | 2160 |
| gcttatgaaa cagatttatg agaaaagttt ttttaaata aattatttaa tcctagctct | 2220 |
| ttgttattca ccagcttttt aaaaaagtgt ttgaaaatta tacattctcg actttgggga | 2280 |
| ttagtttatt cttgtggcat cattataagg cttaattgtg gaaagctaag tacttgcttc | 2340 |
| tattccttcc aatgagagat tataacataa actattaaaa ttattctgct aatatcccta | 2400 |
| gattttatt tttaggtctc tgtccattgc ttttaattaa aattatctgt tttcaaatca | 2460 |
| a | 2461 |

<210> SEQ ID NO 4
<211> LENGTH: 3398
<212> TYPE: DNA
<213> ORGANISM: Homo sapiens

<400> SEQUENCE: 4

| | |
|---|---|
| atttccagga acttcctcct cccccaccgg ccttcacctt ttgttcccta tcctgggcca | 60 |
| gttctctcgc aggtcccaga tgtccagttc cagatgcctg acccagagt gtggggaaa | 120 |
| tatctctgga gaagccctca ctccaaaggc tgtccaggcg caatgtggtg gctgcttctc | 180 |
| tggggagtcc tccaggcttg cccaacccgg ggctccgtcc tcttggccca agagctaccc | 240 |
| cagcagctga catcccccgg gtacccagag ccgtatggca aaggccaaga gagcagcacg | 300 |
| gacatcaagg ctccagaggg ctttgctgtg aggctcgtct tccaggactt cgacctggag | 360 |
| ccgtcccagg actgtgcagg ggactctgtc acaatctcat tcgtcggttc ggatccaagc | 420 |
| cagttctgtg gtcagcaagg ctcccctctg ggcaggcccc ctggtcagag ggagtttgta | 480 |
| tcctcaggga ggagtttgcg gctgaccttc gcacacagc cttcctcgga gaacaagact | 540 |
| gcccacctcc acaagggctt cctggccctc taccaaaccg tggctgtgaa ctatagtcag | 600 |
| cccatcagcg aggccagcag gggctctgag gccatcaacg cacctggaga caaccctgcc | 660 |

```
aaggtccaga accactgcca ggagccctat tatcaggccg cggcagcagg ggcactcacc      720
tgtgcaaccc cagggacctg gaaagacaga caggatgggg aggaggttct tcagtgtatg      780
cctgtctgcg gacggccagt cacccccatt gcccagaatc agacgaccct cggttcttcc      840
agagccaagc tgggcaactt cccctggcaa gccttcacca gtatccacgg ccgtgggggc      900
ggggccctgc tgggggacag atggatcctc actgctgccc acaccatcta ccccaaggac      960
agtgtttctc tcaggaagaa ccagagtgtg aatgtgttct gggccacac agccatagat      1020
gagatgctga aactggggaa ccaccctgtc caccgtgtcg ttgtgcaccc cgactaccgt      1080
cagaatgagt cccataactt tagcggggac atcgccctcc tggagctgca gcacagcatc      1140
cccctgggcc ccaacgtcct cccggtctgt ctgcccgata tgagaccct ctaccgcagc      1200
ggcttgttgg gctacgtcag tgggtttggc atggagatgg gctggctaac tactgagctg      1260
aagtactcga ggctgcctgt agctcccagg gaggcctgca acgcctggct ccaaaagaga      1320
cagagacccg aggtgttttc tgacaatatg ttctgtgttg gggatgagac gcaaaggcac      1380
agtgtctgcc aggggggacag tggcagcgtc tatgtggtat gggacaatca tgcccatcac      1440
tgggtggcca cgggcattgt gtcctggggc ataggggtgtg gcgaagggta tgacttctac      1500
accaaggtgc tcagctatgt ggactggatc aagggagtga tgaatggcaa gaattgaccc      1560
tgggggcttg aacagggact gaccagcaca gtggaggccc caggcaacag agggcctgga      1620
gtgaggactg aacactgggg taggggttgg gggtgggggg ttgggggagg cagggaaatc      1680
ctattcacat cactgttgca ccaagccact gcaagagaaa ccccaccccg gcaagcccgc      1740
cccatcccag acaggaagca gagtcccaca gaccgctcct cctcaccctc tacctccctg      1800
tgctcatgca ctaggccccg ggaagcctgt acatctcaac aactttcgcc ttgaatgtcc      1860
ttagaaccgc cttcccctac ttcatctgtt gacacagctt ttatactcac ctgtggaaga      1920
gtcagctact cacccgctat tagagtatgg aggaaggggt tttcattgca ttgcatttct      1980
gaaacattcc taagacccttt tagttgacct tcaaatattc aagctattct gcagctccaa      2040
gatgcaatta tagaaacagc tcctttttta ttttatgtcc tctatatgcc aggtgcttca      2100
cctgttattt cacttaatcc tcataccata tttgcaaagg atgtgttatt atctatgtgt      2160
gacaaatgag gaaactgagg ctcaggggat aaagggactt gcccaagtcc cacagctggt      2220
gtgtgactgc agagactgtg ctcttcccag tgtgctgcaa tacttctcaa ccctcctcta      2280
acctgctgtg tcacccgctt tccctcccag cccccacatc cttaccattt tccctccctg      2340
ggaattcctg cttctgcgaa aatggtatcc tctagctcac actttcctaa tggccccatc      2400
tcctgcagaa gccaggtgag cccagcactg gactgaagtt cttgcagaca ccccacctgt      2460
gccccctatca tcagggaac tgctccacct gagaggacca actctttaat ttttagtaaa      2520
acctggaggt gatgggccgg gcgcagtggc tcacgcctgt aatcccaaca ccttaggagt      2580
ccgaggtggg tggatcacga ggtcaggaga tccagcccat cctggccaac atggtgaaac      2640
cccatctcta ctaaaaatac aaaaattagc cgggcgtggt gacacgtgcc tgtagtccca      2700
gctactcggg aggctgaggc aggagaatca cttgaacctg ggaggcggag gttgcagtga      2760
gctaagatca cgccactgca ctccagcctg cggacagacc aagacttcat cccccccaaa      2820
aaaaaaagat tggaggtgat ttacagtgaa agacacaaat aaaatacaac tgttcaatgg      2880
aaatagaaaa taaacaccat aaaagagaga agagaggtaa tttgttagca tcaagagtca      2940
agttgctata tggtcaaagg ttaaatttat ctctaaaaaa tggcaggatt caaagttgta      3000
```

```
catacatgtg attacttctg tttttacac ccacatacag tacaaaagat tattaaaaat    3060
attcccaaaa ggcaggtgca atgatgcaca cttatacccc cagccactca ggaggctgat    3120
gcaagaggat cgcttgagcc caggagttga agtccagcct aagcaacata gtgaaacccc    3180
atcgccaaaa atataataat aattctctca aaatactaaa cagaggtggt tttattgata    3240
agattttggc tgtttggttt tccactattc tctattggct aaaatttgtt taatgagcat    3300
gaaatgtttt tattttattt tgcttatttt tatgattgca aaaaatgata tgagtttctc    3360
cctgccaagg caaaaaaata tatatatacc tatattta                          3398

<210> SEQ ID NO 5
<211> LENGTH: 1456
<212> TYPE: DNA
<213> ORGANISM: Homo sapiens

<400> SEQUENCE: 5
atgaaggcca ctatcatcct ccttctgctt gcacaagttt cctgggctgg accgtttcaa     60
cagagaggct tatttgactt tatgctagaa gatgaggctc tgggataggg cccagaagtt    120
cctgatgacc gcgacttcga gccctcccta ggcccagtgt gccccttccg ctgtcaatgc    180
catcttcgag tggtccagtg ttctgatttg ggtcttcctc cttcccttac ggaattacat    240
cttgatggca acaaaatcag cagagttgat gcagctagcc tgaaaggact gaataatttg    300
gctaagttgg gattgagttt caacagcatc tctgctgttg acaatggctc tctggccaac    360
acgcctcatc tgagggagct tcacttggac aacaacaagc ttaccagagt acctggtggg    420
ctggcagagc ataagtacat ccaggttgtc taccttcata caacaatat ctctgtagtt    480 ggatcaagtg acttctgccc acctggacac aacaccaaaa aggcttctta ttcgggtgtg    540
agtcttttca gcaacccggt ccagtactgg gagatacagc catccacctt cagatgtgtc    600
tacgtgcgct ctgccattca actcggaaac tataagtaat tctcaagaaa gccctcattt    660
ttataacctg gcaaaatctt gttaatgtca ttgctaaaaa ataaataaaa gctagatact    720
ggaaacctaa ctgcaatgtg gatgttttac ccacatgact tattatgcat aaagccaaat    780
ttccagttta gtaattgcc tacaataaaa agaaattttg cctgccattt tcagaatcat     840
cttttgaagc tttctgttga tgttaactga gctactagag atattcttat ttcactaaat    900
gtaaaatttg gagtaaatat atatgtcaat atttagtaaa gcttttcttt tttaatttcc    960
aggaaaaaat aaaagagta tgagtcttct gtaattcatt gagcagttag ctcatttgag    1020
ataaagtcaa atgccaaaca ctagctctgt attaatcccc atcattactg gtaaagcctc    1080
atttgaatgt gtgaattcaa tacaggctat gtaaaatttt tactaatgtc attattttga    1140 aaaaataat ttaaaaatac attcaaaatt actattgtat acaagcttaa ttgttaatat    1200
tccctaaaca caattttatg aagggagaag acattggttt gttgacaata acagtacatc    1260
ttttcaagtt ctcagctatt tcttctacct ctccctatct tacatttgag tatggtaact    1320
tatgtcatct atgttgaatg taagcttata aagcacaaag catacatttc ctgactggtc    1380
tagagaactg atgtttcaat ttaccccctct gctaaataaa tattaaaact atcatgtgaa    1440
aaaaaaaaaa aaaaa                                                   1456

<210> SEQ ID NO 6
<211> LENGTH: 1223
<212> TYPE: DNA
<213> ORGANISM: Homo sapiens

<400> SEQUENCE: 6
```

```
atgaaggcca ctatcatcct ccttctgctt gcacaagttt cctgggctgg accgtttcaa      60
cagagaggct tatttgactt tatgctagaa gatgaggctc tgggatagg cccagaagtt      120 cctgatgacc gcgacttcga gccctcccta ggcccagtgt gccccttccg ctgtcaatgc     180
catcttcgag tggtccagtg ttctgatttg ggttgtctac cttcataaca acaatatctc     240
tgtagttgga tcaagtgact tctgcccacc tggacacaac accaaaaagg cttcttattc     300
gggtgtgagt cttttcagca acccggtcca gtactgggag atacagccat ccaccttcag     360
atgtgtctac gtgcgctctg ccattcaact cggaaactat aagtaattct caagaaagcc     420
ctcattttta aacctggca aatcttgtt aatgtcattg ctaaaaata aataaaagct        480 agatactgga aacctaactg caatgtggat gttttaccca catgacttat tatgcataaa     540
gccaaatttc cagtttaagt aattgcctac aataaaaaga aattttgcct gccattttca    600
gaatcatctt ttgaagcttt ctgttgatgt taactgagct actagagata ttcttatttc    660
actaaatgta aaatttggag taaatatata tgtcaatatt tagtaaagct tttctttttt    720
aatttccagg aaaaaataaa aagagtatga gtcttctgta attcattgag cagttagctc    780
atttgagata aagtcaaatg ccaaacacta gctctgtatt aatccccatc attactggta    840
aagcctcatt tgaatgtgtg aattcaatac aggctatgta aaattttttac taatgtcatt   900 attttgaaaa aataaattta aaatacatt caaaattact attgtataca agcttaattg     960
ttaatattcc ctaaacacaa ttttatgaag ggagaagaca ttggtttgtt gacaataaca    1020
gtacatcttt tcaagttctc agctatttct tctacctctc cctatcttac atttgagtat    1080
ggtaacttat gtcatctatg ttgaatgtaa gcttataaag cacaaagcat acatttcctg    1140
actggtctag agaactgatg tttcaattta cccctctgct aaataaatat taaaactatc    1200
atgtgaaaaa aaaaaaaaa aaa                                              1223

<210> SEQ ID NO 7
<211> LENGTH: 1336
<212> TYPE: DNA
<213> ORGANISM: Homo sapiens

<400> SEQUENCE: 7
atgaaggcca ctatcatcct ccttctgctt gcacaagttt cctgggctgg accgtttcaa      60
cagagaggct tatttgactt tatgctagaa gatgaggctc tgggatagg cccagaagtt     120 cctgatgacc gcgacttcga gccctcccta ggcccagtgt gccccttccg ctgtcaatgc    180
catcttcgag tggtccagtg ttctgatttg gtctggaca aagtgccaaa ggatcttccc     240
cctgacacaa ctctgctaga cctgcaaaac aacaaaataa ccgaaatcaa agatggagac    300
tttaagaacc tgaagaacct tcacgttgtc taccttcata acaacaatat ctctgtagtt    360
ggatcaagtg acttctgccc acctggacac aacaccaaaa aggcttctta ttcgggtgtg    420
agtcttttca gcaacccggt ccagtactgg gagatacagc catccacctt cagatgtgtc    480
tacgtgcgct ctgccattca actcggaaac tataagtaat tctcaagaaa gccctcattt    540
ttataacctg gcaaatcttg ttaatgtca ttgctaaaaa ataaataaaa gctagatact     600
ggaaacctaa ctgcaatgtg gatgttttac ccacatgact tattatgcat aaagccaaat    660
ttccagttta gtaattgcc tacaataaaa agaaattttg cctgccattt tcagaatcat     720
cttttgaagc tttctgttga tgttaactga gctactagag atattcttat ttcactaaat    780
gtaaaatttg gagtaaatat atatgtcaat atttagtaaa gcttttcttt tttaatttcc    840
```

-continued

| | |
|---|---|
| aggaaaaaat aaaaagagta tgagtcttct gtaattcatt gagcagttag ctcatttgag | 900 |
| ataaagtcaa atgccaaaca ctagctctgt attaatcccc atcattactg gtaaagcctc | 960 |
| atttgaatgt gtgaattcaa tacaggctat gtaaaatttt tactaatgtc attattttga | 1020 |
| aaaaataaat ttaaaaatac attcaaaatt actattgtat acaagcttaa ttgttaatat | 1080 |
| tccctaaaca caattttatg aagggagaag acattggttt gttgacaata acagtacatc | 1140 |
| ttttcaagtt ctcagctatt tcttctacct ctccctatct tacatttgag tatggtaact | 1200 |
| tatgtcatct atgttgaatg taagcttata aagcacaaag catacatttc ctgactggtc | 1260 |
| tagagaactg atgtttcaat ttacccctct gctaaataaa tattaaaact atcatgtgaa | 1320 |
| aaaaaaaaaa aaaaaa | 1336 |

<210> SEQ ID NO 8
<211> LENGTH: 1570
<212> TYPE: DNA
<213> ORGANISM: Homo sapiens

<400> SEQUENCE: 8

| | |
|---|---|
| atgaaggcca ctatcatcct ccttctgctt gcacaagttt cctgggctgg accgtttcaa | 60 |
| cagagaggct tatttgactt tatgctagaa gatgaaggct ctgggatagg cccagaagtt | 120 |
| cctgatgacc gcgacttcga gccctcccta ggcccagtgt gccccttccg ctgtcaatgc | 180 |
| catcttcgag tggtccagtg ttctgatttg gaactgggca ccaatccgct gaagagctca | 240 |
| ggaattgaaa atggggcttt ccagggaatg aagaagctct cctacatccg cattgctgat | 300 |
| accaatatca ccagcattcc tcaaggtctt cctccttccc ttacggaatt acatcttgat | 360 |
| ggcaacaaaa tcagcagagt tgatgcagct agcctgaaag gactgaataa tttggctaag | 420 |
| ttgggattga gtttcaacag catctctgct gttgacaatg gctctctggc caacacgcct | 480 |
| catctgaggg agcttcactt ggacaacaac aagcttacca gagtacctgg tgggctggca | 540 |
| gagcataagt acatccaggt tgtctacctt cataacaaca atatctctgt agttggatca | 600 |
| agtgacttct gcccacctgg acacaacacc aaaaaggctt cttattcggg tgtgagtctt | 660 |
| ttcagcaacc cggtccagta ctgggagata cagccatcca ccttcagatg tgtctacgtg | 720 |
| cgctctgcca ttcaactcgg aaactataag taattctcaa gaaagccctc attttttataa | 780 |
| cctggcaaaa tcttgttaat gtcattgcta aaaataaaat aaaagctaga tactggaaac | 840 |
| ctaactgcaa tgtggatgtt ttacccacat gacttattat gcataaagcc aaatttccag | 900 |
| tttaagtaat tgcctacaat aaaaagaaat tttgcctgcc attttcagaa tcatcttttg | 960 |
| aagctttctg ttgatgttaa ctgagctact agagatattc ttatttcact aaatgtaaaa | 1020 |
| tttggagtaa atatatatgt caatatttag taaagctttt ctttttttaat ttccaggaaa | 1080 |
| aaataaaaag agtatgagtc ttctgtaatt cattgagcag ttagctcatt tgagataaag | 1140 |
| tcaaatgcca acactagct ctgtattaat ccccatcatt actggtaaag cctcatttga | 1200 |
| atgtgtgaat tcaatacagg ctatgtaaaa ttttttactaa tgtcattatt ttgaaaaaat | 1260 |
| aaatttaaaa atacattcaa aattactatt gtatacaagc ttaattgtta atattcccta | 1320 |
| aacacaattt tatgaaggga agacattg gtttgttgac aataacagta catcttttca | 1380 |
| agttctcagc tatttcttct acctctccct atcttacatt tgagtatggt aacttatgtc | 1440 |
| atctatgttg aatgtaagct tataaagcac aaagcataca tttcctgact ggtctagaga | 1500 |
| actgatgttt caatttaccc ctctgctaaa taaatattaa aactatcatg tgaaaaaaaa | 1560 |
| aaaaaaaaaa | 1570 |

<210> SEQ ID NO 9
<211> LENGTH: 2305
<212> TYPE: DNA
<213> ORGANISM: Homo sapiens

<400> SEQUENCE: 9

| | | | | | |
|---|---|---|---|---|---|
| gaatctacaa | taagacaaat | ttcaaatcaa | gttgctccac | tatactgcat | aagcagttta | 60 |
| gaatcttaag | cagatgcaaa | aagaataaag | caaatgggag | gaaaaaaaag | gccgataaag | 120 |
| tttctggcta | caatacaaga | gacatatcat | taccatatga | tctaatgtgg | gtgtcagccg | 180 |
| gattgtgttc | attgagggaa | accttatttt | ttaactgtgc | tatggagtag | aagcaggagg | 240 |
| ttttcaacct | agtcacagag | cagcacctac | cccctcctcc | tttccacacc | tgcaaactct | 300 |
| tttacttggg | ctgaatattt | agtgtaatta | catctcagct | ttgagggctc | ctgtggcaaa | 360 |
| ttcccggatt | aaaaggttcc | ctggttgtga | aaatacatga | gataaatcat | gaaggccact | 420 |
| atcatcctcc | ttctgcttgc | acaagtttcc | tgggctggac | cgtttcaaca | gagaggctta | 480 |
| tttgacttta | tgctagaaga | tgaggcttct | gggataggcc | cagaagttcc | tgatgaccgc | 540 |
| gacttcgagc | cctccctagg | cccagtgtgc | cccttccgct | gtcaatgcca | tcttcgagtg | 600 |
| gtccagtgtt | ctgatttggg | tctggacaaa | gtgccaaagg | atcttccccc | tgacacaact | 660 |
| ctgctagacc | tgcaaaacaa | caaaataacc | gaaatcaaag | atggagactt | taagaacctg | 720 |
| aagaaccttc | acgcattgat | tcttgtcaac | aataaaatta | gcaaagttag | tcctggagca | 780 |
| tttacccctt | tggtgaagtt | ggaacgactt | tatctgtcca | agaatcagct | gaaggaattg | 840 |
| ccagaaaaaa | tgcccaaaac | tcttcaggag | ctgcgtgccc | atgagaatga | gatcaccaaa | 900 |
| gtgcgaaaag | ttactttcaa | tggactgaac | cagatgattg | tcatagaact | gggcaccaat | 960 |
| ccgctgaaga | gctcaggaat | tgaaaatggg | gctttccagg | gaatgaagaa | gctctcctac | 1020 |
| atccgcattg | ctgataccaa | tatcaccagc | attcctcaag | gtcttcctcc | ttcccttacg | 1080 |
| gaattacatc | ttgatggcaa | caaaatcagc | agagttgatg | cagctagcct | gaaaggactg | 1140 |
| aataatttgg | ctaagttggg | attgagtttc | aacagcatct | ctgctgttga | caatggctct | 1200 |
| ctggccaaca | cgcctcatct | gagggagctt | cacttggaca | caacaagct | taccagagta | 1260 |
| cctggtgggc | tggcagagca | taagtacatc | caggttgtct | accttcataa | caacaatatc | 1320 |
| tctgtagttg | gatcaagtga | cttctgccca | cctggacaca | acaccaaaaa | ggcttcttat | 1380 |
| tcgggtgtga | gtcttttcag | caacccggtc | cagtactggg | agatacagcc | atccaccttc | 1440 |
| agatgtgtct | acgtgcgctc | tgccattcaa | ctcggaaact | ataagtaatt | ctcaagaaag | 1500 |
| ccctcatttt | tataacctgg | caaaatcttg | ttaatgtcat | tgctaaaaaa | taaataaaag | 1560 |
| ctagatactg | gaaacctaac | tgcaatgtgg | atgttttacc | cacatgactt | attatgcata | 1620 |
| aagccaaatt | tccagtttaa | gtaattgcct | acaataaaaa | gaaatttgc | ctgccatttt | 1680 |
| cagaatcatc | ttttgaagct | ttctgttgat | gttaactgag | ctactagaga | tattcttatt | 1740 |
| tcactaaatg | taaaatttgg | agtaaatata | tatgtcaata | tttagtaaag | cttttctttt | 1800 |
| ttaatttcca | ggaaaaaata | aaagagtat | gagtcttctg | taattcattg | agcagttagc | 1860 |
| tcatttgaga | taaagtcaaa | tgccaaacac | tagctctgta | ttaatcccca | tcattactgg | 1920 |
| taaagcctca | tttgaatgtg | tgaattcaat | acaggctatg | taaaattttt | actaatgtca | 1980 |
| ttattttgaa | aaaataaatt | taaaaataca | ttcaaaatta | ctattgtata | caagcttaat | 2040 |
| tgttaatatt | ccctaaacac | aatttttatga | agggagaaga | cattggtttg | ttgacaataa | 2100 |

| cagtacatct | tttcaagttc | tcagctattt | cttctacctc | tccctatctt | acatttgagt | 2160 |
| atggtaactt | atgtcatcta | tgttgaatgt | aagcttataa | agcacaaagc | atacatttcc | 2220 |
| tgactggtct | agagaactga | tgtttcaatt | taccccctctg | ctaaataaat | attaaaacta | 2280 |
| tcatgtgaaa | aaaaaaaaaa | aaaaa | | | | 2305 |

<210> SEQ ID NO 10
<211> LENGTH: 2151
<212> TYPE: DNA
<213> ORGANISM: Homo sapiens

<400> SEQUENCE: 10

| ggaataataa | gacacgccct | gaaggagtac | atcgtctagt | gagggacaga | ccaagcacgc | 60 |
| aaaacaaatt | gcaatataat | gtgataagtt | ctttaaaaga | ggtaagagca | acgtgctttg | 120 |
| ggagcagaga | agagggagaa | agcagcatct | tgcctggatg | agccagggga | cacagaagag | 180 |
| aagcccacta | tctcatttaa | tctttacaac | tctcttgcaa | ggttccctgg | ttgtgaaaat | 240 |
| acatgagata | aatcatgaag | gccactatca | tcctccttct | gcttgcacaa | gtttcctggg | 300 |
| ctggaccgtt | tcaacagaga | ggcttatttg | actttatgct | agaagatgag | gcttctggga | 360 |
| taggcccaga | agttcctgat | gaccgcgact | tcgagccctc | cctaggccca | gtgtgcccct | 420 |
| tccgctgtca | atgccatctt | cgagtggtcc | agtgttctga | tttgggtctg | gacaaagtgc | 480 |
| caaaggatct | tccccctgac | acaactctgc | tagacctgca | aaacaacaaa | ataaccgaaa | 540 |
| tcaaagatgg | agactttaag | aacctgaaga | accttcacgc | attgattctt | gtcaacaata | 600 |
| aaattagcaa | agttagtcct | ggagcattta | cacctttggt | gaagttggaa | cgactttatc | 660 |
| tgtccaagaa | tcagctgaag | gaattgccag | aaaaaatgcc | caaaactctt | caggagctgc | 720 |
| gtgcccatga | gaatgagatc | accaaagtgc | gaaaagttac | tttcaatgga | ctgaaccaga | 780 |
| tgattgtcat | agaactgggc | accaatccgc | tgaagagctc | aggaattgaa | atggggctt | 840 |
| tccagggaat | gaagaagctc | tcctacatcc | gcattgctga | taccaatatc | accagcattc | 900 |
| ctcaaggtct | tcctccttcc | cttacggaat | tacatcttga | tggcaacaaa | atcagcagag | 960 |
| ttgatgcagc | tagcctgaaa | ggactgaata | atttggctaa | gttgggattg | agtttcaaca | 1020 |
| gcatctctgc | tgttgacaat | ggctctctgg | ccaacacgcc | tcatctgagg | gagcttcact | 1080 |
| tggacaacaa | caagcttacc | agagtacctg | gtgggctggc | agagcataag | tacatccagg | 1140 |
| ttgtctacct | tcataacaac | aatatctctg | tagttggatc | aagtgacttc | tgcccacctg | 1200 |
| gacacaaacac | caaaaaggct | tcttattcgg | gtgtgagtct | tttcagcaac | ccggtccagt | 1260 |
| actgggagat | acagccatcc | accttcagat | gtgtctacgt | gcgctctgcc | attcaactcg | 1320 |
| gaaactataa | gtaattctca | agaaagccct | cattttttata | acctggcaaa | atcttgttaa | 1380 |
| tgtcattgct | aaaaaataaa | taaaagctag | atactggaaa | cctaactgca | atgtggatgt | 1440 |
| tttacccaca | tgacttatta | tgcataaagc | caaatttcca | gtttaagtaa | ttgcctacaa | 1500 |
| taaaaagaaa | ttttgcctgc | cattttcaga | atcatctttt | gaagctttct | gttgatgtta | 1560 |
| actgagctac | tagagatatt | cttatttcac | taaatgtaaa | atttggagta | aatatatatg | 1620 |
| tcaatattta | gtaaagcttt | tctttttttaa | tttccaggaa | aaaataaaaa | gagtatgagt | 1680 |
| cttctgtaat | tcattgagca | gttagctcat | ttgagataaa | gtcaaatgcc | aaacactagc | 1740 |
| tctgtattaa | tccccatcat | tactggtaaa | gcctcatttg | aatgtgtgaa | ttcaatacag | 1800 |
| gctatgtaaa | attttactta | atgtcattat | tttgaaaaaa | taaatttaaa | aatacattca | 1860 |
| aaattactat | tgtatacaag | cttaattgtt | aatattccct | aaacacaatt | ttatgaaggg | 1920 |

| agaagacatt | ggtttgttga | caataacagt | acatctttc | aagttctcag | ctatttcttc | 1980 |
| tacctctccc | tatcttacat | ttgagtatgg | taacttatgt | catctatgtt | gaatgtaagc | 2040 |
| ttataaagca | caaagcatac | atttcctgac | tggtctagag | aactgatgtt | tcaatttacc | 2100 |
| cctctgctaa | ataaatatta | aaactatcat | gtgaaaaaaa | aaaaaaaaaa | a | 2151 |

```
<210> SEQ ID NO 11
<211> LENGTH: 2096
<212> TYPE: DNA
<213> ORGANISM: Homo sapiens

<400> SEQUENCE: 11
```

| gggcctgtgg | ctggccgggg | gcggagaagc | gggggtcgg | ggtccctccc | cctggcgctg | 60 |
| gctcaggaat | ccgccgaagg | gcgggcgag | gcgccgggt | gggccgcgcc | gcggcaggcg | 120 |
| ggcgggcggg | gggcgcttcc | tggggccgcg | cgtccaggga | gctgtgccgt | ccgcccgtcc | 180 |
| gtctgcccgc | aggcattgcc | cgagccagcc | gagccgccag | agccgcgggc | cgcggggtg | 240 |
| tcgcgggccc | aaccccagga | tgctcccctg | cgcctcctgc | ctacccgggt | ctctactgct | 300 |
| ctgggcgctg | ctactgttgc | tcttgggatc | agcttctcct | caggattctg | aagagcccga | 360 |
| cagctacacg | gaatgcacag | atggctatga | gtgggaccca | gacagccagc | actgccggga | 420 |
| tgtcaacgag | tgtctgacca | tccctgaggc | ctgcaagggg | gaaatgaagt | gcatcaacca | 480 |
| ctacgggggc | tacttgtgcc | tgccccgctc | cgctgccgtc | atcaacgacc | tacacggcga | 540 |
| gggacccccg | ccaccagtgc | ctcccgctca | acacccaac | ccctgcccac | caggctatga | 600 |
| gcccgacgat | caggacagct | gtgtggatgt | ggacgagtgt | gcccaggccc | tgcacgactg | 660 |
| tcgcccagc | caggactgcc | ataacttgcc | tggctcctat | cagtgcacct | gccctgatgg | 720 |
| ttaccgcaag | atcgggcccg | agtgtgtgga | catagacgag | tgccgctacc | gctactgcca | 780 |
| gcaccgctgc | gtgaacctgc | ctggctcctt | ccgctgccag | tgcgagccgg | gcttccagct | 840 |
| ggggcctaac | aaccgctcct | gtgttgatgt | gaacgagtgt | gacatggggg | ccccatgcga | 900 |
| gcagcgctgc | ttcaactcct | atgggacctt | cctgtgtcgc | tgccaccagg | gctatgagct | 960 |
| gcatcgggat | ggcttctcct | gcagtgatat | tgatgagtgt | agctactcca | gctacctctg | 1020 |
| tcagtaccgc | tgcatcaacg | agccaggccg | tttctcctgc | cactgcccac | agggttacca | 1080 |
| gctgctggcc | acacgcctct | gccaagacat | tgatgagtgt | gagtctggtg | cgcaccagtg | 1140 |
| ctcccgaggcc | caaacctgtg | tcaacttcca | tggggctac | cgctgcgtgg | acaccaaccg | 1200 |
| ctgcgtggag | ccctacatcc | aggtctctga | gaaccgctgt | ctctgcccgg | cctccaaccc | 1260 |
| tctatgtcga | gagcagcctt | catccattgt | gcaccgctac | atgaccatca | cctcggagcg | 1320 |
| gagcgtgccc | gctgacgtgt | tccagatcca | ggcgacctcc | gtctacccg | gtgcctacaa | 1380 |
| tgcctttcag | atccgtgctg | gaaactcgca | ggggactttt | acattaggc | aaatcaacaa | 1440 |
| cgtcagcgcc | atgctggtcc | tcgcccggcc | ggtgacgggc | cccgggagt | acgtgctgga | 1500 |
| cctggagatg | gtcaccatga | attccctcat | gagctaccgg | gccagctctg | tactgaggct | 1560 |
| caccgtctttt | gtaggggcct | acaccttctg | aggagcagga | gggagccacc | ctccctgcag | 1620 |
| ctaccctagc | tgaggagcct | gttgtgaggg | gcagaatgag | aaaggcaata | aagggagaaa | 1680 |
| gaaagtcctg | gtggctgagg | tgggcgggtc | acactgcagg | aagcctcagg | ctggggcagg | 1740 |
| gtggcacttg | gggggcagg | ccaagttcac | ctaaatgggg | gtctctatat | gttcaggccc | 1800 |
| aggggccccc | attgacagga | gctggagct | ctgcaccacg | agcttcagtc | accccgagag | 1860 |

| | | | | |
|---|---|---|---|---|
| gagaggaggt | aacgaggagg | gcggactcca | ggccccggcc | cagagatttg gacttggctg | 1920 |
| gcttgcaggg | gtcctaagaa | actccactct | ggacagcgcc | aggaggccct gggttccatt | 1980 |
| cctaactctg | cctcaaactg | tacatttgga | taagccctag | tagttccctg ggcctgtttt | 2040 |
| tctataaaac | gaggcaactg | gactgttaaa | aaaaaaaaa | aaaaaaaaa aaaaaa | 2096 |

<210> SEQ ID NO 12
<211> LENGTH: 4404
<212> TYPE: DNA
<213> ORGANISM: Homo sapiens

<400> SEQUENCE: 12

| | | | | |
|---|---|---|---|---|
| aggattgggg | gtcccagcct | gcgtcccgtc | agtcccttct | tggcccggag tgcgcggagc | 60 |
| tgggagtggc | ttcgccatgg | ctgtgagaag | ggactccgtg | tggaagtact gctgggggtgt | 120 |
| tttgatggtt | ttatgcagaa | ctgcgatttc | caaatcgata | gttttagagc ctatctattg | 180 |
| gaattcctcg | aactccaaat | ttctacctgg | acaaggactg | tactatacc cacagatagg | 240 |
| agacaaattg | gatattattt | gccccaaagt | ggactctaaa | actgttggcc agtatgaata | 300 |
| ttataaagtt | tatatggttg | ataaagacca | agcagacaga | tgcactatta agaaggaaaa | 360 |
| taccccctctc | ctcaactgtg | ccaaaccaga | ccaagatatc | aaattcacca tcaagtttca | 420 |
| agaattcagc | cctaacctct | ggggtctaga | atttcagaag | aacaaagatt attacattat | 480 |
| atctacatca | aatgggtctt | tggagggcct | ggataaccag | gagggagggg tgtgccagac | 540 |
| aagagccatg | aagatcctca | tgaaagttgg | acaagatgca | agttctgctg gatcaaccag | 600 |
| gaataaagat | ccaacaagac | gtccagaact | agaagctggt | acaaatggaa gaagttcgac | 660 |
| aacaagtccc | tttgtaaaac | caaatccagg | ttctagcaca | gacggcaaca gcgccggaca | 720 |
| ttcggggaac | aacatcctcg | gttccgaagt | ggccttattt | gcagggattg cttcaggatg | 780 |
| catcatcttc | atcgtcatca | tcatcacgct | ggtggtcctc | ttgctgaagt accggaggag | 840 |
| acacaggaag | cactcgccgc | agcacacgac | cacgctgtcg | ctcagcacac tggccacacc | 900 |
| caagcgcagc | ggcaacaaca | acggctcaga | gcccagtgac | attatcatcc cgctaaggac | 960 |
| tgcggacagc | gtcttctgcc | ctcactacga | gaaggtcagc | ggggactacg gcacccggt | 1020 |
| gtacatcgtc | caggagatgc | ccccgcagag | cccggcgaac | atttactaca aggtctgaga | 1080 |
| gggaccctgg | tggtacctgt | gctttcccag | aggacaccta | atgtcccgat gcctcccttg | 1140 |
| agggtttgag | agcccgcgtg | ctggagaatt | gactgaagca | cagcaccggg ggagagggac | 1200 |
| actcctcctc | ggaagagccc | gtcgcgctgg | acagcttacc | tagtcttgta gcattcggcc | 1260 |
| ttggtgaaca | cacacgctcc | ctggaagctg | gaagactgtg | cagaagacgc ccattcggac | 1320 |
| tgctgtgccg | cgtcccacgt | ctcctcctcg | aagccatgtg | ctgcggtcac tcaggcctct | 1380 |
| gcagaagcca | agggaagaca | gtggtttgtg | gacgagaggg | ctgtgagcat cctggcaggt | 1440 |
| gccccaggat | gccacgcctg | gaagggccgg | cttctgcctg | gggtgcattt ccccgcagt | 1500 |
| gcataccgga | cttgtcacac | ggacctcggg | ctagttaagg | tgtgcaaaga tctctagagt | 1560 |
| ttagtcctta | ctgtctcact | cgttctgtta | cccagggctc | tgcagcacct cacctgagac | 1620 |
| ctccactcca | catctgcatc | actcatggaa | cactcatgtc | tggagtcccc tcctccagcc | 1680 |
| gctggcaaca | acagcttcag | tccatgggta | atccgttcat | agaaattgtg tttgctaaca | 1740 |
| aggtgccctt | tagccagatg | ctaggctgtc | tgcgaagaag | gctaggagtt catagaaggg | 1800 |
| agtggggctg | gggaaagggc | tggctgcaat | tgcagctcac | tgctgctgcc tctgaaacag | 1860 |
| aaagttggaa | aggaaaaaag | aaaaaagcaa | ttaggtagca | cagcactttg gttttgctga | 1920 |

-continued

```
gatcgaagag gccagtagga gacacgacag cacacacagt ggattccagt gcatggggag    1980
gcactcgctg ttatcaaata gcgatgtgca ggaagaaaag cccctcttca ttccggggaa    2040
caaagacggg tattgttggg aaaggaacag gcttggaggg aagggagaaa gtaggccgct    2100
gatgatatat tcgggcagga ctgttgtggt actggcaata agatacacag ctccgagctg    2160
taggagagtc ggtctgcttt ggatgatttt ttaagcagac tcagctgcta tacttatcac    2220
attttattaa acacagggaa agcatttagg agaatagcag agagccaaat ctgacctaaa    2280
agttgaaaag ccaaaggtca aacaggctgt aattccatca tcatcgttgt tattaaagaa    2340
tccttatcta taaaaggtag gtcagatccc cctcccccca ggttcctcct tcccctcccg    2400
attgagcctt acgacacttt ggtttatgcg gtgctgtccg ggtgccaggg ctgcagggtc    2460
ggtactgatg gaggctgcag cgcccggtgc tctgtgtcaa ggtgaagcac atacggcaga    2520
cctcttagag tccttaagac ggaagtaaat tatgatgtcc aggggagaa ggaagatagg     2580 acgtatttat aataggtata tagaacacaa gggatataaa atgaaagatt tttactaata    2640
tatattttaa ggttgcacac agtacacacc agaagatgtg aaattcattt gtggcaatta    2700
agtggtccca atgctcagcg cttaaaaaaa caaattggac agctacttct gggaaaaaca    2760
acatcattcc aaaagaaaca ataatgagag caaatgcaaa aataaccaag tcctccgaag    2820
gcatctcacg gaaccgtaga ctaggaagta cgagccccac agagcaggaa gccgatgtga    2880
ctgcatcata tatttaacaa tgacaagatg ttccggcgtt tatttctgcg ttgggttttc     2940
ccttgcctta tgggctgaag tgttctctag aatccagcag gtcacactgg ggcttcagg     3000 tgacgattta gctgtggctc cctcctcctg tcctcccccg caccccctcc cttctgggaa    3060
acaagaagag taaacaggaa acctactttt tatgtgctat gcaaaataga catctttaac    3120
atagtcctgt tactatggta acactttgct ttctgaattg gaagggaaaa aaaatgtagc    3180
gacagcattt taaggttctc agacctccag tgagtacctg caaaaatgag ttgtcacaga    3240
aattatgatc ctctatttcc tgaacctgga aatgatgttg gtccaaagtg cgtgtgtgta    3300
tgtgtgagtg ggtgcgtggt atacatgtgt acatatatgt ataatatata tctacaatat    3360
atattatata tatctatatc atatttctgt ggagggttgc catggtaacc agccacagta    3420
catatgtaat tctttccatc accccaacct ctcctttctg tgcattcatg caagagtttc    3480
ttgtaagcca tcagaagtta cttttaggat ggggagagg ggcgagaagg ggaaaaatgg     3540
gaaatagtct gattttaatg aaatcaaatg tatgtatcat cagttggcta cgttttggtt    3600
ctatgctaaa ctgtgaaaaa tcagatgaat tgataaaaga gttccctgca accaattgaa    3660
aagtgttctg tgcgtctgtt ttgtgtctgg tgcagaatat gacaatctac caactgtccc    3720
tttgtttgaa gttggtttag cttttggaaag ttactgtaaa tgccttgctt gtatgatcgt    3780
ccctggtcac ccgactttgg aatttgcacc atcatgtttc agtgaagatg ctgtaaatag    3840
gttcagattt tactgtctat ggatttgggg tgttacagta gccttattca cctttttaat    3900
aaaaatacac atgaaaacaa gaaagaaatg gcttttctta cccagattgt gtacatagag    3960
caatgttggt tttttataaa gtctaagcaa gatgttttgt ataaaatctg aattttgcaa    4020
tgtatttagc tacagcttgt ttaacggcag tgtcattccc ctttgcactg taatgaggaa    4080
aaaatggtat aaaaggttgc caaattgctg catatttgtg ccgtaattat gtaccatgaa    4140
tatttattta aaatttcgtt gtccaatttg taagtaacac agtattatgc ctgagttata    4200
aatatttttt tctttctttg ttttatttta atagcctgtc ataggtttta aatctgcttt    4260
```

| | |
|---|---:|
| agtttcacat tgcagttagc cccagaaaat gaaatccgtg aagtcacatt ccacatctgt | 4320 |
| ttcaaactga atttgttctt aaaaaaataa aatatttttt tcctatggaa aaagtgcctt | 4380 |
| caaagtaaaa aaaaaaaaaa aaaa | 4404 |

<210> SEQ ID NO 13
<211> LENGTH: 7554
<212> TYPE: DNA
<213> ORGANISM: Homo sapiens

<400> SEQUENCE: 13

| | |
|---|---:|
| ggggcctcgc ggccggcgag gggctgagct gacagggccg catcggctta ccccaccttta | 60 |
| ctttatcgga acgtgcctaa gctgctgcag ctggcacccg gttgcgctcg gcgaagaggg | 120 |
| ctggggcgg gagatgacgg tggtcttctc cctgcttggc accctgcgag caccagctcc | 180 |
| cttctcctcg ccactccaag gttgcagacg aagcaggtac tgtcctagat gttaaggaca | 240 |
| caacattgag caaaaacatg catagtccct gcttccgtga cacttgagtg aactgaatgt | 300 |
| gcaaagtccc tgtggcacaa agtccctggg gccagtgtgt gtggcgggtg tagaaggagc | 360 |
| taaagagatc tggttggagt tggagggtga gagaaaatga attctaattt acctgcagag | 420 |
| aacttaacca ttgcagtcaa tatgaccaag actttgccta cagcagtaac gcatggatt | 480 |
| aattccacta atgacccacc ttcaatgtca attacaaggc ttttccagc cttactggaa | 540 |
| tgctttggca ttgtccttg tggctacata gcaggaaggg ccaatgtcat aacatcaacc | 600 |
| caggccaaag gactaggaaa ttttgtctcc agatttgcac ttccagcttt attattcaaa | 660 |
| aacatggttg tacttaattt ttccaatgtg gactggtcct tcctatatag tatcttaatt | 720 |
| gccaaagctt ctgtattttt cattgtatgt gtattaacct tattggttgc cagtcctgat | 780 |
| agtcgattta gcaaagctgg actattccct attttgcta cacaaagtaa tgactttgca | 840 |
| tgggatacc ctatagttga agctttatat caaactacat acccagaata tctccagtac | 900 |
| atttatttgg tggcaccaat atctcttatg atgttaaacc ctatagggtt tattttctgt | 960 |
| gaaatccaaa agtggaaaga cactcaaaat gcttctcaaa ataaaataaa aattgtggga | 1020 |
| ctcggactcc tgcgtgtatt acagaaccca atagtatta tggtcttcat tggcatcgcc | 1080 |
| ttcaatttta ttcttgatcg aaaggtacct gtatatgtcg aaaattttct tgatggactt | 1140 |
| ggaaattctt tttctggatc agccctattt tatcttggtc tcacgatggt gggaaaaata | 1200 |
| aagagactga agaagtcggc atttgtagta ctaattcttc tcatcacagc taaacttctg | 1260 |
| gtgctgccac ttctgtgcag agaaatggtg gaactcttgg acaagggcga cagtgtggtg | 1320 |
| aaccatacaa gtttatcaaa ttatgcattt ctgtatggtg tatttcctgt agcaccagga | 1380 |
| gtggctatct tgcaacaca attcaacatg gaagtagaaa ttataacctc agggatggtg | 1440 |
| ataagcacat ttgtgtctgc tcccatcatg tacgtttctg cctggttact gaccttccc | 1500 |
| actatggacc ctaagccatt ggcatatgcc atccagaatg ttagttttga tataagtatt | 1560 |
| gtcagcctga tctccttgat ctggtctctg gctattcttc ttttgagtaa gaaatataaa | 1620 |
| cagcttcctc atatgcttac aactaattta ctcattgctc agtctattgt ctgtgctgga | 1680 |
| atgatgatat ggaattttgt taaagaaaaa aattttgttg acaaatttt ggtgtttgtt | 1740 |
| ctattgtaca gctccctcta tagcacctac ctgtggacag gccttctagc aatttctttg | 1800 |
| tttctttga aaagcgaga gagggtacaa attcctgttg gaataatcat aatatctggc | 1860 |
| tggggaattc ctgctctcct tgttggtgtt cttttgataa ctggaaaaca caatggagat | 1920 |
| agcattgact cagccttctt ttatggaaaa gaacagatga tcaccacagc agtcaccctg | 1980 |

| | |
|---|---|
| ttctgcagca tcctgatagc tggcatatcc ctcatgtgca tgaaccagac tgcccaagca | 2040 |
| ggaagctatg aaggtttcga tcagtctcag agccacaaag tggtggagcc tggaaatact | 2100 |
| gcttttgagg agagtccagc accagtaaat gaaccagaac ttttacaag ctctattcca | 2160 |
| gaaacaagtt gctgctcctg ctccatggga aatggtgaat tacactgccc atcaatagag | 2220 |
| ccaatagcaa acacaagcac cagtgagcct gtgattcctt cgtttgagaa aaacaatcat | 2280 |
| tgtgtgagtc gctgtaactc ccagagctgc atattagccc aggaagaaga acagtatcta | 2340 |
| cagagtggag accagcaact gacccgacat gtgttgctgt gtttacttct catcattggc | 2400 |
| ctgttcgcta atctttccag ttgtttatgg tggctattca accaagagcc tggaagactt | 2460 |
| tatgttgagt tacagttttt ctgtgccgtg tttaactttg gtcagggatt tatttccttt | 2520 |
| ggaatctttg gattagataa acatttaatc atcctgcctt tcaaaagaag acttgaattc | 2580 |
| ctatggaaca ataaagacac agcagaaaac agggattctc ctgtttcaga ggaaataaaa | 2640 |
| atgacctgtc aacaatttat ccattatcac cgtgacctct gtatccgaaa cattgtcaaa | 2700 |
| gaaagaaggt gtggtgcaaa gacttctgct ggaactttct gtggctgtga cctggtgagc | 2760 |
| tggctaattg aagtcggcct tgcctccgac cgtggtgaag ctgtgatata cggagacagg | 2820 |
| ctggtacaag ggggagtcat ccaacatatt accaacgagt atgaattccg ggatgagtac | 2880 |
| ttgttttaca gatttcttca aaagagtcct gaacagagtc ctcctgctat taatgcaaac | 2940 |
| actctccaac aggaaagata taagaaatt gagcattcat ccccacccct acattcccct | 3000 |
| aagacctaaa ttatgcaggg gagaaccccta catggaatca tattctagcc gcgtattcat | 3060 |
| tagttttag ctgggtgacc ttgggcaagt taacagaggc aacctctctg agcctcagtt | 3120 |
| gtctcttctg taaaatgtga aaagatgtgc tcccaccaca tgcgcagggt ctgtgatttt | 3180 |
| acatgtatgt aaaacacata ggaagctgac ttaggaaaaa gagaaaacca aattaaagtt | 3240 |
| ctgataatga atataatata gtcatccttt agtatccaag gggattggtt ccaggactcc | 3300 |
| tgaagatccc aaaatctgag gatactcaag tcccttatat aaaatggtgt aggccgggca | 3360 |
| tggtggctca cgcctgtaat cccagtactt gggaggccg agtcaggtgg atcacctgag | 3420 |
| gtcaggagtt caagaccagc ctggccaaca tggcgaaacc ccgtctctac tataaaatac | 3480 |
| aaaaaattag ttgggtgtgg tggcgggtgc ctgtaatccc agctactcag gaggctgagg | 3540 |
| caggagaatc gcttgaatct gggaggcaga ggttgctgtg agccgagatc gtgccactgc | 3600 |
| actccagcct gagcaacaga gcaagactct atctcaaaaa taaataaaa taaataaaa | 3660 |
| taattaataa aatggtgtag tatttgcata taacctatgc acattctccc atatagttta | 3720 |
| atcatcttta gatacttata atgcctaata caatgtaaat gctatgtaaa tagttgttgt | 3780 |
| tatactgtat tgtttaggga ataacaataa gaaaaacagt ctgtacatgt tcactacaga | 3840 |
| tgcaaccatt gttaagcctg actacatctt tttatctgcg gttgattgaa tctatggatg | 3900 |
| tggaacctgt gcatatggag ggtcaactgt actataaata tacgaatat gccaacatta | 3960 |
| tataatcatt gctttctgca actgtttact ataatttcaa aattaatatc ctattaactg | 4020 |
| ttcctataaa ttatcaaatt tggcaagtgt attactagca ggagatggac cttaaattat | 4080 |
| gacaacttta tattttttga tagcatctct tgaaaaagaa ttttaatgat tctaataaga | 4140 |
| ggttctttt cttttttcca tttccttgac aaatagtact catttaaaaa ctagagggct | 4200 |
| aggcttagtg gctcacgcct gtaatctcag cactttggga ggctgaggcg ggcagatcgc | 4260 |
| ttgaggtcag gagttcaaga ccagcccggg caacgtggtg aaaccccgtc tgtactaaaa | 4320 |

```
aaaaaaaaaa agaaaagaa aaagaaaaaa gaatacccag gtgtggtagt gcatgcctgt      4380
agtcccagct actttggaga ctgaggtggg agtaccccct gagcctggga ggcgcaggtt      4440
gcagtgaacc aagatcacat cactgcactt caacctgggt gacagagcaa gaccctgtct      4500 caaaacaaa aaacaagcaa aaaaaaccta gaggcactat ttttttttaa agtttgtctt      4560
ttcttttcta cccaaattac taatctatgc cattaaggaa aggaataaga acctccatat      4620
gtattattat ctccacagtc ctgcagaagt acaatctgat ctttaacttt catgctacaa      4680
ataataattt gagtagatta atttgaattt tatcaacaaa attattgcca tatgatgtat      4740
catttctgtg tttgaacaaa gcatcgtaat gcaggataac ttctacttta ttccctgtag      4800
ttaaaaaaaa aaaactata tagttcaagc caatatttaa aaattctaaa cctaggctgg      4860
gcatggtgac tcatacctgt aatcccagca ctttgggagg ccgaggcagg tgaattgctt      4920
cagcccagga gttcgagacc agcctggcca atgtggtgaa accccatctc tactaaaaaa      4980
aaaaaaaaaa aaaaaaatta gccaggtgtg gtggtgtgca cctgtaatcc cagctaccca      5040
ggaggctgag gcaggaaaat tgcttgaaac caggaggcag aggttgcagt gagctgagat      5100
cgtgccactg cactccagcc tgagtgtcag agtgagactc tgtctcagaa aaaaaaaaaa      5160
aaattctaaa gattacattt agaatttagt ctttttaaag tgtccatgta taaaaatata      5220 taattttaa aattactaaa tgttgccttt tctcttagtc taatattta gctactaaaa      5280 caaatataa actggatagc ttataaacaa cataaactta tttctcacag ttttggaggc      5340
tgtgaagtcc aagattaagg cactaacaga tctagtgtct ggtaaggcaa atttctggct      5400
catagatggt accttcttgc tgtgtcccca catggtagat gggaagaact ggtctcattg      5460 gcccccttata aggacattaa ttccactcaa taggctccac cctcatgatc taataacctc      5520 tcaaggccc tacctcctaa tactaacaca ttgaggatgt gacttcaact ttacatttct      5580
acaggcagag aagtggggct gtgtaaattc ttcccatcag tacttgaatg ttcatttaac      5640
aaataactta tcgagcatct agcatgttcc agacacaatc tgaacactga gcacacaaca      5700
gttggaacaa atatgattcc tatcctcatg gagcttctat tctcctgtga aaaacagatg      5760
ttaaacatga ttgaggatta ggtttcaaca taagaattct aggaggacac agacatttag      5820
accatagcat cttcaggtaa actttatctt cagtaaatta aagagatcta tttagatgac      5880
ctttgagcat cttaattatt agatgtcagt gctagtttaa cttatttaa acgtttcaga      5940 tatttattta attatacttt aagtgtctca tgtaaaaaag ttatttataa aataatttat      6000
agggttagag tcattgccct tttaatgcaa caaataaaca gttttttaaa aacctgcatg      6060
ggggccaggc gcggtggttc atacctgcaa tcccagcact tgggaggtc gaggctggcg      6120 gatcacgagg tcaggagatc gagaccaccc tgattaatgc ggtgaaatcc cgtctctact      6180
aaaaatacaa aaaattagcc agacgtggtg gtgggcacct atagtcccag ctactcggga      6240
ggctgaggca ggagaatggc atgaacccgg aaggcggagc ttgcagtgaa ccaagatcgc      6300
gccactgcac tccagcctgg gcgacagagt gagactccat cgcaaaaaaa aaaaaaaaaa      6360
aacctgcatg gaagcctagt atatttatta ataacaaata aattatactt tagtgtacta      6420
ttaacctata ccaattttaa gttgtgatta gggaatgggg atgttttaa gctgaattgt      6480 cttgctgcgg aactttcctt ttttaataag accatattat gactctgaat gctcaagggt      6540
aagtctaagg cctcattgct gttaccagga gattttttcta gttacagtaa taaagatgtt      6600
aattcacatg catgcagaca actgaaactc aagtggagaa tttgtttgtg aacaagtcat      6660
actacttctg ttatttgcat gaatggaatc tgcaatatct ttttccatgg gagaccctaa      6720
```

```
aagaaaaccc tggatcagaa tgatctgcag tttcagataa taaaggcttt taagagacat    6780
ttttagaatt aaaaatatgc taattttatt aaatgaaaat atttgtaact gttaactttc    6840
tcactgacaa agcaagtttc tcaataaaat acctatttta acttgcatta ctgacatctt    6900
ttctttgagt aatctgaata atgcagaagc catcatagag gtcttttcta tacattctca    6960
atgttttctt aaatgggttt cctgagttct gttcttcatg actctgggct ctgcaaacag    7020
ggtttcccaa ttacgcattc tataaacact tttatgaatg agtcaatatg acattgagtc    7080
cttttcatac atttcatcat ttccaatatg tagagtgaca gctagaaaaa tgataaaatt    7140
ttgattaaaa cctatctctt tttcttcagc atagtcaatt gttttcttaa ctctcaatga    7200
gtaactccat gcctagcttg tgcttagctt tcaatatttt tagactaaga caaagtgtat    7260
ttggcatttt gagaacaaca attaatggtc agtaaatttc taaagcaaga aaatgtgaa     7320 actagtgttt tatatgtttg ttacgcagca gaatgcggct cttagtgttt gccccttcat    7380
atctcatcat gtaaaatatt aaattacttt aggccactgc acataggtag tcctgtcatg    7440
agtgatggct ggagaaaagt tcaggatcat aaatgttatc atcattcttc aagaaaagat    7500
gagattataa atttctgcaa ttggtatgat aaaaggttga ataattaat  gaaa           7554

<210> SEQ ID NO 14
<211> LENGTH: 7405
<212> TYPE: DNA
<213> ORGANISM: Homo sapiens

<400> SEQUENCE: 14
ggggcctcgc ggccggcgag gggctgagct gacagggccg catcggctta ccccaccttc    60
ctttatcgga acgtgcctaa gctgctgcag ctggcacccg gttgcgctcg gcgaagaggg    120 ctggggcgg gagatgacgg tggtcttctc cctgcttggc accctgcgag caccagctcc     180
cttctcctcg ccactccaag gttgcagacg aagcagagat ctggttggag ttggagggtg    240
agagaaaatg aattctaatt tacctgcaga gaacttaacc attgcagtca atatgaccaa    300
gactttgcct acagcagtaa cgcatggatt taattccact aatgacccac cttcaatgtc    360
aattacaagg ctttttccag ccttactgga atgctttggc attgtccttt gtggctacat    420
agcaggaagg gccaatgtca taacatcaac ccaggccaaa ggactaggaa attttgtctc    480
cagatttgca cttccagctt tattattcaa aaacatggtt gtacttaatt tttccaatgt    540
ggactggtcc ttcctatata gtatcttaat tgccaaagct tctgtatttt tcattgtatg    600
tgtattaacc ttattggttg ccagtcctga tagtcgattt agcaaagctg gactattccc    660 tattttgct acacaaagta atgactttgc attgggatac cctatagttg aagctttata    720
tcaaactaca tacccagaat atctccagta catttatttg gtggcaccaa tatctcttat    780
gatgttaaac cctatagggt ttattttctg tgaaatccaa aagtggaaag acactcaaaa    840
tgcttctcaa aataaaataa aaattgtggg actcggactc ctgcgtgtat tacagaaccc    900
aatagtattt atggtcttca ttggcatcgc cttcaatttt attcttgatc gaaaggtacc    960
tgtatatgtc gaaattttc ttgatggact tggaaattct ttttctggat cagccctatt    1020
ttatcttggt ctcacgatgg tgggaaaaat aaagagactg aagaagtcgg catttgtagt    1080
actaattctt ctcatcacag ctaaacttct ggtgctgcca cttctgtgca gagaaatggt    1140
ggaactcttg gacaagggcg acagtgtggt gaaccatcac agtttatcaa attatgcatt    1200
tctgtatggt gtatttcctg tagcaccagg agtggctatc tttgcaacac aattcaacat    1260
```

```
ggaagtagaa attataacct cagggatggt gataagcaca tttgtgtctg ctcccatcat    1320
gtacgtttct gcctggttac tgaccttcc cactatggac cctaagccat tggcatatgc     1380
catccagaat gttagttttg atataagtat tgtcagcctg atctccttga tctggtctct    1440
ggctattctt cttttgagta agaaatataa acagcttcct catatgctta caactaattt    1500
actcattgct cagtctattg tctgtgctgg aatgatgata tggaattttg ttaaagaaaa    1560
aaattttgtt ggacaaattt tggtgtttgt tctattgtac agctcccctct atagcaccta   1620
cctgtggaca ggccttctag caatttcttt gtttcttttg aaaaagcgag agagggtaca    1680
aattcctgtt ggaataatca taatatctgg ctggggaatt cctgctctcc ttgttggtgt    1740
tcttttgata actggaaaac acaatggaga tagcattgac tcagccttct tttatggaaa    1800
agaacagatg atcaccacag cagtcaccct gttctgcagc atcctgatag ctggcatatc    1860
cctcatgtgc atgaaccaga ctgcccaagc aggaagctat gaaggtttcg atcagtctca    1920
gagccacaaa gtggtggagc ctggaaatac tgcttttgag gagagtccag caccagtaaa    1980
tgaaccagaa cttttacaa gctctattcc agaaacaagt tgctgctcct gctccatggg     2040
aaatggtgaa ttacactgcc catcaataga gccaatagca acacaagca ccagtgagcc      2100
tgtgattcct tcgtttgaga aaaacaatca ttgtgtgagt cgctgtaact cccagagctg    2160
catattagcc caggaagaag aacagtatct acagagtgga gaccagcaac tgacccgaca    2220
tgtgttgctg tgtttacttc tcatcattgg cctgttcgct aatctttcca gttgtttatg    2280
gtggctattc aaccaagagc ctggaagact ttatgttgag ttacagtttt tctgtgccgt    2340
gtttaacttt ggtcagggat ttatttcctt tggaatcttt ggattagata acatttaat     2400
catcctgcct ttcaaaagaa gacttgaatt cctatggaac aataaagaca cagcagaaaa    2460
cagggattct cctgtttcag aggaaataaa aatgacctgt caacaattta tccattatca    2520
ccgtgacctc tgtatccgaa acattgtcaa agaaagaagg tgtggtgcaa agacttctgc    2580
tggaactttc tgtggctgtg acctggtgag ctggctaatt gaagtcggcc ttgcctccga    2640
ccgtggtgaa gctgtgatat acggagacag gctggtacaa gggggagtca tccaacatat    2700
taccaacgag tatgaattcc gggatgagta cttgttttac agatttcttc aaaagagtcc    2760
tgaacagagt cctcctgcta ttaatgcaaa cactctccaa caggaaagat ataaagaaat    2820
tgagcattca tccccaccct cacattcccc taagacctaa attatgcagg ggagaaccct    2880
acatggaatc atattctagc cgcgtattca ttagttttta gctgggtgac cttgggcaag    2940
ttaacagagg caacctctct gagcctcagt tgtctcttct gtaaaatgtg aaagatgtg     3000
ctcccaccac atgcgcaggg tctgtgattt tacatgtatg taaaacacat aggaagctga    3060
cttaggaaaa agagaaaacc aaattaaagt tctgataatg aatataatat agtcatcctt    3120
tagtatccaa ggggattggt tccaggactc ctgaagatcc caaaatctga ggatactcaa    3180
gtcccttata taaatggtg taggccgggc atggtggctc acgcctgtaa tcccagtact     3240
tgggaggcc gagtcaggtg gatcacctga ggtcaggagt tcaagaccag cctggccaac     3300
atggcgaaac cccgtctcta ctataaaata caaaaaatta gttgggtgtg gtggcgggtg    3360
cctgtaatcc cagctactca ggaggctgag gcaggagaat cgcttgaatc tgggaggcag    3420
aggttgctgt gagccgagat cgtgccactg cactccagcc tgagcaacag agcaagactc    3480
tatctcaaaa ataaaataaa ataaaataaa ataattaata aaatggtgta gtatttgcat    3540
ataacctatg cacattctcc catatagttt aatcatcttt agatacttat aatgcctaat    3600
acaatgtaaa tgctatgtaa atagttgttg ttatactgta ttgtttaggg aataacaata    3660
```

```
agaaaaacag tctgtacatg ttcactacag atgcaaccat tgttaagcct gactacatct    3720
ttttatctgc ggttgattga atctatggat gtggaacctg tgcatatgga gggtcaactg    3780
tactataaat aatacgaata tgccaacatt atataatcat tgctttctgc aactgtttac    3840
tataatttca aaattaatat cctattaact gttcctataa attatcaaat ttggcaagtg    3900
tattactagc aggagatgga ccttaaatta tgacaacttt atattttttg atagcatctc    3960
ttgaaaaaga attttaatga ttctaataag aggttctttt tcttttttcc atttccttga    4020
caaatagtac tcatttaaaa actagagggc taggcttagt ggctcacgcc tgtaatctca    4080
gcactttggg aggctgaggc gggcagatcg cttgaggtca ggagttcaag accagcccgg    4140
gcaacgtggt gaaacccggt ctgtactaaa aaaaaaaaa aagaaaaaga aaagaaaaa     4200 agaatacccca ggtgtggtag tgcatgcctg tagtcccagc tactttggag actgaggtgg   4260
gagtacccct tgagcctggg aggcgcaggt tgcagtgaac caagatcaca tcactgcact    4320
tcaacctggg tgacagagca agaccctgtc tcaaaaacaa aaaacaagca aaaaaaacct    4380
agaggcacta tttttttta aagtttgtct tttcttttct acccaaatta ctaatctatg     4440
ccattaagga aaggaataag aacctccata tgtattatta tctccacagt cctgcagaag    4500
tacaatctga tctttaactt tcatgctaca aataataatt tgagtagatt aatttgaatt    4560
ttatcaacaa aattattgcc atatgatgta tcatttctgt gtttgaacaa agcatcgtaa    4620
tgcaggataa cttctacttt attccctgta gttaaaaaaa aaaaaactat atagttcaag    4680
ccaatattta aaaattctaa acctaggctg ggcatggtga ctcatacctg taatcccagc    4740
actttgggag gccgaggcag gtgaattgct tcagcccagg agttcgagac cagcctggcc    4800
aatgtggtga aaccccatct ctactaaaaa aaaaaaaaa aaaaaaaatt agccaggtgt     4860
ggtggtgtgc acctgtaatc ccagctaccc aggaggctga ggcaggaaaa ttgcttgaaa    4920
ccaggaggca gaggttgcag tgagctgaga tcgtgccact gcactccagc ctgagtgtca    4980
gagtgagact ctgtctcaga aaaaaaaaaa aaaattctaa agattacatt tagaatttag    5040 tcttttttaaa gtgtccatgt ataaaaatat ataatttta aaattactaa atgttgcctt    5100
ttctcttagt ctaatatttt agctactaaa acaaatatata aactggatag cttataaaca    5160
acataaactt atttctcaca gttttggagg ctgtgaagtc caagattaag gcactaacag    5220
atctagtgtc tggtaaggca aatttctggc tcatagatgg taccttcttg ctgtgtcccc    5280
acatggtaga tgggaagaac tggtctcatt ggcccttat aaggacatta attccactca     5340
ataggctcca ccctcatgat ctaataacct ctcaaaggcc ctacctccta atactaacac     5400
attgaggatg tgacttcaac tttacatttc tacaggcaga gaagtggggc tgtgtaaatt     5460
cttcccatca gtacttgaat gttcatttaa caaataactt atcgagcatc tagcatgttc    5520
cagacacaat ctgaacactg agcacacaac agttggaaca aatatgattc ctatcctcat    5580
ggagcttcta ttctcctgtg aaaaacagat gttaaacatg attgaggatt aggtttcaac    5640
ataagaattc taggaggaca cagacattta gaccatagca tcttcaggta aactttatct    5700
tcagtaaatt aaagagatct atttagatga cctttgagca tcttaattat tagatgtcag    5760
tgctagttta acttatttta aacgtttcag atatttattt aattatactt taagtgtctc    5820
atgtaaaaaa gttatttata aaataattta tagggttaga gtcattgccc ttttaatgca    5880
acaaataaac agttttttaa aaacctgcat gggggccagg cgcggtggtt catacctgca    5940
atcccagcac tttgggaggt cgaggctggc ggatcacgag gtcaggagat cgagaccacc    6000
```

```
ctgattaatg cggtgaaatc ccgtctctac taaaaataca aaaaattagc cagacgtggt    6060
ggtgggcacc tatagtccca gctactcggg aggctgaggc aggagaatgg catgaacccg    6120
gaaggcggag cttgcagtga accaagatcg cgccactgca ctccagcctg ggcgacagag    6180
tgagactcca tcgcaaaaaa aaaaaaaaaa aaacctgcat ggaagcctag tatatttatt    6240
aataacaaat aaattatact ttagtgtact attaacctat accaattta agttgtgatt     6300
agggaatggg gatgttttta agctgaattg tcttgctgcg gaactttcct tttttaataa    6360
gaccatatta tgactctgaa tgctcaaggg taagtctaag gcctcattgc tgttaccagg    6420
agatttttct agttcagta ataaagatgt taattcacat gcatgcagac aactgaaact     6480
caagtggaga atttgtttgt gaacaagtca tactacttct gttatttgca tgaatggaat    6540
ctgcaatatc ttttccatg ggagacccta aagaaaaacc ctggatcaga atgatctgca     6600
gtttcagata ataaaggctt ttaagagaca ttttagaat taaaaatatg ctaatttat     6660
taaatgaaaa tatttgtaac tgttaacttt ctcactgaca aagcaagttt ctcaataaaa    6720
tacctatttt aacttgcatt actgcatct tttctttgag taatctgaat aatgcagaag     6780
ccatcataga ggtcttttct atacattctc aatgttttct taaatgggtt tcctgagttc    6840
tgttcttcat gactctgggc tctgcaaaca gggtttccca attacgcatt ctataaacac    6900
ttttatgaat gagtcaatat gacattgagt ccttttcata catttcatca tttccaatat    6960
gtagagtgac agctagaaaa atgataaaat tttgattaaa acctatctct ttttcttcag    7020
catagtcaat tgttttctta actctcaatg agtaactcca tgcctagctt gtgcttagct    7080
ttcaatattt ttagactaag acaaagtgta tttggcattt tgagaacaac aattaatggt    7140
cagtaaattt ctaaagcaag aaaaatgtga aactagtgtt ttatatgttt gttacgcagc    7200
agaatgcggc tcttagtgtt tgccccttca tatctcatca tgtaaaatat taaattactt    7260
taggccactg cacataggta gtcctgtcat gagtgatggc tggagaaaag ttcaggatca    7320
taaatgttat catcattctt caagaaaaga tgagattata aatttctgca attggtatga    7380
taaaaggttg aaataattaa tgaaa                                          7405

<210> SEQ ID NO 15
<211> LENGTH: 7451
<212> TYPE: DNA
<213> ORGANISM: Homo sapiens

<400> SEQUENCE: 15
ggggcctcgc ggccggcgag gggctgagct gacagggccg catcggctta ccccaccttaa    60
ctttatcgga acgtgcctaa gctgctgcag ctggcacccg gttgcgctcg gcgaagaggg    120
ctggggggcgg gagatgacgg tggtcttctc cctgcttggc accctgcgag caccagctcc    180
cttctcctcg ccactccaag gttgcagacg aagcagatgt gattataaag acttcagtgg    240
aataatcgca agttcccatg tgagatctgg ttggagttgg agggtgagag aaaatgaatt    300
ctaatttacc tgcagagaac ttaaccattg cagtcaatat gaccaagact ttgcctacag    360
cagtaacgca tggatttaat tccactaatg acccaccttc aatgtcaatt acaaggcttt    420
ttccagcctt actggaatgc tttggcattg tcctttgtgg ctacatagca ggaagggcca    480
atgtcataac atcaacccag gccaaaggac taggaaattt tgtctccaga tttgcacttc    540
cagctttatt attcaaaaac atggttgtac ttaattttc caatgtggac tggtccttcc    600
tatatagtat cttaattgcc aaagcttctg tattttcat tgtatgtgta ttaaccttat    660
tggttgccag tcctgatagt cgatttagca aagctggact attccctatt tttgctacac    720
```

```
aaagtaatga ctttgcattg ggatacccta tagttgaagc tttatatcaa actacatacc      780
cagaatatct ccagtacatt tatttggtgg caccaatatc tcttatgatg ttaaacccta      840
tagggtttat tttctgtgaa atccaaaagt ggaaagacac tcaaaatgct tctcaaaata      900
aaataaaaat tgtgggactc ggactcctgc gtgtattaca gaacccaata gtatttatgg      960
tcttcattgg catcgccttc aattttattc ttgatcgaaa ggtacctgta tatgtcgaaa     1020
attttcttga tggacttgga aattctttt ctggatcagc cctatttat cttggtctca       1080 cgatggtggg aaaaataaag agactgaaga agtcggcatt tgtagtacta attcttctca     1140
tcacagctaa acttctggtg ctgccacttc tgtgcagaga aatggtggaa ctcttggaca     1200
agggcgacag tgtggtgaac catacaagtt tatcaaatta tgcatttctg tatggtgtat     1260
ttcctgtagc accaggagtg gctatctttg caacacaatt caacatggaa gtagaaatta     1320
taacctcagg gatggtgata agcacatttg tgtctgctcc catcatgtac gtttctgcct     1380
ggttactgac ctttcccact atggacccta agccattggc atatgccatc cagaatgtta     1440
gttttgatat aagtattgtc agcctgatct ccttgatctg gtctctggct attcttcttt     1500
tgagtaagaa atataaacag cttcctcata tgcttacaac taatttactc attgctcagt     1560
ctattgtctg tgctggaatg atgatatgga attttgttaa agaaaaaaat tttgttggac     1620
aaattttggt gtttgttcta ttgtacagct ccctctatag cacctacctg tggacaggcc     1680
ttctagcaat ttcttttgttt cttttgaaaa agcgagagag ggtacaaatt cctgttggaa     1740
taatcataat atctggctgg ggaattcctg ctctccttgt tggtgttctt ttgataactg     1800
gaaaacacaa tggagatagc attgactcag ccttctttta tggaaaagaa cagatgatca     1860
ccacagcagt caccctgttc tgcagcatcc tgatagctgg catatccctc atgtgcatga     1920
accagactgc ccaagcagga agctatgaag gttttcgatca gtctcagagc cacaaagtgg     1980
tggagcctgg aaatactgct tttgaggaga gtccagcacc agtaaatgaa ccagaacttt     2040
ttacaagctc tattccagaa acaagttgct gctcctgctc catgggaaat ggtgaattac     2100
actgcccatc aatagagcca atagcaaaca caagcaccag tgagcctgtg attccttcgt     2160
ttgagaaaaa caatcattgt gtgagtcgct gtaactccca gagctgcata ttagcccagg     2220
aagaagaaca gtatctacag agtggagacc agcaactgac ccgacatgtg ttgctgtgtt     2280
tacttctcat cattggcctg ttcgctaatc tttccagttg tttatggtgg ctattcaacc     2340
aagagcctgg aagactttat gttgagttac agttttttctg tgccgtgttt aactttggtc     2400
agggatttat ttcctttgga atctttggat tagataaaca tttaatcatc ctgcctttca     2460
aaagaagact tgaattccta tggaacaata agacacagc agaaaacagg gattctcctg      2520
tttcagagga aataaaaatg acctgtcaac aatttatcca ttatcaccgt gacctctgta     2580
tccgaaacat tgtcaaagaa agaaggtgtg gtgcaaagac ttctgctgga actttctgtg     2640
gctgtgacct ggtgagctgg ctaattgaag tcggccttgc ctccgaccgt ggtgaagctg     2700
tgatatacgg agacaggctg gtacaagggg gagtcatcca acatattacc aacgagtatg     2760
aattccggga tgagtacttg ttttacagat ttcttcaaaa gagtcctgaa cagagtcctc     2820
ctgctattaa tgcaaacact ctccaacagg aaagatataa agaaattgag cattcatccc     2880
caccctcaca ttcccctaag acctaaatta tgcaggggag aaccctacat ggaatcatat     2940
tctagccgcg tattcattag ttttagctg ggtgaccttg ggcaagttaa cagaggcaac     3000
ctctctgagc ctcagttgtc tcttctgtaa aatgtgaaaa gatgtgctcc caccacatgc     3060
```

-continued

```
gcagggtctg tgattttaca tgtatgtaaa acacatagga agctgactta ggaaaaagag    3120
aaaaccaaat taaagttctg ataatgaata taatatagtc atcctttagt atccaagggg    3180
attggttcca ggactcctga agatcccaaa atctgaggat actcaagtcc cttatataaa    3240
atggtgtagg ccgggcatgg tggctcacgc ctgtaatccc agtactttgg gaggccgagt    3300
caggtggatc acctgaggtc aggagttcaa gaccagcctg gccaacatgg cgaaaccccg    3360
tctctactat aaaatacaaa aaattagttg ggtgtggtgg cgggtgcctg taatcccagc    3420
tactcaggag gctgaggcag gagaatcgct tgaatctggg aggcagaggt tgctgtgagc    3480
cgagatcgtg ccactgcact ccagcctgag caacagagca agactctatc tcaaaaataa    3540
aataaaataa aataaaataa ttaataaaat ggtgtagtat ttgcatataa cctatgcaca    3600
ttctcccata tagtttaatc atctttagat acttataatg cctaatacaa tgtaaatgct    3660
atgtaaatag ttgttgttat actgtattgt ttagggaata acaataagaa aaacagtctg    3720
tacatgttca ctacagatgc aaccattgtt aagcctgact acatcttttt atctgcggtt    3780
gattgaatct atggatgtgg aacctgtgca tatggagggt caactgtact ataaataata    3840
cgaatatgcc aacattatat aatcattgct ttctgcaact gtttactata atttcaaaat    3900
taatatccta ttaactgttc ctataaatta tcaaatttgg caagtgtatt actagcagga    3960
gatggacctt aaattatgac aactttatat ttttgatag catctcttga aaagaattt    4020 taatgattct aataagaggt tcttttctt ttttccattt ccttgacaaa tagtactcat    4080
ttaaaaacta gagggctagg cttagtggct cacgcctgta atctcagcac tttgggaggc    4140
tgaggcgggc agatcgcttg aggtcaggag ttcaagacca gccgggcaa cgtggtgaaa    4200 cccggtctgt actaaaaaaa aaaaaaaga aaagaaaaa gaaaaaagaa tacccaggtg    4260
tggtagtgca tgcctgtagt cccagctact ttggagactg aggtgggagt acccttgag    4320 cctgggaggc gcaggttgca gtgaaccaag atcacatcac tgcacttcaa cctgggtgac    4380
agagcaagac cctgtctcaa aaacaaaaa caagcaaaaa aaacctagag gcactatttt    4440
tttttaaagt ttgtcttttc ttttctaccc aaattactaa tctatgccat taaggaaagg    4500
aataagaacc tccatatgta ttattatctc cacagtcctg cagaagtaca atctgatctt    4560
taactttcat gctacaaata ataatttgag tagattaatt tgaatttat caacaaaatt    4620 attgccatat gatgtatcat ttctgtgttt gaacaaagca tcgtaatgca ggataacttc    4680
tactttattc cctgtagtta aaaaaaaaaa aactatatag ttcaagccaa tatttaaaaa    4740
ttctaaacct aggctgggca tggtgactca tacctgtaat cccagcactt tgggaggccg    4800
aggcaggtga attgcttcag cccaggagtt cgagaccagc ctggccaatg tggtgaaacc    4860
ccatctctac taaaaaaaaa aaaaaaaaaa aaaattagcc aggtgtggtg gtgtgcacct    4920
gtaatcccag ctacccagga ggctgaggca ggaaaattgc ttgaaaccag gaggcagagg    4980
ttgcagtgag ctgagatcgt gccactgcac tccagcctga gtgtcagagt gagactctgt    5040
ctcagaaaaa aaaaaaaaa ttctaaagat tacatttaga atttagtctt tttaaagtgt    5100
ccatgtataa aaatatataa ttttttaaat tactaaatgt tgccttttct cttagtctaa    5160 tatttttagct actaaaacaa aatataaact ggatagctta taaacaacat aaacttattt    5220
ctcacagttt tggaggctgt gaagtccaag attaaggcac taacagatct agtgtctggt    5280
aaggcaaatt tctggctcat agatggtacc ttcttgctgt gtccccacat ggtagatggg    5340
aagaactggt ctcattggcc ccttataagg acattaattc cactcaatag gctccaccct    5400
catgatctaa taacctctca aaggccctac ctcctaatac taacacattg aggatgtgac    5460
```

```
ttcaacttta catttctaca ggcagagaag tggggctgtg taaattcttc ccatcagtac    5520
ttgaatgttc atttaacaaa taacttatcg agcatctagc atgttccaga cacaatctga    5580
acactgagca cacaacagtt ggaacaaata tgattcctat cctcatggag cttctattct    5640
cctgtgaaaa acagatgtta aacatgattg aggattaggg ttcaacataa gaattctagg    5700
aggacacaga catttagacc atagcatctt caggtaaact ttatcttcag taaattaaag    5760
agatctattt agatgacctt tgagcatctt aattattaga tgtcagtgct agtttaactt    5820
attttaaacg tttcagatat ttatttaatt atactttaag tgtctcatgt aaaaaagtta    5880
tttataaaat aatttatagg gttagagtca ttgccctttt aatgcaacaa ataaacagtt    5940
ttttaaaaac ctgcatgggg gccaggcgcg gtggttcata cctgcaatcc cagcactttg    6000
ggaggtcgag gctggcggat cacgaggtca ggagatcgag accacccctga ttaatgcggt    6060 gaaatcccgt ctctactaaa aatacaaaaa attagccaga cgtggtggtg gcacctata    6120 gtcccagcta ctcgggaggc tgaggcagga gaatggcatg aacccggaag gcggagcttg    6180
cagtgaacca agatcgcgcc actgcactcc agcctgggcg acagagtgag actccatcgc    6240
aaaaaaaaaa aaaaaaaaac ctgcatggaa gcctagtata tttattaata acaaataaat    6300
tatactttag tgtactatta acctatacca attttaagtt gtgattaggg aatggggatg    6360
tttttaagct gaattgtctt gctgcggaac tttcctttt taataagacc atattatgac    6420
tctgaatgct caagggtaag tctaaggcct cattgctgtt accaggagat ttttctagtt    6480
acagtaataa agatgttaat tcacatgcat gcagacaact gaaactcaag tggagaattt    6540
gtttgtgaac aagtcatact acttctgtta tttgcatgaa tggaatctgc aatatctttt    6600
tccatgggag accctaaaag aaaaccctgg atcagaatga tctgcagttt cagataataa    6660
aggcttttaa gagacatttt tagaattaaa aatatgctaa ttttattaaa tgaaaatatt    6720
tgtaactgtt aactttctca ctgacaaagc aagtttctca ataaaatacc tattttaact    6780
tgcattactg acatcttttc tttgagtaat ctgaataatg cagaagccat catagaggtc    6840
ttttctatac attctcaatg ttttcttaaa tgggtttcct gagttctgtt cttcatgact    6900
ctgggctctg caaacagggt ttcccaatta cgcattctat aaaacatttt atgaatgagt    6960
caatatgaca ttgagtcctt ttcatacatt tcatcatttc caatatgtag agtgacagct    7020
agaaaaatga taaaattttg attaaaacct atctctttt cttcagcata gtcaattgtt    7080
ttcttaactc tcaatgagta actccatgcc tagcttgtgc ttagctttca atattttag    7140 actaagacaa agtgtatttg gcattttgag aacaacaatt aatggtcagt aaatttctaa    7200
agcaagaaaa atgtgaaact agtgttttat atgtttgtta cgcagcagaa tgcggctctt    7260
agtgtttgcc ccttcatatc tcatcatgta aaatattaaa ttactttagg ccactgcaca    7320
taggtagtcc tgtcatgagt gatggctgga gaaaagttca ggatcataaa tgttatcatc    7380
attcttcaag aaaagatgag attataaatt tctgcaattg gtatgataaa aggttgaaat    7440
aattaatgaa a                                                          7451
```

<210> SEQ ID NO 16
<211> LENGTH: 7321
<212> TYPE: DNA
<213> ORGANISM: Homo sapiens

<400> SEQUENCE: 16

```
ggggcctcgc ggccggcgag gggctgagct gacagggccg catcggctta ccccaccttg      60
```

```
ctttatcgga acgtgcctaa gctgctgcag ctggcacccg gttgcgctcg gcgaagaggg    120 ctggggcgg gagatgacgg tggtcttctc cctgcttggc accctgcgag caccagctcc    180
cttctcctcg ccactccaag gttgcagacg aagcagagat ctggttggag ttggagggtg    240
agagaaaatg aattctaatt tacctgcaga gaacttaacc attgcagtca atatgaccaa    300
gactttgcct acagcagtaa cgcatggatt taattccact aatgacccac cttcaatgtc    360
aattacaagg ctttttccag ccttactgga atgcttggc attgtccttt gtggctacat    420
agcaggaagg gccaatgtca taacatcaac ccaggccaaa ggactaggaa attttgtctc    480
cagatttgca cttccagctt tattattcaa aaacatggtt gtacttaatt tttccaatgt    540
ggactggtcc ttcctatata gtatcttaat tgccaaagct tctgtatttt tcattgtatg    600
tgtattaacc ttattggttg ccagtcctga tagtcgattt agcaaagctg gactattccc    660
tatttttgct acacaaagta atgactttgc attgggatac cctatagttg aagctttata    720
tcaaactaca tacccagaat atctccagta catttatttg gtggaccaa tatctcttat    780 gatgttaaac cctatagggt ttattttctg tgaaatccaa aagtggaaag acactcaaaa    840
tgcttctcaa aataaaataa aaattgtggg actcggactc ctgcgtgtat tacagaaccc    900
aatagtattt atggtcttca ttggcatcgc cttcaatttt attcttgatc gaaaggtacc    960
tgtatatgtc gaaaattttc ttgatggact tggaaattct ttttctggat cagccctatt   1020
ttatcttggt ctcacgatgg tgggaaaaat aaagagactg aagaagtcgg catttgtagt   1080
actaattctt ctcatcacag ctaaacttct ggtgctgcca cttctgtgca gagaaatggt   1140
ggaactcttg gacaagggcg acagtgtggt gaaccataca agtttatcaa attatgcatt   1200
tctgtatggt gtatttcctg tagcaccagg agtggctatc tttgcaacac aattcaacat   1260
ggaagtagaa attataaacct cagggatggt gataagcaca tttgtgtctg ctcccatcat   1320
gtacgtttct gcctggttac tgacctttcc cactatggac cctaagccat ggcatatgc    1380 catccagaat gttagttttg atataagtat tgtcagcctg atctccttgt ctattgtctg   1440
tgctggaatg atgatatgga attttgttaa agaaaaaaat tttgttggac aaattttggt   1500
gtttgttcta ttgtacagct ccctctatag cacctacctg tggacaggcc ttctagcaat   1560
ttctttgttt cttttgaaaa agcgagagag ggtacaaatt cctgttggaa taatcataat   1620
atctggctgg ggaattcctg ctctccttgt tggtgttctt ttgataactg aaaacacaa    1680 tggagatagc attgactcag ccttcttta tggaaaagaa cagatgatca ccacagcagt   1740
caccctgttc tgcagcatcc tgatagctgg catatccctc atgtgcatga accagactgc   1800
ccaagcagga agctatgaag gtttcgatca gtctcagagc cacaaagtgg tggagcctgg   1860
aaatactgct tttgaggaga gtccagcacc agtaaatgaa ccagaacttt ttacaagctc   1920
tattccagaa acaagttgct gctcctgctc catgggaaat ggtgaattac actgcccatc   1980
aatagagcca atagcaaaca caagcaccag tgagcctgtg attccttcgt ttgagaaaaa   2040
caatcattgt gtgagtcgct gtaactccca gagctgcata ttagcccagg aagaagaaca   2100
gtatctacag agtggagacc agcaactgac ccgacatgtg ttgctgtgtt acttctcat    2160 cattggcctg ttcgctaatc tttccagttg tttatggtgg ctattcaacc aagagcctgg   2220
aagactttat gttgagttac agttttctg tgccgtgttt aactttggtc agggatttat   2280
ttcctttgga atctttggat tagataaaca tttaatcatc ctgcctttca aaagaagact   2340
tgaattccta tggaacaata aagacacagc agaaaacagg gattctcctg tttcaggaga   2400
aataaaaatg acctgtcaac aatttatcca ttatcaccgt gacctctgta tccgaaacat   2460
```

```
tgtcaaagaa agaaggtgtg gtgcaaagac ttctgctgga actttctgtg gctgtgacct      2520
ggtgagctgg ctaattgaag tcggccttgc ctccgaccgt ggtgaagctg tgatatacgg      2580
agacaggctg gtacaagggg gagtcatcca acatattacc aacgagtatg aattccggga      2640
tgagtacttg ttttacagat ttcttcaaaa gagtcctgaa cagagtcctc ctgctattaa      2700
tgcaaacact ctccaacagg aaagatataa agaaattgag cattcatccc caccctcaca      2760
ttcccctaag acctaaatta tgcagggag aaccctacat ggaatcatat tctagccgcg      2820
tattcattag ttttagctg ggtgaccttg ggcaagttaa cagaggcaac ctctctgagc      2880
ctcagttgtc tcttctgtaa aatgtgaaaa gatgtgctcc caccacatgc gcagggtctg      2940
tgattttaca tgtatgtaaa acacatagga agctgactta ggaaaaagag aaaaccaaat      3000
taaagttctg ataatgaata taatatagtc atcctttagt atccaagggg attggttcca      3060
ggactcctga agatcccaaa atctgaggat actcaagtcc cttatataaa atggtgtagg      3120
ccgggcatgt ggctcacgc ctgtaatccc agtactttgg gaggccgagt caggtggatc      3180
acctgaggtc aggagttcaa gaccagcctg gccaacatgg cgaaaccccg tctctactat      3240
aaaatacaaa aaattagttg ggtgtggtgg cgggtgcctg taatcccagc tactcaggag      3300
gctgaggcag gagaatcgct tgaatctggg aggcagaggt tgctgtgagc cgagatcgtg      3360
ccactgcact ccagcctgag caacagagca agactctatc tcaaaaataa aataaaataa      3420
aataaaataa ttaataaaat ggtgtagtat ttgcatataa cctatgcaca ttctcccata      3480
tagtttaatc atctttagat acttataatg cctaatacaa tgtaaatgct atgtaaaatag     3540 ttgttgttat actgtattgt ttagggaata acaataagaa aaacagtctg tacatgttca      3600
ctacagatgc aaccattgtt aagcctgact acatcttttt atctgcggtt gattgaatct      3660
atggatgtgg aacctgtgca tatggagggt caactgtact ataaataata cgaatatgcc      3720
aacattatat aatcattgct ttctgcaact gtttactata atttcaaaat taatatccta      3780
ttaactgttc ctataaatta tcaaatttgg caagtgtatt actagcagga gatggacctt      3840
aaattatgac aactttatat tttttgatag catctcttga aaaagaattt taatgattct      3900
aataagaggt tctttttctt ttttccattt ccttgacaaa tagtactcat ttaaaaacta      3960
gagggctagg cttagtggct cacgcctgta atctcagcac tttgggaggc tgaggcgggc      4020
agatcgcttg aggtcaggag ttcaagacca gcccgggcaa cgtggtgaaa cccgtctgt      4080 actaaaaaaa aaaaaaaga aaagaaaaa gaaaaagaa tacccaggtg tggtagtgca       4140
tgcctgtagt cccagctact ttggagactg aggtgggagt accccttgag cctgggaggc      4200
gcaggttgca gtgaaccaag atcacatcac tgcacttcaa cctgggtgac agagcaagac      4260
cctgtctcaa aaacaaaaaa caagcaaaaa aaacctagag gcactatttt tttttaaagt      4320
ttgtcttttc ttttctaccc aaattactaa tctatgccat taaggaaagg aataagaacc      4380
tccatatgta ttattatctc cacagtcctg cagaagtaca atctgatctt taactttcat      4440
gctacaaata ataatttgag tagattaatt tgaattttat caacaaaatt attgccatat      4500
gatgtatcat ttctgtgttt gaacaaagca tcgtaatgca ggataacttc tactttattc      4560
cctgtagtta aaaaaaaaaa aactatatag ttcaagccaa tatttaaaaa ttctaaacct      4620
aggctgggca tggtgactca tacctgtaat cccagcactt tgggaggccg aggcaggtga      4680
attgcttcag cccaggagtt cgagaccagc ctggccaatg tggtgaaacc ccatctctac      4740
taaaaaaaaa aaaaaaaaa aaaattagcc aggtgtggtg gtgtgcacct gtaatcccag      4800
```

```
ctacccagga ggctgaggca ggaaaattgc ttgaaaccag gaggcagagg ttgcagtgag   4860
ctgagatcgt gccactgcac tccagcctga gtgtcagagt gagactctgt ctcagaaaaa   4920
aaaaaaaaaa ttctaaagat tacatttaga atttagtctt tttaaagtgt ccatgtataa   4980
aaatatataa ttttttaaaat tactaaatgt tgccttttct cttagtctaa tattttagct   5040
actaaaacaa aatataaact ggatagctta taaacaacat aaacttattt ctcacagttt   5100
tggaggctgt gaagtccaag attaaggcac taacagatct agtgtctggt aaggcaaatt   5160
tctggctcat agatggtacc ttcttgctgt gtccccacat ggtagatggg aagaactggt   5220
ctcattggcc ccttataagg acattaattc cactcaatag gctccaccct catgatctaa   5280
taacctctca aaggccctac ctcctaatac taacacattg aggatgtgac ttcaacttta   5340
catttctaca ggcagagaag tggggctgtg taaattcttc ccatcagtac ttgaatgttc   5400
atttaacaaa taacttatcg agcatctagc atgttccaga cacaatctga acactgagca   5460
cacaacagtt ggaacaaata tgattcctat cctcatggag cttctattct cctgtgaaaa   5520
acagatgtta aacatgattg aggattaggt ttcaacataa gaattctagg aggacacaga   5580
catttagacc atagcatctt caggtaaaact ttatcttcag taaattaaag agatctattt   5640
agatgacctt tgagcatctt aattattaga tgtcagtgct agtttaactt attttaaacg   5700
tttcagatat ttatttaatt atactttaag tgtctcatgt aaaaaagtta tttataaaat   5760
aatttatagg gttagagtca ttgcccttt aatgcaacaa ataaacagtt ttttaaaaac   5820
ctgcatgggg gccaggcgcg gtggttcata cctgcaatcc cagcactttg ggaggtcgag   5880
gctggcggat cacgaggtca ggagatcgag accaccctga ttaatgcggt gaaatcccgt   5940
ctctactaaa aatacaaaaa attagccaga cgtggtggtg ggcacctata gtcccagcta   6000
ctcgggaggc tgaggcagga gaatggcatg aacccggaag gcggagcttg cagtgaacca   6060
agatcgcgcc actgcactcc agcctgggcg acagagtgag actccatcgc aaaaaaaaaa   6120
aaaaaaaaac ctgcatggaa gcctagtata tttattaata acaaataaat tatactttag   6180
tgtactatta acctatacca atttaagtt gtgattaggg aatggggatg ttttttaagct   6240
gaattgtctt gctgcggaac tttccttttt taataagacc atattatgac tctgaatgct   6300
caagggtaag tctaaggcct cattgctgtt accaggagat ttttctagtt acagtaataa   6360
agatgttaat tcacatgcat gcagacaact gaaactcaag tggagaattt gtttgtgaac   6420
aagtcatact acttctgtta tttgcatgaa tggaatctgc aatatctttt tccatgggag   6480
accctaaaag aaaaccctgg atcagaatga tctgcagttt cagataataa aggcttttaa   6540
gagacatttt tagaattaaa aatatgctaa ttttattaaa tgaaatatatt tgtaactgtt   6600
aactttctca ctgacaaagc aagtttctca ataaaatacc tattttaact tgcattactg   6660
acatctttc tttgagtaat ctgaataatg cagaagccat catagaggtc ttttctatac   6720
attctcaatg ttttcttaaa tgggtttcct gagttctgtt cttcatgact ctgggctctg   6780
caaacagggt ttcccaatta cgcattctat aaacactttt atgaatgagt caatatgaca   6840
ttgagtcctt ttcatacatt tcatcatttc caatatgtag agtgacagct agaaaaatga   6900
taaaattttg attaaaacct atctcttttt cttcagcata gtcaattgtt tcttaactc   6960
tcaatgagta actccatgcc tagcttgtgc ttagctttca atattttag actaagacaa   7020
agtgtatttg gcattttgag aacaacaatt aatggtcagt aaatttctaa agcaagaaaa   7080
atgtgaaact agtgttttat atgttgttta cgcagcagaa tgcggctctt agtgtttgcc   7140
ccttcatatc tcatcatgta aaatattaaa ttactttagg ccactgcaca taggtagtcc   7200
```

-continued

| | | |
|---|---|---|
| tgtcatgagt gatggctgga gaaaagttca ggatcataaa tgttatcatc attcttcaag | 7260 | |
| aaaagatgag attataaatt tctgcaattg gtatgataaa aggttgaaat aattaatgaa | 7320 | |
| a | 7321 | |

<210> SEQ ID NO 17
<211> LENGTH: 4725
<212> TYPE: DNA
<213> ORGANISM: Homo sapiens

<400> SEQUENCE: 17

| | |
|---|---|
| cccagctcag acactcctag ccttggggca gctgccgggc gagtcagcgg agtagcggcc | 60 |
| agcgggcgat ggagacagag agacacccga cgagaggagg cggggtgggg gaggcgggga | 120 |
| gagtgcgggg gcggaggctg gcaggggggcg ctggaagctg gagcggtccg tgcgctcccc | 180 |
| gcgcccgagg gtgcaggagg ctctgaagcg gctgctgcac cgcggggccc aggcggcggc | 240 |
| tgggggggctg gggggcgctg ccgccgccgc cgccggggggc gtcgctggcc tcggccccctt | 300 |
| tgttctcgcg cgctccccct cgccgcccac tcccctgctg tcgcgcggcg cggcggtgg | 360 |
| cggcggcggc tcctcccgcc cgaggcagtc gggctcggcg ccggggggcgg gaggggggcgg | 420 |
| ggggagcacg ccagccgccg agagtggggg gcgatggcga agctccgggt ggcttacgag | 480 |
| tacacggaag ccgaggacaa gagcatccgg ctcggcttgt ttctcatcat ctccggcgtc | 540 |
| gtgtcgctct tcatcttcgg cttctgctgg ctgagtcccg cgctgcagga tctgcaagcc | 600 |
| acggaggcca attgcacggt gctgtcggtg cagcagatcg gcgaggtgtt cgagtgcacc | 660 |
| ttcacctgtg gcgccgactg caggggcacc tcgcagtacc cctgcgtcca ggtctacgtg | 720 |
| aacaactctg agtccaactc tagggcgctg ctgcacagcg acgagcacca gctcctgacc | 780 |
| aaccccaagt gctcctatat ccctcccctgt aagagagaaa atcagaagaa tttggaaagt | 840 |
| gtcatgaatt ggcaacagta ctggaaagat gagattggtt cccagccatt tacttgctat | 900 |
| tttaatcaac atcaaagacc agatgatgtg cttctgcatc gcactcatga tgagattgtc | 960 |
| ctcctgcatt gcttcctctg gcccctggtg acatttgtgg tgggcgttct cattgtggtc | 1020 |
| ctgaccatct gtgccaagag cttggcggtc aaggcggaag ccatgaagaa gcgcaagttc | 1080 |
| tcttaaaggg gaaggaggct tgtagaaagc aaagtacaga agctgtactc atcggcacgc | 1140 |
| gtccacctgc ggaacctgtg tttcctggcg caggagatgg acagggccac gacagggctc | 1200 |
| tgagaggctc atccctcagt ggcaacagaa acaggcacaa ctggaagact tggaacctca | 1260 |
| aagcttgtat tccatctgct gtagcaatgg ctaaagggtc aagatcttag ctgtatggag | 1320 |
| taactatttc agaaaaccct ataagaagtt catttctctt caaaagtaac agtatattat | 1380 |
| ttgtacagtg tagtatacaa accattatga tttatgctac ttaaaaatat taaaatagag | 1440 |
| tggtctgtgt tattttctat ttccttttttt atgcttagaa caccagggtt taaaaaaaaa | 1500 |
| aaaaaggtga ggacatctgg gtctcatttg cttctgctag gttaaacttt tacttgacaa | 1560 |
| caaggattcc tgctgaagtc tgaaccttac tgtgtaaccc tcagtttcca ctattaaaga | 1620 |
| gtatcttttg acgtctgctt ggaaaatgaa tagtatactg gtaactcagt ctccagtcac | 1680 |
| ctctgtgtct cttaagcaag agattctaaa agattgggaa aacatatcct ccaacacctg | 1740 |
| cctttgccta accattattt ttccaccagat tacttcttaa gagagggagg tgattctgaa | 1800 |
| gaaggcttct atctcaaaaa gcactgggct tccttattca tctgttcttg ttgttttga | 1860 |
| cggagttaaa aaagtttgtg tgcaatacaa tatacatgat gtgaaggaca ctcttcagct | 1920 |

```
tagtgaaacg ctgttttcat tttttttttt ttttgtaggt cagaaaaaaa caacaaaatc    1980
agttcaagca ttttttttc tttgtccttg ccttgatgtt atgagtatta aaaccaggag    2040
gattgctgcc attgtgcagt tgcttagac aaacctggag atgcaaccca gctcacatca    2100
ttgctactga tgagctttct gtgcctttat caaaagttga ttgagaagac catatttctt    2160
tgtatctttt tataaactca aattccaagt atcaaatcgc aggtctcagt gaacatcaaa    2220
cctatttact acatagaatc aaaccttgt ttaggtgaga tgtacatcgt tagtggagga    2280
aaaactgaca acctaatttc atttgttttc ttctgatact cttcagacat gcctctatta    2340
gaataaaggt aaactggaat ttaaagacaa gttcccctca gttatttcca tggagctgta    2400
atatgtatat atggagtgat ggtttcctga cctttagtcc ataccaat gttttctttt    2460 ttcttttttt tttttttttt tgagatggtg tctcactctg ttgccaggct ggagtgcagt    2520
ggcacgatct cggctcacta cagtctccac ctcctgggtt caagtcattc ctctgcctca    2580
gcctcccgag tagctgggac tacaggcacg caccaccacg cctggctaat ttttttgtat    2640
ttttagtaga cgggggttt caccgtgtta gccaggatgg tctcaatctc ctgaccttgt    2700
gatctgccca cttcacctcc caaagtgctg ggattacagg ccaatgtttt cttaatctta    2760
gaatgtgaat aactgaaaat catagtctgt ggaaaggtgt tgaattgagt ataatcttct    2820
tctgtttatt tttgtgtttt gttttttaac agatgggtat cttgctatgt tgcccaggat    2880
ggagtgcagt agctattcac aggtatgatc atagcacact gcagcctcaa gctcctgggc    2940
tcaagcgatc cccctccctc agcctcccaa gtatctgggg ttactggtgt gcaccaccgt    3000
gcttggctcc aataatttt tttctaattc aaaagttaca gtttcactgt gaaaaaggcc    3060
ttgaacacac tatttatgac atcttttgag gcagctccag tgccttgact tcaatcccag    3120
tttccggttg cagcatcctt gttgtcttag caacacagtg aactattctg aagcatagag    3180
taacacgaaa ctgggagtcc gagaaataat catctctgca tcacattatg ggagacgaag    3240
tctgctttat ccattttatc tttattcagt tgtctatgat taattgatta cagagtagta    3300
gattagaata gtgcatggat atacatttgt gttgaaaaaa ggggaagttg atatatatca    3360
atcttagttt tcatttatca gtttgatatt catgcattta cactaaacgc ttccatttat    3420
cccgaaaaag tatatgcaac tgtattctgt aggttgattt ttggaaaagg ggagaagcac    3480
actgaattca taaggtcaca tgtagtctta aggtcttact tgcttacagc caattaaatt    3540
tgaagcacct tatttatact tgttaaaggt aaaacccaaa agaacaagca gaggacattt    3600
taaggtcata aaaggtaaat aagcttacct tcttaatgtt ttcattctct ttttgtataa    3660
atcagaaaat gatctaaact gctgtaacaa agagacccca aaatatgatg gctcatgtaa    3720
gataatttat ttttttctca catagcaatc cagaagtggc ttcatttcac aaggtattca    3780
agggatatag gagtcatcta ccttgttagt tctcttaata cccaagggta ttgttctttc    3840
catggtcaaa gctggctcaa gacttcctag cctgtgaaaa aagaagaagg tggagcaagc    3900
catttccttt ttaggaaatt acagccatca cttctgccca ccgtccattc atgaatactt    3960
actatatagc tatacctagc ttcaagaaag cctgggacgt gtctctaact agatggacat    4020
gtgccctact aaaactccag ggaaagggtt ctattactaa agctaaaaag aggggaatga    4080
atactagagt taaagacaaa aatgatagca gccaatggcc catgccgtga taatctgctg    4140
agcaggcatg atggagatcc cttgcccagc agaaagtgtt ccttggtgaa atcatgaatc    4200
tgctatctag gagaaactcc cttgtccatt gtcttctgtg gccactagtt tgacctctag    4260
gaaagtcttg ctcgtcagct tctgtggccc cgtctgaaac ttttgaggga catcgcagct    4320
```

| | |
|---|---|
| tttgcagccc ctgcttgctg gtgcagactt ttagacctag attgccttag agactgaaaa | 4380 |
| atatacgctt ttataggccg gggttttagt tcatttgact gtaataaaga cgtcaatgcc | 4440 |
| gtttttaatg tttgactgct gacatctttc aagactcacc tttcccttct cccttatgct | 4500 |
| gcacatctgg gcaagctgat ggaagcatgg gtgcctcctc ctttggcccc agcaggaagt | 4560 |
| tcaaatcacg caagccctgg catgcatgca ggaagcttca ccccagcctc acactctaag | 4620 |
| acggataaaa gccaaaccaa ttaagccgtt tctcgaccct cctgggagcc tgccctatct | 4680 |
| ccctggaaag tctcagtatg tgagtaataa accttttat accca | 4725 |

<210> SEQ ID NO 18
<211> LENGTH: 3987
<212> TYPE: DNA
<213> ORGANISM: Homo sapiens

<400> SEQUENCE: 18

| | |
|---|---|
| cttcctggac tggggatccc ggctaaatat agctgtttct gtcttacaac acaggctcca | 60 |
| gtatataaat caggcaaatt ccccatttga gcatgaacct ctgaaaactg ccggcatctg | 120 |
| aggtttcctc caaggccctc tgaagtgcag cccataatga aggtcttggc ggcaggagtt | 180 |
| gtgccctgc tgttggttct gcactggaaa catggggcgg ggagccccct ccccatcacc | 240 |
| cctgtcaacg ccacctgtgc catacgccac ccatgtcaca acaacctcat gaaccagatc | 300 |
| aggagccaac tggcacagct caatggcagt gccaatgccc tctttattct ctattacaca | 360 |
| gcccagggg agccgttccc caacaacctg gacaagctat gtggccccaa cgtgacggac | 420 |
| ttcccgccct tccacgccaa cggcacggag aaggccaagc tggtggagct gtaccgcata | 480 |
| gtcgtgtacc ttggcacctc cctgggcaac atcacccggg accagaagat cctcaacccc | 540 |
| agtgccctca gcctccacag caagctcaac gccaccgccg acatcctgcg aggcctcctt | 600 |
| agcaacgtgc tgtgccgcct gtgcagcaag taccacgtgg gccatgtgga cgtgacctac | 660 |
| ggccctgaca cctcgggtaa ggatgtcttc cagaagaaga agctgggctg tcaactcctg | 720 |
| gggaagtata agcagatcat cgccgtgttg gcccaggcct tctagcagga ggtcttgaag | 780 |
| tgtgctgtga accgagggat ctcaggagtt gggtccagat gtgggggcct gtccaagggt | 840 |
| ggctggggcc cagggcatcg ctaaacccaa atggggggctg ctggcagacc ccgagggtgc | 900 |
| ctggccagtc cactccactc tgggctgggc tgtgatgaag ctgagcagag tggaaacttc | 960 |
| catagggagg gagctagaag aaggtgcccc ttcctctggg agattgtgga ctggggagcg | 1020 |
| tgggctggac ttctgcctct acttgtccct ttggccccctt gctcactttg tgcagtgaac | 1080 |
| aaactacaca agtcatctac aagagccctg accacagggt gagacagcag ggcccagggg | 1140 |
| agtggaccag cccccagcaa attatcacca tctgtgcctt tgctgccct taggttggga | 1200 |
| cttaggtggg ccagaggggc taggatccca aaggactcct tgtcccctag aagtttgatg | 1260 |
| agtggaagat agagagggc ctctgggatg gaaggctgtc ttcttttgag gatgatcaga | 1320 |
| gaacttgggc ataggaacaa tctggcagaa gtttccagaa ggaggtcact tggcattcag | 1380 |
| gctcttgggg aggcagagaa gccaccttca ggcctgggaa ggaagacact gggaggagga | 1440 |
| gaggcctgga aagctttggt aggttcttcg ttctcttccc cgtgatcttc cctgcagcct | 1500 |
| gggatggcca gggtctgatg gctggacctg cagcaggggt ttgtggaggt gggtagggca | 1560 |
| ggggcaggtt gctaagtcag gtgcagaggt tctgagggac ccaggctctt cctctgggta | 1620 |
| aaggtctgta agaaggggct ggggtagctc agagtagcag ctcacatctg aggccctggg | 1680 |

```
aggccttgtg aggtcacaca gaggtacttg aggggggactg gaggccgtct ctggtcccca    1740
gggcaaggga acagcagaac ttagggtcag ggtctcaggg aaccctgagc tccaagcgtg    1800
ctgtgcgtct gacctggcat gatttctatt tattatgata tcctatttat attaacttat    1860
tggtgctttc agtggccaag ttaattcccc tttccctggt ccctactcaa caaaatatga    1920
tgatggctcc cgacacaagc gccagggcca gggcttagca gggcctggtc tggaagtcga    1980
caatgttaca agtggaataa gccttacggg tgaagctcag agaagggtcg gatctgagag    2040
aatggggagg cctgagtggg agtgggggggc cttgctccac cccccccat cccctactgt    2100
gacttgcttt agggtgtcag ggtccaggct gcaggggctg ggccaatttg tggagaggcc    2160
gggtgccttt ctgtcttgat tccagggggc tggttcacac tgttcttggg cgccccagca    2220
ttgtgttgtg aggcgcactg ttcctggcag atattgtgcc ccctggagca gtgggcaaga    2280
cagtccttgt ggcccaccct gtccttgttt ctgtgtcccc atgctgcctc tgaaatagcg    2340
ccctggaaca accctgcccc tgcacccagc atgctccgac acagcaggga agctcctcct    2400
gtggcccgga cacccataga cggtgcgggg ggcctggctg ggccagaccc caggaaggtg    2460
gggtagactg ggggggatcag ctgcccattg ctcccaagag gaggagaggg aggctgcaga    2520
tgcctgggac tcagaccagg aagctgtggg ccctcctgct ccaccccat cccactccca    2580
cccatgtctg ggctcccagg cagggaaccc gatctcttcc tttgtgctgg ggccaggcga    2640
gtggagaaac gccctccagt ctgagagcag ggggaggaag gaggcagcag agttggggca    2700
gctgctcaga gcagtgttct ggcttcttct caaaccctga gcgggctgcc ggcctccaag    2760
ttcctccgac aagatgatgg tactaattat ggtactttc actcactttg caccctttccc    2820
tgtcgctctc taagcacttt acctggatgg cgcgtgggca gtgtgcaggc aggtcctgag    2880
gcctggggtt ggggtggagg gtgcggcccg gagttgtcca tctgtccatc ccaacagcaa    2940
gacgaggatg tggctgttga gatgtgggcc acactcaccc ttgtccagga tgcagggact    3000
gccttctcct tcctgcttca tccggcttag cttggggctg gctgcattcc cccaggatgg    3060
gcttcgagaa agacaaactt gtctggaaac cagagttgct gattccaccc gggggggcccg    3120
gctgactcgc ccatcacctc atctccctgt ggacttggga gctctgtgcc aggcccacct    3180
tgcggccctg gctctgagtc gctctcccac ccagcctgga cttggcccca tgggacccat    3240
cctcagtgct ccctccagat cccgtccggc agcttggcgt ccaccctgca cagcatcact    3300
gaatcacaga gcctttgcgt gaaacagctc tgccaggccg ggagctgggt ttctcttccc    3360
tttttatctg ctggtgtgga ccacacctgg gcctggccgg aggaagagag agtttaccaa    3420
gagagatgtc tccgggccct tatttattat ttaaacattt ttttaaaaag cactgctagt    3480
ttacttgtct ctcctcccca tcgtccccat cgtcctcctt gtccctgact tggggcactt    3540
ccaccctgac ccagccagtc cagctctgcc ttgccggctc tccagagtag acatagtgtg    3600
tggggttgga gctctggcac ccggggaggt agcatttccc tgcagatggt acagatgttc    3660
ctgccttaga gtcatctcta gttccccacc tcaatcccgg catccagcct tcagtcccgc    3720
ccacgtgcta gctccgtggg cccaccgtgc ggccttagag gtttccctcc ttcctttcca    3780
ctgaaaagca catggccttg ggtgacaaat tcctctttga tgaatgtacc ctgtggggat    3840
gtttcatact gacagattat ttttatttat tcaatgtcat atttaaaata tttattttttt    3900
ataccaaatg aatacttttt tttttaagaa aaaaagaga atgaataaa gaatctactc    3960
ttggctggca aaaaaaaaaa aaaaaaa                                        3987
```

<210> SEQ ID NO 19
<211> LENGTH: 3808
<212> TYPE: DNA
<213> ORGANISM: Homo sapiens

<400> SEQUENCE: 19

| | | | | | |
|---|---|---|---|---|---|
| cttcctggac | tggggatccc | ggctaaatat | agctgtttct | gtcttacaac | acaggctcca | 60 |
| gtatataaat | caggcaaatt | ccccatttga | gcatgaacct | ctgaaaactg | ccggcatctg | 120 |
| aggtttcctc | caaggccctc | tgaagtgcag | cccataatga | aggtcttggc | ggcagtacac | 180 |
| agcccagggg | gagccgttcc | ccaacaacct | ggacaagcta | tgtggcccca | acgtgacgga | 240 |
| cttcccgccc | ttccacgcca | acggcacgga | gaaggccaag | ctggtggagc | tgtaccgcat | 300 |
| agtcgtgtac | cttggcacct | ccctgggcaa | catcacccgg | gaccagaaga | tcctcaaccc | 360 |
| cagtgccctc | agcctccaca | gcaagctcaa | cgccaccgcc | gacatcctgc | gaggcctcct | 420 |
| tagcaacgtg | ctgtgccgcc | tgtgcagcaa | gtaccacgtg | ggccatgtgg | acgtgaccta | 480 |
| cggccctgac | acctcgggta | aggatgtctt | ccagaagaag | aagctgggct | gtcaactcct | 540 |
| ggggaagtat | aagcagatca | tcgccgtgtt | ggcccaggcc | ttctagcagg | aggtcttgaa | 600 |
| gtgtgctgtg | aaccgaggga | tctcaggagt | tgggtccaga | tgtgggggcc | tgtccaaggg | 660 |
| tggctggggc | cagggcatc | gctaaaccca | aatgggggct | gctggcagac | cccgagggtg | 720 |
| cctggccagt | ccactccact | ctgggctggg | ctgtgatgaa | gctgagcaga | gtggaaactt | 780 |
| ccatagggag | ggagctagaa | gaaggtgccc | cttcctctgg | gagattgtgg | actggggagc | 840 |
| gtgggctgga | cttctgcctc | tacttgtccc | tttggcccct | tgctcacttt | gtgcagtgaa | 900 |
| caaactacac | aagtcatcta | caagagccct | gaccacaggg | tgagacagca | gggcccaggg | 960 |
| gagtggacca | gccccagca | aattatcacc | atctgtgcct | ttgctgcccc | ttaggttggg | 1020 |
| acttaggtgg | gccagagggg | ctaggatccc | aaaggactcc | ttgtcccta | gaagtttgat | 1080 |
| gagtggaaga | tagagagggg | cctctgggat | ggaaggctgt | cttcttttga | ggatgatcag | 1140 |
| agaacttggg | cataggaaca | atctggcaga | agtttccaga | aggaggtcac | ttggcattca | 1200 |
| ggctcttggg | gaggcagaga | agccaccttc | aggcctggga | aggaagacac | tgggaggagg | 1260 |
| agaggcctgg | aaagctttgg | taggttcttc | gttctcttcc | ccgtgatctt | ccctgcagcc | 1320 |
| tgggatggcc | agggtctgat | ggctggacct | gcagcagggg | tttgtggagg | tgggtagggc | 1380 |
| aggggcaggt | tgctaagtca | ggtgcagagg | ttctgaggga | cccaggctct | tcctctgggt | 1440 |
| aaaggtctgt | aagaaggggc | tggggtagct | cagagtagca | gctcacatct | gaggccctgg | 1500 |
| gaggccttgt | gaggtcacac | agaggtactt | gagggggact | ggaggccgtc | tctggtcccc | 1560 |
| agggcaaggg | aacagcagaa | cttagggtca | gggtctcagg | gaaccctgag | ctccaagcgt | 1620 |
| gctgtgcgtc | tgacctggca | tgatttctat | ttattatgat | atcctattta | tattaactta | 1680 |
| ttggtgcttt | cagtggccaa | gttaattccc | ctttccctgg | tccctactca | acaaaatatg | 1740 |
| atgatggctc | ccgacacaag | cgccagggcc | agggcttagc | agggcctggt | ctggaagtcg | 1800 |
| acaatgttac | aagtggaata | agccttacgg | gtgaagctca | gagaagggtc | ggatctgaga | 1860 |
| gaatggggag | gcctgagtgg | gagtgggggg | ccttgctcca | ccccccccca | tccctactg | 1920 |
| tgacttgctt | tagggtgtca | gggtccaggc | tgcagggct | gggccaattt | gtggagaggc | 1980 |
| cgggtgcctt | tctgtcttga | ttccaggggg | ctggttcaca | ctgttcttgg | gcgccccagc | 2040 |
| attgtgttgt | gaggcgcact | gttcctggca | gatattgtgc | ccctggagc | agtgggcaag | 2100 |
| acagtccttg | tggcccaccc | tgtccttgtt | tctgtgtccc | catgctgcct | ctgaaatagc | 2160 |

| | |
|---|---|
| gccctggaac aaccctgccc ctgcacccag catgctccga cacagcaggg aagctcctcc | 2220 |
| tgtggcccgg acacccatag acggtgcggg gggcctggct gggccagacc ccaggaaggt | 2280 |
| ggggtagact gggggggatca gctgcccatt gctcccaaga ggaggagagg gaggctgcag | 2340 |
| atgcctggga ctcagaccag gaagctgtgg gccctcctgc tccacccca tcccactccc | 2400 |
| acccatgtct gggctcccag gcagggaacc cgatctcttc ctttgtgctg gggccaggcg | 2460 |
| agtggagaaa cgccctccag tctgagagca ggggagggaa ggaggcagca gagttggggc | 2520 |
| agctgctcag agcagtgttc tggcttcttc tcaaaccctg agcgggctgc cggcctccaa | 2580 |
| gttcctccga caagatgatg gtactaatta tggtactttt cactcacttt gcacctttcc | 2640 |
| ctgtcgctct ctaagcactt tacctggatg gcgcgtgggc agtgtgcagg caggtcctga | 2700 |
| ggcctggggt tggggtggag ggtgcggccc ggagttgtcc atctgtccat cccaacagca | 2760 |
| agacgaggat gtggctgttg agatgtgggc cacactcacc cttgtccagg atgcagggac | 2820 |
| tgccttctcc ttcctgcttc atccggctta gcttgggct ggctgcattc ccccaggatg | 2880 |
| ggcttcgaga aagacaaaact tgtctggaaa ccagagttgc tgattccacc cggggggccc | 2940 |
| ggctgactcg cccatcacct catctccctg tggacttggg agctctgtgc caggcccacc | 3000 |
| ttgcggccct ggctctgagt cgctctccca cccagcctgg acttggcccc atgggaccca | 3060 |
| tcctcagtgc tccctccaga tcccgtccgg cagcttggcg tccaccctgc acagcatcac | 3120 |
| tgaatcacag agcctttgcg tgaaacagct ctgccaggcc gggagctggg tttctcttcc | 3180 |
| cttttatct gctggtgtgg accacacctg ggcctggccg gaggaagaga gagtttacca | 3240 |
| agagagatgt ctccgggccc ttatttatta tttaaacatt tttttaaaaa gcactgctag | 3300 |
| tttacttgtc tctcctcccc atcgtcccca tcgtcctcct tgtccctgac ttggggcact | 3360 |
| tccaccctga cccagccagt ccagctctgc cttgccggct ctccagagta gacatagtgt | 3420 |
| gtggggttgg agctctggca cccggggagg tagcatttcc ctgcagatgg tacagatgtt | 3480 |
| cctgccttag agtcatctct agttcccac ctcaatcccg gcatccagcc ttcagtcccg | 3540 |
| cccacgtgct agctccgtgg gcccaccgtg cggccttaga ggtttccctc cttccttttcc | 3600 |
| actgaaaagc acatggcctt gggtgacaaa ttcctctttg atgaatgtac cctgtgggga | 3660 |
| tgtttcatac tgacagatta ttttttattta ttcaatgtca tatttaaaat atttattttt | 3720 |
| tataccaaat gaatactttt ttttttaaga aaaaaagag aaatgaataa agaatctact | 3780 |
| cttggctggc aaaaaaaaaa aaaaaaa | 3808 |

<210> SEQ ID NO 20
<211> LENGTH: 1668
<212> TYPE: DNA
<213> ORGANISM: Homo sapiens

<400> SEQUENCE: 20

| | |
|---|---|
| attctcagca cagcctttaa ggttccaaac atctgctaga agaggaatgc agatttaaac | 60 |
| tgagtgaggt gtggagtggg ggaagttgat tgggtctaga ccaaagaact ttgaggaact | 120 |
| tgcccagagc cctgcatgca tcagacctac agcagacatt gcaggcctga agaaagcacc | 180 |
| ttttctgctg ccatgacaac catgcaagga atggaacagg ccatgccagg ggctggccct | 240 |
| ggtgtgcccc agctgggaaa catggctgtc atacattcac atctgtggaa aggattgcaa | 300 |
| gagaagttct tgaagggaga acccaaagtc cttggggttg tgcagattct gactgccctg | 360 |
| atgagcctta gcatgggaat aacaatgatg tgtatggcat ctaatactta tggaagtaac | 420 |
| cctatttccg tgtatatcgg gtacacaatt tggggtcag taatgtttat tatttcagga | 480 |

| | |
|---|---|
| tccttgtcaa ttgcagcagg aattagaact acaaaaggcc tggtccgagg tagtctagga | 540 |
| atgaatatca ccagctctgt actggctgca tcagggatct taatcaacac atttagcttg | 600 |
| gcgttttatt cattccatca cccttactgt aactactatg gcaactcaaa taattgtcat | 660 |
| gggactatgt ccatcttaat gggtctggat ggcatggtgc tcctcttaag tgtgctggaa | 720 |
| ttctgcattg ctgtgtccct ctctgccttt ggatgtaaag tgctctgttg taccccctggt | 780 |
| ggggttgtgt taattctgcc atcacattct cacatggcag aaacagcatc tcccacacca | 840 |
| cttaatgagg tttgaggcca ccaaaagatc aacagacaaa tgctccagaa atctatgctg | 900 |
| actgtgacac aagagcctca catgagaaat taccagtatc caacttcgat actgatagac | 960 |
| ttgttgatat tattattata tgtaatccaa ttatgaactg tgtgtgtata gagagataat | 1020 |
| aaattcaaaa ttatgttctc attttttttcc ctggaactca ataactcatt tcactggctc | 1080 |
| tttatcgaga gtactagaag ttaaattaat aaataatgca tttaatgagg caacagcact | 1140 |
| tgaaagttttt tcattcatca taagaacttt atataaaggc attacattgg caaataaggt | 1200 |
| ttggaagcag aagagcaaaa aaaagatatt gttaaaatga ggcctccatg caaaacacat | 1260 |
| acttccctcc catttattta actttttttt tctcctacct atggggacca aagtgctttt | 1320 |
| tccttcagga agtggagatg catggccatc tcccccctccc tttttccttc tcctgctttt | 1380 |
| ctttccccat agaaagtacc ttgaagtagc acagtccgtc cttgcatgtg cacgagctat | 1440 |
| catttgagta aaagtataca tggagtaaaa atcatattaa gcatcagatt caacttatat | 1500 |
| tttctatttc atcttcttcc tttcccttct cccaccttct actgggcata attatatctt | 1560 |
| aatcatatat ggaaatgtgc aacatatggt atttgttaaa tacgtttgtt tttattgcag | 1620 |
| agcaaaaata aatcaaatta gaagcaataa aaaaaaaaaa aaaaaaaa | 1668 |

<210> SEQ ID NO 21
<211> LENGTH: 1814
<212> TYPE: DNA
<213> ORGANISM: Homo sapiens

<400> SEQUENCE: 21

| | |
|---|---|
| attctcagca cagcctttaa ggttccaaac atctgctaga agaggaatgc agatttaaac | 60 |
| tgagtgaggt gtggagtggg ggaagttgat tgggtctaga ccaaagaact ttgaggaact | 120 |
| tgcccagagc cctgcatgca tcagacctac agcagacatt gcaggcctga agaaaggtgg | 180 |
| tcacaagagg ggtggaacat tcctgcaaat ggtttcaata tatgcagatg tctcaatata | 240 |
| ggaatgaaat tacgtctttg gaacaactta ataagtcaa atatacttgg agctttaaaa | 300 |
| attaaaagga gagagattcg agcacctttt ctgctgccat gacaaccatg caaggaatgg | 360 |
| aacaggccat gccaggggct ggccctggtg tgccccagct gggaaacatg gctgtcatac | 420 |
| attcacatct gtggaaagga ttgcaagaga agttcttgaa gggagaaccc aaagtccttg | 480 |
| gggttgtgca gattctgact gccctgatga gccttagcat gggaataaca atgatgtgta | 540 |
| tggcatctaa tacttatgga agtaaaccta tttccgtgta tatcgggtac acaatttggg | 600 |
| ggtcagtaat gttttattatt tcaggatcct tgtcaattgc agcaggaatt agaactacaa | 660 |
| aaggcctggt ccgaggtagt ctaggaatga atatcaccag ctctgtactg ctgcatcag | 720 |
| ggatcttaat caacacattt agcttggcgt tttattcatt ccatcaccct tactgtaact | 780 |
| actatgcaa ctcaaataat tgtcatggga ctatgtccat cttaatgggt ctggatggca | 840 |
| tggtgctcct cttaagtgtg ctggaattct gcattgctgt gtccctctct gcctttggat | 900 |

| | |
|---|---|
| gtaaagtgct ctgttgtacc cctggtgggg ttgtgttaat tctgccatca cattctcaca | 960 |
| tggcagaaac agcatctccc acaccactta atgaggtttg aggccaccaa aagatcaaca | 1020 |
| gacaaatgct ccagaaatct atgctgactg tgacacaaga gcctcacatg agaaattacc | 1080 |
| agtatccaac ttcgatactg atagacttgt tgatattatt attatatgta atccaattat | 1140 |
| gaactgtgtg tgtatagaga gataataaat tcaaaattat gttctcattt ttttccctgg | 1200 |
| aactcaataa ctcatttcac tggctcttta tcgagagtac tagaagttaa attaataaat | 1260 |
| aatgcattta atgaggcaac agcacttgaa agttttcat tcatcataag aactttatat | 1320 |
| aaaggcatta cattggcaaa taaggtttgg aagcagaaga gcaaaaaaaa gatattgtta | 1380 |
| aaatgaggcc tccatgcaaa acacatactt ccctcccatt tatttaactt ttttttttctc | 1440 |
| ctacctatgg ggaccaaagt gcttttcct tcaggaagtg gagatgcatg gccatctccc | 1500 |
| cctccctttt tccttctcct gcttttcttt ccccatagaa agtaccttga agtagcacag | 1560 |
| tccgtccttg catgtgcacg agctatcatt tgagtaaaag tatacatgga gtaaaaatca | 1620 |
| tattaagcat cagattcaac ttatatttc tatttcatct tcttcctttc ccttctccca | 1680 |
| ccttctactg ggcataatta tatcttaatc atatatggaa atgtgcaaca tatggtattt | 1740 |
| gttaaatacg tttgttttta ttgcagagca aaataaatc aaattagaag caataaaaaa | 1800 |
| aaaaaaaaaa aaaa | 1814 |

<210> SEQ ID NO 22
<211> LENGTH: 1509
<212> TYPE: DNA
<213> ORGANISM: Homo sapiens

<400> SEQUENCE: 22

| | |
|---|---|
| attctcagca cagcctttaa ggttccaaac atctgctaga agaggaatgc agatttaaac | 60 |
| tgagtgaggt gtggagtggg ggaagttgat tgggtctaga ccaaagaact ttgaggaact | 120 |
| tgcccagagc cctgcatgca tcagacctac agcagacatt gcaggcctga agaaagcacc | 180 |
| ttttctgctg ccatgacaac catgcaagga atggaacagg ccatgccagg ggctggccct | 240 |
| ggtgtgcccc agctgggaaa catggctgtc atacattcac atctgtggaa aggattgcaa | 300 |
| gagaagttct tgaagggaga acccaaagtc cttggggttg tgcagattct gactgccctg | 360 |
| atgagcctta gcatgggaat aacaatgatg tgtatggcat ctaatactta tggaagtaac | 420 |
| cctatttccg tgtatatcgg gtacacaatt tgggggtcag taatgtttat tatttcagga | 480 |
| tccttgtcaa ttgcagcagg aattagaact acaaaaggcc tgggtctgga tggcatggtg | 540 |
| ctcctcttaa gtgtgctgga attctgcatt gctgtgtccc tctctgcctt tggatgtaaa | 600 |
| gtgctctgtt gtaccctgg tggggttgtg ttaattctgc catcacattc tcacatggca | 660 |
| gaaacagcat ctcccacacc acttaatgag gtttgaggcc accaaaagat caacagacaa | 720 |
| atgctccaga aatctatgct gactgtgaca agagcctc acatgagaaa ttaccagtat | 780 |
| ccaacttcga tactgataga cttgttgata ttattattat atgtaatcca attatgaact | 840 |
| gtgtgtgtat agagagataa taaattcaaa attatgttct cattttttc cctggaactc | 900 |
| aataactcat ttcactggct ctttatcgag agtactagaa gttaaattaa taataatgc | 960 |
| atttaatgag gcaacagcac ttgaaagttt ttcattcatc ataagaactt tatataaagg | 1020 |
| cattacattg gcaaataagg tttggaagca gaagagcaaa aaaagatat tgttaaaatg | 1080 |
| aggcctccat gcaaaacaca tacttccctc ccatttattt aacttttttt ttctcctacc | 1140 |
| tatggggacc aaagtgcttt ttccttcagg aagtggagat gcatggccat ctccccctcc | 1200 |

```
cttttttcctt ctcctgcttt tctttcccca tagaaagtac cttgaagtag cacagtccgt    1260
ccttgcatgt gcacgagcta tcatttgagt aaaagtatac atggagtaaa aatcatatta    1320
agcatcagat tcaacttata ttttctattt catcttcttc ctttcccttc tcccaccttc    1380
tactgggcat aattatatct taatcatata tggaaatgtg caacatatgg tatttgttaa    1440
atacgtttgt ttttattgca gagcaaaaat aaatcaaatt agaagcaata aaaaaaaaaa    1500
aaaaaaaaa                                                             1509

<210> SEQ ID NO 23
<211> LENGTH: 3291
<212> TYPE: DNA
<213> ORGANISM: Homo sapiens

<400> SEQUENCE: 23
agaatcggag agccggtggc gtcgcaggtc gggaggacga gcaccgagtc gagggctcgc      60
tcgtctgggc cgcccgagag tcttaatcgc gggcgcttgg gccgccatct tagatggcgg     120
gagtaagagg aaaacgattg tgaggcggga acggctttct gctgcctttt ttgggccccg     180
aaaagggtca gctggccggg cttggggcg cgtgccctga ggcgcggagc gcgtttgcta      240
cgatgcgggg gctgctcggg gctccgtccc ctgggctggg gacgcgccga atgtgaccgc     300
ctcccgctcc ctcacccgcc gcggggagga ggagcgggcg agaagctgcc gccgaacgac     360
aggacgttgg ggcggcctgg ctccctcagg tttaagaatt gtttaagctg catcaatgga     420
gcacatacag ggagcttgga agacgatcag caatggtttt ggattcaaag atgccgtgtt     480
tgatggctcc agctgcatct ctcctacaat agttcagcag tttggctatc agcgccgggc     540
atcagatgat ggcaaactca cagatccttc taagacaagc aacactatcc gtgttttctt     600
gccgaacaag caaagaacag tggtcaatgt gcgaaatgga atgagcttgc atgactgcct     660
tatgaaagca ctcaaggtga ggggcctgca accagagtgc tgtgcagtgt tcagacttct     720
ccacgaacac aaaggtaaaa agcacgcctt agattggaat actgatgctg cgtctttgat     780
tggagaagaa cttcaagtag atttcctgga tcatgttccc ctcacaacac acaactttgc     840
tcggaagacg ttcctgaagc ttgccttctg tgacatctgt cagaaattcc tgctcaatgg     900
atttcgatgt cagacttgtg gctacaaaat tcatgagcac tgtagcacca agtacctac      960 tatgtgtgtg gactggagta acatcagaca actcttattg tttccaaatt ccactattgg    1020
tgatagtgga gtcccagcac taccttcttt gactatgcgt cgtatgcgag agtctgttc     1080 caggatgcct gttagttctc agcacagata ttctacacct cacgccttca cctttaacac    1140
ctccagtccc tcatctgaag gttccctctc ccagaggcag aggtcgacat ccacacctaa    1200
tgtccacatg gtcagcacca ccctgcctgt ggacagcagg atgattgagg atgcaattcg    1260
aagtcacagc gaatcagcct caccttcagc cctgtccagt agccccaaca atctgagccc    1320
aacaggctgg tcagagccga aaccccccgt gccagcacaa agagagcggg caccagtatc    1380
tgggacccag gagaaaaaca aaattaggcc tcgtggacag agagattcaa gctattattg    1440
ggaaatagaa gccagtgaag tgatgctgtc cactcggatt gggtcaggct cttttggaac    1500
tgtttataag ggtaaatggc acggagatgt tgcagtaaag atcctaaagg ttgtcgaccc    1560 aacccccagag caattccagg ccttcaggaa tgaggtggct gttctgcgca aaacacggca    1620
tgtgaacatt ctgctttca tggggtacat gacaaaggac aacctggcaa ttgtgaccca    1680
gtggtgcgag ggcagcagcc tctacaaaca cctgcatgtc caggagacca gtttcgagat    1740
```

```
gttccagcta attgacattg cccggcagac ggctcaggga atggactatt tgcatgcaaa    1800
gaacatcatc catagagaca tgaaatccaa caatatattt ctccatgaag gcttaacagt    1860
gaaaattgga gattttggtt tggcaacagt aaagtcacgc tggagtggtt ctcagcaggt    1920
tgaacaacct actggctctg tcctctggat ggcccagag gtgatccgaa tgcaggataa     1980
caacccattc agtttccagt cggatgtcta ctcctatggc atcgtattgt atgaactgat    2040
gacgggggag cttccttatt ctcacatcaa caaccgagat cagatcatct tcatggtggg    2100
ccgaggatat gcctccccag atcttagtaa gctatataag aactgcccca agcaatgaa    2160 gaggctggta gctgactgtg tgaagaaagt aaaggaagag aggcctcttt tcccccagat    2220
cctgtcttcc attgagctgc tccaacactc tctaccgaag atcaaccgga gcgcttccga    2280
gccatccttg catcgggcag cccacactga ggatatcaat gcttgcacgc tgaccacgtc    2340
cccgaggctg cctgtcttct agttgacttt gcacctgtct tcaggctgcc aggggaggag    2400
gagaagccag caggcaccac ttttctgctc cctttctcca gaggcagaac acatgttttc    2460
agagaagctg ctgctaagga ccttctagac tgctcacagg gccttaactt catgttgcct    2520
tcttttctat ccctttgggc cctgggagaa ggaagccatt tgcagtgctg gtgtgtcctg    2580
ctccctcccc acattcccca tgctcaaggc ccagccttct gtagatgcgc aagtggatgt    2640
tgatggtagt acaaaaagca gggccccagc cccagctgtt ggctacatga gtatttagag    2700
gaagtaaggt agcaggcagt ccagccctga tgtggagaca catgggattt tggaaatcag    2760
cttctggagg aatgcatgtc acaggcggga cttcttcag agagtggtgc agcgccagac    2820
attttgcaca taaggcacca acagcccag gactgccgag actctggccg cccgaaggag    2880
cctgctttgg tactatggaa cttttcttag gggacacgtc ctcctttcac agcttctaag    2940
gtgtccagtg cattgggatg gttttccagg caaggcactc ggccaatccg catctcagcc    3000
ctctcaggga gcagtcttcc atcatgctga attttgtctt ccaggagctg cccctatggg    3060
gcggggccgc agggccagcc ttgtttctct aacaaacaaa caaacaaaca gccttgtttc    3120
tctagtcaca tcatgtgtat acaaggaagc caggaataca ggttttcttg atgatttggg    3180
ttttaatttt gttttttattg cacctgacaa aatacagtta tctgatggtc cctcaattat    3240
gttattttaa taaataaat taaatttagg tgtaaaaaaa aaaaaaaaa a               3291
```

<210> SEQ ID NO 24
<211> LENGTH: 2134
<212> TYPE: DNA
<213> ORGANISM: Homo sapiens

<400> SEQUENCE: 24

```
ggagttgaga attagggagg aggtggtaga gtccgggtag tgagcggagg gacaggaagg     60
gtagggcaag aaagggagag gggacaggag ggaagggtgg gccaaagcgg tgagaaagga    120
gggccagcca gttgggtggg ggagagggcc gaggcccggg ggcaggagtg cagggctctg    180
aggcggggag aggagaggag agaagagccg cgggggccc agcccggagc caggatgccc     240
gcgccgcgcg cccgggagca gccccgcgtg cccggggagc gccagccgct gctgcctcgc    300
ggtgcgcggg gccctcgacg gtggcggcgg cggcgggcg cggccgtgct gctggtggag    360
atgctggagc gcgccgcctt cttcggcgtc accgccaacc tcgtgctgta cctcaacagc    420
accaacttca ctggaccggg cgagcaggcg acgcgcgccg cgctggtatt cctgggcgcc    480
tcctacctgc tggcgcccgt gggcggctgg ctggccgacg tgtacctggg ccgctaccgc    540
gcggtcgcgc tcagcctgct gctctacctg gccgcctcgg gcctgctgcc cgccaccgcc    600
```

```
ttccccgacg gccgcagctc cttctgcgga gagatgcccg cgtcgccgct gggacctgcc    660
tgcccctcgg ccggctgccc gcgctcctcg cccagcccct actgcgcgcc cgtcctctac    720
gcgggcctgc tgctactcgg cctggccgcc agctccgtcc ggagcaacct cacctccttc    780
ggtgccgacc aggtgatgga tctcggccgc gacgccaccc gccgcttctt caactggttt    840
tactggagca tcaacctggg tgctgtgctg tcgctgctgg tggtggcgtt tattcagcag    900
aacatcagct tcctgctggg ctacagcatc cctgtgggct gtgtgggcct ggcattttc    960 atcttcctct ttgccacccc cgtcttcatc accaagcccc cgatgggcag ccaagtgtcc   1020
tctatgctta agctcgctct ccaaaactgc tgccccagc tgtggcaacg acactcggcc    1080
agagaccgtc aatgtgcccg cgtgctggcc gacgagaggt ctccccagcc aggggcttcc   1140
ccgcaagagg acatcgccaa cttccaggtg ctggtgaaga tcttgcccgt catggtgacc   1200
ctggtgccct actggatggt ctacttccag atgcagtcca cctatgtcct gcagggtctt   1260
cacctccaca tcccaaacat tttcccagcc aacccggcca acatctctgt ggccctgaga   1320
gcccagggca gcagctacac gatcccggaa gcctggctcc tcctggccaa tgttgtggtg   1380
gtgctgattc tggtccctct gaaggaccgc ttgatcgacc ctttactgct gcggtgcaag   1440
ctgcttccct ctgctctgca aagatggcg ctggggatgt tctttggttt tacctccgtc   1500
attgtggcag gagtcctgga gatggagcgc ttacactaca tccaccacaa cgagaccgtg   1560
tcccagcaga ttggggaggt cctgtacaac gcggcaccac tgtccatctg gtggcagatc   1620
cctcagtacc tgctcattgg gatcagtgag atctttgcca gcatcccagg cctggagttt   1680
gcctactcag aggccccgcg ctccatgcag gcgccatca tgggcatctt cttctgcctg   1740 tcggggtgg gctcactgtt gggctccagc ctagtggcac tgctgtcctt gcccggggc    1800 tggctgcact gccccaagga cttgggaac atcaacaatt gccggatgga cctctacttc   1860
ttcctgctgg ctggcattca ggccgtcacg gctctcctat ttgtctggat cgctggacgc   1920
tatgagaggg cgtcccaggg cccagcctcc cacagccgtt tcagcaggga caggggctga   1980
acaggcccta ttccagcccc cttgcttcac tctaccggac agacggcagc agtcccagct   2040
ctggtttcct tctcggttta ttctgttaga atgaaatggt tccataaat aagggcatg    2100 agcccttcct cacgacaaaa aaaaaaaaaa aaaa                               2134
```

<210> SEQ ID NO 25
<211> LENGTH: 3165
<212> TYPE: DNA
<213> ORGANISM: Homo sapiens

<400> SEQUENCE: 25

```
gcttttcctg tagaaactag gagggactag ggagagtctg caaggggaag agtgtgtctg     60
tgacactgcc agcagcgcgc agagggaggg atggggcgg gtatcggcgt aggggccctc    120
ggaaagaacg gatattgctg tgacaccgcg ggacgctct gaaggacga gtgtcggtgt    180 ggcaccggtg cacgctgaag gagccggcgg aaccgggtgg ccatggggat gtgggcatcg    240
ctggacgctt tgtgggagat gccggccgag aagcgtatct tcgggccgt gctgctcttt    300 tcctggacag tgtatctttg ggagaccttc ctagcacagc ggcagagaag gatatataaa    360
acaacaactc atgtaccacc ggagttagga cagatcatgg attctgaaac atttgagaaa    420
tctcgactct atcaactgga taaaagcact ttcagcttct ggtcaggact ctattcagag    480
actgaaggca ctcttattct tctctttgga ggaatacctt atctctggag actttctgga    540
```

```
cggttctgtg gttatgctgg cttttggacca gaatatgaga tcactcagtc cctggtgttt    600
ctgctgttgg ctacactttt cagtgcattg actggtttgc catggagtct ttataatact    660
tttgtgatag aagaaaaaca tggcttcaat caacagactt tggggttctt catgaaagat    720
gcaatcaaga aatttgttgt gactcagtgt attttgttgc ctgtgtcttc acttctactt    780
tacattatta aaattggggg tgactatttt tttatttatg cctggctgtt cacattagtt    840
gtgtctctgg ttcttgtcac aatctatgct gattatattg ccccttattt tgacaaattc    900
acacctctgc ctgagggaaa gcttaaagaa gaaattgaag taatggcaaa gagtattgac    960
tttcctttga cgaaggtgta tgttgtggaa ggatctaaac gctcttccca cagcaatgct   1020
tatttttatg gcttcttcaa gaacaagcga atagttttgt tgacactct actagaagag   1080
tactctgtac taaacaaaga catccaggag gattctggca tggaaccccg caatgaggaa   1140
gaagggaaca gtgaagaaat aaaagctaaa gttaaaaata gaaacaagg atgtaaaaat   1200
gaggaggtac tcgctgtact aggccatgaa ctggggcact ggaagttggg acatacagtc   1260
aaaaatatca ttattagcca gatgaattct ttcctgtgtt tttttttatt tgctgtatta   1320
attggtcgaa aggagctttt tgctgcattt ggttttatg atagccaacc cactcttatt   1380
ggactattga tcatcttcca gtttattttt tcaccttaca atgaggttct ttcttttgc   1440
ctaacagtcc taagccgcag atttgagttt caagctgatg catttgccaa gaaactttggg   1500
aaggctaaag acttatattc tgctttaatc aaacttaaca agataactt gggattccct   1560
gtttctgact ggttgttctc aatgtggcat tattctcatc ctccactgct agagagactt   1620
caagctttga aaactatgaa gcaacactga gatgtccagg atctgtgact gaagacattt   1680
ctgattattt ctgtcctggc agcatgttcc agctcttgat gttttaaac ttttttttag   1740
aagaaaaatt aagtacagaa aagcccagat ttaaatacat ttaatatgtc attttaaaaa   1800
tgattttaat aattcatttc ttaaaacact gaatgaattt tgaagcttaa tgttttaaa   1860
ggcatagttt tatctttgac atctaattta ccatcaagtt gtaaaattat ttggaaaaat   1920
acagaactcg ttttatttgt atacttatat ggaatctgca tgtgaggtgt tgagggcat   1980
atgtttgaaa gagggagcat caccacagga atcctttctg tgaggtggaa acagtggtcc   2040
tgaatcattg tgctcacacc taacttgaaa tctggtctta ctttcatgct gttatgattt   2100
cacctggtga atcagtgttt taaataagaa aggtaatagt tggtaaggcc aatgttattt   2160
aaatgaaagt agttagaaaa atgctctcct attctaccaa attttaatt tctttcttcc   2220
ctttcttgct acacagtgat caagagtttc tcatagtgct ttgaagttag aaattatgta   2280
taggatattt taaatcattg agttttgtgg ggttttttg tttgtttgtt tcttttgttt   2340
tttgaaaat ccgtgtcttt atcttttttt cccacgtggt agatatgatc ccattggagg   2400
taaattgtag cttcttctca ttcatgcagt aaataataca tcctttcact cagcagagat   2460
ggccatatta aacacgtttt gctatgttaa aagtggcaga acaggaaaga cgaattaaaa   2520
ataacatttt ttaagcgaca taaggatgaa atactgatga atctctgtga cattacaggg   2580
aaaaaaatat agttttctat ctctttcaag ggcagaagag ttttcatttt tattttttgta   2640
attttatctg taagtcataa atattactta atcaggcctg attctactt tgaaaattac   2700
agttcttgaa atgcagataa tgtttacttt gaaacaaat gtcatgaatg atttccagtt   2760
tttaaagcta tatgtttcac tgcttcatat ctctgtccac tttctgaatg agaacttatt   2820
ttgtgcctag agctctcact cactgataat gcttattacc ttctgggcat ttattccaaa   2880
gtgggatcaa ctgtacgcct ttggtatctg accataaagt cttttgctcc gctgacattt   2940
```

```
gggtgatgtc ttcacatgga aatataataa aaataaaaat ctagtttaat actgcattat    3000 ttatttcct aaggctaaag aggagcagtc ctatgctttt attcagcatc ctttatctgt    3060
gacttcatgc tctgataact gcctttcctt ccttctgtgc ctttgaatac aaatttcagt    3120
tctgcaaaag tgaaacatta aacattgcca acgcaaatgt atgta                    3165
```

```
<210> SEQ ID NO 26
<211> LENGTH: 353
<212> TYPE: PRT
<213> ORGANISM: Homo sapiens

<400> SEQUENCE: 26
```

| | | | | | | | | | | | | | | | |
|---|---|---|---|---|---|---|---|---|---|---|---|---|---|---|---|
| Met | Gly | Ser | Leu | Tyr | Ser | Glu | Tyr | Leu | Asn | Pro | Asn | Lys | Val | Gln | Glu |
| 1 | | | | 5 | | | | | 10 | | | | | 15 | |
| His | Tyr | Asn | Tyr | Thr | Lys | Glu | Thr | Leu | Glu | Thr | Gln | Glu | Thr | Thr | Ser |
| | | | 20 | | | | | 25 | | | | | 30 | | |
| Arg | Gln | Val | Ala | Ser | Ala | Phe | Ile | Val | Ile | Leu | Cys | Cys | Ala | Ile | Val |
| | | 35 | | | | | 40 | | | | | 45 | | | |
| Val | Glu | Asn | Leu | Leu | Val | Leu | Ile | Ala | Val | Ala | Arg | Asn | Ser | Lys | Phe |
| | 50 | | | | | 55 | | | | | 60 | | | | |
| His | Ser | Ala | Met | Tyr | Leu | Phe | Leu | Gly | Asn | Leu | Ala | Ala | Ser | Asp | Leu |
| 65 | | | | | 70 | | | | | 75 | | | | | 80 |
| Leu | Ala | Gly | Val | Ala | Phe | Val | Ala | Asn | Thr | Leu | Leu | Ser | Gly | Ser | Val |
| | | | | 85 | | | | | 90 | | | | | 95 | |
| Thr | Leu | Arg | Leu | Thr | Pro | Val | Gln | Trp | Phe | Ala | Arg | Glu | Gly | Ser | Ala |
| | | | 100 | | | | | 105 | | | | | 110 | | |
| Phe | Ile | Thr | Leu | Ser | Ala | Ser | Val | Phe | Ser | Leu | Leu | Ala | Ile | Ala | Ile |
| | | 115 | | | | | 120 | | | | | 125 | | | |
| Glu | Arg | His | Val | Ala | Ile | Ala | Lys | Val | Lys | Leu | Tyr | Gly | Ser | Asp | Lys |
| | 130 | | | | | 135 | | | | | 140 | | | | |
| Ser | Cys | Arg | Met | Leu | Leu | Leu | Ile | Gly | Ala | Ser | Trp | Leu | Ile | Ser | Leu |
| 145 | | | | | 150 | | | | | 155 | | | | | 160 |
| Val | Leu | Gly | Gly | Leu | Pro | Ile | Leu | Gly | Trp | Asn | Cys | Leu | Gly | His | Leu |
| | | | | 165 | | | | | 170 | | | | | 175 | |
| Glu | Ala | Cys | Ser | Thr | Val | Leu | Pro | Leu | Tyr | Ala | Lys | His | Tyr | Val | Leu |
| | | | 180 | | | | | 185 | | | | | 190 | | |
| Cys | Val | Val | Thr | Ile | Phe | Ser | Ile | Ile | Leu | Leu | Ala | Ile | Val | Ala | Leu |
| | | 195 | | | | | 200 | | | | | 205 | | | |
| Tyr | Val | Arg | Ile | Tyr | Cys | Val | Val | Arg | Ser | Ser | His | Ala | Asp | Met | Ala |
| | 210 | | | | | 215 | | | | | 220 | | | | |
| Ala | Pro | Gln | Thr | Leu | Ala | Leu | Leu | Lys | Thr | Val | Thr | Ile | Val | Leu | Gly |
| 225 | | | | | 230 | | | | | 235 | | | | | 240 |
| Val | Phe | Ile | Val | Cys | Trp | Leu | Pro | Ala | Phe | Ser | Ile | Leu | Leu | Leu | Asp |
| | | | | 245 | | | | | 250 | | | | | 255 | |
| Tyr | Ala | Cys | Pro | Val | His | Ser | Cys | Pro | Ile | Leu | Tyr | Lys | Ala | His | Tyr |
| | | | 260 | | | | | 265 | | | | | 270 | | |
| Phe | Phe | Ala | Val | Ser | Thr | Leu | Asn | Ser | Leu | Leu | Asn | Pro | Val | Ile | Tyr |
| | | 275 | | | | | 280 | | | | | 285 | | | |
| Thr | Trp | Arg | Ser | Arg | Asp | Leu | Arg | Arg | Glu | Val | Leu | Arg | Pro | Leu | Gln |
| | 290 | | | | | 295 | | | | | 300 | | | | |
| Cys | Trp | Arg | Pro | Gly | Val | Gly | Val | Gln | Gly | Arg | Arg | Gly | Gly | Thr | |
| 305 | | | | | 310 | | | | | 315 | | | | | 320 |
| Pro | Gly | His | His | Leu | Leu | Pro | Leu | Arg | Ser | Ser | Ser | Leu | Glu | Arg | |
| | | | | 325 | | | | | 330 | | | | | 335 | |

```
Gly Met His Met Pro Thr Ser Pro Thr Phe Leu Glu Gly Asn Thr Val
            340                 345                 350
Val

<210> SEQ ID NO 27
<211> LENGTH: 525
<212> TYPE: PRT
<213> ORGANISM: Homo sapiens

<400> SEQUENCE: 27

Met Val Ser Arg Pro Glu Pro Gly Glu Ala Met Asp Ala Glu Leu
1               5                   10                  15

Ala Val Ala Pro Pro Gly Cys Ser His Leu Gly Ser Phe Lys Val Asp
                20                  25                  30

Asn Trp Lys Gln Asn Leu Arg Ala Ile Tyr Gln Cys Phe Val Trp Ser
            35                  40                  45

Gly Thr Ala Glu Ala Arg Lys Arg Lys Ala Lys Ser Cys Ile Cys His
    50                  55                  60

Val Cys Gly Val His Leu Asn Arg Leu His Ser Cys Leu Tyr Cys Val
65                  70                  75                  80

Phe Phe Gly Cys Phe Thr Lys Lys His Ile His Glu His Ala Lys Ala
                85                  90                  95

Lys Arg His Asn Leu Ala Ile Asp Leu Met Tyr Gly Gly Ile Tyr Cys
                100                 105                 110

Phe Leu Cys Gln Asp Tyr Ile Tyr Asp Lys Asp Met Glu Ile Ala
            115                 120                 125

Lys Glu Glu Gln Arg Lys Ala Trp Lys Met Gln Gly Val Gly Glu Lys
130                 135                 140

Phe Ser Thr Trp Glu Pro Thr Lys Arg Glu Leu Glu Leu Leu Lys His
145                 150                 155                 160

Asn Pro Lys Arg Arg Lys Ile Thr Ser Asn Cys Thr Ile Gly Leu Arg
                165                 170                 175

Gly Leu Ile Asn Leu Gly Asn Thr Cys Phe Met Asn Cys Ile Val Gln
            180                 185                 190

Ala Leu Thr His Thr Pro Leu Leu Arg Asp Phe Phe Leu Ser Asp Arg
        195                 200                 205

His Arg Cys Glu Met Gln Ser Pro Ser Ser Cys Leu Val Cys Glu Met
210                 215                 220

Ser Ser Leu Phe Gln Glu Phe Tyr Ser Gly His Arg Ser Pro His Ile
225                 230                 235                 240

Pro Tyr Lys Leu Leu His Leu Val Trp Thr His Ala Arg His Leu Ala
                245                 250                 255

Gly Tyr Glu Gln Gln Asp Ala His Glu Phe Leu Ile Ala Ala Leu Asp
            260                 265                 270

Val Leu His Arg His Cys Lys Gly Asp Asp Asn Gly Lys Lys Ala Asn
        275                 280                 285

Asn Pro Asn His Cys Asn Cys Ile Ile Asp Gln Ile Phe Thr Gly Gly
    290                 295                 300

Leu Gln Ser Asp Val Thr Cys Gln Val Cys His Gly Val Ser Thr Thr
305                 310                 315                 320

Ile Asp Pro Phe Trp Asp Ile Ser Leu Asp Leu Pro Gly Ser Ser Thr
                325                 330                 335

Pro Phe Trp Pro Leu Ser Pro Gly Ser Glu Gly Asn Val Val Asn Gly
            340                 345                 350
```

Glu Ser His Val Ser Gly Thr Thr Thr Leu Thr Asp Cys Leu Arg Arg
                355                 360                 365

Phe Thr Arg Pro Glu His Leu Gly Ser Ser Ala Lys Ile Lys Cys Ser
            370                 375                 380

Gly Cys His Ser Tyr Gln Glu Ser Thr Lys Gln Leu Thr Met Lys Lys
385                 390                 395                 400

Leu Pro Ile Val Ala Cys Phe His Leu Lys Arg Phe Glu His Ser Ala
                405                 410                 415

Lys Leu Arg Arg Lys Ile Thr Thr Tyr Val Ser Phe Pro Leu Glu Leu
            420                 425                 430

Asp Met Thr Pro Phe Met Ala Ser Ser Lys Glu Ser Arg Met Asn Gly
            435                 440                 445

Gln Tyr Gln Gln Pro Thr Asp Ser Leu Asn Asn Asp Asn Lys Tyr Ser
            450                 455                 460

Leu Phe Ala Val Val Asn His Gln Gly Thr Leu Glu Ser Gly His Tyr
465                 470                 475                 480

Thr Ser Phe Ile Arg Gln His Lys Asp Gln Trp Phe Lys Cys Asp Asp
                485                 490                 495

Ala Ile Ile Thr Lys Ala Ser Ile Lys Asp Val Leu Asp Ser Glu Gly
                500                 505                 510

Tyr Leu Leu Phe Tyr His Lys Gln Phe Leu Glu Tyr Glu
            515                 520                 525

<210> SEQ ID NO 28
<211> LENGTH: 308
<212> TYPE: PRT
<213> ORGANISM: Homo sapiens

<400> SEQUENCE: 28

Met Ala Ser Ser Asn Thr Val Leu Met Arg Leu Val Ala Ser Ala Tyr
1               5                   10                  15

Ser Ile Ala Gln Lys Ala Gly Met Ile Val Arg Arg Val Ile Ala Glu
                20                  25                  30

Gly Asp Leu Gly Ile Val Glu Lys Thr Cys Ala Thr Asp Leu Gln Thr
            35                  40                  45

Lys Ala Asp Arg Leu Ala Gln Met Ser Ile Cys Ser Ser Leu Ala Arg
        50                  55                  60

Lys Phe Pro Lys Leu Thr Ile Ile Gly Glu Glu Asp Leu Pro Ser Glu
65                  70                  75                  80

Glu Val Asp Gln Glu Leu Ile Glu Asp Ser Gln Trp Glu Glu Ile Leu
                85                  90                  95

Lys Gln Pro Cys Pro Ser Gln Tyr Ser Ala Ile Lys Glu Glu Asp Leu
            100                 105                 110

Val Val Trp Val Asp Pro Leu Asp Gly Thr Lys Glu Tyr Thr Glu Gly
        115                 120                 125

Leu Leu Asp Asn Val Thr Val Leu Ile Gly Ile Ala Tyr Glu Gly Lys
        130                 135                 140

Ala Ile Ala Gly Val Ile Asn Gln Pro Tyr Tyr Asn Tyr Glu Ala Gly
145                 150                 155                 160

Pro Asp Ala Val Leu Gly Arg Thr Ile Trp Gly Val Leu Gly Leu Gly
                165                 170                 175

Ala Phe Gly Phe Gln Leu Lys Glu Val Pro Ala Gly Lys His Ile Ile
            180                 185                 190

Thr Thr Thr Arg Ser His Ser Asn Lys Leu Val Thr Asp Cys Val Ala

```
                    195                 200                 205
Ala Met Asn Pro Asp Ala Val Leu Arg Val Gly Gly Ala Gly Asn Lys
    210                 215                 220

Ile Ile Gln Leu Ile Glu Gly Lys Ala Ser Ala Tyr Val Phe Ala Ser
225                 230                 235                 240

Pro Gly Cys Lys Lys Trp Asp Thr Cys Ala Pro Glu Val Ile Leu His
                245                 250                 255

Ala Val Gly Gly Lys Leu Thr Asp Ile His Gly Asn Val Leu Gln Tyr
            260                 265                 270

His Lys Asp Val Lys His Met Asn Ser Ala Gly Val Leu Ala Thr Leu
        275                 280                 285

Arg Asn Tyr Asp Tyr Tyr Ala Ser Arg Val Pro Glu Ser Ile Lys Asn
    290                 295                 300

Ala Leu Val Pro
305

<210> SEQ ID NO 29
<211> LENGTH: 487
<212> TYPE: PRT
<213> ORGANISM: Homo sapiens

<400> SEQUENCE: 29

Met Pro Gly Pro Arg Val Trp Gly Lys Tyr Leu Trp Arg Ser Pro His
1               5                   10                  15

Ser Lys Gly Cys Pro Gly Ala Met Trp Trp Leu Leu Leu Trp Gly Val
                20                  25                  30

Leu Gln Ala Cys Pro Thr Arg Gly Ser Val Leu Leu Ala Gln Glu Leu
            35                  40                  45

Pro Gln Gln Leu Thr Ser Pro Gly Tyr Pro Glu Pro Tyr Gly Lys Gly
        50                  55                  60

Gln Glu Ser Ser Thr Asp Ile Lys Ala Pro Glu Gly Phe Ala Val Arg
65                  70                  75                  80

Leu Val Phe Gln Asp Phe Asp Leu Glu Pro Ser Gln Asp Cys Ala Gly
                85                  90                  95

Asp Ser Val Thr Ile Ser Phe Val Gly Ser Asp Pro Ser Gln Phe Cys
            100                 105                 110

Gly Gln Gln Gly Ser Pro Leu Gly Arg Pro Pro Gly Gln Arg Glu Phe
        115                 120                 125

Val Ser Ser Gly Arg Ser Leu Arg Leu Thr Phe Arg Thr Gln Pro Ser
130                 135                 140

Ser Glu Asn Lys Thr Ala His Leu His Lys Gly Phe Leu Ala Leu Tyr
145                 150                 155                 160

Gln Thr Val Ala Val Asn Tyr Ser Gln Pro Ile Ser Glu Ala Ser Arg
                165                 170                 175

Gly Ser Glu Ala Ile Asn Ala Pro Gly Asp Asn Pro Ala Lys Val Gln
            180                 185                 190

Asn His Cys Gln Glu Pro Tyr Tyr Gln Ala Ala Ala Gly Ala Leu
        195                 200                 205

Thr Cys Ala Thr Pro Gly Thr Trp Lys Asp Arg Gln Asp Gly Glu Glu
    210                 215                 220

Val Leu Gln Cys Met Pro Val Cys Gly Arg Pro Val Thr Pro Ile Ala
225                 230                 235                 240

Gln Asn Gln Thr Thr Leu Gly Ser Ser Arg Ala Lys Leu Gly Asn Phe
                245                 250                 255
```

```
Pro Trp Gln Ala Phe Thr Ser Ile His Gly Arg Gly Gly Ala Leu
            260                 265                 270

Leu Gly Asp Arg Trp Ile Leu Thr Ala Ala His Thr Ile Tyr Pro Lys
        275                 280                 285

Asp Ser Val Ser Leu Arg Lys Asn Gln Ser Val Asn Val Phe Leu Gly
    290                 295                 300

His Thr Ala Ile Asp Glu Met Leu Lys Leu Gly Asn His Pro Val His
305                 310                 315                 320

Arg Val Val Val His Pro Asp Tyr Arg Gln Asn Glu Ser His Asn Phe
                325                 330                 335

Ser Gly Asp Ile Ala Leu Leu Glu Leu Gln His Ser Ile Pro Leu Gly
            340                 345                 350

Pro Asn Val Leu Pro Val Cys Leu Pro Asp Asn Glu Thr Leu Tyr Arg
        355                 360                 365

Ser Gly Leu Leu Gly Tyr Val Ser Gly Phe Gly Met Glu Met Gly Trp
    370                 375                 380

Leu Thr Thr Glu Leu Lys Tyr Ser Arg Leu Pro Val Ala Pro Arg Glu
385                 390                 395                 400

Ala Cys Asn Ala Trp Leu Gln Lys Arg Gln Arg Pro Glu Val Phe Ser
                405                 410                 415

Asp Asn Met Phe Cys Val Gly Asp Glu Thr Gln Arg His Ser Val Cys
            420                 425                 430

Gln Gly Asp Ser Gly Ser Val Tyr Val Val Trp Asp Asn His Ala His
        435                 440                 445

His Trp Val Ala Thr Gly Ile Val Ser Trp Gly Ile Gly Cys Gly Glu
    450                 455                 460

Gly Tyr Asp Phe Tyr Thr Lys Val Leu Ser Tyr Val Asp Trp Ile Lys
465                 470                 475                 480

Gly Val Met Asn Gly Lys Asn
                485

<210> SEQ ID NO 30
<211> LENGTH: 212
<212> TYPE: PRT
<213> ORGANISM: Homo sapiens

<400> SEQUENCE: 30

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Pro Pro Ser Leu Thr Glu Leu His
65                  70                  75                  80

Leu Asp Gly Asn Lys Ile Ser Arg Val Asp Ala Ala Ser Leu Lys Gly
                85                  90                  95

Leu Asn Asn Leu Ala Lys Leu Gly Leu Ser Phe Asn Ser Ile Ser Ala
            100                 105                 110

Val Asp Asn Gly Ser Leu Ala Asn Thr Pro His Leu Arg Glu Leu His
        115                 120                 125

Leu Asp Asn Asn Lys Leu Thr Arg Val Pro Gly Gly Leu Ala Glu His
    130                 135                 140
```

-continued

```
Lys Tyr Ile Gln Val Val Tyr Leu His Asn Asn Ile Ser Val Val
145                 150                 155                 160

Gly Ser Ser Asp Phe Cys Pro Pro Gly His Asn Thr Lys Lys Ala Ser
                165                 170                 175

Tyr Ser Gly Val Ser Leu Phe Ser Asn Pro Val Gln Tyr Trp Glu Ile
            180                 185                 190

Gln Pro Ser Thr Phe Arg Cys Val Tyr Val Arg Ser Ala Ile Gln Leu
        195                 200                 205

Gly Asn Tyr Lys
    210

<210> SEQ ID NO 31
<211> LENGTH: 75
<212> TYPE: PRT
<213> ORGANISM: Homo sapiens

<400> SEQUENCE: 31

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Cys Leu Pro Ser
65                  70                  75

<210> SEQ ID NO 32
<211> LENGTH: 172
<212> TYPE: PRT
<213> ORGANISM: Homo sapiens

<400> SEQUENCE: 32

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Val Val Tyr Leu
            100                 105                 110

His Asn Asn Asn Ile Ser Val Val Gly Ser Ser Asp Phe Cys Pro Pro
        115                 120                 125

Gly His Asn Thr Lys Lys Ala Ser Tyr Ser Gly Val Ser Leu Phe Ser
    130                 135                 140

Asn Pro Val Gln Tyr Trp Glu Ile Gln Pro Ser Thr Phe Arg Cys Val
145                 150                 155                 160

Tyr Val Arg Ser Ala Ile Gln Leu Gly Asn Tyr Lys
                165                 170
```

<210> SEQ ID NO 33
<211> LENGTH: 250
<212> TYPE: PRT
<213> ORGANISM: Homo sapiens

<400> SEQUENCE: 33

```
Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Glu Leu Gly Thr Asn Pro Leu Lys Ser Ser
65                  70                  75                  80

Gly Ile Glu Asn Gly Ala Phe Gln Gly Met Lys Lys Leu Ser Tyr Ile
                85                  90                  95

Arg Ile Ala Asp Thr Asn Ile Thr Ser Ile Pro Gln Gly Leu Pro Pro
            100                 105                 110

Ser Leu Thr Glu Leu His Leu Asp Gly Asn Lys Ile Ser Arg Val Asp
        115                 120                 125

Ala Ala Ser Leu Lys Gly Leu Asn Asn Leu Ala Lys Leu Gly Leu Ser
    130                 135                 140

Phe Asn Ser Ile Ser Ala Val Asp Asn Gly Ser Leu Ala Asn Thr Pro
145                 150                 155                 160

His Leu Arg Glu Leu His Leu Asp Asn Asn Lys Leu Thr Arg Val Pro
                165                 170                 175

Gly Gly Leu Ala Glu His Lys Tyr Ile Gln Val Val Tyr Leu His Asn
            180                 185                 190

Asn Asn Ile Ser Val Val Gly Ser Ser Asp Phe Cys Pro Pro Gly His
        195                 200                 205

Asn Thr Lys Lys Ala Ser Tyr Ser Gly Val Ser Leu Phe Ser Asn Pro
    210                 215                 220

Val Gln Tyr Trp Glu Ile Gln Pro Ser Thr Phe Arg Cys Val Tyr Val
225                 230                 235                 240

Arg Ser Ala Ile Gln Leu Gly Asn Tyr Lys
                245                 250
```

<210> SEQ ID NO 34
<211> LENGTH: 359
<212> TYPE: PRT
<213> ORGANISM: Homo sapiens

<400> SEQUENCE: 34

```
Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60

Val Gln Cys Ser Asp Leu Gly Leu Asp Lys Val Pro Lys Asp Leu Pro
65                  70                  75                  80
```

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
            130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
            195                 200                 205

Asp Thr Asn Ile Thr Ser Ile Pro Gln Gly Leu Pro Pro Ser Leu Thr
210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
            245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
            275                 280                 285

Ala Glu His Lys Tyr Ile Gln Val Val Tyr Leu His Asn Asn Asn Ile
            290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
            325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 35
<211> LENGTH: 359
<212> TYPE: PRT
<213> ORGANISM: Homo sapiens

<400> SEQUENCE: 35

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
            50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile

```
                85                  90                  95
Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
    130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
        195                 200                 205

Asp Thr Asn Ile Thr Ser Ile Pro Gln Gly Leu Pro Pro Ser Leu Thr
    210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
        275                 280                 285

Ala Glu His Lys Tyr Ile Gln Val Val Tyr Leu His Asn Asn Asn Ile
    290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 36
<211> LENGTH: 443
<212> TYPE: PRT
<213> ORGANISM: Homo sapiens

<400> SEQUENCE: 36

Met Leu Pro Cys Ala Ser Cys Leu Pro Gly Ser Leu Leu Leu Trp Ala
1               5                   10                  15

Leu Leu Leu Leu Leu Leu Gly Ser Ala Ser Pro Gln Asp Ser Glu Glu
            20                  25                  30

Pro Asp Ser Tyr Thr Glu Cys Thr Asp Gly Tyr Glu Trp Asp Pro Asp
        35                  40                  45

Ser Gln His Cys Arg Asp Val Asn Glu Cys Leu Thr Ile Pro Glu Ala
    50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95
```

Pro Pro Pro Val Pro Pro Ala Gln His Pro Asn Pro Cys Pro Pro Gly
                            100                 105                 110

Tyr Glu Pro Asp Asp Gln Asp Ser Cys Val Asp Val Asp Glu Cys Ala
                    115                 120                 125

Gln Ala Leu His Asp Cys Arg Pro Ser Gln Asp Cys His Asn Leu Pro
                130                 135                 140

Gly Ser Tyr Gln Cys Thr Cys Pro Asp Gly Tyr Arg Lys Ile Gly Pro
            145                 150                 155                 160

Glu Cys Val Asp Ile Asp Glu Cys Arg Tyr Arg Tyr Cys Gln His Arg
                            165                 170                 175

Cys Val Asn Leu Pro Gly Ser Phe Arg Cys Gln Cys Glu Pro Gly Phe
                        180                 185                 190

Gln Leu Gly Pro Asn Asn Arg Ser Cys Val Asp Val Asn Glu Cys Asp
                    195                 200                 205

Met Gly Ala Pro Cys Glu Gln Arg Cys Phe Asn Ser Tyr Gly Thr Phe
                210                 215                 220

Leu Cys Arg Cys His Gln Gly Tyr Glu Leu His Arg Asp Gly Phe Ser
            225                 230                 235                 240

Cys Ser Asp Ile Asp Glu Cys Ser Tyr Ser Ser Tyr Leu Cys Gln Tyr
                            245                 250                 255

Arg Cys Ile Asn Glu Pro Gly Arg Phe Ser Cys His Cys Pro Gln Gly
                        260                 265                 270

Tyr Gln Leu Leu Ala Thr Arg Leu Cys Gln Asp Ile Asp Glu Cys Glu
                    275                 280                 285

Ser Gly Ala His Gln Cys Ser Glu Ala Gln Thr Cys Val Asn Phe His
                290                 295                 300

Gly Gly Tyr Arg Cys Val Asp Thr Asn Arg Cys Val Glu Pro Tyr Ile
            305                 310                 315                 320

Gln Val Ser Glu Asn Arg Cys Leu Cys Pro Ala Ser Asn Pro Leu Cys
                            325                 330                 335

Arg Glu Gln Pro Ser Ser Ile Val His Arg Tyr Met Thr Ile Thr Ser
                        340                 345                 350

Glu Arg Ser Val Pro Ala Asp Val Phe Gln Ile Gln Ala Thr Ser Val
                    355                 360                 365

Tyr Pro Gly Ala Tyr Asn Ala Phe Gln Ile Arg Ala Gly Asn Ser Gln
                370                 375                 380

Gly Asp Phe Tyr Ile Arg Gln Ile Asn Asn Val Ser Ala Met Leu Val
            385                 390                 395                 400

Leu Ala Arg Pro Val Thr Gly Pro Arg Glu Tyr Val Leu Asp Leu Glu
                            405                 410                 415

Met Val Thr Met Asn Ser Leu Met Ser Tyr Arg Ala Ser Ser Val Leu
                        420                 425                 430

Arg Leu Thr Val Phe Val Gly Ala Tyr Thr Phe
                    435                 440

<210> SEQ ID NO 37
<211> LENGTH: 333
<212> TYPE: PRT
<213> ORGANISM: Homo sapiens

<400> SEQUENCE: 37

Met Ala Val Arg Arg Asp Ser Val Trp Lys Tyr Cys Trp Gly Val Leu
1               5                   10                  15

Met Val Leu Cys Arg Thr Ala Ile Ser Lys Ser Ile Val Leu Glu Pro
            20                  25                  30

-continued

```
Ile Tyr Trp Asn Ser Ser Asn Ser Lys Phe Leu Pro Gly Gln Gly Leu
             35                  40                  45

Val Leu Tyr Pro Gln Ile Gly Asp Lys Leu Asp Ile Ile Cys Pro Lys
 50                  55                  60

Val Asp Ser Lys Thr Val Gly Gln Tyr Glu Tyr Tyr Lys Val Tyr Met
 65                  70                  75                  80

Val Asp Lys Asp Gln Ala Asp Arg Cys Thr Ile Lys Lys Glu Asn Thr
                 85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
            115                 120                 125

Asn Lys Asp Tyr Tyr Ile Ile Ser Thr Ser Asn Gly Ser Leu Glu Gly
            130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
            195                 200                 205

Asp Gly Asn Ser Ala Gly His Ser Gly Asn Asn Ile Leu Gly Ser Glu
            210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Leu Lys Tyr Arg Arg Arg His
                245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
            275                 280                 285

Ile Ile Ile Pro Leu Arg Thr Ala Asp Ser Val Phe Cys Pro His Tyr
            290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330

<210> SEQ ID NO 38
<211> LENGTH: 870
<212> TYPE: PRT
<213> ORGANISM: Homo sapiens

<400> SEQUENCE: 38

Met Asn Ser Asn Leu Pro Ala Glu Asn Leu Thr Ile Ala Val Asn Met
 1               5                  10                  15

Thr Lys Thr Leu Pro Thr Ala Val Thr His Gly Phe Asn Ser Thr Asn
             20                  25                  30

Asp Pro Pro Ser Met Ser Ile Thr Arg Leu Phe Pro Ala Leu Leu Glu
             35                  40                  45

Cys Phe Gly Ile Val Leu Cys Gly Tyr Ile Ala Gly Arg Ala Asn Val
 50                  55                  60

Ile Thr Ser Thr Gln Ala Lys Gly Leu Gly Asn Phe Val Ser Arg Phe
```

-continued

```
            65                  70                  75                  80
Ala Leu Pro Ala Leu Leu Phe Lys Asn Met Val Val Leu Asn Phe Ser
                    85                  90                  95

Asn Val Asp Trp Ser Phe Leu Tyr Ser Ile Leu Ile Ala Lys Ala Ser
                100                 105                 110

Val Phe Phe Ile Val Cys Val Leu Thr Leu Leu Val Ala Ser Pro Asp
            115                 120                 125

Ser Arg Phe Ser Lys Ala Gly Leu Phe Pro Ile Phe Ala Thr Gln Ser
    130                 135                 140

Asn Asp Phe Ala Leu Gly Tyr Pro Ile Val Glu Ala Leu Tyr Gln Thr
145                 150                 155                 160

Thr Tyr Pro Glu Tyr Leu Gln Tyr Ile Tyr Leu Val Ala Pro Ile Ser
                165                 170                 175

Leu Met Met Leu Asn Pro Ile Gly Phe Ile Phe Cys Glu Ile Gln Lys
            180                 185                 190

Trp Lys Asp Thr Gln Asn Ala Ser Gln Asn Lys Ile Lys Ile Val Gly
    195                 200                 205

Leu Gly Leu Leu Arg Val Leu Gln Asn Pro Ile Val Phe Met Val Phe
210                 215                 220

Ile Gly Ile Ala Phe Asn Phe Ile Leu Asp Arg Lys Val Pro Val Tyr
225                 230                 235                 240

Val Glu Asn Phe Leu Asp Gly Leu Gly Asn Ser Phe Ser Gly Ser Ala
                245                 250                 255

Leu Phe Tyr Leu Gly Leu Thr Met Val Gly Lys Ile Lys Arg Leu Lys
            260                 265                 270

Lys Ser Ala Phe Val Val Leu Ile Leu Leu Ile Thr Ala Lys Leu Leu
    275                 280                 285

Val Leu Pro Leu Leu Cys Arg Glu Met Val Glu Leu Leu Asp Lys Gly
290                 295                 300

Asp Ser Val Val Asn His Thr Ser Leu Ser Asn Tyr Ala Phe Leu Tyr
305                 310                 315                 320

Gly Val Phe Pro Val Ala Pro Gly Val Ala Ile Phe Ala Thr Gln Phe
                325                 330                 335

Asn Met Glu Val Glu Ile Ile Thr Ser Gly Met Val Ile Ser Thr Phe
            340                 345                 350

Val Ser Ala Pro Ile Met Tyr Val Ser Ala Trp Leu Leu Thr Phe Pro
    355                 360                 365

Thr Met Asp Pro Lys Pro Leu Ala Tyr Ala Ile Gln Asn Val Ser Phe
370                 375                 380

Asp Ile Ser Ile Val Ser Leu Ile Ser Leu Ile Trp Ser Leu Ala Ile
385                 390                 395                 400

Leu Leu Leu Ser Lys Lys Tyr Lys Gln Leu Pro His Met Leu Thr Thr
                405                 410                 415

Asn Leu Leu Ile Ala Gln Ser Ile Val Cys Ala Gly Met Met Ile Trp
            420                 425                 430

Asn Phe Val Lys Glu Lys Asn Phe Val Gly Gln Ile Leu Val Phe Val
    435                 440                 445

Leu Leu Tyr Ser Ser Leu Tyr Ser Thr Tyr Leu Trp Thr Gly Leu Leu
450                 455                 460

Ala Ile Ser Leu Phe Leu Leu Lys Lys Arg Glu Arg Val Gln Ile Pro
465                 470                 475                 480

Val Gly Ile Ile Ile Ser Gly Trp Gly Ile Pro Ala Leu Leu Val
                485                 490                 495
```

```
Gly Val Leu Leu Ile Thr Gly Lys His Asn Gly Asp Ser Ile Asp Ser
            500                 505                 510

Ala Phe Phe Tyr Gly Lys Glu Gln Met Ile Thr Thr Ala Val Thr Leu
            515                 520                 525

Phe Cys Ser Ile Leu Ile Ala Gly Ile Ser Leu Met Cys Met Asn Gln
            530                 535                 540

Thr Ala Gln Ala Gly Ser Tyr Glu Gly Phe Asp Gln Ser Gln Ser His
545                 550                 555                 560

Lys Val Val Glu Pro Gly Asn Thr Ala Phe Glu Ser Pro Ala Pro
                565                 570                 575

Val Asn Glu Pro Glu Leu Phe Thr Ser Ser Ile Pro Glu Thr Ser Cys
            580                 585                 590

Cys Ser Cys Ser Met Gly Asn Gly Glu Leu His Cys Pro Ser Ile Glu
            595                 600                 605

Pro Ile Ala Asn Thr Ser Thr Ser Glu Pro Val Ile Pro Ser Phe Glu
            610                 615                 620

Lys Asn Asn His Cys Val Ser Arg Cys Asn Ser Gln Ser Cys Ile Leu
625                 630                 635                 640

Ala Gln Glu Glu Gln Tyr Leu Gln Ser Gly Asp Gln Gln Leu Thr
                645                 650                 655

Arg His Val Leu Leu Cys Leu Leu Ile Ile Gly Leu Phe Ala Asn
            660                 665                 670

Leu Ser Ser Cys Leu Trp Trp Leu Phe Asn Gln Glu Pro Gly Arg Leu
            675                 680                 685

Tyr Val Glu Leu Gln Phe Phe Cys Ala Val Phe Asn Phe Gly Gln Gly
            690                 695                 700

Phe Ile Ser Phe Gly Ile Phe Gly Leu Asp Lys His Leu Ile Ile Leu
705                 710                 715                 720

Pro Phe Lys Arg Arg Leu Glu Phe Leu Trp Asn Asn Lys Asp Thr Ala
                725                 730                 735

Glu Asn Arg Asp Ser Pro Val Ser Glu Glu Ile Lys Met Thr Cys Gln
            740                 745                 750

Gln Phe Ile His Tyr His Arg Asp Leu Cys Ile Arg Asn Ile Val Lys
            755                 760                 765

Glu Arg Arg Cys Gly Ala Lys Thr Ser Ala Gly Thr Phe Cys Gly Cys
            770                 775                 780

Asp Leu Val Ser Trp Leu Ile Glu Val Gly Leu Ala Ser Asp Arg Gly
785                 790                 795                 800

Glu Ala Val Ile Tyr Gly Asp Arg Leu Val Gln Gly Gly Val Ile Gln
                805                 810                 815

His Ile Thr Asn Glu Tyr Glu Phe Arg Asp Glu Tyr Leu Phe Tyr Arg
            820                 825                 830

Phe Leu Gln Lys Ser Pro Glu Gln Ser Pro Pro Ala Ile Asn Ala Asn
            835                 840                 845

Thr Leu Gln Gln Glu Arg Tyr Lys Glu Ile Glu His Ser Ser Pro Pro
            850                 855                 860

Ser His Ser Pro Lys Thr
865                 870

<210> SEQ ID NO 39
<211> LENGTH: 870
<212> TYPE: PRT
<213> ORGANISM: Homo sapiens
```

<400> SEQUENCE: 39

Met Asn Ser Asn Leu Pro Ala Glu Asn Leu Thr Ile Ala Val Asn Met
1               5                   10                  15

Thr Lys Thr Leu Pro Thr Ala Val Thr His Gly Phe Asn Ser Thr Asn
            20                  25                  30

Asp Pro Pro Ser Met Ser Ile Thr Arg Leu Phe Pro Ala Leu Leu Glu
        35                  40                  45

Cys Phe Gly Ile Val Leu Cys Gly Tyr Ile Ala Gly Arg Ala Asn Val
    50                  55                  60

Ile Thr Ser Thr Gln Ala Lys Gly Leu Gly Asn Phe Val Ser Arg Phe
65                  70                  75                  80

Ala Leu Pro Ala Leu Leu Phe Lys Asn Met Val Val Leu Asn Phe Ser
                85                  90                  95

Asn Val Asp Trp Ser Phe Leu Tyr Ser Ile Leu Ile Ala Lys Ala Ser
            100                 105                 110

Val Phe Phe Ile Val Cys Val Leu Thr Leu Leu Val Ala Ser Pro Asp
        115                 120                 125

Ser Arg Phe Ser Lys Ala Gly Leu Phe Pro Ile Phe Ala Thr Gln Ser
    130                 135                 140

Asn Asp Phe Ala Leu Gly Tyr Pro Ile Val Glu Ala Leu Tyr Gln Thr
145                 150                 155                 160

Thr Tyr Pro Glu Tyr Leu Gln Tyr Ile Tyr Leu Val Ala Pro Ile Ser
            165                 170                 175

Leu Met Met Leu Asn Pro Ile Gly Phe Ile Phe Cys Glu Ile Gln Lys
        180                 185                 190

Trp Lys Asp Thr Gln Asn Ala Ser Gln Asn Lys Ile Lys Ile Val Gly
    195                 200                 205

Leu Gly Leu Leu Arg Val Leu Gln Asn Pro Ile Val Phe Met Val Phe
210                 215                 220

Ile Gly Ile Ala Phe Asn Phe Ile Leu Asp Arg Lys Val Pro Val Tyr
225                 230                 235                 240

Val Glu Asn Phe Leu Asp Gly Leu Gly Asn Ser Phe Ser Gly Ser Ala
            245                 250                 255

Leu Phe Tyr Leu Gly Leu Thr Met Val Gly Lys Ile Lys Arg Leu Lys
        260                 265                 270

Lys Ser Ala Phe Val Val Leu Ile Leu Leu Ile Thr Ala Lys Leu Leu
    275                 280                 285

Val Leu Pro Leu Leu Cys Arg Glu Met Val Glu Leu Leu Asp Lys Gly
290                 295                 300

Asp Ser Val Val Asn His Thr Ser Leu Ser Asn Tyr Ala Phe Leu Tyr
305                 310                 315                 320

Gly Val Phe Pro Val Ala Pro Gly Val Ala Ile Phe Ala Thr Gln Phe
            325                 330                 335

Asn Met Glu Val Glu Ile Ile Thr Ser Gly Met Val Ile Ser Thr Phe
        340                 345                 350

Val Ser Ala Pro Ile Met Tyr Val Ser Ala Trp Leu Leu Thr Phe Pro
    355                 360                 365

Thr Met Asp Pro Lys Pro Leu Ala Tyr Ala Ile Gln Asn Val Ser Phe
370                 375                 380

Asp Ile Ser Ile Val Ser Leu Ile Ser Leu Ile Trp Ser Leu Ala Ile
385                 390                 395                 400

Leu Leu Leu Ser Lys Lys Tyr Lys Gln Leu Pro His Met Leu Thr Thr
            405                 410                 415

```
Asn Leu Leu Ile Ala Gln Ser Ile Val Cys Ala Gly Met Met Ile Trp
            420                 425                 430

Asn Phe Val Lys Glu Lys Asn Phe Val Gly Gln Ile Leu Val Phe Val
            435                 440                 445

Leu Leu Tyr Ser Ser Leu Tyr Ser Thr Tyr Leu Trp Thr Gly Leu Leu
        450                 455                 460

Ala Ile Ser Leu Phe Leu Lys Lys Arg Glu Arg Val Gln Ile Pro
465                 470                 475                 480

Val Gly Ile Ile Ile Ile Ser Gly Trp Gly Ile Pro Ala Leu Leu Val
                485                 490                 495

Gly Val Leu Leu Ile Thr Gly Lys His Asn Gly Asp Ser Ile Asp Ser
            500                 505                 510

Ala Phe Phe Tyr Gly Lys Glu Gln Met Ile Thr Thr Ala Val Thr Leu
        515                 520                 525

Phe Cys Ser Ile Leu Ile Ala Gly Ile Ser Leu Met Cys Met Asn Gln
    530                 535                 540

Thr Ala Gln Ala Gly Ser Tyr Glu Gly Phe Asp Gln Ser Gln Ser His
545                 550                 555                 560

Lys Val Val Glu Pro Gly Asn Thr Ala Phe Glu Glu Ser Pro Ala Pro
                565                 570                 575

Val Asn Glu Pro Glu Leu Phe Thr Ser Ser Ile Pro Glu Thr Ser Cys
            580                 585                 590

Cys Ser Cys Ser Met Gly Asn Gly Glu Leu His Cys Pro Ser Ile Glu
        595                 600                 605

Pro Ile Ala Asn Thr Ser Thr Ser Glu Pro Val Ile Pro Ser Phe Glu
    610                 615                 620

Lys Asn Asn His Cys Val Ser Arg Cys Asn Ser Gln Ser Cys Ile Leu
625                 630                 635                 640

Ala Gln Glu Glu Glu Gln Tyr Leu Gln Ser Gly Asp Gln Gln Leu Thr
                645                 650                 655

Arg His Val Leu Leu Cys Leu Leu Ile Ile Gly Leu Phe Ala Asn
            660                 665                 670

Leu Ser Ser Cys Leu Trp Trp Leu Phe Asn Gln Glu Pro Gly Arg Leu
        675                 680                 685

Tyr Val Glu Leu Gln Phe Phe Cys Ala Val Phe Asn Phe Gly Gln Gly
    690                 695                 700

Phe Ile Ser Phe Gly Ile Phe Gly Leu Asp Lys His Leu Ile Ile Leu
705                 710                 715                 720

Pro Phe Lys Arg Arg Leu Glu Phe Leu Trp Asn Asn Lys Asp Thr Ala
                725                 730                 735

Glu Asn Arg Asp Ser Pro Val Ser Glu Glu Ile Lys Met Thr Cys Gln
            740                 745                 750

Gln Phe Ile His Tyr His Arg Asp Leu Cys Ile Arg Asn Ile Val Lys
        755                 760                 765

Glu Arg Arg Cys Gly Ala Lys Thr Ser Ala Gly Thr Phe Cys Gly Cys
    770                 775                 780

Asp Leu Val Ser Trp Leu Ile Glu Val Gly Leu Ala Ser Asp Arg Gly
785                 790                 795                 800

Glu Ala Val Ile Tyr Gly Asp Arg Leu Val Gln Gly Gly Val Ile Gln
                805                 810                 815

His Ile Thr Asn Glu Tyr Glu Phe Arg Asp Glu Tyr Leu Phe Tyr Arg
            820                 825                 830
```

```
Phe Leu Gln Lys Ser Pro Glu Gln Ser Pro Pro Ala Ile Asn Ala Asn
            835                 840                 845

Thr Leu Gln Gln Glu Arg Tyr Lys Glu Ile Glu His Ser Ser Pro Pro
    850                 855                 860

Ser His Ser Pro Lys Thr
865                 870

<210> SEQ ID NO 40
<211> LENGTH: 870
<212> TYPE: PRT
<213> ORGANISM: Homo sapiens

<400> SEQUENCE: 40

Met Asn Ser Asn Leu Pro Ala Glu Asn Leu Thr Ile Ala Val Asn Met
1               5                   10                  15

Thr Lys Thr Leu Pro Thr Ala Val Thr His Gly Phe Asn Ser Thr Asn
            20                  25                  30

Asp Pro Pro Ser Met Ser Ile Thr Arg Leu Phe Pro Ala Leu Leu Glu
        35                  40                  45

Cys Phe Gly Ile Val Leu Cys Gly Tyr Ile Ala Gly Arg Ala Asn Val
    50                  55                  60

Ile Thr Ser Thr Gln Ala Lys Gly Leu Gly Asn Phe Val Ser Arg Phe
65                  70                  75                  80

Ala Leu Pro Ala Leu Leu Phe Lys Asn Met Val Val Leu Asn Phe Ser
                85                  90                  95

Asn Val Asp Trp Ser Phe Leu Tyr Ser Ile Leu Ile Ala Lys Ala Ser
            100                 105                 110

Val Phe Phe Ile Val Cys Val Leu Thr Leu Leu Val Ala Ser Pro Asp
        115                 120                 125

Ser Arg Phe Ser Lys Ala Gly Leu Phe Pro Ile Phe Ala Thr Gln Ser
    130                 135                 140

Asn Asp Phe Ala Leu Gly Tyr Pro Ile Val Glu Ala Leu Tyr Gln Thr
145                 150                 155                 160

Thr Tyr Pro Glu Tyr Leu Gln Tyr Ile Tyr Leu Val Ala Pro Ile Ser
                165                 170                 175

Leu Met Met Leu Asn Pro Ile Gly Phe Ile Phe Cys Glu Ile Gln Lys
            180                 185                 190

Trp Lys Asp Thr Gln Asn Ala Ser Gln Asn Lys Ile Lys Ile Val Gly
        195                 200                 205

Leu Gly Leu Leu Arg Val Leu Gln Asn Pro Ile Val Phe Met Val Phe
    210                 215                 220

Ile Gly Ile Ala Phe Asn Phe Ile Leu Asp Arg Lys Val Pro Val Tyr
225                 230                 235                 240

Val Glu Asn Phe Leu Asp Gly Leu Gly Asn Ser Phe Ser Gly Ser Ala
                245                 250                 255

Leu Phe Tyr Leu Gly Leu Thr Met Val Gly Lys Ile Lys Arg Leu Lys
            260                 265                 270

Lys Ser Ala Phe Val Val Leu Ile Leu Ile Thr Ala Lys Leu Leu
        275                 280                 285

Val Leu Pro Leu Leu Cys Arg Glu Met Val Glu Leu Leu Asp Lys Gly
    290                 295                 300

Asp Ser Val Val Asn His Thr Ser Leu Ser Asn Tyr Ala Phe Leu Tyr
305                 310                 315                 320

Gly Val Phe Pro Val Ala Pro Gly Val Ala Ile Phe Ala Thr Gln Phe
                325                 330                 335
```

-continued

Asn Met Glu Val Glu Ile Ile Thr Ser Gly Met Val Ile Ser Thr Phe
            340                 345                 350

Val Ser Ala Pro Ile Met Tyr Val Ser Ala Trp Leu Leu Thr Phe Pro
            355                 360                 365

Thr Met Asp Pro Lys Pro Leu Ala Tyr Ala Ile Gln Asn Val Ser Phe
            370                 375                 380

Asp Ile Ser Ile Val Ser Leu Ile Ser Leu Ile Trp Ser Leu Ala Ile
385                 390                 395                 400

Leu Leu Leu Ser Lys Lys Tyr Lys Gln Leu Pro His Met Leu Thr Thr
            405                 410                 415

Asn Leu Leu Ile Ala Gln Ser Ile Val Cys Ala Gly Met Met Ile Trp
            420                 425                 430

Asn Phe Val Lys Glu Lys Asn Phe Val Gly Gln Ile Leu Val Phe Val
            435                 440                 445

Leu Leu Tyr Ser Ser Leu Tyr Ser Thr Tyr Leu Trp Thr Gly Leu Leu
            450                 455                 460

Ala Ile Ser Leu Phe Leu Leu Lys Lys Arg Glu Arg Val Gln Ile Pro
465                 470                 475                 480

Val Gly Ile Ile Ile Ser Gly Trp Gly Ile Pro Ala Leu Leu Val
            485                 490                 495

Gly Val Leu Leu Ile Thr Gly Lys His Asn Gly Asp Ser Ile Asp Ser
            500                 505                 510

Ala Phe Phe Tyr Gly Lys Glu Gln Met Ile Thr Thr Ala Val Thr Leu
            515                 520                 525

Phe Cys Ser Ile Leu Ile Ala Gly Ile Ser Leu Met Cys Met Asn Gln
            530                 535                 540

Thr Ala Gln Ala Gly Ser Tyr Glu Gly Phe Asp Gln Ser Gln Ser His
545                 550                 555                 560

Lys Val Val Glu Pro Gly Asn Thr Ala Phe Glu Ser Pro Ala Pro
            565                 570                 575

Val Asn Glu Pro Glu Leu Phe Thr Ser Ser Ile Pro Glu Thr Ser Cys
            580                 585                 590

Cys Ser Cys Ser Met Gly Asn Gly Glu Leu His Cys Pro Ser Ile Glu
            595                 600                 605

Pro Ile Ala Asn Thr Ser Thr Ser Glu Pro Val Ile Pro Ser Phe Glu
            610                 615                 620

Lys Asn Asn His Cys Val Ser Arg Cys Asn Ser Gln Ser Cys Ile Leu
625                 630                 635                 640

Ala Gln Glu Glu Gln Tyr Leu Gln Ser Gly Asp Gln Gln Leu Thr
            645                 650                 655

Arg His Val Leu Leu Cys Leu Leu Leu Ile Ile Gly Leu Phe Ala Asn
            660                 665                 670

Leu Ser Ser Cys Leu Trp Trp Leu Phe Asn Gln Glu Pro Gly Arg Leu
            675                 680                 685

Tyr Val Glu Leu Gln Phe Phe Cys Ala Val Phe Asn Phe Gly Gln Gly
            690                 695                 700

Phe Ile Ser Phe Gly Ile Phe Gly Leu Asp Lys His Leu Ile Ile Leu
705                 710                 715                 720

Pro Phe Lys Arg Arg Leu Glu Phe Leu Trp Asn Asn Lys Asp Thr Ala
            725                 730                 735

Glu Asn Arg Asp Ser Pro Val Ser Glu Glu Ile Lys Met Thr Cys Gln
            740                 745                 750

```
Gln Phe Ile His Tyr His Arg Asp Leu Cys Ile Arg Asn Ile Val Lys
            755                 760                 765

Glu Arg Arg Cys Gly Ala Lys Thr Ser Ala Gly Thr Phe Cys Gly Cys
770                 775                 780

Asp Leu Val Ser Trp Leu Ile Glu Val Gly Leu Ala Ser Asp Arg Gly
785                 790                 795                 800

Glu Ala Val Ile Tyr Gly Asp Arg Leu Val Gln Gly Val Ile Gln
                805                 810                 815

His Ile Thr Asn Glu Tyr Glu Phe Arg Asp Glu Tyr Leu Phe Tyr Arg
            820                 825                 830

Phe Leu Gln Lys Ser Pro Glu Gln Ser Pro Ala Ile Asn Ala Asn
            835                 840                 845

Thr Leu Gln Gln Glu Arg Tyr Lys Glu Ile Glu His Ser Pro Pro
850                 855                 860

Ser His Ser Pro Lys Thr
865                 870

<210> SEQ ID NO 41
<211> LENGTH: 842
<212> TYPE: PRT
<213> ORGANISM: Homo sapiens

<400> SEQUENCE: 41

Met Asn Ser Asn Leu Pro Ala Glu Asn Leu Thr Ile Ala Val Asn Met
1               5                   10                  15

Thr Lys Thr Leu Pro Thr Ala Val Thr His Gly Phe Asn Ser Thr Asn
            20                  25                  30

Asp Pro Pro Ser Met Ser Ile Thr Arg Leu Phe Pro Ala Leu Leu Glu
        35                  40                  45

Cys Phe Gly Ile Val Leu Cys Gly Tyr Ile Ala Gly Arg Ala Asn Val
    50                  55                  60

Ile Thr Ser Thr Gln Ala Lys Gly Leu Gly Asn Phe Val Ser Arg Phe
65                  70                  75                  80

Ala Leu Pro Ala Leu Leu Phe Lys Asn Met Val Val Leu Asn Phe Ser
                85                  90                  95

Asn Val Asp Trp Ser Phe Leu Tyr Ser Ile Leu Ile Ala Lys Ala Ser
            100                 105                 110

Val Phe Phe Ile Val Cys Val Leu Thr Leu Leu Val Ala Ser Pro Asp
        115                 120                 125

Ser Arg Phe Ser Lys Ala Gly Leu Phe Pro Ile Phe Ala Thr Gln Ser
    130                 135                 140

Asn Asp Phe Ala Leu Gly Tyr Pro Ile Val Glu Ala Leu Tyr Gln Thr
145                 150                 155                 160

Thr Tyr Pro Glu Tyr Leu Gln Tyr Ile Tyr Leu Val Ala Pro Ile Ser
                165                 170                 175

Leu Met Met Leu Asn Pro Ile Gly Phe Ile Phe Cys Glu Ile Gln Lys
            180                 185                 190

Trp Lys Asp Thr Gln Asn Ala Ser Gln Asn Lys Ile Lys Ile Val Gly
        195                 200                 205

Leu Gly Leu Leu Arg Val Leu Gln Asn Pro Ile Val Phe Met Val Phe
    210                 215                 220

Ile Gly Ile Ala Phe Asn Phe Ile Leu Asp Arg Lys Val Pro Val Tyr
225                 230                 235                 240

Val Glu Asn Phe Leu Asp Gly Leu Gly Asn Ser Phe Ser Gly Ser Ala
                245                 250                 255
```

-continued

```
Leu Phe Tyr Leu Gly Leu Thr Met Val Gly Lys Ile Lys Arg Leu Lys
            260                 265                 270

Lys Ser Ala Phe Val Val Leu Ile Leu Leu Ile Thr Ala Lys Leu Leu
        275                 280                 285

Val Leu Pro Leu Leu Cys Arg Glu Met Val Glu Leu Leu Asp Lys Gly
290                 295                 300

Asp Ser Val Val Asn His Thr Ser Leu Ser Asn Tyr Ala Phe Leu Tyr
305                 310                 315                 320

Gly Val Phe Pro Val Ala Pro Gly Val Ala Ile Phe Ala Thr Gln Phe
                325                 330                 335

Asn Met Glu Val Glu Ile Ile Thr Ser Gly Met Val Ile Ser Thr Phe
            340                 345                 350

Val Ser Ala Pro Ile Met Tyr Val Ser Ala Trp Leu Leu Thr Phe Pro
        355                 360                 365

Thr Met Asp Pro Lys Pro Leu Ala Tyr Ala Ile Gln Asn Val Ser Phe
    370                 375                 380

Asp Ile Ser Ile Val Ser Leu Ile Ser Leu Ser Ile Val Cys Ala Gly
385                 390                 395                 400

Met Met Ile Trp Asn Phe Val Lys Glu Lys Asn Phe Val Gly Gln Ile
                405                 410                 415

Leu Val Phe Val Leu Leu Tyr Ser Ser Leu Tyr Ser Thr Tyr Leu Trp
            420                 425                 430

Thr Gly Leu Leu Ala Ile Ser Leu Phe Leu Leu Lys Lys Arg Glu Arg
        435                 440                 445

Val Gln Ile Pro Val Gly Ile Ile Ile Ser Gly Trp Gly Ile Pro
    450                 455                 460

Ala Leu Leu Val Gly Val Leu Leu Ile Thr Gly Lys His Asn Gly Asp
465                 470                 475                 480

Ser Ile Asp Ser Ala Phe Phe Tyr Gly Lys Glu Gln Met Ile Thr Thr
                485                 490                 495

Ala Val Thr Leu Phe Cys Ser Ile Leu Ile Ala Gly Ile Ser Leu Met
            500                 505                 510

Cys Met Asn Gln Thr Ala Gln Ala Gly Ser Tyr Glu Gly Phe Asp Gln
        515                 520                 525

Ser Gln Ser His Lys Val Val Glu Pro Gly Asn Thr Ala Phe Glu Glu
    530                 535                 540

Ser Pro Ala Pro Val Asn Glu Pro Glu Leu Phe Thr Ser Ser Ile Pro
545                 550                 555                 560

Glu Thr Ser Cys Cys Ser Cys Ser Met Gly Asn Gly Glu Leu His Cys
                565                 570                 575

Pro Ser Ile Glu Pro Ile Ala Asn Thr Ser Thr Ser Gly Pro Val Ile
            580                 585                 590

Pro Ser Phe Glu Lys Asn Asn His Cys Val Ser Arg Cys Asn Ser Gln
        595                 600                 605

Ser Cys Ile Leu Ala Gln Glu Glu Gln Tyr Leu Gln Ser Gly Asp
    610                 615                 620

Gln Gln Leu Thr Arg His Val Leu Leu Cys Leu Leu Ile Ile Gly
625                 630                 635                 640

Leu Phe Ala Asn Leu Ser Ser Cys Leu Trp Trp Leu Phe Asn Gln Glu
                645                 650                 655

Pro Gly Arg Leu Tyr Val Glu Leu Gln Phe Cys Ala Val Phe Asn
            660                 665                 670
```

```
Phe Gly Gln Gly Phe Ile Ser Phe Gly Ile Phe Gly Leu Asp Lys His
            675                 680                 685

Leu Ile Ile Leu Pro Phe Lys Arg Arg Leu Glu Phe Leu Trp Asn Asn
        690                 695                 700

Lys Asp Thr Ala Glu Asn Arg Asp Ser Pro Val Ser Glu Glu Ile Lys
705                 710                 715                 720

Met Thr Cys Gln Gln Phe Ile His Tyr His Arg Asp Leu Cys Ile Arg
            725                 730                 735

Asn Ile Val Lys Glu Arg Arg Cys Gly Ala Lys Thr Ser Ala Gly Thr
                740                 745                 750

Phe Cys Gly Cys Asp Leu Val Ser Trp Leu Ile Glu Val Gly Leu Ala
        755                 760                 765

Ser Asp Arg Gly Glu Ala Val Ile Tyr Gly Asp Arg Leu Val Gln Gly
    770                 775                 780

Gly Val Ile Gln His Ile Thr Asn Glu Tyr Glu Phe Arg Asp Glu Tyr
785                 790                 795                 800

Leu Phe Tyr Arg Phe Leu Gln Lys Ser Pro Glu Gln Ser Pro Pro Ala
            805                 810                 815

Ile Asn Ala Asn Thr Leu Gln Gln Glu Arg Tyr Lys Glu Ile Glu His
                820                 825                 830

Ser Ser Pro Pro Ser His Ser Pro Lys Thr
            835                 840

<210> SEQ ID NO 42
<211> LENGTH: 210
<212> TYPE: PRT
<213> ORGANISM: Homo sapiens

<400> SEQUENCE: 42

Met Ala Lys Leu Arg Val Ala Tyr Glu Tyr Thr Glu Ala Glu Asp Lys
1               5                   10                  15

Ser Ile Arg Leu Gly Leu Phe Leu Ile Ile Ser Gly Val Val Ser Leu
            20                  25                  30

Phe Ile Phe Gly Phe Cys Trp Leu Ser Pro Ala Leu Gln Asp Leu Gln
        35                  40                  45

Ala Thr Glu Ala Asn Cys Thr Val Leu Ser Val Gln Gln Ile Gly Glu
    50                  55                  60

Val Phe Glu Cys Thr Phe Thr Cys Gly Ala Asp Cys Arg Gly Thr Ser
65                  70                  75                  80

Gln Tyr Pro Cys Val Gln Val Tyr Val Asn Asn Ser Glu Ser Asn Ser
            85                  90                  95

Arg Ala Leu Leu His Ser Asp Glu His Gln Leu Leu Thr Asn Pro Lys
            100                 105                 110

Cys Ser Tyr Ile Pro Pro Cys Lys Arg Glu Asn Gln Lys Asn Leu Glu
        115                 120                 125

Ser Val Met Asn Trp Gln Gln Tyr Trp Lys Asp Glu Ile Gly Ser Gln
    130                 135                 140

Pro Phe Thr Cys Tyr Phe Asn Gln His Gln Arg Pro Asp Asp Val Leu
145                 150                 155                 160

Leu His Arg Thr His Asp Glu Ile Val Leu Leu His Cys Phe Leu Trp
            165                 170                 175

Pro Leu Val Thr Phe Val Val Gly Val Leu Ile Val Val Leu Thr Ile
                180                 185                 190

Cys Ala Lys Ser Leu Ala Val Lys Ala Glu Ala Met Lys Lys Arg Lys
        195                 200                 205
```

Phe Ser
    210

<210> SEQ ID NO 43
<211> LENGTH: 202
<212> TYPE: PRT
<213> ORGANISM: Homo sapiens

<400> SEQUENCE: 43

Met Lys Val Leu Ala Ala Gly Val Val Pro Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65              70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
            180                 185                 190

Gln Ile Ile Ala Val Leu Ala Gln Ala Phe
        195                 200

<210> SEQ ID NO 44
<211> LENGTH: 88
<212> TYPE: PRT
<213> ORGANISM: Homo sapiens

<400> SEQUENCE: 44

Met Lys Val Leu Ala Ala Val His Ser Pro Gly Gly Ala Val Pro Gln
1               5                   10                  15

Gln Pro Gly Gln Ala Met Trp Pro Gln Arg Asp Gly Leu Pro Ala Leu
            20                  25                  30

Pro Arg Gln Arg His Gly Glu Gly Gln Ala Gly Gly Ala Val Pro His
        35                  40                  45

Ser Arg Val Pro Trp His Leu Pro Gly Gln His His Pro Gly Pro Glu
    50                  55                  60

Asp Pro Gln Pro Gln Cys Pro Gln Pro Gln Gln Ala Gln Arg His
65                  70                  75                  80

Arg Arg His Pro Ala Arg Pro Pro
            85

<210> SEQ ID NO 45

<211> LENGTH: 239
<212> TYPE: PRT
<213> ORGANISM: Homo sapiens

<400> SEQUENCE: 45

Met His Gln Thr Tyr Ser Arg His Cys Arg Pro Glu Glu Ser Thr Phe
1               5                   10                  15

Ser Ala Ala Met Thr Thr Met Gln Gly Met Glu Gln Ala Met Pro Gly
            20                  25                  30

Ala Gly Pro Gly Val Pro Gln Leu Gly Asn Met Ala Val Ile His Ser
        35                  40                  45

His Leu Trp Lys Gly Leu Gln Glu Lys Phe Leu Lys Gly Glu Pro Lys
50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
            100                 105                 110

Ile Ser Gly Ser Leu Ser Ile Ala Ala Gly Ile Arg Thr Thr Lys Gly
        115                 120                 125

Leu Val Arg Gly Ser Leu Gly Met Asn Ile Thr Ser Ser Val Leu Ala
130                 135                 140

Ala Ser Gly Ile Leu Ile Asn Thr Phe Ser Leu Ala Phe Tyr Ser Phe
145                 150                 155                 160

His His Pro Tyr Cys Asn Tyr Tyr Gly Asn Ser Asn Asn Cys His Gly
                165                 170                 175

Thr Met Ser Ile Leu Met Gly Leu Asp Gly Met Val Leu Leu Leu Ser
            180                 185                 190

Val Leu Glu Phe Cys Ile Ala Val Ser Leu Ser Ala Phe Gly Cys Lys
        195                 200                 205

Val Leu Cys Cys Thr Pro Gly Gly Val Val Leu Ile Leu Pro Ser His
    210                 215                 220

Ser His Met Ala Glu Thr Ala Ser Pro Thr Pro Leu Asn Glu Val
225                 230                 235

<210> SEQ ID NO 46
<211> LENGTH: 220
<212> TYPE: PRT
<213> ORGANISM: Homo sapiens

<400> SEQUENCE: 46

Met Thr Thr Met Gln Gly Met Glu Gln Ala Met Pro Gly Ala Gly Pro
1               5                   10                  15

Gly Val Pro Gln Leu Gly Asn Met Ala Val Ile His Ser His Leu Trp
            20                  25                  30

Lys Gly Leu Gln Glu Lys Phe Leu Lys Gly Glu Pro Lys Val Leu Gly
        35                  40                  45

Val Val Gln Ile Leu Thr Ala Leu Met Ser Leu Ser Met Gly Ile Thr
    50                  55                  60

Met Met Cys Met Ala Ser Asn Thr Tyr Gly Ser Asn Pro Ile Ser Val
65                  70                  75                  80

Tyr Ile Gly Tyr Thr Ile Trp Gly Ser Val Met Phe Ile Ile Ser Gly
                85                  90                  95

Ser Leu Ser Ile Ala Ala Gly Ile Arg Thr Thr Lys Gly Leu Val Arg
            100                 105                 110

```
Gly Ser Leu Gly Met Asn Ile Thr Ser Ser Val Leu Ala Ala Ser Gly
            115                 120                 125

Ile Leu Ile Asn Thr Phe Ser Leu Ala Phe Tyr Ser Phe His His Pro
            130                 135                 140

Tyr Cys Asn Tyr Tyr Gly Asn Ser Asn Asn Cys His Gly Thr Met Ser
145                 150                 155                 160

Ile Leu Met Gly Leu Asp Gly Met Val Leu Leu Ser Val Leu Glu
                165                 170                 175

Phe Cys Ile Ala Val Ser Leu Ser Ala Phe Gly Cys Lys Val Leu Cys
                180                 185                 190

Cys Thr Pro Gly Gly Val Val Leu Ile Leu Pro Ser His Ser His Met
            195                 200                 205

Ala Glu Thr Ala Ser Pro Thr Pro Leu Asn Glu Val
    210                 215                 220

<210> SEQ ID NO 47
<211> LENGTH: 186
<212> TYPE: PRT
<213> ORGANISM: Homo sapiens

<400> SEQUENCE: 47

Met His Gln Thr Tyr Ser Arg His Cys Arg Pro Glu Glu Ser Thr Phe
1               5                   10                  15

Ser Ala Ala Met Thr Thr Met Gln Gly Met Glu Gln Ala Met Pro Gly
                20                  25                  30

Ala Gly Pro Gly Val Pro Gln Leu Gly Asn Met Ala Val Ile His Ser
            35                  40                  45

His Leu Trp Lys Gly Leu Gln Glu Lys Phe Leu Lys Gly Glu Pro Lys
        50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
                100                 105                 110

Ile Ser Gly Ser Leu Ser Ile Ala Ala Gly Ile Arg Thr Thr Lys Gly
            115                 120                 125

Leu Gly Leu Asp Gly Met Val Leu Leu Ser Val Leu Glu Phe Cys
        130                 135                 140

Ile Ala Val Ser Leu Ser Ala Phe Gly Cys Lys Val Leu Cys Cys Thr
145                 150                 155                 160

Pro Gly Gly Val Val Leu Ile Leu Pro Ser His Ser His Met Ala Glu
                165                 170                 175

Thr Ala Ser Pro Thr Pro Leu Asn Glu Val
            180                 185

<210> SEQ ID NO 48
<211> LENGTH: 648
<212> TYPE: PRT
<213> ORGANISM: Homo sapiens

<400> SEQUENCE: 48

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
                20                  25                  30
```

-continued

```
Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
 50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
                115                 120                 125

Asp Phe Leu Asp His Val Pro Leu Thr Thr His Asn Phe Ala Arg Lys
            130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
                180                 185                 190

Leu Leu Leu Phe Pro Asn Ser Thr Ile Gly Asp Ser Gly Val Pro Ala
                195                 200                 205

Leu Pro Ser Leu Thr Met Arg Arg Met Arg Glu Ser Val Ser Arg Met
            210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
                260                 265                 270

Asp Ser Arg Met Ile Glu Asp Ala Ile Arg Ser His Ser Glu Ser Ala
            275                 280                 285

Ser Pro Ser Ala Leu Ser Ser Pro Asn Asn Leu Ser Pro Thr Gly
            290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
                340                 345                 350

Thr Arg Ile Gly Ser Gly Ser Phe Gly Thr Val Tyr Lys Gly Lys Trp
            355                 360                 365

His Gly Asp Val Ala Val Lys Ile Leu Lys Val Val Asp Pro Thr Pro
            370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
            435                 440                 445
```

```
Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
                500                 505                 510

Ala Pro Glu Val Ile Arg Met Gln Asp Asn Asn Pro Phe Ser Phe Gln
                515                 520                 525

Ser Asp Val Tyr Ser Tyr Gly Ile Val Leu Tyr Glu Leu Met Thr Gly
530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
                580                 585                 590

Lys Glu Glu Arg Pro Leu Phe Pro Gln Ile Leu Ser Ser Ile Glu Leu
                595                 600                 605

Leu Gln His Ser Leu Pro Lys Ile Asn Arg Ser Ala Ser Glu Pro Ser
610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 49
<211> LENGTH: 581
<212> TYPE: PRT
<213> ORGANISM: Homo sapiens

<400> SEQUENCE: 49

Met Pro Ala Pro Arg Ala Arg Glu Gln Pro Arg Val Pro Gly Glu Arg
1               5                   10                  15

Gln Pro Leu Leu Pro Arg Gly Ala Arg Gly Pro Arg Arg Trp Arg Arg
                20                  25                  30

Ala Ala Gly Ala Ala Val Leu Leu Val Glu Met Leu Glu Arg Ala Ala
            35                  40                  45

Phe Phe Gly Val Thr Ala Asn Leu Val Leu Tyr Leu Asn Ser Thr Asn
50                  55                  60

Phe Asn Trp Thr Gly Glu Gln Ala Thr Arg Ala Ala Leu Val Phe Leu
65                  70                  75                  80

Gly Ala Ser Tyr Leu Leu Ala Pro Val Gly Gly Trp Leu Ala Asp Val
                85                  90                  95

Tyr Leu Gly Arg Tyr Arg Ala Val Ala Leu Ser Leu Leu Leu Tyr Leu
                100                 105                 110

Ala Ala Ser Gly Leu Leu Pro Ala Thr Ala Phe Pro Asp Gly Arg Ser
            115                 120                 125

Ser Phe Cys Gly Glu Met Pro Ala Ser Pro Leu Gly Pro Ala Cys Pro
            130                 135                 140

Ser Ala Gly Cys Pro Arg Ser Ser Pro Tyr Cys Ala Pro Val
145                 150                 155                 160

Leu Tyr Ala Gly Leu Leu Leu Gly Leu Ala Ala Ser Ser Val Arg
                165                 170                 175
```

```
Ser Asn Leu Thr Ser Phe Gly Ala Asp Gln Val Met Asp Leu Gly Arg
            180                 185                 190

Asp Ala Thr Arg Arg Phe Phe Asn Trp Phe Tyr Trp Ser Ile Asn Leu
        195                 200                 205

Gly Ala Val Leu Ser Leu Leu Val Val Ala Phe Ile Gln Gln Asn Ile
        210                 215                 220

Ser Phe Leu Leu Gly Tyr Ser Ile Pro Val Gly Cys Val Gly Leu Ala
225                 230                 235                 240

Phe Phe Ile Phe Leu Phe Ala Thr Pro Val Phe Ile Thr Lys Pro Pro
                245                 250                 255

Met Gly Ser Gln Val Ser Ser Met Leu Lys Leu Ala Leu Gln Asn Cys
            260                 265                 270

Cys Pro Gln Leu Trp Gln Arg His Ser Ala Arg Asp Arg Gln Cys Ala
        275                 280                 285

Arg Val Leu Ala Asp Glu Arg Ser Pro Gln Pro Gly Ala Ser Pro Gln
        290                 295                 300

Glu Asp Ile Ala Asn Phe Gln Val Leu Val Lys Ile Leu Pro Val Met
305                 310                 315                 320

Val Thr Leu Val Pro Tyr Trp Met Val Tyr Phe Gln Met Gln Ser Thr
                325                 330                 335

Tyr Val Leu Gln Gly Leu His Leu His Ile Pro Asn Ile Phe Pro Ala
            340                 345                 350

Asn Pro Ala Asn Ile Ser Val Ala Leu Arg Ala Gln Gly Ser Ser Tyr
        355                 360                 365

Thr Ile Pro Glu Ala Trp Leu Leu Ala Asn Val Val Val Val Leu
        370                 375                 380

Ile Leu Val Pro Leu Lys Asp Arg Leu Ile Asp Pro Leu Leu Leu Arg
385                 390                 395                 400

Cys Lys Leu Leu Pro Ser Ala Leu Gln Lys Met Ala Leu Gly Met Phe
                405                 410                 415

Phe Gly Phe Thr Ser Val Ile Val Ala Gly Val Leu Glu Met Glu Arg
            420                 425                 430

Leu His Tyr Ile His His Asn Glu Thr Val Ser Gln Gln Ile Gly Glu
        435                 440                 445

Val Leu Tyr Asn Ala Ala Pro Leu Ser Ile Trp Trp Gln Ile Pro Gln
        450                 455                 460

Tyr Leu Leu Ile Gly Ile Ser Glu Ile Phe Ala Ser Ile Pro Gly Leu
465                 470                 475                 480

Glu Phe Ala Tyr Ser Glu Ala Pro Arg Ser Met Gln Gly Ala Ile Met
                485                 490                 495

Gly Ile Phe Phe Cys Leu Ser Gly Val Gly Ser Leu Leu Gly Ser Ser
            500                 505                 510

Leu Val Ala Leu Leu Ser Leu Pro Gly Gly Trp Leu His Cys Pro Lys
        515                 520                 525

Asp Phe Gly Asn Ile Asn Asn Cys Arg Met Asp Leu Tyr Phe Phe Leu
        530                 535                 540

Leu Ala Gly Ile Gln Ala Val Thr Ala Leu Leu Phe Val Trp Ile Ala
545                 550                 555                 560

Gly Arg Tyr Glu Arg Ala Ser Gln Gly Pro Ala Ser His Ser Arg Phe
                565                 570                 575

Ser Arg Asp Arg Gly
            580
```

<210> SEQ ID NO 50
<211> LENGTH: 475
<212> TYPE: PRT
<213> ORGANISM: Homo sapiens

<400> SEQUENCE: 50

```
Met Gly Met Trp Ala Ser Leu Asp Ala Leu Trp Glu Met Pro Ala Glu
1               5                   10                  15

Lys Arg Ile Phe Gly Ala Val Leu Leu Phe Ser Trp Thr Val Tyr Leu
            20                  25                  30

Trp Glu Thr Phe Leu Ala Gln Arg Gln Arg Ile Tyr Lys Thr Thr
        35                  40                  45

Thr His Val Pro Pro Glu Leu Gly Gln Ile Met Asp Ser Glu Thr Phe
    50                  55                  60

Glu Lys Ser Arg Leu Tyr Gln Leu Asp Lys Ser Thr Phe Ser Phe Trp
65                  70                  75                  80

Ser Gly Leu Tyr Ser Glu Thr Glu Gly Thr Leu Ile Leu Leu Phe Gly
                85                  90                  95

Gly Ile Pro Tyr Leu Trp Arg Leu Ser Gly Arg Phe Cys Gly Tyr Ala
            100                 105                 110

Gly Phe Gly Pro Glu Tyr Glu Ile Thr Gln Ser Leu Val Phe Leu Leu
        115                 120                 125

Leu Ala Thr Leu Phe Ser Ala Leu Thr Gly Leu Pro Trp Ser Leu Tyr
    130                 135                 140

Asn Thr Phe Val Ile Glu Glu Lys His Gly Phe Asn Gln Gln Thr Leu
145                 150                 155                 160

Gly Phe Phe Met Lys Asp Ala Ile Lys Lys Phe Val Val Thr Gln Cys
                165                 170                 175

Ile Leu Leu Pro Val Ser Ser Leu Leu Leu Tyr Ile Ile Lys Ile Gly
            180                 185                 190

Gly Asp Tyr Phe Phe Ile Tyr Ala Trp Leu Phe Thr Leu Val Val Ser
        195                 200                 205

Leu Val Leu Val Thr Ile Tyr Ala Asp Tyr Ile Ala Pro Leu Phe Asp
    210                 215                 220

Lys Phe Thr Pro Leu Pro Glu Gly Lys Leu Lys Glu Glu Ile Glu Val
225                 230                 235                 240

Met Ala Lys Ser Ile Asp Phe Pro Leu Thr Lys Val Tyr Val Val Glu
                245                 250                 255

Gly Ser Lys Arg Ser Ser His Ser Asn Ala Tyr Phe Tyr Gly Phe Phe
            260                 265                 270

Lys Asn Lys Arg Ile Val Leu Phe Asp Thr Leu Leu Glu Glu Tyr Ser
        275                 280                 285

Val Leu Asn Lys Asp Ile Gln Glu Asp Ser Gly Met Glu Pro Arg Asn
    290                 295                 300

Glu Glu Glu Gly Asn Ser Glu Glu Ile Lys Ala Lys Val Lys Asn Lys
305                 310                 315                 320

Lys Gln Gly Cys Lys Asn Glu Glu Val Leu Ala Val Leu Gly His Glu
                325                 330                 335

Leu Gly His Trp Lys Leu Gly His Thr Val Lys Asn Ile Ile Ser
            340                 345                 350

Gln Met Asn Ser Phe Leu Cys Phe Phe Leu Phe Ala Val Leu Ile Gly
        355                 360                 365

Arg Lys Glu Leu Phe Ala Ala Phe Gly Phe Tyr Asp Ser Gln Pro Thr
    370                 375                 380
```

Leu Ile Gly Leu Leu Ile Ile Phe Gln Phe Ile Phe Ser Pro Tyr Asn
385                 390                 395                 400

Glu Val Leu Ser Phe Cys Leu Thr Val Leu Ser Arg Arg Phe Glu Phe
                405                 410                 415

Gln Ala Asp Ala Phe Ala Lys Lys Leu Gly Lys Ala Lys Asp Leu Tyr
            420                 425                 430

Ser Ala Leu Ile Lys Leu Asn Lys Asp Asn Leu Gly Phe Pro Val Ser
        435                 440                 445

Asp Trp Leu Phe Ser Met Trp His Tyr Ser His Pro Pro Leu Leu Glu
    450                 455                 460

Arg Leu Gln Ala Leu Lys Thr Met Lys Gln His
465                 470                 475

<210> SEQ ID NO 51
<211> LENGTH: 19
<212> TYPE: DNA
<213> ORGANISM: Artificial sequence
<220> FEATURE:
<223> OTHER INFORMATION: siRNA target sequence

<400> SEQUENCE: 51
ggttacctaa gggtgtggc                                                19

<210> SEQ ID NO 52
<211> LENGTH: 19
<212> TYPE: DNA
<213> ORGANISM: Artificial sequence
<220> FEATURE:
<223> OTHER INFORMATION: siRNA target sequence

<400> SEQUENCE: 52
gaatcgatat tgttacaac                                                19

<210> SEQ ID NO 53
<211> LENGTH: 19
<212> TYPE: DNA
<213> ORGANISM: Artificial sequence
<220> FEATURE:
<223> OTHER INFORMATION: siRNA target sequence

<400> SEQUENCE: 53
gcataaggct atgaagaga                                                19

<210> SEQ ID NO 54
<211> LENGTH: 19
<212> TYPE: DNA
<213> ORGANISM: Artificial sequence
<220> FEATURE:
<223> OTHER INFORMATION: siRNA target sequence

<400> SEQUENCE: 54
gtctatacct cctggcaga                                                19

<210> SEQ ID NO 55
<211> LENGTH: 19
<212> TYPE: DNA
<213> ORGANISM: Artificial sequence
<220> FEATURE:
<223> OTHER INFORMATION: siRNA target sequence

<400> SEQUENCE: 55
gccaaagacc tgtccattc                                                19

```
<210> SEQ ID NO 56
<211> LENGTH: 19
<212> TYPE: DNA
<213> ORGANISM: Artificial sequence
<220> FEATURE:
<223> OTHER INFORMATION: siRNA target sequence

<400> SEQUENCE: 56
gtcccagcta ccatcaaga                                              19

<210> SEQ ID NO 57
<211> LENGTH: 19
<212> TYPE: DNA
<213> ORGANISM: Artificial sequence
<220> FEATURE:
<223> OTHER INFORMATION: siRNA target sequence

<400> SEQUENCE: 57
cccggcagat ttcagaatc                                              19

<210> SEQ ID NO 58
<211> LENGTH: 19
<212> TYPE: DNA
<213> ORGANISM: Artificial sequence
<220> FEATURE:
<223> OTHER INFORMATION: siRNA target sequence

<400> SEQUENCE: 58
gagtctgtgg tcagcatta                                              19

<210> SEQ ID NO 59
<211> LENGTH: 19
<212> TYPE: DNA
<213> ORGANISM: Artificial sequence
<220> FEATURE:
<223> OTHER INFORMATION: siRNA target sequence

<400> SEQUENCE: 59
ggaacagaca aactatcga                                              19

<210> SEQ ID NO 60
<211> LENGTH: 19
<212> TYPE: DNA
<213> ORGANISM: Artificial sequence
<220> FEATURE:
<223> OTHER INFORMATION: siRNA target sequence

<400> SEQUENCE: 60
gttctggtca tggatctct                                              19

<210> SEQ ID NO 61
<211> LENGTH: 19
<212> TYPE: DNA
<213> ORGANISM: Artificial sequence
<220> FEATURE:
<223> OTHER INFORMATION: siRNA target sequence

<400> SEQUENCE: 61
cgtggagctg agagataac                                              19

<210> SEQ ID NO 62
<211> LENGTH: 19
<212> TYPE: DNA
<213> ORGANISM: Artificial sequence
<220> FEATURE:
<223> OTHER INFORMATION: siRNA target sequence
```

```
<400> SEQUENCE: 62
gacttagcta gcatcaata                                                19

<210> SEQ ID NO 63
<211> LENGTH: 19
<212> TYPE: DNA
<213> ORGANISM: Artificial sequence
<220> FEATURE:
<223> OTHER INFORMATION: siRNA target sequence

<400> SEQUENCE: 63
ggatattgtc cattgaaat                                                19

<210> SEQ ID NO 64
<211> LENGTH: 19
<212> TYPE: DNA
<213> ORGANISM: Artificial sequence
<220> FEATURE:
<223> OTHER INFORMATION: siRNA target sequence

<400> SEQUENCE: 64
tgaagcaacc atgcccatc                                                19

<210> SEQ ID NO 65
<211> LENGTH: 19
<212> TYPE: DNA
<213> ORGANISM: Artificial sequence
<220> FEATURE:
<223> OTHER INFORMATION: siRNA target sequence

<400> SEQUENCE: 65
tgtgttgctg ctatgaacc                                                19

<210> SEQ ID NO 66
<211> LENGTH: 19
<212> TYPE: DNA
<213> ORGANISM: Artificial sequence
<220> FEATURE:
<223> OTHER INFORMATION: siRNA target sequence

<400> SEQUENCE: 66
gagctgattg aagacagtc                                                19

<210> SEQ ID NO 67
<211> LENGTH: 19
<212> TYPE: DNA
<213> ORGANISM: Artificial sequence
<220> FEATURE:
<223> OTHER INFORMATION: siRNA target sequence

<400> SEQUENCE: 67
gtcttcttga caatgtaac                                                19

<210> SEQ ID NO 68
<211> LENGTH: 19
<212> TYPE: DNA
<213> ORGANISM: Artificial sequence
<220> FEATURE:
<223> OTHER INFORMATION: siRNA target sequence

<400> SEQUENCE: 68
gtaccacaag gatgtgaag                                                19

<210> SEQ ID NO 69
```

-continued

```
<211> LENGTH: 19
<212> TYPE: DNA
<213> ORGANISM: Artificial sequence
<220> FEATURE:
<223> OTHER INFORMATION: siRNA target sequence

<400> SEQUENCE: 69
gaatgagtcc cataacttt                                                  19

<210> SEQ ID NO 70
<211> LENGTH: 19
<212> TYPE: DNA
<213> ORGANISM: Artificial sequence
<220> FEATURE:
<223> OTHER INFORMATION: siRNA target sequence

<400> SEQUENCE: 70
ccgtggctgt gaactatag                                                  19

<210> SEQ ID NO 71
<211> LENGTH: 19
<212> TYPE: DNA
<213> ORGANISM: Artificial sequence
<220> FEATURE:
<223> OTHER INFORMATION: siRNA target sequence

<400> SEQUENCE: 71
ggtctgtctg cccgataat                                                  19

<210> SEQ ID NO 72
<211> LENGTH: 19
<212> TYPE: DNA
<213> ORGANISM: Artificial sequence
<220> FEATURE:
<223> OTHER INFORMATION: siRNA target sequence

<400> SEQUENCE: 72
ccagagtgtg aatgtgttc                                                  19

<210> SEQ ID NO 73
<211> LENGTH: 19
<212> TYPE: DNA
<213> ORGANISM: Artificial sequence
<220> FEATURE:
<223> OTHER INFORMATION: siRNA target sequence

<400> SEQUENCE: 73
ggtgctcagc tatgtggac                                                  19

<210> SEQ ID NO 74
<211> LENGTH: 19
<212> TYPE: DNA
<213> ORGANISM: Artificial sequence
<220> FEATURE:
<223> OTHER INFORMATION: siRNA target sequence

<400> SEQUENCE: 74
ggttgtctac cttcataac                                                  19

<210> SEQ ID NO 75
<211> LENGTH: 19
<212> TYPE: DNA
<213> ORGANISM: Artificial sequence
<220> FEATURE:
<223> OTHER INFORMATION: siRNA target sequence

<400> SEQUENCE: 75
```
gaagatgagg cttctggga                                                    19

<210> SEQ ID NO 76
<211> LENGTH: 19
<212> TYPE: DNA
<213> ORGANISM: Artificial sequence
<220> FEATURE:
<223> OTHER INFORMATION: siRNA target sequence

<400> SEQUENCE: 76
ccaaacctgt gtcaacttc                                                    19

<210> SEQ ID NO 77
<211> LENGTH: 19
<212> TYPE: DNA
<213> ORGANISM: Artificial sequence
<220> FEATURE:
<223> OTHER INFORMATION: siRNA target sequence

<400> SEQUENCE: 77
gagatggtca ccatgaatt                                                    19

<210> SEQ ID NO 78
<211> LENGTH: 19
<212> TYPE: DNA
<213> ORGANISM: Artificial sequence
<220> FEATURE:
<223> OTHER INFORMATION: siRNA target sequence

<400> SEQUENCE: 78
tgatggttac cgcaagatc                                                    19

<210> SEQ ID NO 79
<211> LENGTH: 19
<212> TYPE: DNA
<213> ORGANISM: Artificial sequence
<220> FEATURE:
<223> OTHER INFORMATION: siRNA target sequence

<400> SEQUENCE: 79
gcctatctat tggaattcc                                                    19

<210> SEQ ID NO 80
<211> LENGTH: 19
<212> TYPE: DNA
<213> ORGANISM: Artificial sequence
<220> FEATURE:
<223> OTHER INFORMATION: siRNA target sequence

<400> SEQUENCE: 80
aataaagatc caacaagac                                                    19

<210> SEQ ID NO 81
<211> LENGTH: 19
<212> TYPE: DNA
<213> ORGANISM: Artificial sequence
<220> FEATURE:
<223> OTHER INFORMATION: siRNA target sequence

<400> SEQUENCE: 81
gccaaaccag accaagata                                                    19

<210> SEQ ID NO 82
<211> LENGTH: 19
<212> TYPE: DNA

```
<213> ORGANISM: Artificial sequence
<220> FEATURE:
<223> OTHER INFORMATION: siRNA target sequence

<400> SEQUENCE: 82
gatcgaaagg tacctgtat                                                19

<210> SEQ ID NO 83
<211> LENGTH: 19
<212> TYPE: DNA
<213> ORGANISM: Artificial sequence
<220> FEATURE:
<223> OTHER INFORMATION: siRNA target sequence

<400> SEQUENCE: 83
attggcctgt tcgctaatc                                                19

<210> SEQ ID NO 84
<211> LENGTH: 19
<212> TYPE: DNA
<213> ORGANISM: Artificial sequence
<220> FEATURE:
<223> OTHER INFORMATION: siRNA target sequence

<400> SEQUENCE: 84
gagagagggt acaaattcc                                                19

<210> SEQ ID NO 85
<211> LENGTH: 19
<212> TYPE: DNA
<213> ORGANISM: Artificial sequence
<220> FEATURE:
<223> OTHER INFORMATION: siRNA target sequence

<400> SEQUENCE: 85
ccagagctgc atattagcc                                                19

<210> SEQ ID NO 86
<211> LENGTH: 19
<212> TYPE: DNA
<213> ORGANISM: Artificial sequence
<220> FEATURE:
<223> OTHER INFORMATION: siRNA target sequence

<400> SEQUENCE: 86
atttgtggtg ggcgttctc                                                19

<210> SEQ ID NO 87
<211> LENGTH: 19
<212> TYPE: DNA
<213> ORGANISM: Artificial sequence
<220> FEATURE:
<223> OTHER INFORMATION: siRNA target sequence

<400> SEQUENCE: 87
agaagctgta ctcatcggc                                                19

<210> SEQ ID NO 88
<211> LENGTH: 19
<212> TYPE: DNA
<213> ORGANISM: Artificial sequence
<220> FEATURE:
<223> OTHER INFORMATION: siRNA target sequence

<400> SEQUENCE: 88
caacctcatg aaccagatc                                                19
```

<210> SEQ ID NO 89
<211> LENGTH: 19
<212> TYPE: DNA
<213> ORGANISM: Artificial sequence
<220> FEATURE:
<223> OTHER INFORMATION: siRNA target sequence

<400> SEQUENCE: 89
ctcgggtaag gatgtcttc                                                  19

<210> SEQ ID NO 90
<211> LENGTH: 19
<212> TYPE: DNA
<213> ORGANISM: Artificial sequence
<220> FEATURE:
<223> OTHER INFORMATION: siRNA target sequence

<400> SEQUENCE: 90
acaacctgga caagctatg                                                  19

<210> SEQ ID NO 91
<211> LENGTH: 19
<212> TYPE: DNA
<213> ORGANISM: Artificial sequence
<220> FEATURE:
<223> OTHER INFORMATION: siRNA target sequence

<400> SEQUENCE: 91
ccatcaccct tactgtaac                                                  19

<210> SEQ ID NO 92
<211> LENGTH: 19
<212> TYPE: DNA
<213> ORGANISM: Artificial sequence
<220> FEATURE:
<223> OTHER INFORMATION: siRNA target sequence

<400> SEQUENCE: 92
gcatggtgct cctcttaag                                                  19

<210> SEQ ID NO 93
<211> LENGTH: 19
<212> TYPE: DNA
<213> ORGANISM: Artificial sequence
<220> FEATURE:
<223> OTHER INFORMATION: siRNA target sequence

<400> SEQUENCE: 93
gtttggcaac agtaaagtc                                                  19

<210> SEQ ID NO 94
<211> LENGTH: 19
<212> TYPE: DNA
<213> ORGANISM: Artificial sequence
<220> FEATURE:
<223> OTHER INFORMATION: siRNA target sequence

<400> SEQUENCE: 94
gaggatgcaa ttcgaagtc                                                  19

<210> SEQ ID NO 95
<211> LENGTH: 19
<212> TYPE: DNA
<213> ORGANISM: Artificial sequence
<220> FEATURE:

<223> OTHER INFORMATION: siRNA target sequence

<400> SEQUENCE: 95
ccgaatgcag gataacaac                                                                19

<210> SEQ ID NO 96
<211> LENGTH: 19
<212> TYPE: DNA
<213> ORGANISM: Artificial sequence
<220> FEATURE:
<223> OTHER INFORMATION: siRNA target sequence

<400> SEQUENCE: 96
gcacgcttag attggaata                                                                19

<210> SEQ ID NO 97
<211> LENGTH: 19
<212> TYPE: DNA
<213> ORGANISM: Artificial sequence
<220> FEATURE:
<223> OTHER INFORMATION: siRNA target sequence

<400> SEQUENCE: 97
cctgaattcc ctgctcaac                                                                19

<210> SEQ ID NO 98
<211> LENGTH: 19
<212> TYPE: DNA
<213> ORGANISM: Artificial sequence
<220> FEATURE:
<223> OTHER INFORMATION: siRNA target sequence

<400> SEQUENCE: 98
gttccactcg gcaatgtac                                                                19

<210> SEQ ID NO 99
<211> LENGTH: 19
<212> TYPE: DNA
<213> ORGANISM: Artificial sequence
<220> FEATURE:
<223> OTHER INFORMATION: siRNA target sequence

<400> SEQUENCE: 99
gtagccaata ccttgctct                                                                19

<210> SEQ ID NO 100
<211> LENGTH: 19
<212> TYPE: DNA
<213> ORGANISM: Artificial sequence
<220> FEATURE:
<223> OTHER INFORMATION: siRNA target sequence

<400> SEQUENCE: 100
ggactttggg aacatcaac                                                                19

<210> SEQ ID NO 101
<211> LENGTH: 19
<212> TYPE: DNA
<213> ORGANISM: Artificial sequence
<220> FEATURE:
<223> OTHER INFORMATION: siRNA target sequence

<400> SEQUENCE: 101
cctcgtgctg tacctcaac                                                                19

```
<210> SEQ ID NO 102
<211> LENGTH: 19
<212> TYPE: DNA
<213> ORGANISM: Artificial sequence
<220> FEATURE:
<223> OTHER INFORMATION: siRNA target sequence

<400> SEQUENCE: 102
cctctatgct taagctcgc                                                  19

<210> SEQ ID NO 103
<211> LENGTH: 19
<212> TYPE: DNA
<213> ORGANISM: Artificial sequence
<220> FEATURE:
<223> OTHER INFORMATION: siRNA target sequence

<400> SEQUENCE: 103
gatggagcgc ttacactac                                                  19

<210> SEQ ID NO 104
<211> LENGTH: 19
<212> TYPE: DNA
<213> ORGANISM: Artificial sequence
<220> FEATURE:
<223> OTHER INFORMATION: siRNA target sequence

<400> SEQUENCE: 104
ggacagtctc aacaatgac                                                  19

<210> SEQ ID NO 105
<211> LENGTH: 19
<212> TYPE: DNA
<213> ORGANISM: Artificial sequence
<220> FEATURE:
<223> OTHER INFORMATION: siRNA target sequence

<400> SEQUENCE: 105
gctgttgtta accatcaag                                                  19

<210> SEQ ID NO 106
<211> LENGTH: 19
<212> TYPE: DNA
<213> ORGANISM: Artificial sequence
<220> FEATURE:
<223> OTHER INFORMATION: siRNA target sequence

<400> SEQUENCE: 106
gctgaagcac aacccgaaa                                                  19

<210> SEQ ID NO 107
<211> LENGTH: 19
<212> TYPE: DNA
<213> ORGANISM: Artificial sequence
<220> FEATURE:
<223> OTHER INFORMATION: siRNA target sequence

<400> SEQUENCE: 107
tggttgttct caatgtggc                                                  19

<210> SEQ ID NO 108
<211> LENGTH: 19
<212> TYPE: DNA
<213> ORGANISM: Artificial sequence
<220> FEATURE:
<223> OTHER INFORMATION: siRNA target sequence
```

```
-continued

<400> SEQUENCE: 108
gactgaaggc actcttatt                                                  19

<210> SEQ ID NO 109
<211> LENGTH: 19
<212> TYPE: DNA
<213> ORGANISM: Artificial sequence
<220> FEATURE:
<223> OTHER INFORMATION: siRNA target sequence

<400> SEQUENCE: 109
gccatggagt ctttataat                                                  19

<210> SEQ ID NO 110
<211> LENGTH: 12
<212> TYPE: RNA
<213> ORGANISM: Artificial sequence
<220> FEATURE:
<223> OTHER INFORMATION: Loop sequence

<400> SEQUENCE: 110
guuugcuaua ac                                                         12

<210> SEQ ID NO 111
<211> LENGTH: 18
<212> TYPE: DNA
<213> ORGANISM: Artificial sequence
<220> FEATURE:
<223> OTHER INFORMATION: Forward primer

<400> SEQUENCE: 111
accctgtgct gctcaccg                                                   18

<210> SEQ ID NO 112
<211> LENGTH: 23
<212> TYPE: DNA
<213> ORGANISM: Artificial sequence
<220> FEATURE:
<223> OTHER INFORMATION: Reverse primer

<400> SEQUENCE: 112
aggtctcaaa catgatctgg gtc                                             23
```